(12) United States Patent
Tang et al.

(10) Patent No.: US 8,329,682 B2
(45) Date of Patent: Dec. 11, 2012

(54) PYRROLO-NITROGENOUS HETEROCYCLIC DERIVATIVES, THE PREPARATION AND THE PHARMACEUTICAL USE THEREOF

(75) Inventors: Peng Cho Tang, Shanghai (CN); Yidong Su, Shanghai (CN); Yali Li, Shanghai (CN); Lei Zhang, Shanghai (CN); Fuqiang Zhao, Shanghai (CN); Jialiang Yang, Shanghai (CN); Ying Zhou, Shanghai (CN); Pingyan Bie, Shanghai (CN); Guangtao Qian, Shanghai (CN); Minggang Ju, Shanghai (CN)

(73) Assignee: Shanghai Hengrui Pharmaceutical Co., Ltd., Shanghai (CN)

( * ) Notice: Subject to any disclaimer, the term of this patent is extended or adjusted under 35 U.S.C. 154(b) by 267 days.

(21) Appl. No.: 12/451,466

(22) PCT Filed: May 14, 2008

(86) PCT No.: PCT/CN2008/001352
§ 371 (c)(1),
(2), (4) Date: Dec. 3, 2009

(87) PCT Pub. No.: WO2008/138232
PCT Pub. Date: Nov. 20, 2008

(65) Prior Publication Data
US 2010/0075952 A1 Mar. 25, 2010

(30) Foreign Application Priority Data

May 14, 2007 (CN) .......................... 2007 1 0107463
Apr. 11, 2008 (CN) .......................... 2008 1 0087564

(51) Int. Cl.
*C07D 519/00* (2006.01)
*C07D 487/04* (2006.01)
*C07D 471/04* (2006.01)
*A61K 31/41* (2006.01)
*A61K 31/437* (2006.01)
*A61P 35/00* (2006.01)

(52) U.S. Cl. ................... 514/183; 514/212.06; 514/412; 514/414; 540/461; 540/523

(58) Field of Classification Search ................ 540/461, 540/523; 514/183, 212.06, 412, 414
See application file for complete search history.

(56) References Cited

U.S. PATENT DOCUMENTS
6,599,902 B2 7/2003 Cui et al.

FOREIGN PATENT DOCUMENTS
| WO | WO98/05335 | 2/1998 |
| WO | WO01/60814 | 8/2001 |
| WO | WO01/64681 | 9/2001 |
| WO | WO01/94312 | 12/2001 |
| WO | WO 2007/085188 | 8/2007 |

OTHER PUBLICATIONS

Strawn, Laurie M., et al., "Flk-1 as a Target for Tumor Growth Inhibition", (1996),6 pgs.
Jackson, Jeffrey R., et al., "Pharmacological Effects of SB 220025, a Selective Inhibitor of P38 Mitogen-Activated Protein Kinase, in Angiogenesis and Chronic Inflammatory Disease Models", (1998),6 pgs.
Bolen, Joseph B., et al., "Leukocyte Protein Tyrosine Kinases: Potential Targets for Drug Discovery", (1997),34 pgs.
Littler, Edward et al., "Human cytomegalovirus UL97 open reading frame encodes a protein that phosphorylates the antiviral nucleoside analogue ganciclovir", (1992),3 pgs.
Weber, R et al., "Immunohistochemical analysis of c-kit (CD117) expression in solid tumors", (2004),1 pg.
Huang, Steve C., et al., "Duplication of the Mutant RET Allele in Trisomy 10 or Loss of the Wild-Type Allele in Multiple Endocrine Neoplasia Type 2-associated Pheochromocytomas", (2000),4 pgs.
Ma, Patrick C., et al., "c-Met: Structure, functions and potential for therapeutic inhibition", (2003),17 pgs.
Maulik, Gautam et al., "Role of the hepatocyte growth factor receptor, c-Met, in oncogenesis and potential for therapeutic inhibition", (2002),19 pgs.
Ma, Patrick C., et al., "c-Met Mutational Analysis in Small Cell Lung Cancer: Novel Juxtamembrane Domain Mutations Regulating Cytoskeletal Functions", (2003) 10 pgs.
Bolen, Joseph B., "Nonreceptor tyrosine protein kinases", (1993),7 pgs.

(Continued)

*Primary Examiner* — Bruck Kifle
(74) *Attorney, Agent, or Firm* — Jon L. Woodard; MacDonald, Illig, Jones & Britton LLP

(57) ABSTRACT

The invention provides new pyrrolo-nitrogenous heterocyclic derivatives represented by formula (I) or their salts, the preparation thereof, pharmaceutical compositions containing such derivatives and the use of such derivatives as therapeutic agents, especially as protein kinase inhibitors, wherein each substituent in formula (I) is same as defined in the description.

12 Claims, No Drawings

OTHER PUBLICATIONS

Borthwick, Andrew C., et al., "Inhibition of Clycogen Synthase Kinase-3 by Insulin in Cultured Human Skeletal Muscle Myoblasts", (1995),8 pgs.

Salari, Hassan "Erbstatin blocks platelet activating factor-induced protein-tyrosine phosphorylation, polyphosphoinositide hydrolysis, protein kinase C activation, serotonin secretion and aggregation of rabbit platelets", (1990),5 pgs.

Hajjar, David P., et al., "Signal transduction in atherosclerosis: integration of cytokines and the eicosanoid network", (1992),9 pgs.

Hunter, Tony et al., "Cyclins and Cancer II: Cyclin D and CDK Inhibitors Come of Age", (1994),10 pgs.

Tanaka, Sakae et al., "c-Cbl is downstream of c-Src in a signaling pathway necessary for bone resorption", (1996),4 pgs.

Dvir, Arik et al., "The Inhibition of EGF-dependent Proliferation of Keratinocytes by Tyrphostin Tyrosine Kinase Blockers", (1991),9 pgs.

Badger, Alison M., et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function", (1996),9 pgs.

Yashpal, Kiran et al., "Noxious Thermal and Chemical Stimulation Induce Increases in $^3$H-Phorbol 12,13-Dibutyrate Binding in Spinal Cord Dorsal Horn as Well as Persistent Pain and Hyperalgesia, Which Is Reduced by Inhibition of Protein Kinase C", (1995),10 pgs.

Sengupta, Amitabha et al., "Potentiation of GSK-3-catalyzed Alzheimer-like phosphorylation of human tau by cdk5", (1997),7 pgs.

Mandelkow, E et al., "Glycogen synthase kinase-3 and the Alzheimer-like state of microtubule-associated protein tau", (1992),7 pgs.

Schlessinger, J et al., "Growth Factor Signaling by Receptor Tyrosine Kinases", (1992),9 pgs.

Robinson, Dan R., et al., "The protein tyrosine kinase family of the human genome", (2000),10 pgs.

PYRROLO-NITROGENOUS HETEROCYCLIC DERIVATIVES, THE PREPARATION AND THE PHARMACEUTICAL USE THEREOF

FIELD OF THE INVENTION

The invention relates to new pyrrolo-nitrogenous heterocyclic derivatives, the preparation thereof, pharmaceutical compositions containing such derivatives and the use of such derivatives as therapeutic agents, especially as protein kinase inhibitors.

BACKGROUND OF THE INVENTION

Cellular signal transduction is a fundamental mechanism whereby extracellular stimuli are relayed to the interior of cells and subsequently regulate diverse cellular processes. These signals regulate a wide variety of physical responses in the cell including proliferation, differentiation, apoptosis and motility. The extracellular signals take the form of a diverse variety of soluble factors including growth factors as well as paracrine, autocrine and endocrine factors. By binding to specific transmembrane receptors, growth factor ligands communicate extracellular signals to the intracellular signalling pathways, thereby causing the individual cell to respond to extracellular signals. Many of these signal transduction processes utilize the reversible process of the phosphorylation of proteins involving specific protein kinases and phosphatases.

Protein kinases (PKs) are enzymes that catalyze the phosphorylation of hydroxyl groups on tyrosine, serine and threonine residues of proteins, whereas protein phosphatases hydrolyze phosphate moieties from phosphorylated protein substrates. The converse functions of protein kinases and protein phosphatases balance and regulate the flow of signals in signal transduction processes. The phosphorylation state of a protein can affect its conformation, enzymatic activity, and cellular location, is modified through the reciprocal actions of protein kinases and protein phosphatases. Phosphorylation is an important regulatory mechanism in the signal transduction process and aberrations in the process result in abnormal cell differentiation, transformation and growth. For example, it has been discovered that a cell may become cancerous by virtue of the transformation of a portion of its DNA into an oncogene. Several such oncogenes encode proteins which are receptors for growth factors, for example tyrosine kinases. Tyrosine kinases may also be mutated to constitutively active forms that result in the transformation of a variety of human cells. Alternatively, the overexpression of normal tyrosine kinase enzymes may also result in abnodal cell proliferation.

There are two classes of PKs, the protein tyrosine kinases (PTKs) and the serine-threonine kinases (STKs). PTKs phosphorylate tyrosine residue on a protein. STKs phosphorylate serine or/and threonine on a protein. Tyrosine kinases can be of not only the receptor-type (having extracellular, transmembrane and intracellular domains) but the non-receptor type (being wholly intracellular). One of the prime aspects of PTK activity is their involvement with growth factor receptors which are cell-surface proteins. Growth factor receptors with PTK activity are known as receptor tyrosine kinases ("RTKs"). About 90 tyrosine kinases have been identified in the human genome, of which about 60 are of the receptor type and about 30 are of the non-receptor type. These can be categorized into 20 receptor tyrosine kinase sub-families according to the families of growth factors that they bind and into 10 non-receptor tyrosine kinase sub-families (Robinson et al, *Oncogene,* 2000, 19, 5548-5557).

The Receptor Tyrosine Kinases (RTKs) family includes: (1) the EGF family of receptor tyrosine kinases such as the EGF, TGFα, Neu and erbB receptors; (2) the insulin family of receptor tyrosine kinases such as the insulin and IGF1 receptors and insulin-related receptor (IRR); (3) the Class III family of receptor tyrosine kinases such as the platelet-derived growth factor (PDGF) receptor tyrosine kinases, for example the PDGFα and PDGFβ receptors, the stem cell factor receptor tyrosine kinase SCF RTK (commonly known as c-Kit), the fms-related tyrosine kinase 3 (Flt3) receptor tyrosine kinase and the colony-stimulating factor 1 receptor (CSF-1R) tyrosine kinase and the like. They play a critical role in the control of cell growth and differentiation and are key mediators of cellular signals leading to the production of growth factors and cytokines (Schlessinger and Ullrich, *Neuron* 1992, 9, 383). A partial, non-limiting, list of such kinases includes Abl, ARaf, ATK, ATM, bcr-abl, Blk, BRaf, Brk, Btk, CDK1, CDK2, CDK3, CDK4, CDK5, CDK6, CDK7, CDK8, CDK9, CHK, AuroraA, AuroraB, AuroraC, cfms, c-fms, c-Kit, c-Met, cRaf1, CSF1R, CSK, c-Src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, Chk, Axl, Pim-1, Plh-1, IGF-1R, IKK, IKK1, IKK2, IKK3, INS-R, Integrin-linked kinase, Jak, JAK1, JAK2, JAK3, JNK, JNK, Lck, Lyn, MEK, MEK1, MEK2, p38, PDGFR, PIK, PKB1, PKB2, PKB3, PKC, PKCa, PKCb, PKCd, PKCe, PKCg, PKCl, PKCm, PKCz, PLK1, Polo-like kinase, PYK2, $tie_1$, $tie_2$, TrkA, TrkB, TrkC, UL13, UL97, VEGF-R1, VEGF-R2, Yes and Zap70 and the like. Protein kinases have also been implicated as targets in central nervous system disorders such as Alzheimer's (Mandelkow, E. M. et al. *FEBS Lett.* 1992, 314, 315; Sengupta, A. et al. *Mol. Cell. Biochem.* 1997, 167, 99), pain sensation (Yashpal, K. J. *Neurosci.* 1995, 15, 3263-72), inflammatory disorders such as arthritis (Badger, J. *Pharmn Exp. Ther.* 1996, 279, 1453), psoriasis (Dvir, et al. *J. Cell Biol.* 1991, 113, 857), bone diseases such as osteoporosis (Tanaka et al, *Nature,* 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al. *Cancer Res.* 1996, 56, 3540; Jackson et al. *J. Pharm. Exp. Ther.* 1998, 284, 687), autoimmune diseases and transplant rejection (Bolen and Brugge, *Ann. Rev. Immunol.* 1997, 15, 371) and infection diseases such as viral (Littler, E. *Nature* 1992, 358, 160), and fungal infections (Lum, R. T. PCT Int Appl., WO 9805335 A1 980212).

RTKs mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular responses, e.g., cell division (multiplication), and responses to the extracellular microenvironment.

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors. Aberrant expression or mutations in the protein tyrosine kinases have been shown to lead to either uncontrolled cell proliferation (e.g. malignant tumor growth) or to defects in key developmental processes.

It has been identified that such mutated and overexpressed forms of tyrosine kinases are present in a large proportion of common human cancers such as the leukaemia, breast cancer, prostate cancer, non-small cell lung cancer (NSCLC) including adenocarcinomas and squamous cell cancer of the lung, gastrointestinal cancer including colon, rectal and stomach cancer, bladder cancer, oesophageal cancer, ovarian cancer and pancreatic cancer and the like. As further human tumour tissues are tested, it is expected that the widespread prevalence and relevance of tyrosine kinases will be further established. For example, it has been shown that EGFR tyrosine kinase is mutated and overexpressed in several human cancers including in tumours of the lung, head and neck, gastrointestinal tract, breast, oesophagus, ovary, uterus, bladder and thyroid.

One subfamily designated the "HER" or "Erb" RTKs, which include EGFR (epithelial growth factor receptor), HER2, HER3 and HER4. These RTKs consist of an extracellular glycosylated ligand binding domain, a transmembrane domain and an intracellular cytoplasm catalytic domain that can phosphorylate tyrosine residues on proteins. The enzymatic activity of receptor tyrosine kinases can be stimulated by either overexpression of receptor, or by ligand-mediated dimerization. The formation of homodimers as well as heterodimers has been demonstrated for the HER2 receptor family. An example of homodimerization is the dimerization of HER1 (EGF receptor) by the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3 and HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol3-kinase (PI3 kinase). Activation of these pathways has been shown to lead to cell proliferation and the inhibition of apoptosis.

Another RTK subfamily includes insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor (PDGFR) group, which includes PDGFRα, PDGFRβ, CSFIR, c-Kit and c-fms. These receptors consist of glycosylated extracellular domains composed of variable members of immunoglobin-like loops and an intracellular domain wherein the tyrosine kinase domain is interrupted by unrelated amino acid sequences.

Platelet derived growth factor receptors such as PDGFRα and PDGFRβ are also transmembrance tyrosine kinase receptors. Upon binding of the ligand, they form either homodimers (PDGF-AA, PDGF-BB) or heterodimers (PDGF-AB). As the receptor dimerizes, its tyrosine kinase is activated. This leads to downstream signaling and thus may support tumor growth. Mutations in this gene allow for receptor activation independent of ligand binding and appear to be driving forces in oncogenesis. An expression of PDGF, the growth factor that activates PDGFR, was observed in a number of different tumor cell lines, inter alia in mamma, colon, ovarian, prostate carcinoma, sarcoma and glioblastomas cell lines. Among the tumors, brain tumors and prostate carcinoma (including adenocarcinomas and bone metastasis) have found special interest. Interesting data also exist regarding malign gliomes.

c-Kit is a tyrosine kinase receptor which belongs to the PDGF receptor family and becomes activated upon binding of its ligand SCF (stem-cell factor). The expression pattern of c-Kit has been studied e.g. in a panel of different primary solid tumors. A strong expression of c-Kit could be found inter alia in sarcoma, gastrointestinal stromal tumors (GIST), seminoma and carcinoids [Weber et al., J. Clin. Oncol. 22(14S), 9642 (2004)]. GISTs are non-epithelial tumors. Many occur in the stomach, less in the small intestine and still less in the esophagus. Dissemination to the liver, omentum and peritoneal cavity can be observed. GISTS probably arise from Interstitial Cajal Cells (ICC) which normally form part of the autonomic nervous system of the intestine and take part in the control of motility. Most (50 to 80%) of GISTS arise due to c-Kit gene mutation. In the gut, a staining positive for c-Kit/CD117 is likely to be a GIST. Mutations of c-Kit can make c-Kit function independent of activation by SCF, leading to a high cell division rate and possibly genomic instability. Also in mast cell tumors aberrations of c-Kit could be observed, as well as in mastocytosis and associated myeloproliferative syndrome and Urticaria Pigmentosa. An expression and/or aberrations of c-Kit can also be found in acute myeloicanemia (AML) and malign lymphomas. A c-Kit expression can also be demonstrated in small cell bronchial carcinoma, seminomas, dysgerminomas, testicular intraepithelial neoplasias, melanomas, mamma carcinomas, neuroblastomas, Ewing sarcoma, some soft part sarcomas as well as papillary/follicular thyroid carcinoma (see Schütte et al., innovartis 3/2001). Inherited mutations of the RET (rearranged during transfection) proto-oncogene are e.g. known to be tumorigenic in patients with multiple endocrine neoplasia type 2 (MEN 2) which may lead to pheochromocytoma, medullary thyroid carcinoma and parathyroid hyperplasia/adenoma (see Huang et al., Cancer Res. 60, 6223-6 (2000)).

Another group which, because of its similarity to the PDGFR subfamily, is sometimes subsumed into the later group is the fetus liver kinase (Flk) receptor subfamily. This group is believed to be made up of kinase insert domain-receptor fetal liver kinase-1 (KDR/FLK-1, VEGFR2), Flk-1R, Flk-4 and Fms-like tyrosine kinase 1 (Flt-1).

A further member of the tyrosine kinase growth factor receptor family is the fibroblast growth factor (FGF) receptor subgroup. This group consists of four receptors, FGFR1-4, seven ligands, and FGF1-7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor (VEGF) receptor subgroup, VEGF is a dimeric glycoprotein similar to PDGF but has different biological functions and target cell specificity in vivo. In particular, VEGFRs are known to be involved in the control of the onset of angiogenesis. As especially solid tumors depend on good blood supply, inhibition of VEGFRs and thus angiogenesis is under clinical investigation in the treatment of such tumors, showing promising results. VEGF is also a major player in leukemias and lymphomas and highly expressed in a variety of solid malignant tumors, correlating well with malignant disease progression. Examples of tumor diseases with VEGFR-2 (KDR) expression are lung carcinomas, breast carcinomas, Non Hodgkin's lymphomas, ovarian carcinoma, pancreatic cancer, malignant pleural mesothelioma and melanoma. In addition to its angiogenic activity, the ligand of VEGFR, VEGF, may promote tumor growth by direct pro-survival effects in tumor cells. PDGF is also involved in angiogenesis, the process of forming new blood vessels that is critical for continuing tumor growth. Normally, angiogenesis plays an important role in processes such as embryonic development, wound healing and several components of female reproductive function. However, undesirable or pathological angiogenesis has been associated with a number of disease states including diabetic retinopathy, psoriasis, cancer, rheumatoid arthritis, atheroma, Kaposi's sarcoma and haemangioma. Angiogenesis is stimulated via the promotion of the growth of endothelial cells. Several polypeptides with in vitro endothelial cell growth promoting activity have been identified including acidic and basic fibroblast growth factors (aFGF and bFGF) and vascular endothelial growth factor (VEGF). By virtue of the restricted expression of its receptors, the growth factor activity of VEGF, in contrast to that of aFGF and bFGF, is relatively specific towards endothelial cells. Recent evidence indicates that VEGF is an important stimulator of both normal and pathological angiogenesis and vascular permeability. This cytokine induces a vascular sprouting phenotype by inducing endothelial cell proliferation, protease expression and migration which subsequently leads to the formation of capillary tubes that promote the formation of the hyperpermeable, immature vascular network which is the characteristic of pathological angiogenesis. Accordingly, antagonism of the activity of VEGF is expected to be beneficial in the treatment of a number of disease states that are associated with angiogenesis or increased vascular permeability such as cancer, especially in inhibiting the development of tumors.

FLT3 (fms-like tyrosine kinase) is a member of the type III receptor tyrosine kinase (RTK) family. Aberrant expression of the FLT3 gene has inter alia been documented in both adult and childhood leukemias including acute myeloid leukemia (AML), AML with trilineage myelodysplasia (AML/TMDS), acute lymphoblastic leukemia (ALL), and myelodysplastic syndrome (MDS), as well as MLL (mixed-lineage leukemia). Activating mutations of the FLT3 receptor have been found in about 35% of patients with acute myeloblastic leukemia (AML), and are associated with a poor prognosis. The most common mutation involves an in-frame duplication within the juxtamembrane domain, with an additional 5-10% of patients having a point mutation at asparagine 835. Both of these mutations are associated with constitutive activation of the tyrosine kinase activity of FLT3, and result in proliferation and viability signals in the absence of ligand. Patients expressing the mutant form of the receptor have been shown to have a decreased chance for cure. Thus, there is accumulating evidence for a role for hyperactivated (mutated) FLT3 kinase activity in human leukemias and myelodysplastic syndrome.

The hepatocyte growth factor (HGF) receptor (c-MET or HGFR) receptor tyrosine kinase (RTK) has been shown in many human cancers to be involved in oncogenesis, tumor progression with enhanced cell motility and invasion, as well as metastasis (see, Ma, P. C. et al. (2003b). *Cancer Metastasis Rev*, 22, 309-25; Maulik, G. et al. (2002b). *Cytokine Growth Factor Rev*, 13, 41-59). c-MET (HGFR) can be activated through overexpression or mutations in various human cancers including small cell lung cancer (SCLC) (Ma, P. C. et al. (2003a). *Cancer Res*, 63, 6272-6281).

c-MET is a receptor tyrosine kinase that is encoded by the Met proto-oncogene and transduces the biological effects of hepatocyte growth factor (HGF). It is a transmembrane glycoprotein with tyrosine kinase activity, which contribute to multi-cell multiplication and division. The c-Met proto-oncogene is overexpressed in numerous human malignancy especially in thyroid tumour, which is closely related with pathologic staging, tumour invasion and metastasis.

A more complete listing of the known RTK subfamilies is described in Plowman et al., *DN&P* 7(6): 334-339 (1994) which is incorporated by reference, as if fully set forth herein.

Besides PTKs, additional cell enzyme family is present, called as receptor tyrosine kinases inhibitor (abbreviated as "CTK"). At present, over twenty-four CTKs, comprising eleven subfamilies (Src, Frk, Btk, Csk, Abl, Zap70, Fes/Fps, Fak, Jak, Ack and LIMK) have been identified. At present, the Src subfamily of CTKs are comprised of the largest number of PTKs and include Src, Yes, Fyn, Lyn, Lck, Blk, Hck, Fgr and Yrk. The Src subfamily of enzymes has been linked to oncogenesis. A more detailed discussion of CTKs is provided in Bolen, 1993, Oncogen 8: 2025-2031, which is incorporated herein by reference, including any drawings.

The serine/threonine kinases, or STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

A further characteristic of hyperproliferative diseases such as cancer is damage to the cellular pathways that control progress through the cell cycle which, in normal eukaryotic cells, involves an ordered cascade of protein phosphorylation. As for signal transduction mechanisms, several families of protein kinases appear to play critical roles in the cell cycle cascade.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

There is a need for novel viable small-molecule inhibitors which posess anti-tumor cell proliferative activities. These small molecules are expected to inhibit one or more RTKs, CTKs or STKs, and are useful in treating or ameliorating RTKs, CTKs or STKs mediated, angiogenesis mediated or hyperproliferative disorder.

Based on the structure of tyrosine kinase inhibitor SU-11248 and the pyrrolofused heterocycle Formula (X) which showed great bioactivities reported by the patent (U.S. Pat. No. 6,599,902B2), the present invention is directed to design and synthesize the pyrrolofused multiple-membered aza-heterocyclic derivatives and has got a better pharmacological data. In order to improve the pharmacokinetics profile of pyrrolofused multiple-membered aza-heterocyclic derivatives, the present invention is directed to design compounds of formula (I). The compounds of the invention have obvious structure differences with the existing compounds in prior art, and they also show more efficiency and more function.

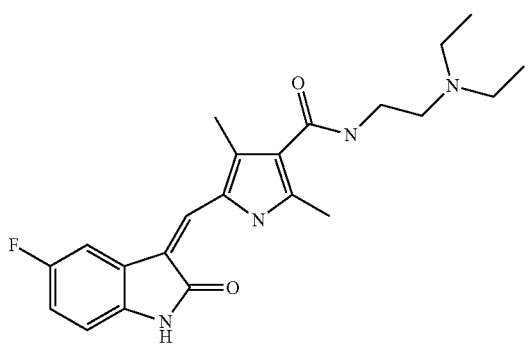

SU-11248

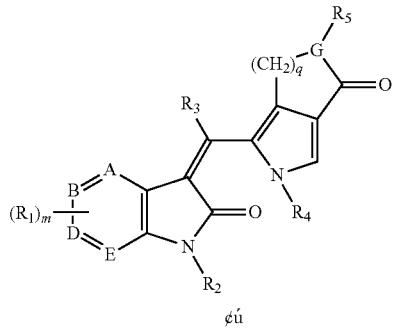

¢ú

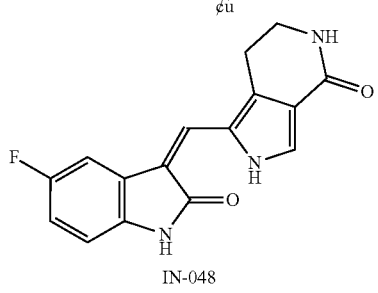

IN-048

SUMMARY OF THE INVENTION

In order to overcome the deficiency of the prior art, the present invention is directed to provide pyrrolo-nitrogenous heterocyclic derivatives having formula (I), their tautomers, enantiomers, diastereomers, racemates or pharmaceutically acceptable salts thereof, and metabolites, precursor or prodrug thereof, wherein said tautomer includes Z configuration and E configuration.

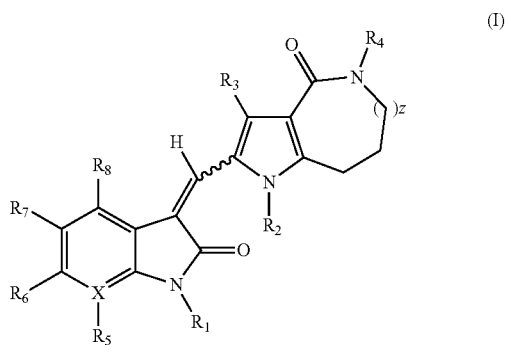

Wherein:

X is selected from the group consisting of carbon and nitrogen;

$R_1$ and $R_2$ are each independently selected from the group consisting of hydrogen and alkyl;

$R_3$ is selected from the group consisting of alkyl, trifluoromethyl, aryl and aralkyl, wherein said alkyl, aryl or aralkyl is further substituted by one or more halogen;

$R_4$ is selected from the group consisting of alkyl, cycloalkyl, heterocyclo alkyl, aryl, heteroaryl, —$(CH_2)_n$ $(OCH_2CH_2)_rR_{11}$, —$[CH_2CH(OH)]_rCH_2NR_9R_{10}$ and —$(CH_2)_nNR_9R_{10}$, wherein said alkyl, cylcoalkyl, heterocyclo alkyl, aryl or heteroaryl is further substituted by one or more groups selected from the group consisting of aryl, hydroxyl, amino, amide group, aminocarbonyl, alkoxyl, aryloxy, aminoalkyl, hydroxyalkyl, heterocyclo alkyl, carboxylic acid, carboxylic ester and —$NR_9R_{10}$;

when X is nitrogen, $R_5$ is absent, $R_6$, $R_7$, $R_8$ are each independently selected from the group consisting of hydrogen and halogen;

when X is carbon atom, $R_5$, $R_6$, $R_7$, $R_8$ are each independently selected from the group consisting of hydrogen, halogen, hydroxyalkyl, alkyl, cycloalkyl, heterocyclo alkyl, aryl, heteroaryl, hydroxyl, cyano, nitro, —$OR_9$, —$O[CH_2CH_2O]_rR_{11}$, —$NR_9R_{10}$, —$(CH_2)_nCO_2R_9$, —$(CH_2)_nCONR_9R_{10}$, —$COR_9$, —$NR_9COR_{10}$, —$SO_2R_9$ and —$NHCO_2R_{10}$, wherein said aryl, heteroaryl, cycloalkyl or heterocyclo alkyl is further substituted by one or more groups selected from the group consisting of alkyl, alkoxyl and halogen;

$R_9$ and $R_{10}$ are each independently selected from the group consisting of hydrogen, alkyl, cycloalkyl, aryl, heterocyclo alkyl and heteroaryl, wherein said alkyl, cycloalkyl, aryl, heterocyclo alkyl or heteroaryl is further substituted by one or more groups selected from the group consisting of alkyl, aryl, haloaryl, hydroxyl, amino, cyano, alkoxyl, aryloxy, hydroxyalkyl, heterocyclo alkyl, carboxylic acid, carboxylic ester and —$NR_9R_{10}$;

$R_9$ and $R_{10}$ are taken together with the attached atom to form 4 to 8 membered hetero rings, wherein said 4 to 8 membered hetero rings may contain one to more heteroatoms selected from the group consisting of N, O and S atom, and said 4 to 8 membered rings are further substituted by one or more groups consisting of alkyl, halogen, aryl, heteroaryl, haloalkyl, hydroxyl, cyano, alkoxyl, aryloxy, aminoalkyl, hydroxyalkyl, heterocyclo alkyl, carboxylic acid, carboxylic ester and —$NR_9R_{10}$;

$R_{11}$ is selected from the group consisting of hydrogen and alkyl;

n is an integer from 2 to 6;

z is an integer from 1 to 4; and r is an integer from 1 to 6;

or pharmaceutically acceptable salts thereof.

The compounds or pharmaceutically acceptable salts thereof of formula (I), wherein $R_3$ is preferably methyl.

The compounds or pharmaceutically acceptable salts thereof of formula (I), wherein $R_1$ and $R_2$ are preferably hydrogen.

Further, the present invention includes the compounds or pharmaceutically acceptable salts having formula (IA):

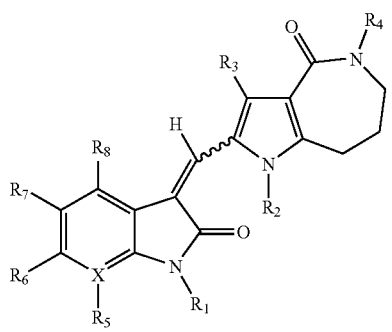

(IA)

Wherein:

X is selected from the group consisting of carbon and nitrogen;

$R_1$ and $R_2$ are each independently selected from the group consisting of hydrogen and alkyl;

$R_3$ is selected from the group consisting of alkyl, trifluoromethyl, aryl and aralkyl, wherein said alkyl, aryl or aralkyl is further substituted by one or more halogen;

$R_4$ is selected from the group consisting of alkyl, cycloalkyl, heterocyclo alkyl, aryl, heteroaryl, —$(CH_2)_n$ $(OCH_2CH_2)_nR_{11}$, —$[CH_2CH(OH)]_rCH_2NR_9R_{10}$ and —$(CH_2)_nNR_9R_{10}$, wherein said alkyl, cylcoalkyl, heterocyclo alkyl, aryl or heteroaryl is further substituted by one or more groups selected from the group consisting of aryl, hydroxyl, amino, amide group, aminocarbonyl, alkoxyl, aryloxy, aminoalkyl, hydroxyalkyl, heterocyclo alkyl, carboxylic acid, carboxylic ester and —$NR_9R_{10}$;

when X is nitrogen, $R_5$ is absent, $R_6$, $R_7$, $R_8$ are each independently selected from the group consisting of hydrogen and halogen;

when X is carbon, $R_5$, $R_6$, $R_7$, $R_8$ are each independently selected from the group consisting of hydrogen, halogen, hydroxyalkyl, alkyl, cycloalkyl, heterocyclo alkyl, aryl, heteroaryl, hydroxyl, cyano, nitro, —$OR_9$, —$O[CH_2CH_2O]_rR_{11}$, —$NR_9R_{10}$, —$(CH_2)_nCO_2R_9$, —$(CH_2)_nCONR_9R_{10}$, —$COR_9$, —$NR_9COR_{10}$, —$SO_2R_9$ and —$NHCO_2R_{10}$, wherein said aryl, heteroaryl, cycloalkyl or heterocyclo alkyl is further substituted by one or more groups selected from the group consisting of alkyl, alkoxyl and halogen;

$R_9$ and $R_{10}$ are each independently selected from the group consisting of hydrogen, alkyl, cycloalkyl, aryl, heterocyclo alkyl and heteroaryl, wherein said alkyl, cycloalkyl, aryl, heterocyclo alkyl or heteroaryl further substituted by one or more groups selected from the group consisting of alkyl, aryl, haloaryl, hydroxyl, amino, cyano, alkoxyl, aryloxy, hydroxyalkyl, heterocyclo alkyl, carboxylic acid, carboxylic ester and —$NR_9R_{10}$;

$R_9$ and $R_{10}$ are taken together with the attached atom to form 4 to 8 membered hetero rings, wherein said 4 to 8 membered hetero rings may contain one or more heteroatoms selected from the group consisting of N, O and S atom, and said 4 to 8 membered rings are further substituted by one or more groups consisting of alkyl, halogen, aryl, heteroaryl, haloalkyl, hydroxyl, cyano, alkoxyl, aryloxy, aminoalkyl, hydroxyalkyl, heterocyclo alkyl, carboxylic acid, carboxylic ester and —$NR_9R_{10}$;

$R_{11}$ is selected from the group consisting of hydrogen and alkyl;

n is an integer from 2 to 6; and r is an integer from 1 to 6; or pharmaceutically acceptable salts thereof.

Further, the present invention includes the compounds or pharmaceutically acceptable salts having formula (IB):

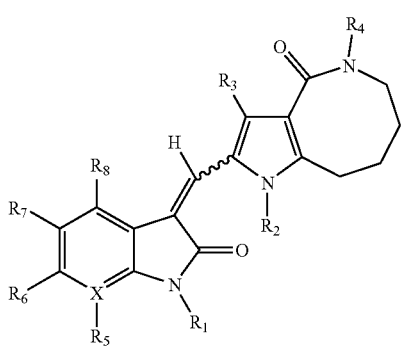

(IB)

Wherein:

X is selected from the group consisting of carbon and nitrogen;

$R_1$ and $R_2$ are each independently selected from the group consisting of hydrogen and alkyl;

$R_3$ is selected from the group consisting of alkyl, trifluoromethyl, aryl and aralkyl, wherein said alkyl, aryl or aralkyl is further substituted by one or more halogen;

$R_4$ is selected from the group consisting of alkyl, cycloalkyl, heterocyclo alkyl, aryl, heteroaryl, —$(CH_2)_n$ $(OCH_2CH_2)_rR_{11}$, —$[CH_2CH(OH)]_rCH_2NR_9R_{10}$ and —$(CH_2)_nNR_9R_{10}$, wherein said alkyl, cylcoalkyl, heterocyclo alkyl, aryl or heteroaryl is further substituted by one or more groups selected from the group consisting of aryl, hydroxyl, amino, amide group, aminocarbonyl, alkoxyl, aryloxy, aminoalkyl, hydroxyalkyl, heterocyclo alkyl, carboxylic acid, carboxylic ester and —$NR_9R_{10}$;

when X is nitrogen, $R_5$ is absent, $R_6$, $R_7$, $R_8$ are each independently selected from the group consisting of hydrogen and halogen;

when X is carbon, $R_5$, $R_6$, $R_7$, $R_8$ are each independently selected from hydrogen, halogen, hydroxyalkyl, alkyl, cycloalkyl, heterocyclo alkyl, aryl, heteroaryl, hydroxyl, cyano, nitro, —$OR_9$, —$O[CH_2CH_2O]_rR_{11}$, —$NR_9R_{10}$, —$(CH_2)_nCO_2R_9$, —$(CH_2)_nCONR_9R_{10}$, —$COR_9$, —$NR_9COR_{10}$, —$SO_2R_9$ and —$NHCO_2R_{10}$, wherein said aryl, heteroaryl, cycloalkyl or heterocyclo alkyl is further substituted by one or more groups selected from the group consisting of alkyl, alkoxyl and halogen;

$R_9$ and $R_{10}$ are each independently selected from the group consisting of hydrogen, alkyl, cycloalkyl, aryl, heterocyclo alkyl and heteroaryl, wherein said alkyl, cycloalkyl, aryl, heterocyclo alkyl or heteroaryl further substituted by one or more groups selected from the group consisting of alkyl, aryl, haloaryl, hydroxyl, amino, cyano, alkoxyl, aryloxy, hydroxyalkyl, heterocyclo alkyl, carboxylic acid, carboxylic ester and —NR$_9$R$_{10}$;

R$_9$ and R$_{10}$ are taken together with the attached atom to form 4 to 8 membered hetero rings, wherein said 4 to 8 membered hetero rings may further optionally contain one or more heteroatoms selected from the group consisting of N, O and S atom, and said 4 to 8 membered rings are further substituted by one or more groups consisting of alkyl, halogen, aryl, heteroaryl, haloalkyl, hydroxyl, cyano, alkoxyl, aryloxy, aminoalkyl, hydroxyalkyl, heterocyclo alkyl, carboxylic acid, carboxylic ester and —NR$_9$R$_{10}$;

R$_{11}$ is selected from the group consisting of hydrogen and alkyl;

n is an integer from 2 to 6; and r is an integer from 1 to 6;

or pharmaceutically acceptable salts thereof.

The compounds of the invention include, but not limited to the following:

| Example No. | Structure | Name |
|---|---|---|
| 1 | 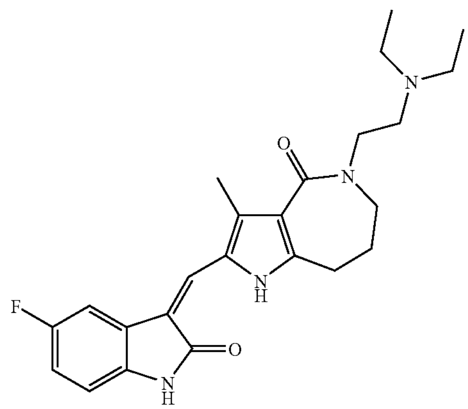 | (Z)-5-(2-diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one |
| 2 | 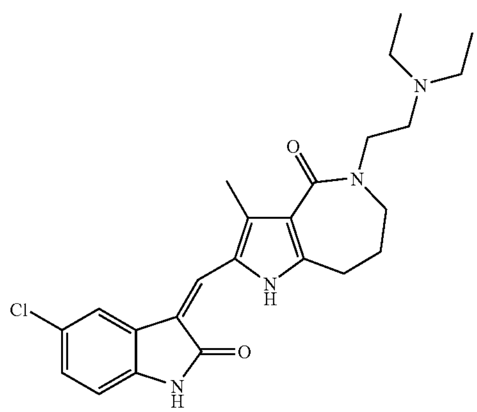 | (Z)-2-(5-chloro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one |
| 3 | 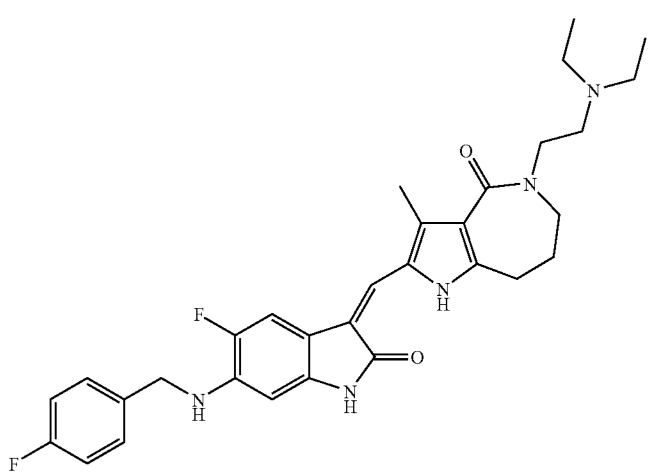 | (Z)-5-(2-diethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one |

-continued

| Example No. | Structure | Name |
|---|---|---|
| 4 | 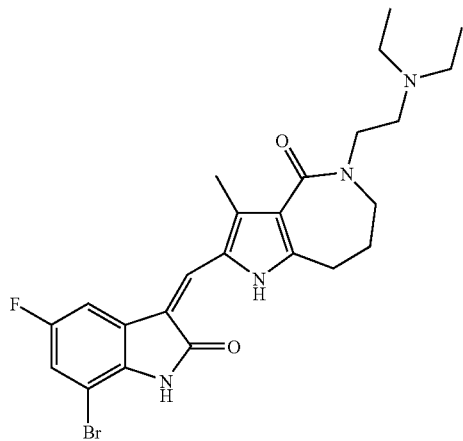 | (Z)-2-(7-bromo-5-fluoro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one |
| 5 | 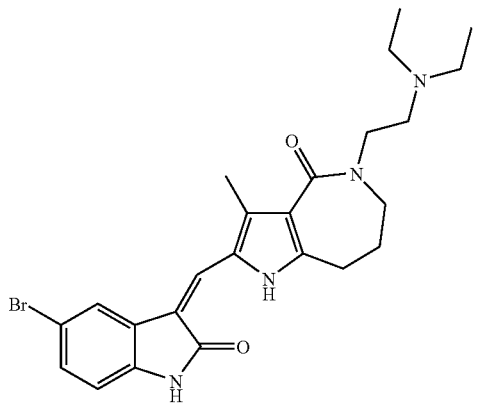 | (Z)-2-(5-bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one |
| 6 | 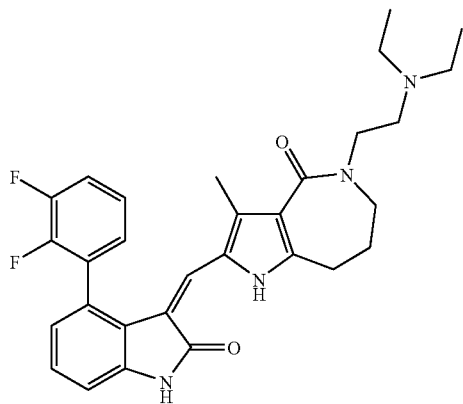 | (Z)-5-(2-diethylamino-ethyl)-2-[4-(2,3-difluoro-phenyl)-2-oxo-1,2-dihydro-indol-3-ylidenemethyl]-3-methyl-5,6,7,8-tetrahydro-1H-pyrrolo[3,2-c]azepin-4-one |

-continued

| Example No. | Structure | Name |
|---|---|---|
| 7 | 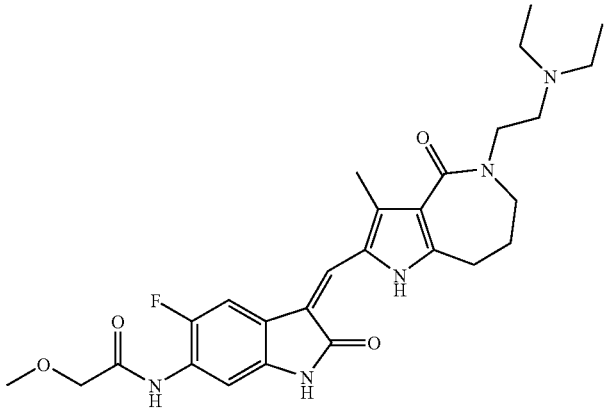 | (Z)-N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide |
| 8 | 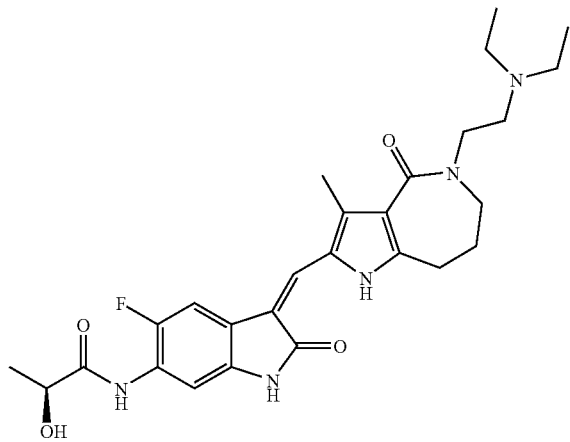 | (S,Z)-N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-propionamide |
| 9 | 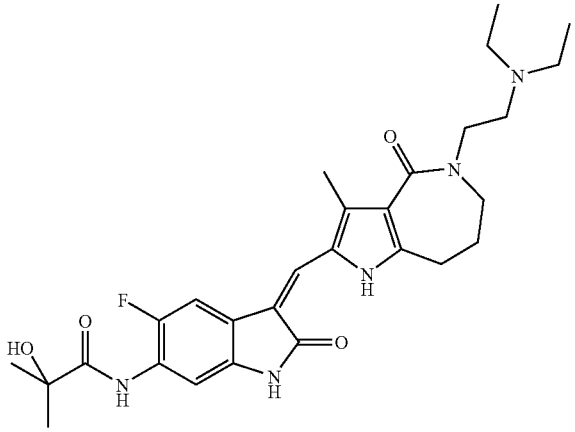 | (Z)-N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-2-methyl-propionamide |

-continued

| Example No. | Structure | Name |
|---|---|---|
| 10 | 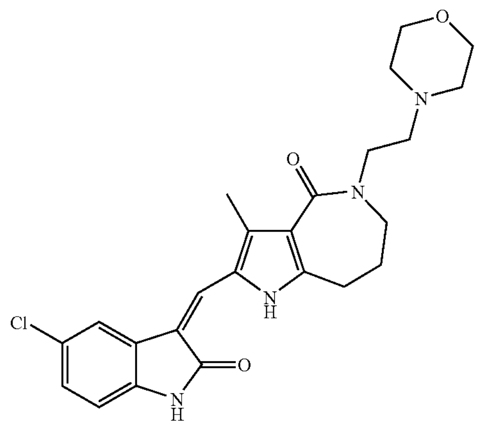 | (Z)-2-(5-chloro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one |
| 11 | 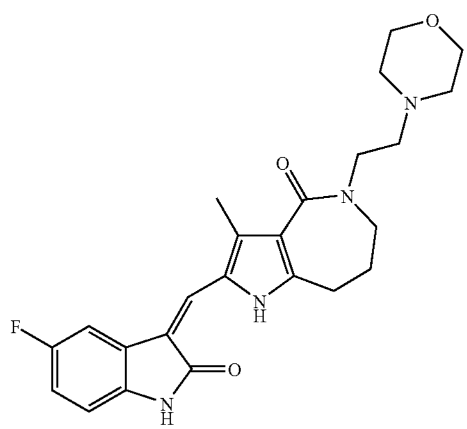 | (Z)-2-(5-fluoro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one |
| 12 | 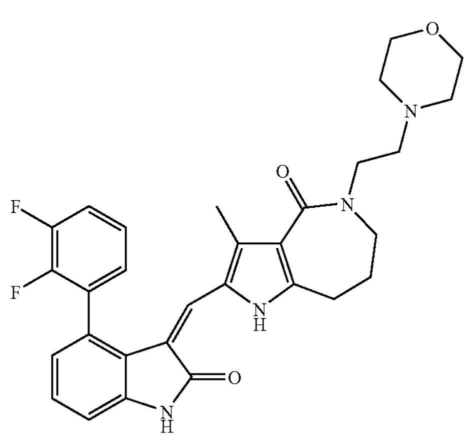 | (Z)-2-[4-(2,3-difluoro-phenyl)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one |

-continued
| Example No. | Structure | Name |
|---|---|---|
| 13 | 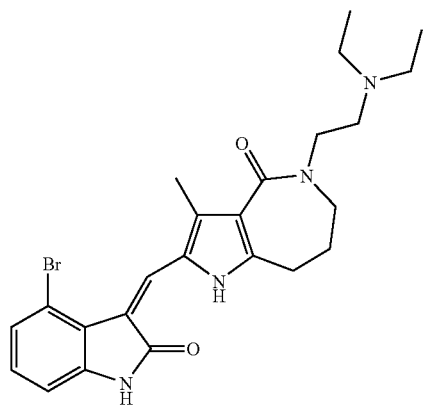 | (Z)-2-(4-bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one |
| 14 | 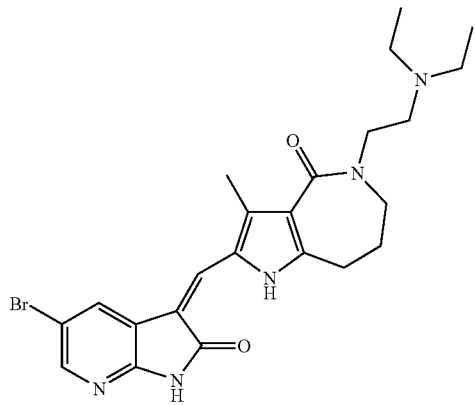 | (Z)-2-(5-bromo-2-oxo-1,2-dihydro-pyrrolo[2,3-b]pyridin-3-ylidenemethyl)-5-(2-diethylamino-ethyl)-3-methyl-5,6,7,8-tetrahydro-1H-pyrrolo[3,2-c]azepin-4-one |
| 15 | 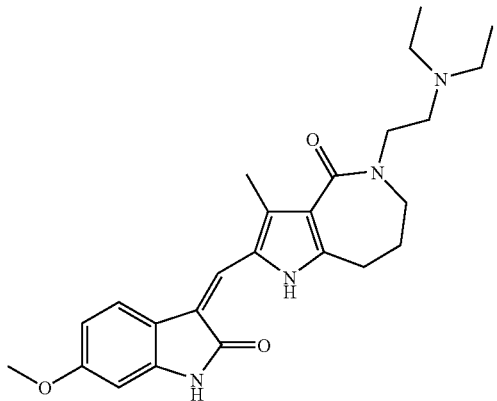 | (Z)-5-(2-diethylamino-ethyl)-2-(6-methoxy-2-oxo-1,2-dihydro-indol-3-ylidenemethyl)-3-methyl-5,6,7,8-tetrahydro-1H-pyrrolo[3,2-c]azepin-4-one |

| Example No. | Structure | Name |
|---|---|---|
| 16 | 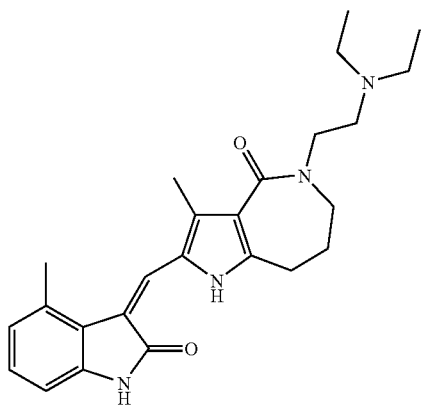 | (Z)-5-(2-diethylamino-ethyl)-3-methyl-2-(4-methyl-2-oxo-1,2-dihydro-indol-3-ylidenemethyl)-5,6,7,8-tetrahydro-1H-pyrrolo[3,2-c]azepin-4-one |
| 17 | 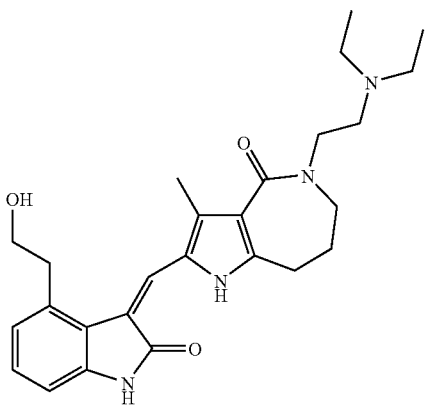 | (Z)-5-(2-diethylamino-ethyl)-2-[4-(2-hydroxy-ethyl)-2-oxo-1,2-dihydro-indol-3-ylidenemethyl]-3-methyl-5,6,7,8-tetrahydro-1H-pyrrolo[3,2-c]azepin-4-one |
| 18 | 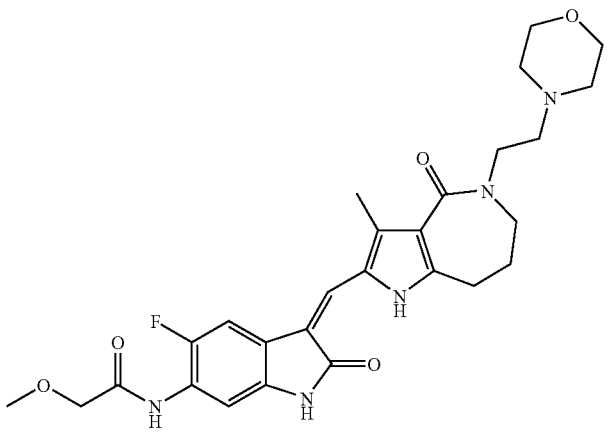 | (Z)-N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-methoxy-acetamide |

| Example No. | Structure | Name |
|---|---|---|
| 19 | 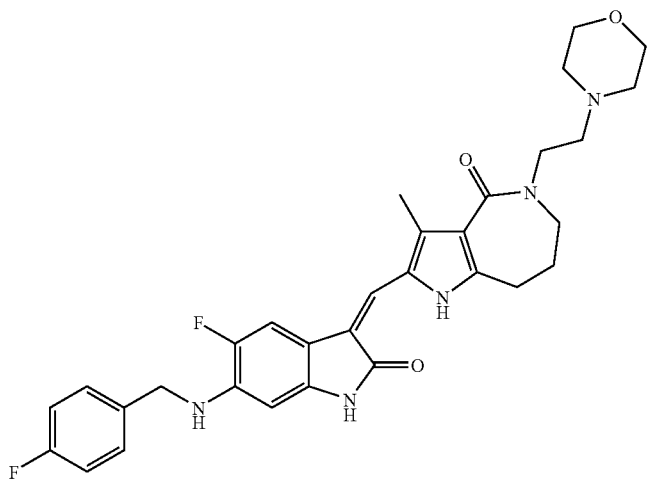 | (Z)-2-[5-fluoro-6-(4-fluoro-benzylamino)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one |
| 20 | 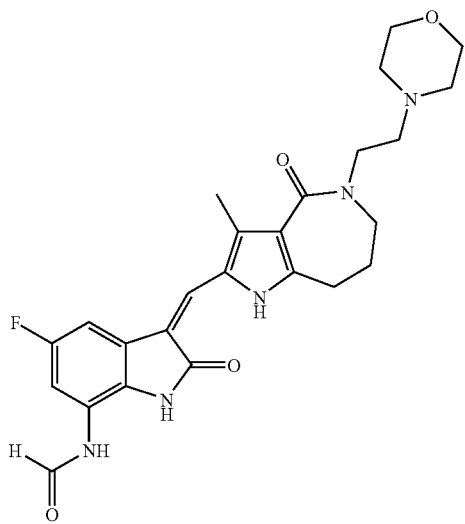 | (Z)-N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-7-yl}-formamide |
| 21 | 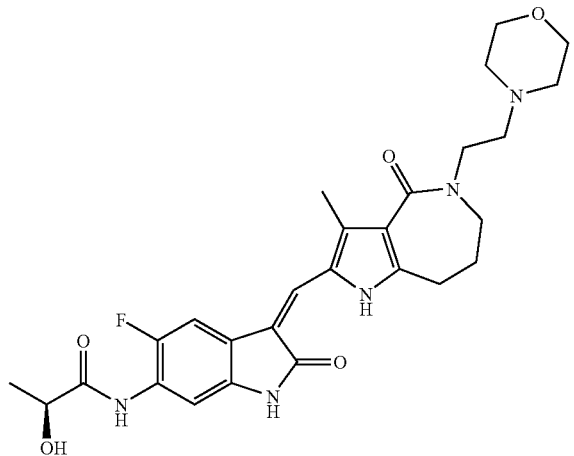 | (S,Z)-N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-hydroxy-propionamide |

-continued

| Example No. | Structure | Name |
|---|---|---|
| 22 | 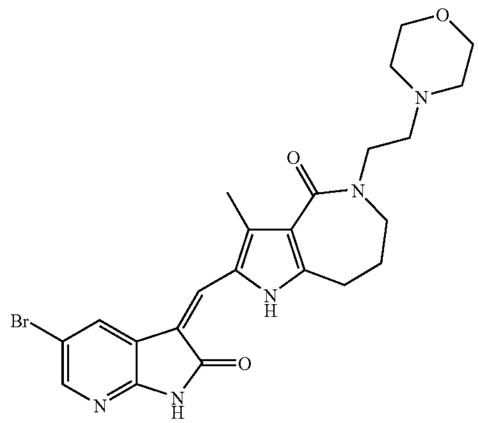 | (Z)-2-(5-bromo-2-oxo-1,2-dihydro-pyrrolo[2,3-b]pyridin-3-ylidenemethyl)-3-methyl-5-(2-morpholin-4-yl-ethyl)-5,6,7,8-tetrahydro-1H-pyrrolo[3,2-c]azepin-4-one |
| 23 | 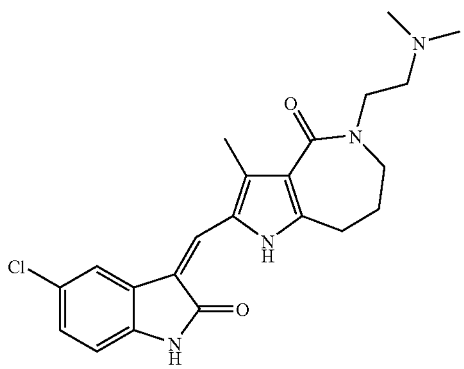 | (Z)-2-(5-chloro-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one |
| 24 | 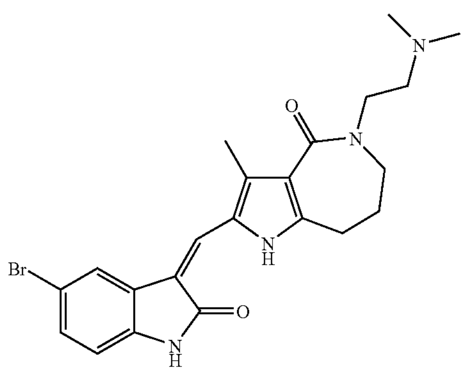 | (Z)-2-(5-bromo-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one |
| 25 | 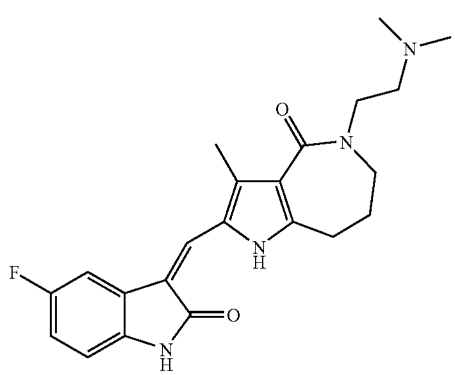 | (Z)-5-(2-dimethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one |

| Example No. | Structure | Name |
|---|---|---|
| 26 | 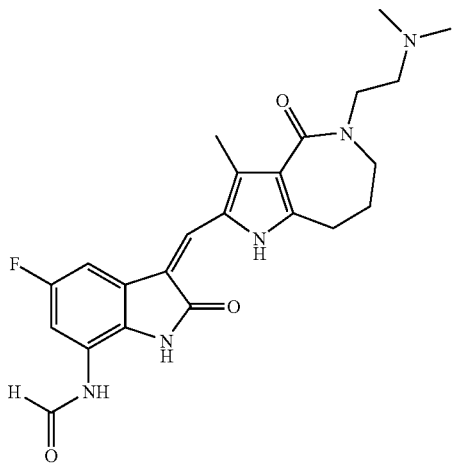 | (Z)-N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-7-yl}-formamide |
| 27 | 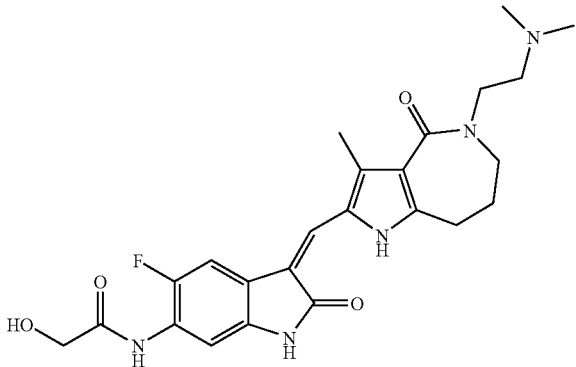 | (Z)-N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-acetamide |
| 28 | 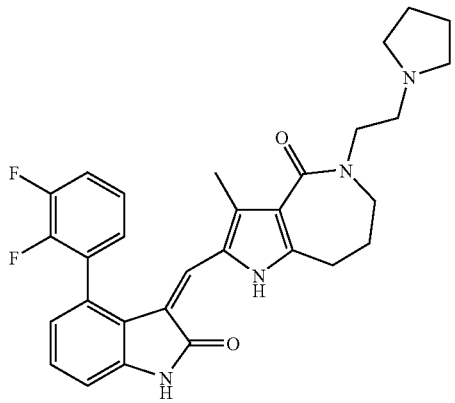 | (Z)-2-[4-(2,3-difluoro-phenyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one |

| Example No. | Structure | Name |
|---|---|---|
| 29 | 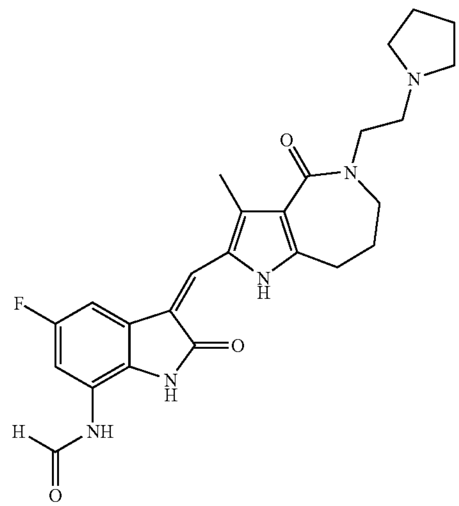 | (Z)-N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-7-yl}-formamide |
| 30 | 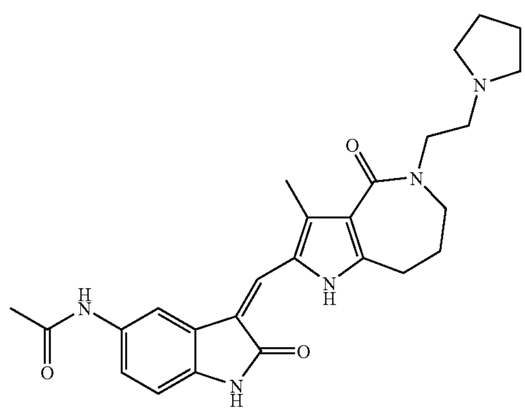 | (Z)-N-{3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-5-yl}-acetamide |
| 31 | 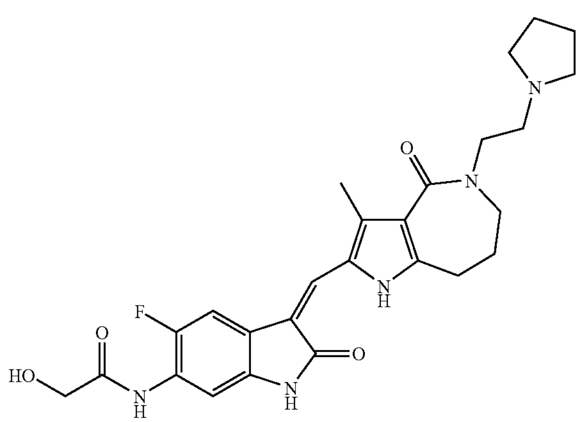 | (Z)-N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-acetamide |

-continued

| Example No. | Structure | Name |
|---|---|---|
| 32 | 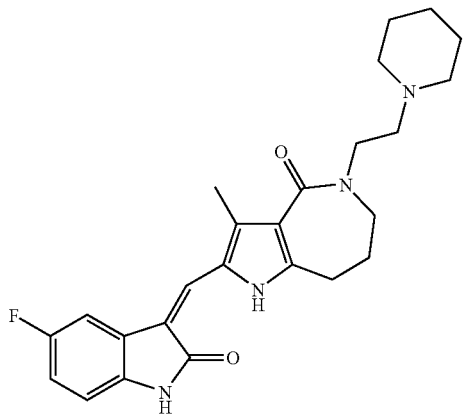 | (Z)-2-(5-fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one |
| 33 | 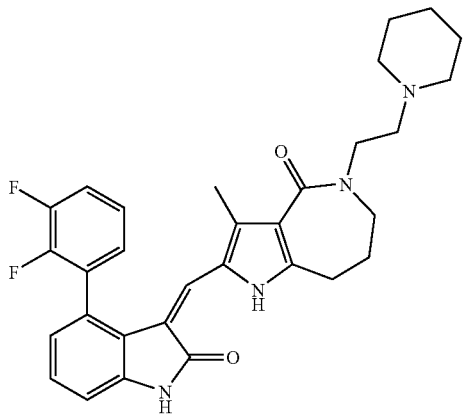 | (Z)-2-[4-(2,3-difluoro-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one |
| 34 | 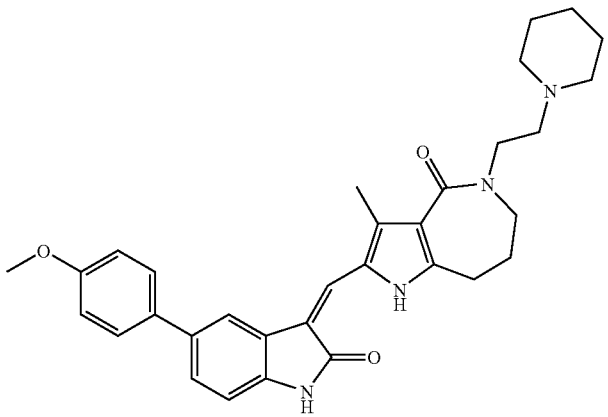 | (Z)-2-[5-(4-methoxy-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one |

| Example No. | Structure | Name |
|---|---|---|
| 35 | 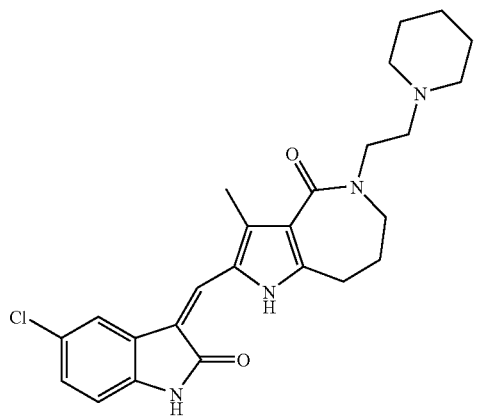 | (Z)-2-(5-chloro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one |
| 36 | 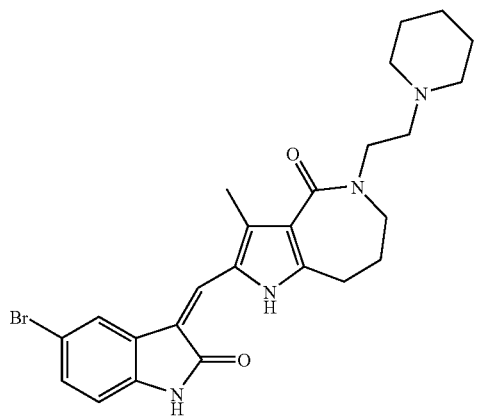 | (Z)-2-(5-bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one |
| 37 | 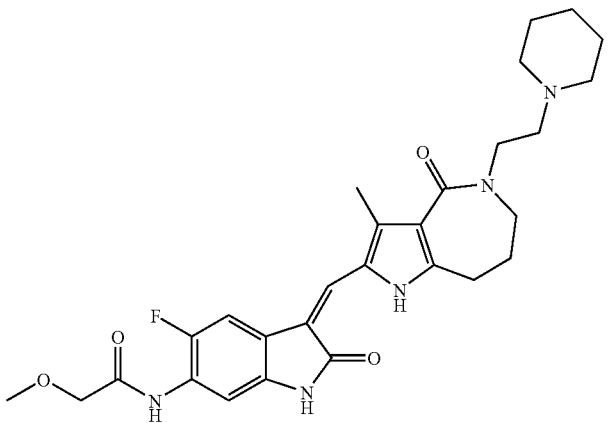 | (Z)-N-{5-fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide |

-continued

| Example No. | Structure | Name |
|---|---|---|
| 38 | 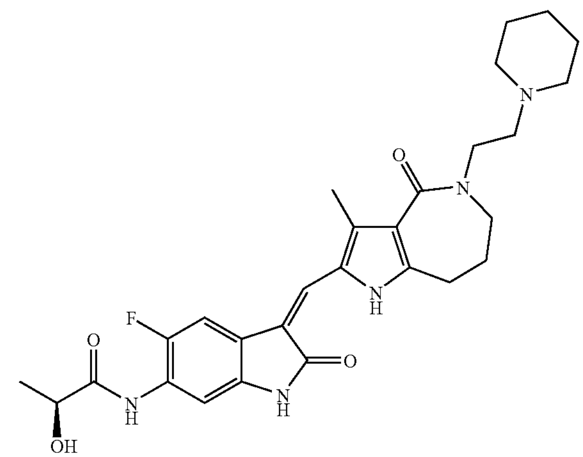 | (S,Z)-N-{5-fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-propionamide |
| 39 | 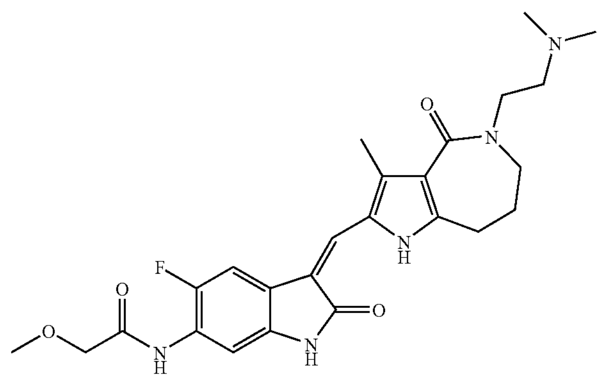 | (Z)-N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide |
| 40 | 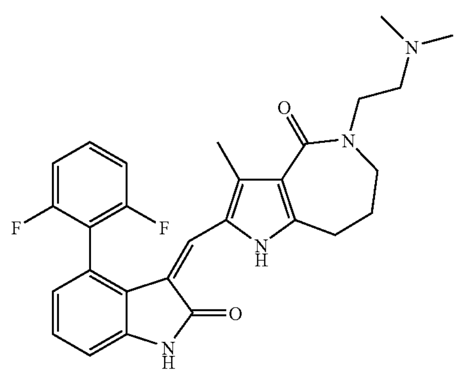 | (Z)-2-[4-(2,6-difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one |
| 41 | 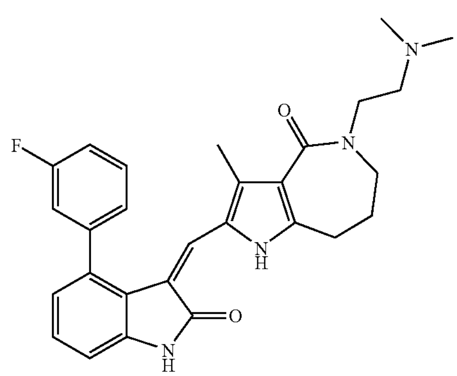 | (Z)-5-(2-dimethylamino-ethyl)-2-[4-(3-fluoro-phenyl)-2-oxo-1,2-dihydro-indol-3-ylidenemethyl]-3-methyl-5,6,7,8-tetrahydro-1H-pyrrolo[3,2-c]azepin-4-one |

-continued

| Example No. | Structure | Name |
|---|---|---|
| 42 | 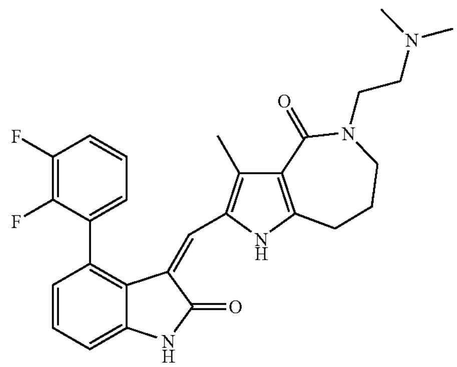 | (Z)-2-[4-(2,3-difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one |
| 43 | 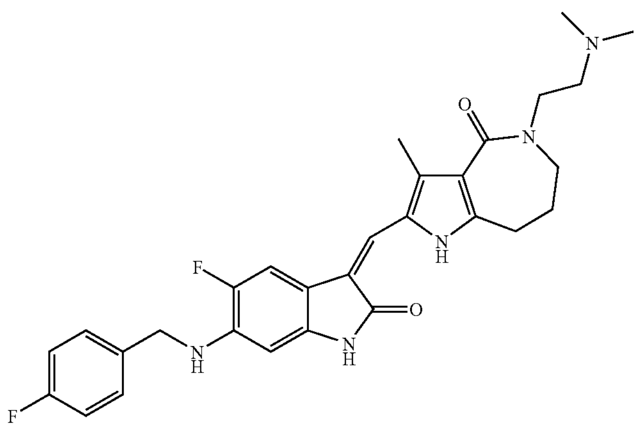 | (Z)-5-(2-dimethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one |
| 44 | 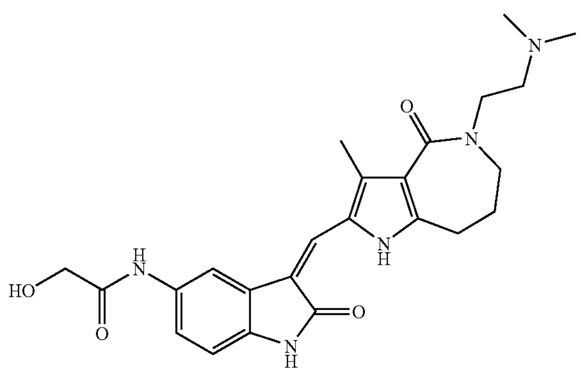 | (Z)-N-{3-[5-(2-dimethylamino-ethyl)-3-methyl-4-oxo-1,4,5,6,7,8-hexahydro-pyrrolo[3,2-c]azepin-2-ylmethylene]-2-oxo-2,3-dihydro-1H-indol-5-yl}-2-hydroxy-acetamide |
| 45 | 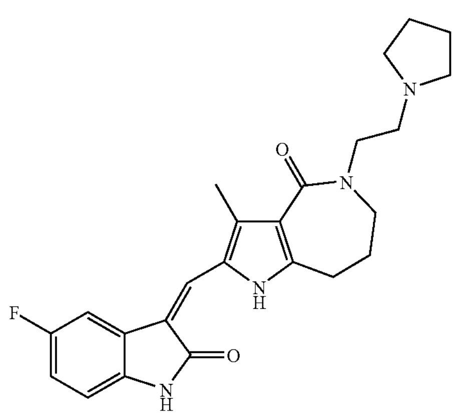 | (Z)-2-(5-fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one |

| Example No. | Structure | Name |
|---|---|---|
| 46 | 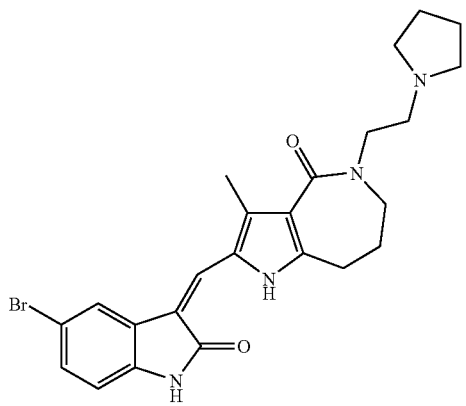 | (Z)-2-(5-bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one |
| 47 | 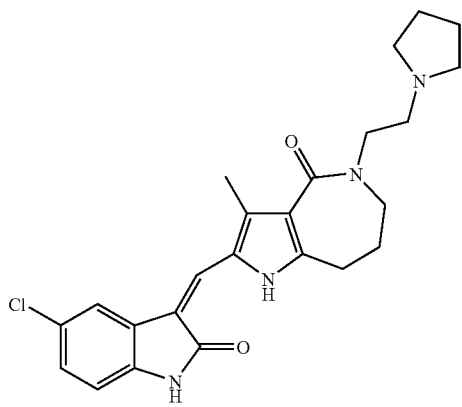 | (Z)-2-(5-chloro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one |
| 48 | 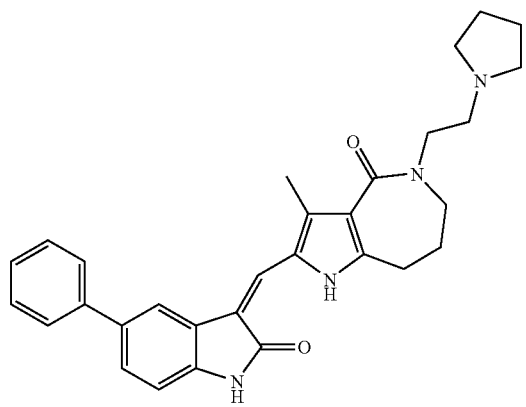 | (Z)-3-methyl-2-(2-oxo-5-phenyl-1,2-dihydro-indol-3-ylidenemethyl)-5-(2-pyrrolidin-1-yl-ethyl)-5,6,7,8-tetrahydro-1H-pyrrolo[3,2-c]azepin-4-one |

-continued

| Example No. | Structure | Name |
|---|---|---|
| 49 | 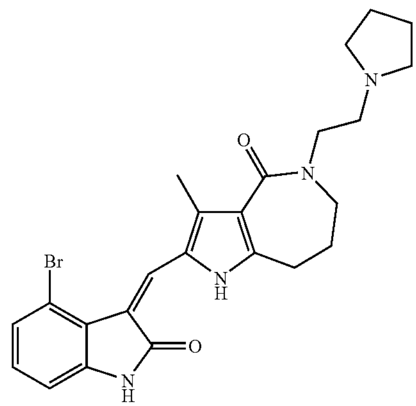 | (Z)-2-(4-bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one |
| 50 | 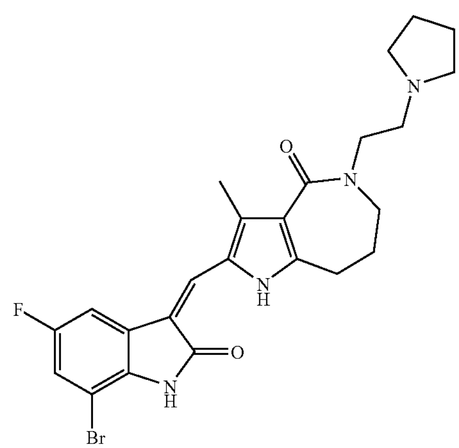 | (Z)-2-(7-bromo-5-fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one |
| 51 | 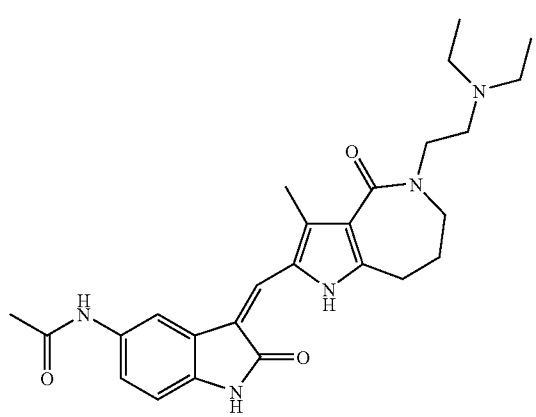 | (Z)-N-{3-[5-(2-diethylamino-ethyl)-3-methyl-4-oxo-1,4,5,6,7,8-hexahydro-pyrrolo[3,2-c]azepin-2-ylmethylene]-2-oxo-2,3-dihydro-1H-indol-5-yl}-acetamide |

| Example No. | Structure | Name |
|---|---|---|
| 52 | 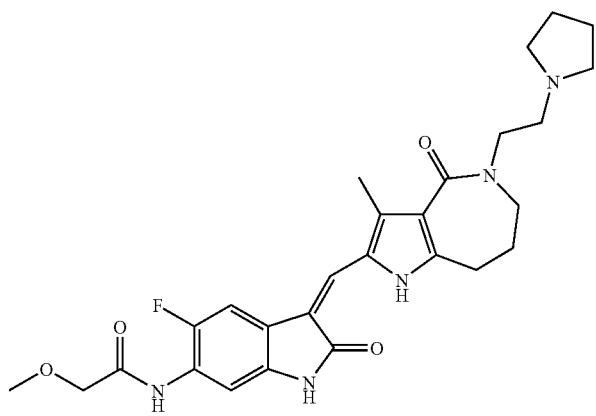 | (Z)-N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide |
| 53 | 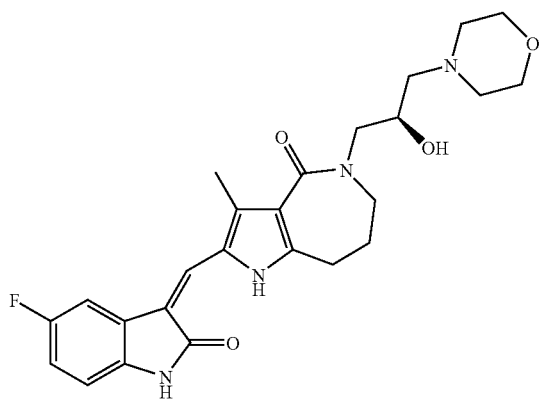 | (R,Z)-2-(5-fluoro-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one |
| 54 | 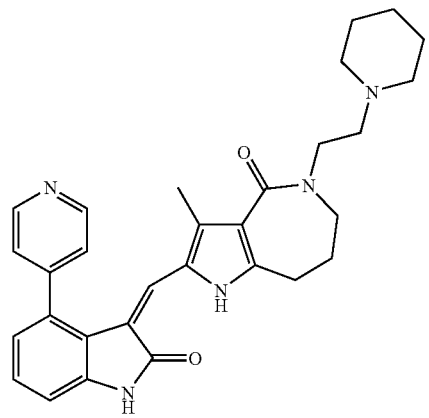 | (Z)-3-methyl-2-(2-oxo-4-pyridin-4-yl-1,2-dihydro-indol-3-ylidenemethyl)-5-(2-piperidin-1-yl-ethyl)-5,6,7,8-tetrahydro-1H-pyrrolo[3,2-c]azepin-4-one |

-continued

| Example No. | Structure | Name |
| --- | --- | --- |
| 55 | 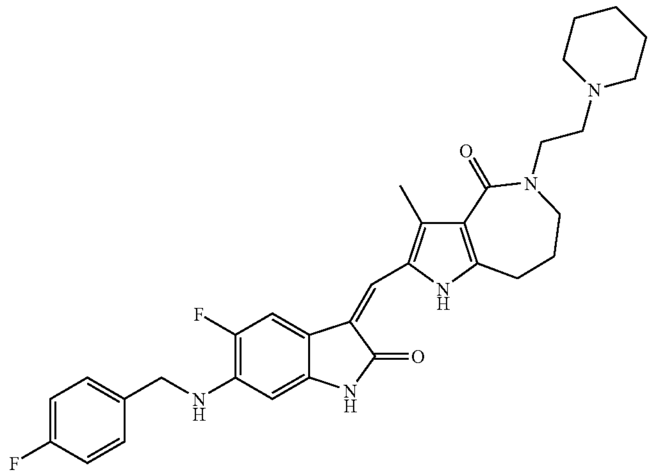 | (Z)-2-[5-fluoro-6-(4-fluoro-benzylamino)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one |
| 56 | 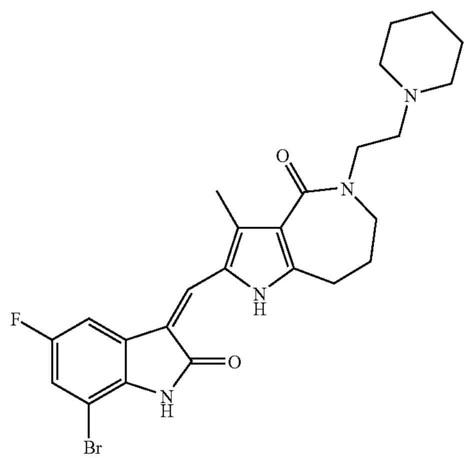 | (Z)-2-(7-bromo-5-fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one |
| 57 | 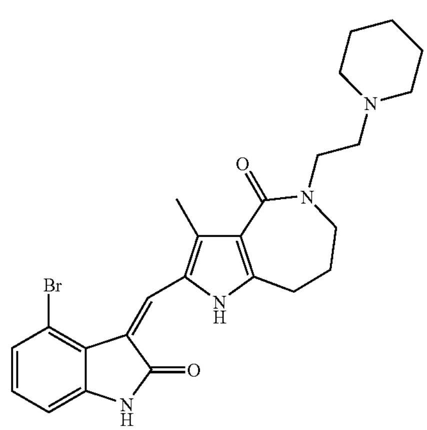 | (Z)-2-(4-bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one |

| Example No. | Structure | Name |
|---|---|---|
| 58 | 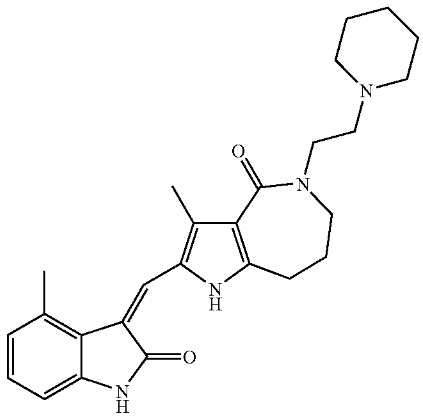 | (Z)-3-methyl-2-(4-methyl-2-oxo-1,2-dihydro-indol-3-ylidenemethyl)-5-(2-piperidin-1-yl-ethyl)-5,6,7,8-tetrahydro-1H-pyrrolo[3,2-c]azepin-4-one |
| 59 | 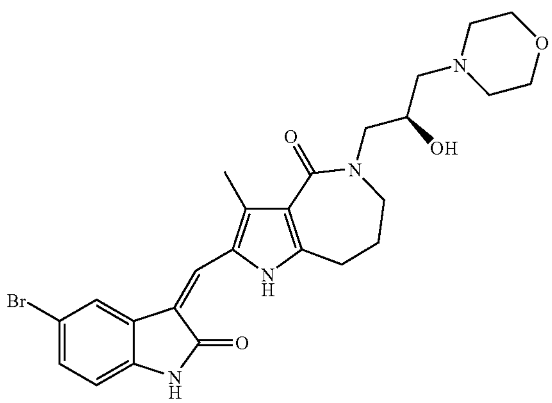 | (R,Z)-2-(5-bromo-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one |
| 60 | 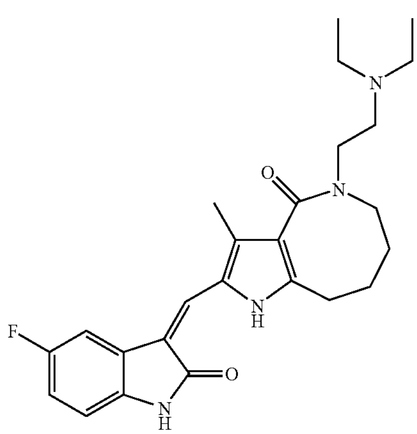 | (Z)-5-(2-diethylamino-ethyl)-2-(5-fluoro-2-oxo-1,2-dihydro-indol-3-ylidenemethyl)-3-methyl-6,7,8,9-tetrahydro-1H,5H-1,5-diaza-cyclopentacycloocten-4-one |

| Example No. | Structure | Name |
|---|---|---|
| 61 | 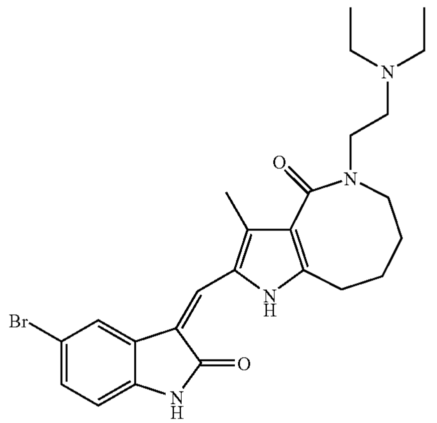 | (Z)-2-(5-bromo-2-oxo-1,2-dihydro-indol-3-ylidenemethyl)-5-(2-diethylamino-ethyl)-3-methyl-6,7,8,9-tetrahydro-1H,5H-1,5-diaza-cyclopentacycloocten-4-one |
| 62 | 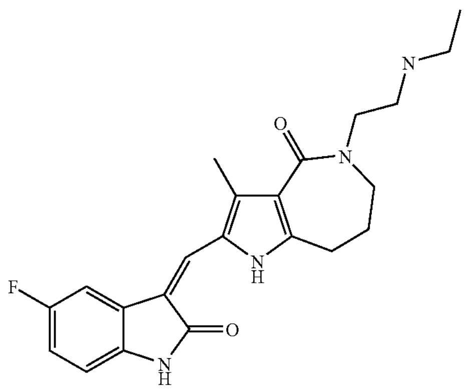 | (Z)-5-(2-ethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one |
| 63 | 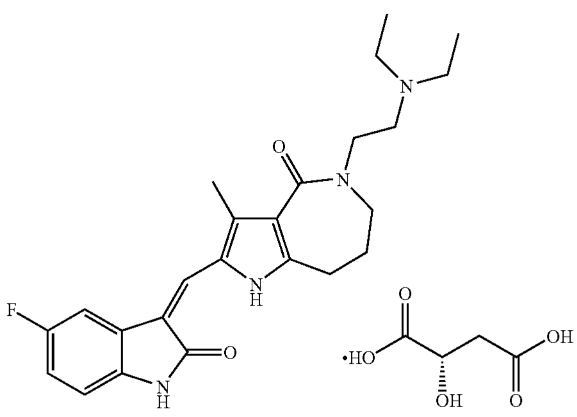 | (Z)-5-(2-diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one malate |
| 64 | 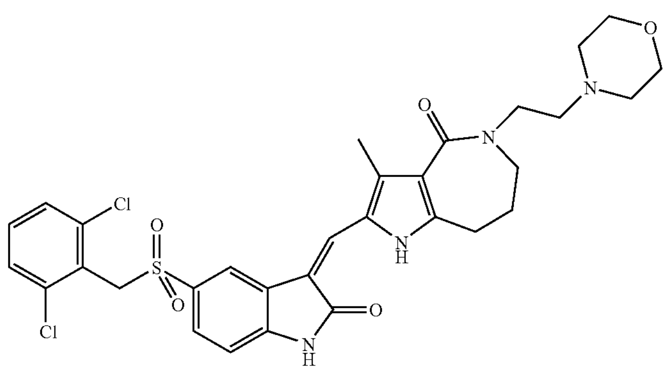 | (Z)-2-((5-(2,6-dichlorobenzylsulfonyl)-2-oxoindolin-3-ylidene)methyl)-3-methyl-5-(2-morpholinoethyl)-5,6,7,8-tetrahydropyrrolo[3,2-c]azepin-4(1H)-one |

| Example No. | Structure | Name |
|---|---|---|
| 65 | 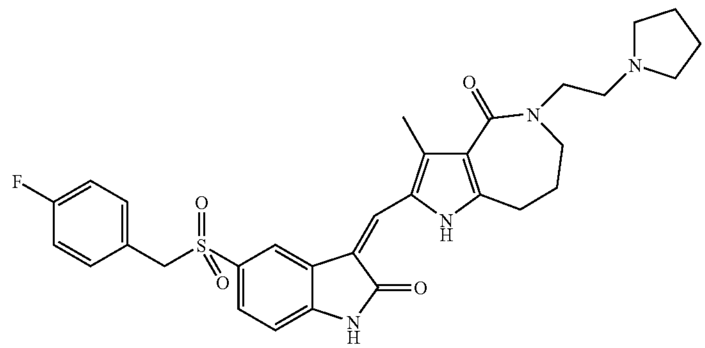 | (Z)-2-[5-(4-fluoro-phenylmethanesulfonyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one |
| 66 | 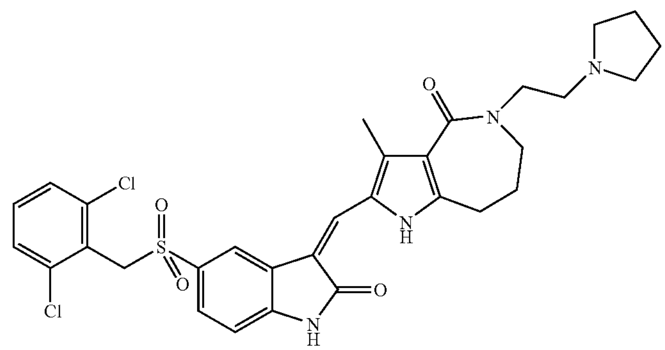 | (Z)-2-((5-(2,6-dichlorobenzylsulfonyl)-2-oxoindolin-3-ylidene)methyl)-3-methyl-5-(2-(pyrrolidin-1-yl)ethyl)-5,6,7,8-tetrahydropyrrolo[3,2-c]azepin-4(1H)-one |
| 67 | 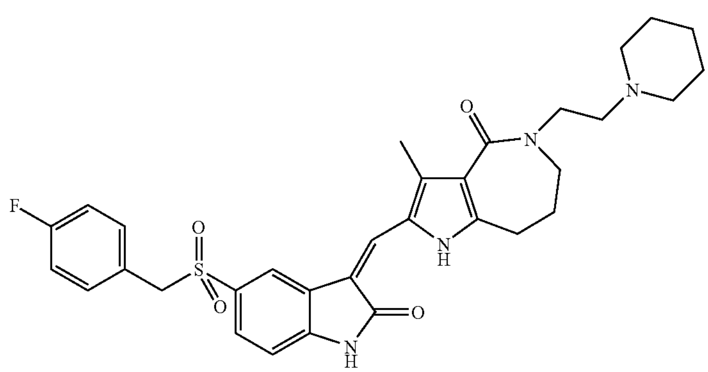 | (Z)-2-((5-(4-fluorobenzylsulfonyl)-2-oxoindolin-3-ylidene)methyl)-3-methyl-5-(2-(piperidin-1-yl)ethyl)-5,6,7,8-tetrahydropyrrolo[3,2-c]azepin-4(1H)-one |
| 68 | 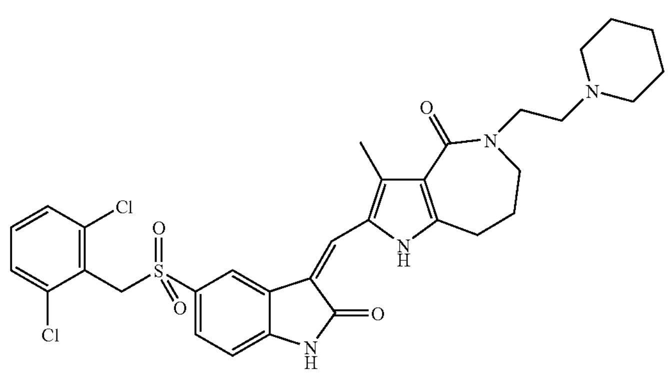 | (Z)-2-((5-(2,6-dichlorobenzylsulfonyl)-2-oxoindolin-3-ylidene)methyl)-3-methyl-5-(2-(piperidin-1-yl)ethyl)-5,6,7,8-tetrahydropyrrolo[3,2-c]azepin-4(1H)-one |

| Example No. | Structure | Name |
|---|---|---|
| 69 | 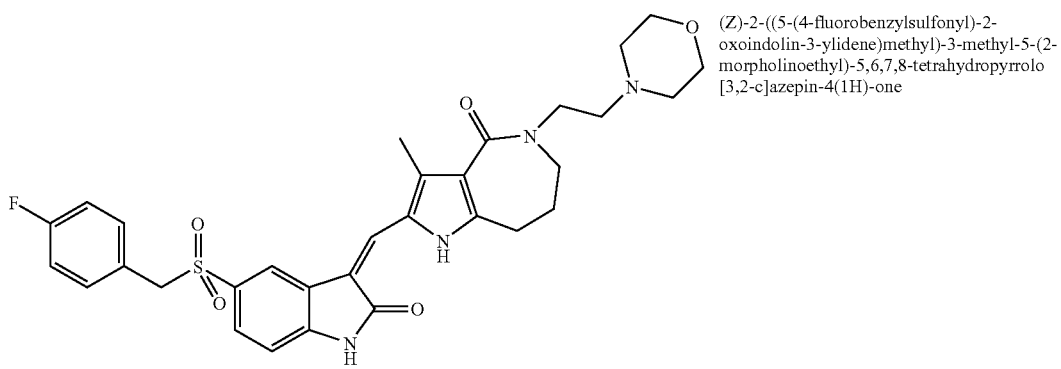 | (Z)-2-((5-(4-fluorobenzylsulfonyl)-2-oxoindolin-3-ylidene)methyl)-3-methyl-5-(2-morpholinoethyl)-5,6,7,8-tetrahydropyrrolo[3,2-c]azepin-4(1H)-one |
| 70 | 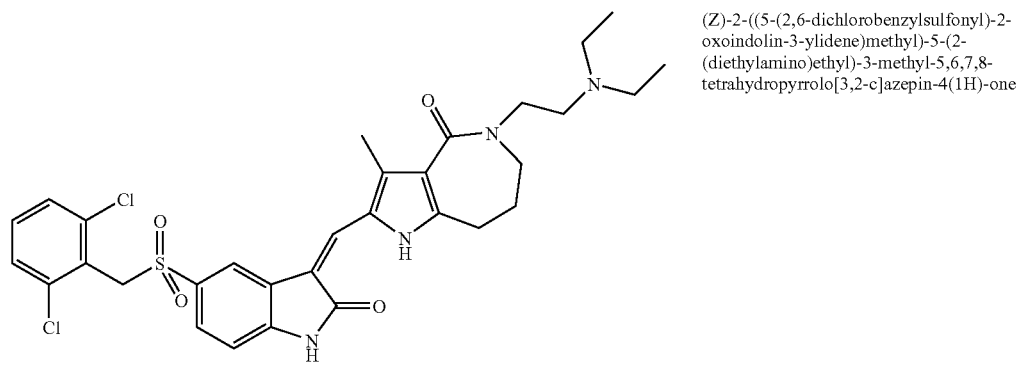 | (Z)-2-((5-(2,6-dichlorobenzylsulfonyl)-2-oxoindolin-3-ylidene)methyl)-5-(2-(diethylamino)ethyl)-3-methyl-5,6,7,8-tetrahydropyrrolo[3,2-c]azepin-4(1H)-one |
| 71 | 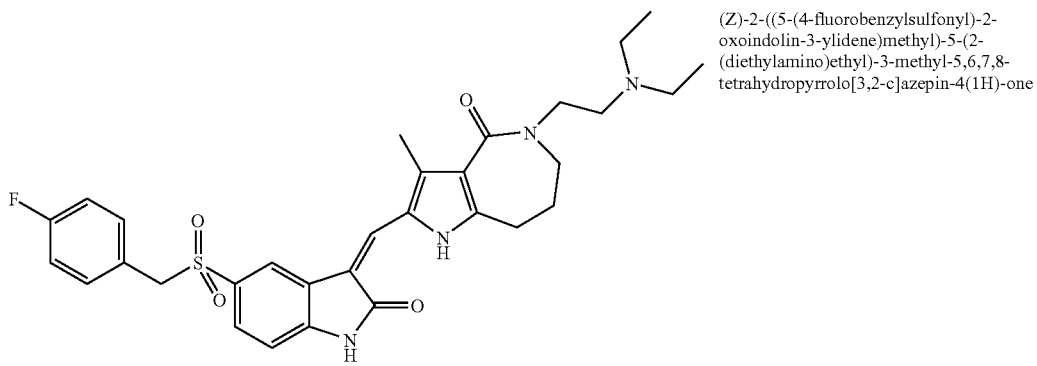 | (Z)-2-((5-(4-fluorobenzylsulfonyl)-2-oxoindolin-3-ylidene)methyl)-5-(2-(diethylamino)ethyl)-3-methyl-5,6,7,8-tetrahydropyrrolo[3,2-c]azepin-4(1H)-one |
| 72 | 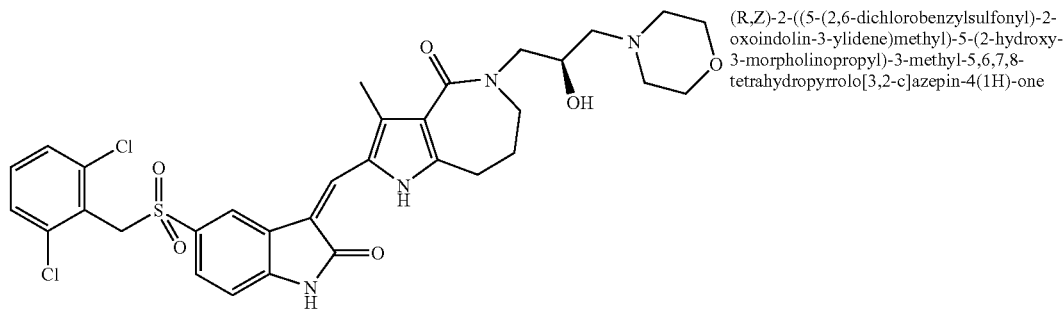 | (R,Z)-2-((5-(2,6-dichlorobenzylsulfonyl)-2-oxoindolin-3-ylidene)methyl)-5-(2-hydroxy-3-morpholinopropyl)-3-methyl-5,6,7,8-tetrahydropyrrolo[3,2-c]azepin-4(1H)-one |

-continued

| Example No. | Structure | Name |
|---|---|---|
| 73 | 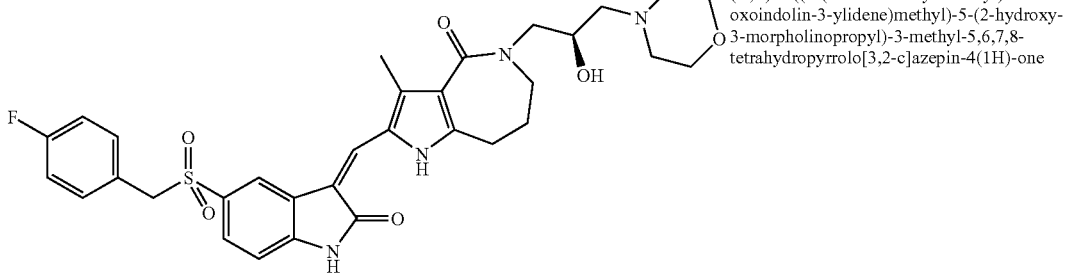 | (R,Z)-2-((5-(4-fluorobenzylsulfonyl)-2-oxoindolin-3-ylidene)methyl)-5-(2-hydroxy-3-morpholinopropyl)-3-methyl-5,6,7,8-tetrahydropyrrolo[3,2-c]azepin-4(1H)-one |
| 74 | 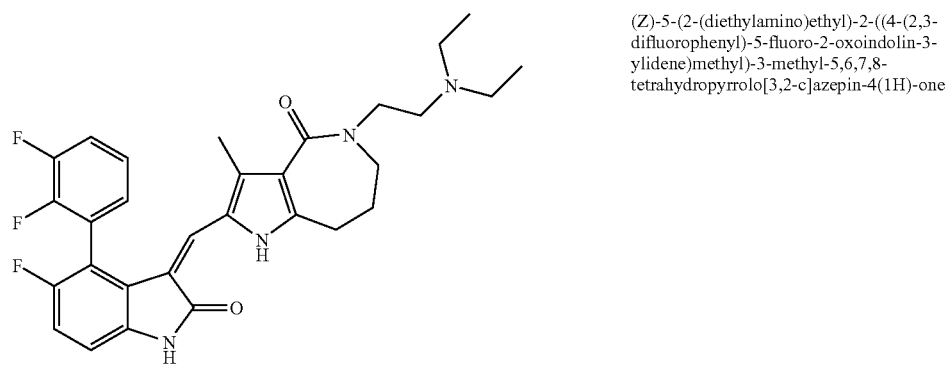 | (Z)-5-(2-(diethylamino)ethyl)-2-((4-(2,3-difluorophenyl)-5-fluoro-2-oxoindolin-3-ylidene)methyl)-3-methyl-5,6,7,8-tetrahydropyrrolo[3,2-c]azepin-4(1H)-one |
| 75 | 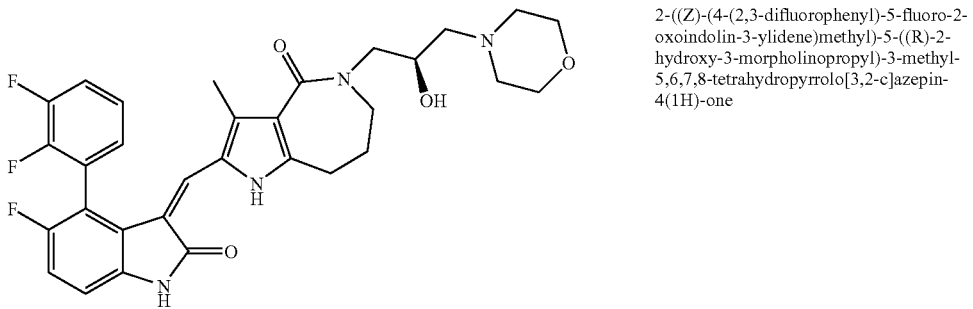 | 2-((Z)-(4-(2,3-difluorophenyl)-5-fluoro-2-oxoindolin-3-ylidene)methyl)-5-((R)-2-hydroxy-3-morpholinopropyl)-3-methyl-5,6,7,8-tetrahydropyrrolo[3,2-c]azepin-4(1H)-one |
| 76 | 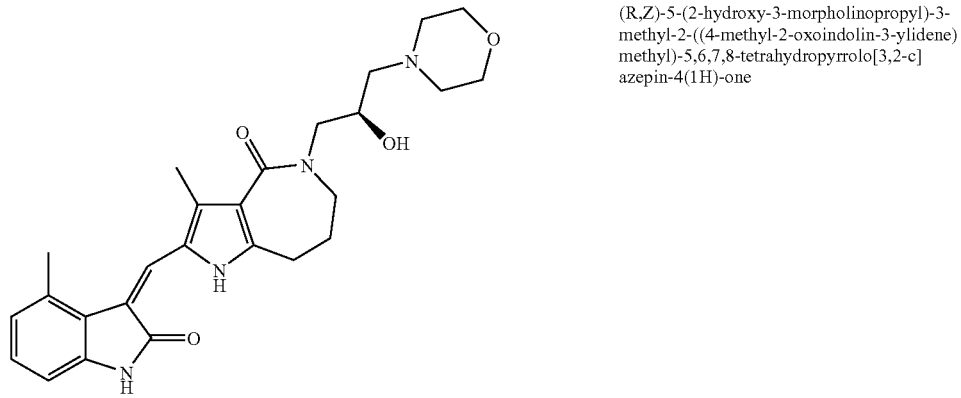 | (R,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one |

-continued

| Example No. | Structure | Name |
|---|---|---|
| 77 | 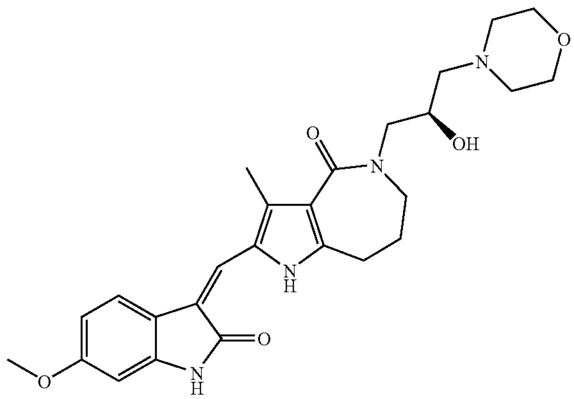 | (R,Z)-5-(2-hydroxy-3-morpholinopropyl)-2-((6-methoxy-2-oxoindolin-3-ylidene)methyl)-3-methyl-5,6,7,8-tetrahydropyrrolo[3,2-c]azepin-4(1H)-one |
| 78 | 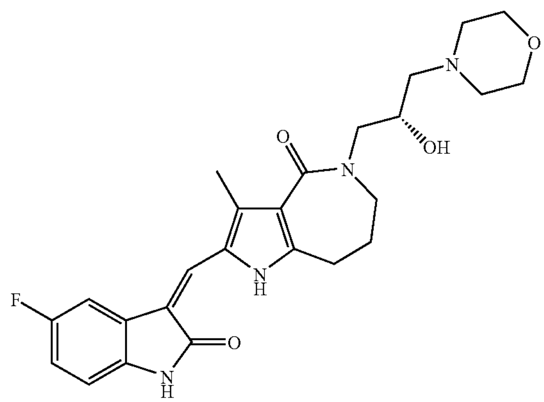 | (S,Z)-2-((5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one |
| 79 | 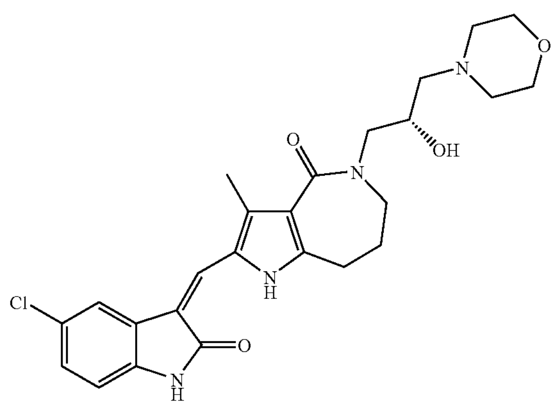 | (S,Z)-2-((5-chloro-2-oxoindolin-3-ylidene)methyl)-5-(2-hydroxy-3-morpholinopropyl)-3-methyl-5,6,7,8-tetrahydropyrrolo[3,2-c]azepin-4(1H)-one |
| 80 | 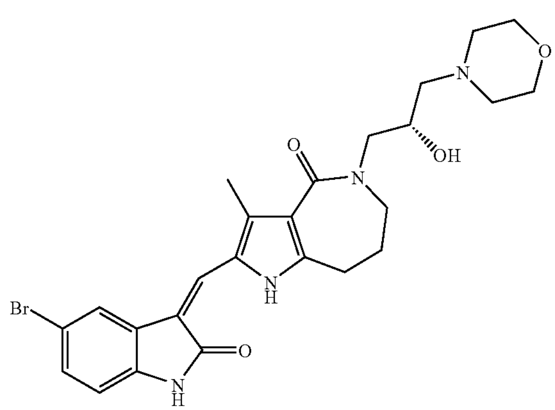 | (S,Z)-2-((5-bromo-2-oxoindolin-3-ylidene)methyl)-5-(2-hydroxy-3-morpholinopropyl)-3-methyl-5,6,7,8-tetrahydropyrrolo[3,2-c]azepin-4(1H)-one |

-continued

| Example No. | Structure | Name |
|---|---|---|
| 81 | 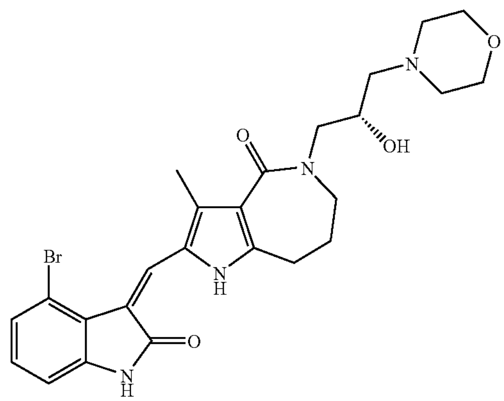 | (S,Z)-2-((4-bromo-2-oxoindolin-3-ylidene)methyl)-5-(2-hydroxy-3-morpholinopropyl)-3-methyl-5,6,7,8-tetrahydropyrrolo[3,2-c]azepin-4(1H)-one |
| 82 | 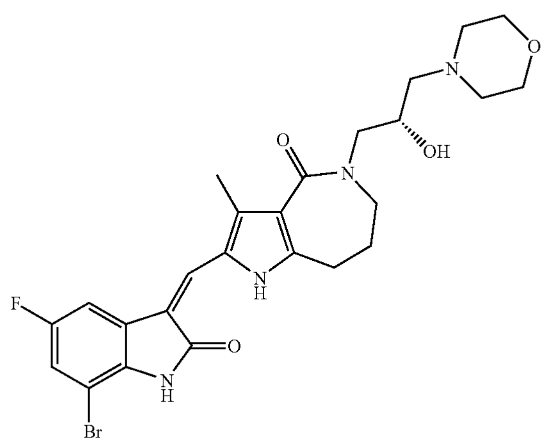 | (S,Z)-2-((7-bromo-5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one |
| 83 | 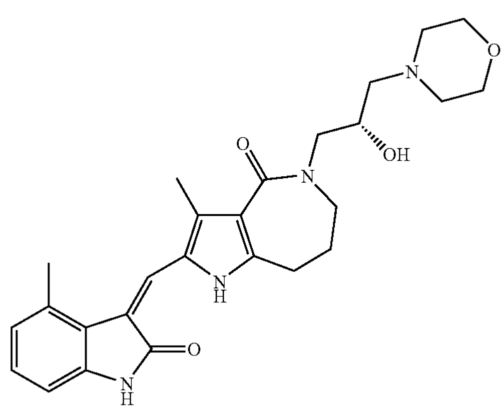 | (S,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one |

Another aspect of this invention is directed to a pharmaceutical composition comprising one or more compound(s) of formula (I), or a pharmaceutically acceptable salt thereof, prodrug thereof and pharmaceutically acceptable carriers.

Another aspect of this invention is directed to a method for modulating the catalytic activity of a protein kinase comprising contacting said protein kinase with a compound of formula (I), or a pharmaceutically acceptable salt thereof. Said protein kinases are selected from the group consisting of receptor tyrosine kinases (RTKs), nonreceptor protein tyrosine kinases (CTKs) and serine-threonine protein kinases (STKs).

Wherein, the pharmaceutically acceptable salts according to present invention are those formed of present compound with the acids selected from the group consisting of malic acid, lactic acid, maleic acid, hydrochloric acid, methanesulfonic acid, sulfuric acid, phosphoric acid, citric acid, tartaric acid, acetic acid and trifluoroacetic acid.

Further, this invention relates to compounds having the following formula (IC) or (ID) as intermediates in the synthesis of compounds of formula (I):

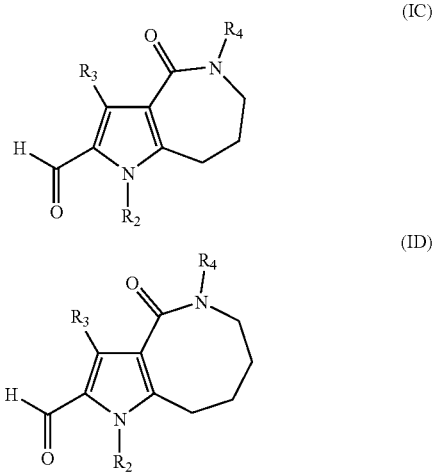

Wherein:

$R_2$ is selected from the group consisting of hydrogen and alkyl;

$R_3$ is selected from the group consisting of alkyl, trifluoromethyl, aryl and aralkyl, wherein said alkyl, aryl or aralkyl is further substituted by one or more halogen;

$R_4$ is selected from the group consisting of alkyl, cycloalkyl, heterocyclo alkyl, aryl, heteroaryl, —$(CH_2)_n$ $(OCH_2CH_2)_rR_{11}$, —$[CH_2CH(OH)]_rCH_2NR_9R_{10}$ and —$(CH_2)_nNR_9R_{10}$, wherein said alkyl, cylcoalkyl, heterocyclo alkyl, aryl or heteroaryl is further substituted by one or more groups selected from the group consisting of aryl, hydroxyl, amino, amide group, aminocarbonyl, alkoxyl, aryloxy, aminoalkyl, hydroxyalkyl, heterocyclo alkyl, carboxylic acid, carboxylic ester and —$NR_9R_{10}$;

$R_9$ and $R_{10}$ are each independently selected from the group consisting of hydrogen, alkyl, cycloalkyl, aryl, heterocyclo alkyl and heteroaryl, wherein said alkyl, cycloalkyl, aryl, heterocyclo alkyl or heteroaryl is further substituted by one or more groups selected from the group consisting of alkyl, aryl, haloaryl, hydroxyl, amino, cyano, alkoxyl, aryloxy, hydroxyalkyl, heterocyclo alkyl, carboxylic acid, carboxylic ester and —$NR_9R_{10}$;

$R_9$ and $R_{10}$ are taken together with the attached atom to form 4 to 8 membered hetero rings, wherein said 4 to 8 membered hetero rings may further optionally contain one to more heteroatoms selected from the group consisting of N, O and S atom, and said 4 to 8 membered rings are further substituted by one or more groups consisting of alkyl, halogen, aryl, heteroaryl, haloalkyl, hydroxyl, cyano, alkoxyl, aryloxy, aminoalkyl, hydroxyalkyl, heterocyclo alkyl, carboxylic acid, carboxylic ester and —$NR_9R_{10}$;

$R_{11}$ is selected from the group consisting of hydrogen and alkyl;

n is an integer from 2 to 6;

z is an integer from 1 to 4; and r is an integer from 1 to 6.

In another aspect, this invention is directed to a method for preventing or treating a mammal from protein kinase related disorders comprising administering to the mammal a therapeutically effective amount of the pharmaceutical composition of the invention, which comprises the compound(s) of the invention or pharmaceutically acceptable salts thereof, as well as pharmaceutically acceptable carriers and excipients. The protein kinase related disorders are selected from the group consisting of the disorders related to VEGFR-2, EGFR, HER-2, HER-3, HER-4, PDGFR, c-Kit, c-Met, FGFR, and Flt3. The protein kinases related disorders also are leukemias, diabete, autoimmune diseases, hyperplasias, psoriasis, osteoarthritis, rheumatoid arthritis, angiogenesis, cardiovascular diseases, von Heppel-Lindau disease, inflammatory diseases, and fibrosis. More preferably, said protein kinase related disorders are squamous cell carcinoma, renal cell carcinoma, Kaposi's sarcoma, non-small cell lung cancer, small cell lung cancer, lymphoma, thyroid adenocarcinoma, breast cancer, head and neck cancer, uterine cancer, esophageal cancer, melanoma, bladder cancer, carcinosarcoma in urinary and genital system, gastrointestinal carcinoma, gliomas, colorectal cancer, ovarian cancer. Preferably, said mammal is a human.

Further, the method for treating a mammal from protein kianse related disorders according to the present invention is preferably the method for treating a mammal from cancer. The present method further comprises co-administering the mammal a therapeutically effective amount of anti-tumor agent selected from the group consisting of taxol or carboplatin. Preferably, said mammal is a human. In still another aspect, this invention is directed to a use of the compounds according to the present invention in the preparation of a medicament for the treatment of protein kinase related disorders. The protein kinase related disorders are selected from the group consisting of the disorders related to VEGFR-2, EGFR, HER-2, HER-3, HER-4, PDGFR, c-Kit, c-Met, FGFR and Flt3. Alternatively, the protein kinases related disorders are selected from the group consisting of leukemias, diabete, autoimmune diseases, hyperplasia, psoriasis, osteoarthritis, rheumatoid arthritis, angiogenesis, cardiovascular diseases, von Heppel-Lindau disease, inflammatory diseases, and fibrosis. More preferably, said protein kinase related disorders are cancer selected from the group consisting of squamous cell carcinoma, renal cell carcinoma, Kaposi's sarcoma, non-small cell lung cancer, small cell lung cancer, lymphoma, thyroid adenocarcinoma, breast cancer, head and neck cancer, uterine cancer, esophageal cancer, melanoma, bladder cancer, carcinosarcoma in the urinary and genital systems, gastrointestinal carcinoma, gliomas, colorectal cancer, and ovarian cancer.

In another aspect, the invention relates to the preparation process of the compound of intermediate formula (IC), comprising the following steps of:

reacting starting material pyrrole methyl carboxylic diester IC-1 in tetrahydrofuran in the presence of acetic acid with ammonium ceric nitrate at room temperature to obtain pyrrole aldehyde carboxylic diester IC-2; and

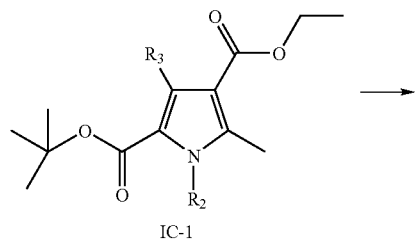

IC-1

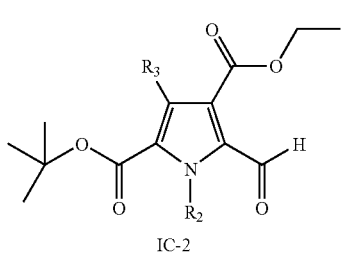

IC-2 reacting pyrrole aldehyde carboxylic diester IC-2 in anhydrous tetrahydrofuran with (carbethoxy methylene)triphenylphosphorane via Witting reaction to obtain pyrrole ethoxycarbonyl ethenyl dicarboxylic ester IC-3;

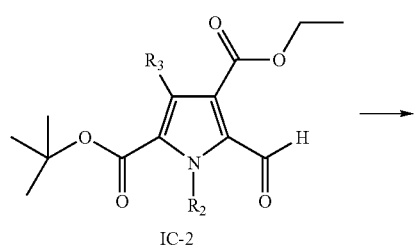

IC-2

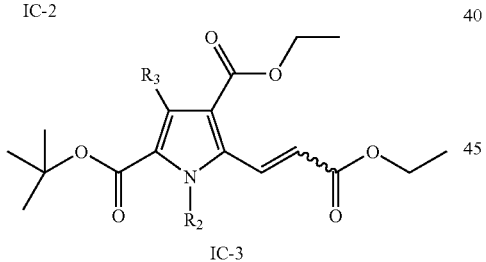

IC-3 reducing pyrrole ethoxycarbonyl ethenyl dicarboxylic ester IC-3 in anhydrous ethanol by hydrogen catalyzed by palladium/carbon at room temperature to obtain pyrrole ethoxycarbony ethyl dicarboxylic ester IC-4;

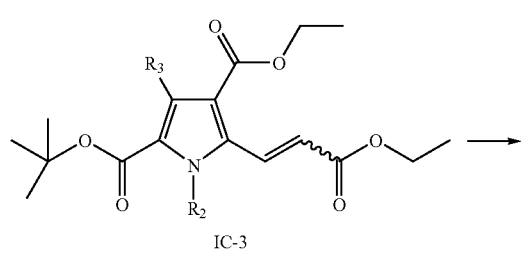

IC-3

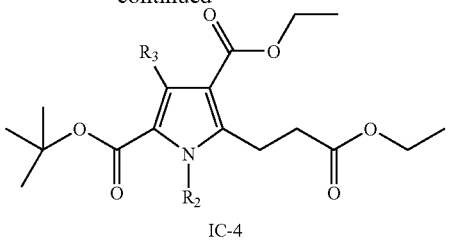

IC-4 hydrolyzing pyrrole ethoxycarbony ethyl dicarboxylic ester IC-4 in aqueous lithium hydroxide solution to obtain pyrrole carboxylethyl dicarboxylic ester IC-5;

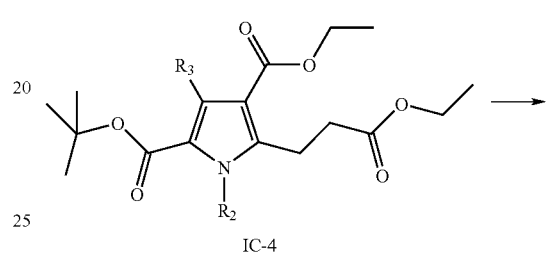

IC-4

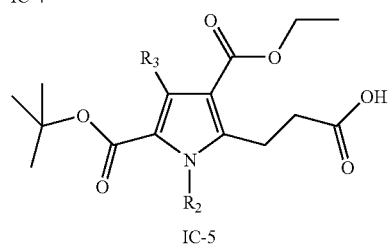

IC-5 reducing pyrrole carboxylethyl dicarboxylic ester IC-5 in anhydrous tetrahydrofuran by borane-tertrahydrofuran solution at −20~−5° C. (degree centigrade) to obtain pyrrole hydroxypropyl dicarboxylic ester IC-6;

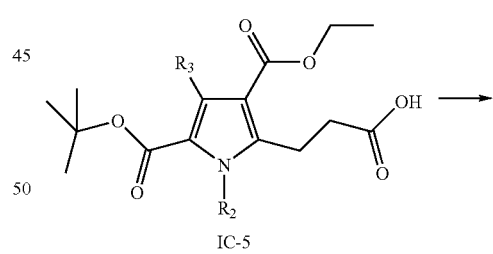

IC-5

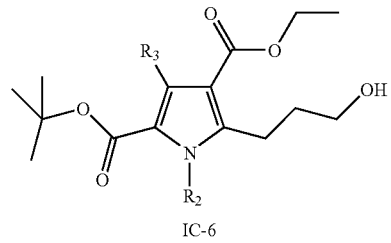

IC-6 mesylating pyrrole hydroxypropyl dicarboxylic ester IC-6 in anhydrous dichloromethane in the presence of triethylamine at −20~−5° C. to obtain pyrrole methylsulfonyloxypropyl dicarboxylic ester IC-7;

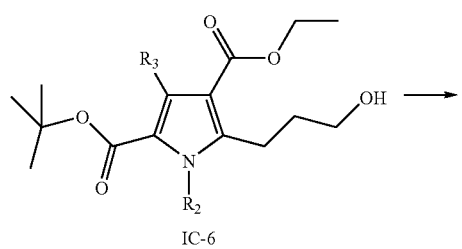

IC-6

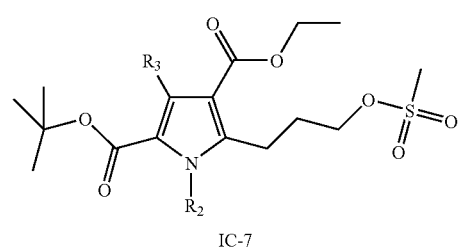

IC-7 reacting pyrrole methylsulfonyloxy-propyl dicarboxylic ester IC-7 with different amines to obtain pyrrole amide dicarboxylic ester IC-8;

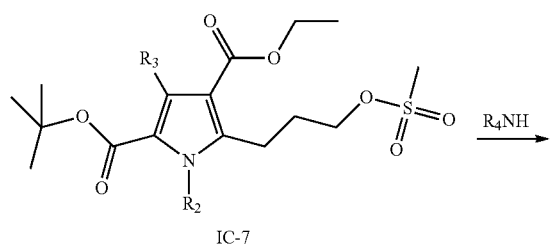

IC-7

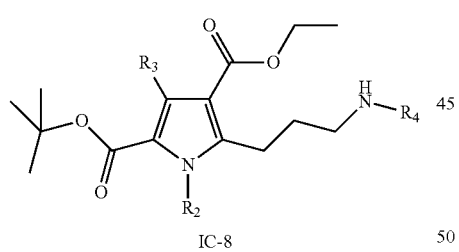

IC-8 reacting pyrrole amide dicarboxylic ester IC-8 with trimethyl aluminmum in toluene under reflux to obtain the pyrrolofused seven-membered aza-heterocyclic ester IC-9;

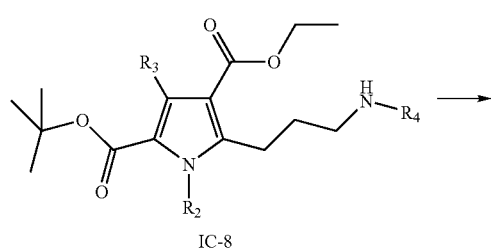

IC-8

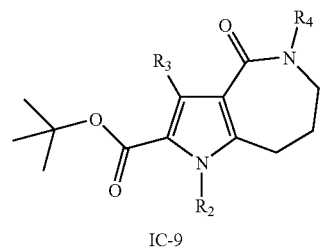

IC-9 reacting pyrrolofused seven-membered aza-heterocyclic ester IC-9 with trifluoroacetic acid at 30~50° C. under an argon atmosphere to obtain pyrrolofused seven-membered aza-heterocyclic formaldehyde IC

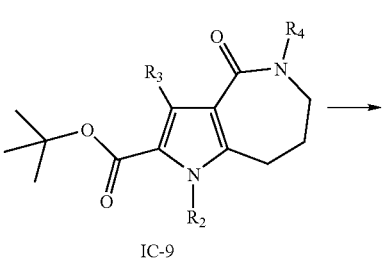

IC-9

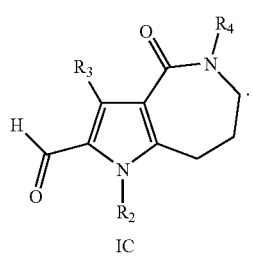

IC

Wherein:

$R_2$, $R_3$ and $R_4$ are as defined above.

In another aspect, the invention relates to preparation process of the compound of intermediate formula (ID), comprising the following steps of:

reacting pyrrole aldehyde carboxylic diester IC-2 with Grignard reagent cyclopropylmagnesium bromide in anhydrous tetrahydrofuran at room temperature under an argon atmosphere to obtain pyrrole cyclopropyl hydroxycarboxylic diester ID-1

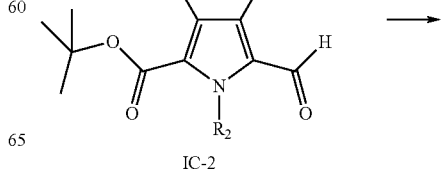

IC-2

-continued

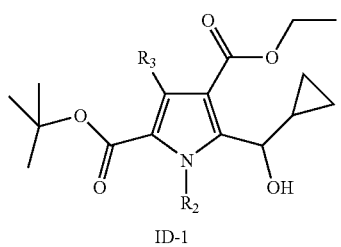

ID-1 reacting pyrrole cyclopropyl hydroxycarboxylic diester ID-1 with hydrobromic acid in methanol to obtain bromo-butenyl pyrrole diester ID-2;

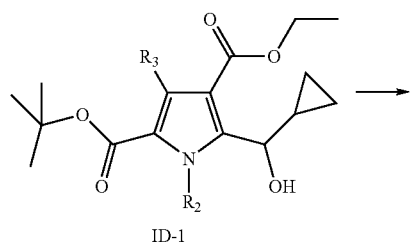

ID-1

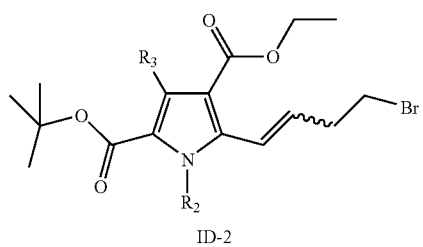

ID-2 reducing bromo-butenyl pyrrole diester ID-2 in anhydrous ethanol by hydrogen catalyzed by palladium/carbon at room temperature to obtain bromo-butyl pyrrole diester ID-3;

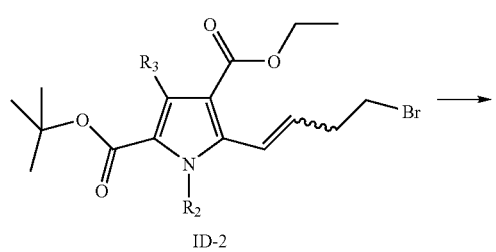

ID-2

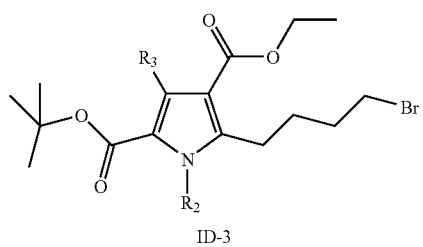

ID-3 reacting bromo-butyl pyrrole diester ID-3 with different amines in dichloromethane under reflux to obtain pyrrole amide dicarboxylic diester ID-4;

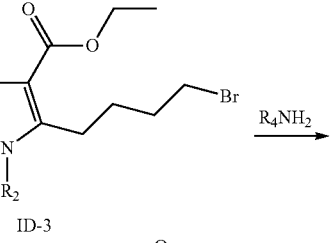

ID-3

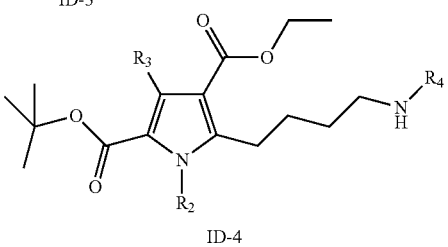

ID-4 reacting pyrrole amide dicarboxylic diester ID-4 with trimethyl aluminmum in toluene under reflux to obtain the pyrrolofused eight-membered aza-heterocyclic aldehyde ID;

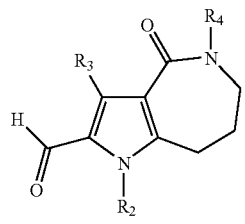

ID-4

(ID)

Wherein:

R$_2$, R$_3$ and R$_4$ are as defined above.

Furthermore, another aspect of this invention is directed to a preparation process of pyrrolo-nitrogenous heterocyclic derivatives, comprising the step of reacting an oxindole with an aldehyde in the presence of base (such as triethylamine, piperidine), and the reaction mixture is heated for 2~12 hours, wherein said aldehyde has the following formula:

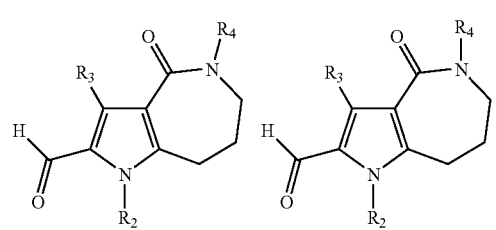

and said oxindole has the following formula:

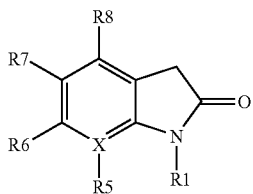

Wherein:

X, $R_1$, $R_2$, $R_3$, $R_4$, $R_5$, $R_6$, $R_7$ and $R_8$ are as defined above.

In still another aspect, this invention is directed to the compounds which can distinguish the protein kinase activity by contacting cells which express the protein kinase with a compound of the invention or a pharmaceutically acceptable salt thereof, and determining the effect to the cell.

In still another aspect, this invention is directed to the compounds which can distinguish protein kinase activity by contacting man-made recombinant protein kinase with a compound of the invention or a pharmaceutically acceptable salt thereof, and determining kinase activity by ELISA method.

DETAILED DESCRIPTION OF THE INVENTION

Unless otherwise stated, the following terms used in the specification and claims have the meanings discussed below.

"Alkyl" refers to a saturated aliphatic hydrocarbon radical including $C_1$~$C_{20}$ straight chain and branched chain groups. Preferably, an alkyl group is a medium size alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl, or tert-butyl, and the like. The alkyl group may be substituted or unsubstituted. When substituted, the preferable substituent group(s) is halo, hydroxyl, lower alkoxyl, aryl, aryloxyl, heteroaryl, heterocyclo alkyl, —$OR_9$, —$NR_9R_{10}$, —$COR_9$, —$O[CH_2CH_2O]_rR_{11}$, —$NR_9COR_{10}$, —$SO_2R_9$ or —$NHCO_2R_{10}$.

"Cycloalkyl" refers to a 3 to 8 membered all-carbon monocyclic ring, an all-carbon 5-membered/6-membered or 6-membered/6-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated pi-electron system. Examples of cycloalkyl groups are cyclopropane, cyclobutane, cyclopentane, cyclopentene, cyclohexane, cyclohexadiene, adamantane, cycloheptane, cycloheptatriene, and the like. The cycloalkyl group may be substituted or unsubstituted. When substituted, the substituent group(s) is preferably one or more independently selected from the group consisting of lower alkyl, trihalo alkyl, halo, hydroxyl, lower alkoxyl, aryl (optionally substituted with one or more groups which each independently is halo, hydroxyl, lower alkyl or lower alkoxyl groups), aryloxy (optionally substituted with one or more groups which each independently is halo, hydroxyl, lower alkyl or lower alkoxyl groups), 6-membered heteroaryl (having 1 to 3 nitrogen atoms in the ring, the carbons in the ring being optionally substituted with one or more groups which each independently is halo, hydroxyl, lower alkyl or lower alkoxyl groups), 5-membered heteroaryl (having 1 to 3 heteroatoms selected from the group consisting of nitrogen, oxygen and sulfur, the carbon and nitrogen atoms of the group being optionally substituted with one or more groups which each independently is halo, hydroxyl, lower alkyl or lower alkoxyl groups), 5- or 6-membered heterocyclo alkyl (having 1 to 3 heteroatoms selected from nitrogen, oxygen and sulfur, the carbon and nitrogen (if present) atoms in the group being optionally substituted with one or more groups which each independently is halo, hydroxyl, lower alkyl or lower alkoxyl groups), mercapto, cyano, nitro, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Alkenyl" refers to an alkyl group as defined above having at least 2 carbon atoms and at least one carbon-carbon double bond. Illustrative examples of alkenyl are derived from, but not limited to the following: ethenyl, 1-propenyl, 2-propenyl, 1-, 2-, or 3-butenyl, and the like. Said alkenyl may be optionally substituted with one or more groups selected from the group consisting of halo, trihalomethyl, hydroxyl, nitro, cyano, alkoxyl, alkyl, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Alkynyl" refers to refers to an alkyl group as defined above having at least 2 carbon atoms and at least one carbon-carbon triple bond. Illustrative examples of alkynyl are derived from, but not limited to the following: ethynyl, 1-propynyl, 2-propynyl, 1-, 2-, or 3-butynyl, and the like. Said alkynyl may be optionally substituted with one or more groups selected from the group consisting of halo, trihalomethyl, hydroxyl, nitro, cyano, alkoxyl, alkyl, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Aryl" refers to groups having at least one aromatic ring, i.e., having a completely conjugated pi-electron system, including all-carbon cyclic aryl, heteroaryl, fused-ring polycyclic aryl. Said aryl may be optionally substituted with one or more groups selected from the group consisting of halo, trihalomethyl, hydroxyl, nitro, cyano, alkoxyl, alkyl, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Heteroaryl" refers to an aryl having 1 to 3 ring heteroatoms selected from the group consisting of O, S, and N as ring atoms, the remaining ring atoms being C. Said ring is 5 or 6 membered ring. Examples, without limitation, of heteroaryl groups are furan, thiophene, pyridine, pyrrole, N-alkyl pyrrole, pyrimidine, pyrazine, imidazole, and the like. Said heteroaryl may be optionally substituted with one or more groups selected from the group consisting of halo, trihalomethyl, hydroxyl, nitro, cyano, alkoxyl, alkyl, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Heterocyclo alkyl" group refers to a monocyclic or fused ring group of 5 to 9 ring atoms having in the ring(s) one or more atoms selected from the group consisting of nitrogen, oxygen and $S(O)n$ (n is integer from 0 to 2), the remaining ring atoms being C. The rings may also have one or more double bonds, However, the rings may or may not have a completely conjugated pi-electron system. Examples, without limitation, of unsubstituted heterocyclo alkyl groups are pyrrolidine, piperidine, piperazine, morpholine, thiomorpholine, homopiperazine, and the like. The heterocyclo alkyl may be substituted or unsubstituted. When substituted, the substituent group(s) is preferably one or more selected from halo, trihalomethyl, hydroxyl, nitro, cyano, alkoxyl, alkyl, carboxylic acid, carboxylic ester, —$OR_9$, —$NR_9R_{10}$, —$COR_9$, —$O[CH_2CH_2O]_rR_{11}$, —$NR_9COR_{10}$, —$SO_2R_9$ and —$NHCO_2R_{10}$.

"Hydroxyl" refers to an —OH group.

"Alkoxyl" refers to both an —O-(alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like. Said alkoxyl group may be optionally substituted with one or more groups selected from the group consisting of halo, trihalomethyl, hydroxyl, nitro, cyano, alkoxyl, alkyl, carboxylic acid, carboxylic ester, —OR$_9$, —NR$_9$R$_{10}$, —COR$_9$, —O[CH$_2$CH$_2$O]$_r$R$_{11}$, —NR$_9$COR$_{10}$, —SO$_2$R$_9$ and —NHCO$_2$R$_{10}$.

"Haloalkoxy" refers to an —O-(haloalkyl). Representative examples include, but are not limited to, trifluoromethoxy, tribromoethoxy, and the like.

"Aryloxyl" refers to both an —O-aryl and an —O-heteroaryl group, as defined above. Representative examples include, but are not limited to, phenoxy, [0094] and derivatives thereof. Said aryloxyl group may be optionally substituted with one or more groups selected from the group consisting of halo, trihalomethyl, hydroxyl, nitro, cyano, alkoxyl, alkyl, carboxylic acid, carboxylic ester, —OR$_9$, —NR$_9$R$_{10}$, —COR$_9$, —O[CH$_2$CH$_2$O]$_r$R$_{11}$, —NR$_9$COR$_{10}$, —SO$_2$R$_9$ and —NHCO$_2$R$_{10}$.

"Hydroxyalkyl" refers to a —(CH$_2$)$_n$OH group.

"Halo" refers to fluoro, chloro, bromo, or iodo, preferably fluoro or chloro.

"Trihalomethyl" refers to a —CX$_3$, with X as defined above.

"Optional" or "optionally" means that the subsequently described event or circumstance may or may not occur, and that the description includes instances where the event or circumstance may or may not occur. For example, "heterocycle group optionally substituted with an alkyl group" means that the alkyl may or may not be present, and the description includes situations where the heterocycle group is substituted with an alkyl group and situations where the heterocyclo group is not substituted with the alkyl group.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

Synthesis Method of the Invention Compound

In order to complete the object of the invention, the invention applies the following technical solution:

The compounds of the invention can be prepared by methods known in the art. The suitable synthetic methods are provided in the following examples. Generally, the compounds can be prepared according to the following scheme:

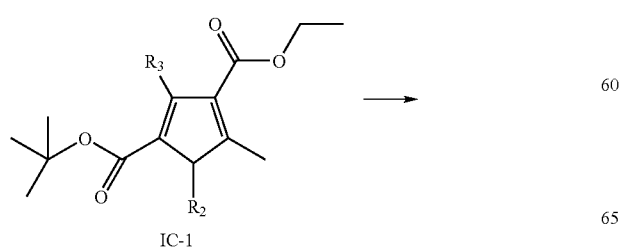

IC-1

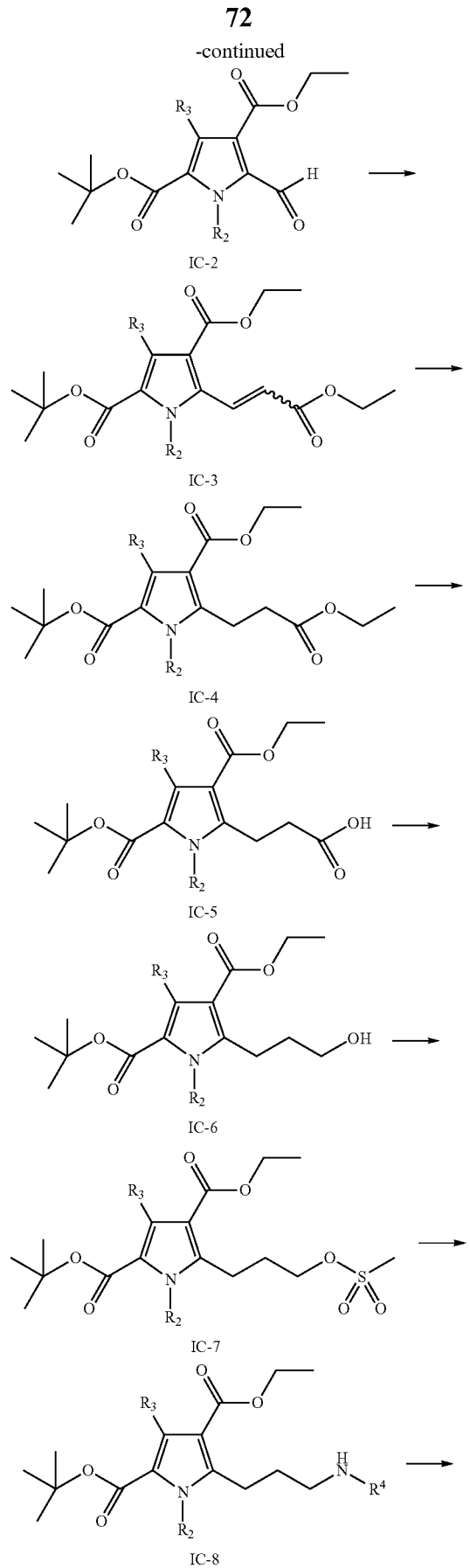

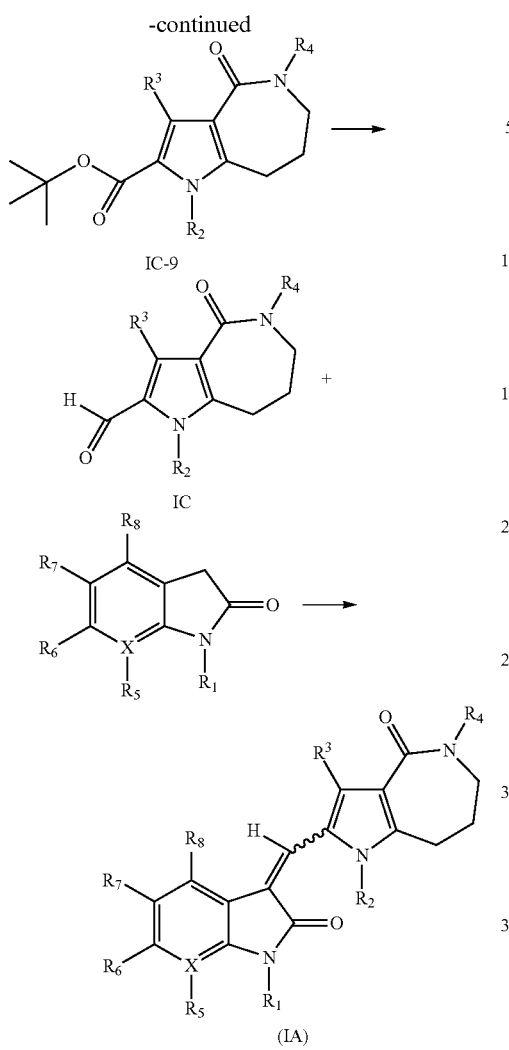

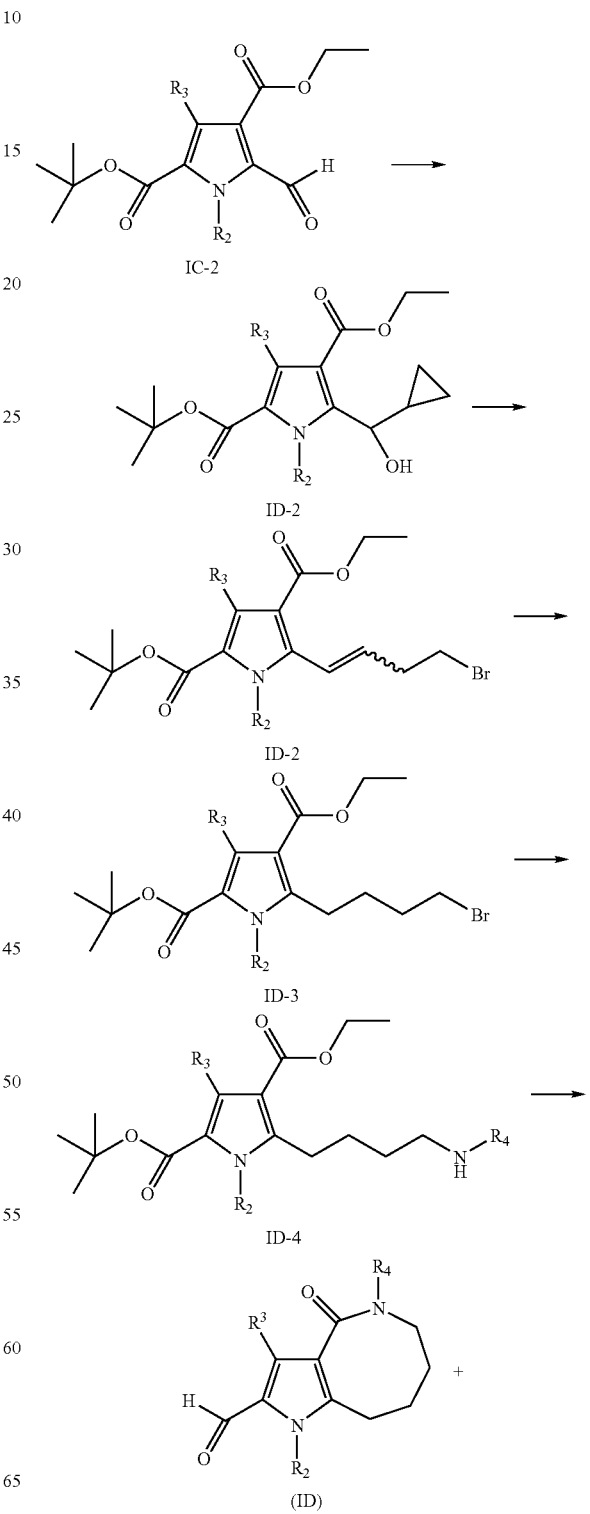

IC-9; reacting pyrrolofused seven-membered aza-heterocyclic ester IC-9 with trifluoroacetic acid at 30~50° C. under an argon atmosphere to obtain pyrrolofused seven-membered aza-heterocyclic formaldehyde IC; reacting pyrrolofused seven-membered aza-heterocyclic formaldehyde IC with indolinones in the presence of a base such as triethylamine or piperidine under reflux for 2~12 hours to obtain pyrrolofused seven-membered aza-heterocyclic derivatives (IA).

Reacting starting material pyrrole methyl carboxylic diester IC-1 in tetrahydrofuran in the presence of acetic acid with ammonium ceric nitrate at room temperature to obtain pyrrole aldehyde carboxylic diester IC-2; reacting pyrrole aldehyde carboxylic diester IC-2 in anhydrous tetrahydrofuran with (carbethoxy methylene)triphenylphosphorane via Witting reaction to obtain pyrrole ethoxycarbonyl ethenyl dicarboxylic ester IC-3; reducing pyrrole ethoxycarbonyl ethenyl dicarboxylic ester IC-3 in anhydrous ethanol by hydrogen catalyzed by palladium/carbon at room temperature to obtain pyrrole ethoxycarbony ethyl dicarboxylic ester IC-4; hydrolyzing pyrrole ethoxycarbony ethyl dicarboxylic ester IC-4 in aqueous lithium hydroxide solution to obtain pyrrole carboxylethyl dicarboxylic ester IC-5; reducing pyrrole carboxylethyl dicarboxylic ester IC-5 in anhydrous tetrahydrofuran by borane-tertrahydrofuran solution at −20~−5° C. to obtain pyrrole hydroxypropyl dicarboxylic ester IC-6; furthermore, mesylating of pyrrole hydroxypropyl dicarboxylic ester IC-6 in anhydrous dichloromethane in the presence of triethylamine at −20~−5° C. to obtain pyrrole methylsulfonyloxy-propyl dicarboxylic ester IC-7; reacting pyrrole methylsulfonyloxy-propyl dicarboxylic ester IC-7 with different amines to obtain pyrrole amide dicarboxylic ester IC-8; reacting pyrrole amide dicarboxylic ester IC-8 with trimethyl aluminmum in toluene under reflux to obtain the pyrrolofused seven-membered aza-heterocyclic ester

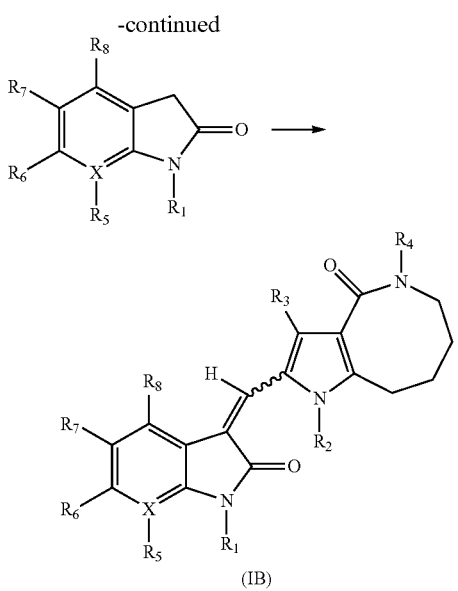

Reacting pyrrole aldehyde carboxylic diester IC-2 was with Grignard reagent cyclopropylmagnesium bromide in anhydrous tetrahydrofuran at room temperature under an argon atmosphere to obtain pyrrole cyclopropyl hydroxycarboxylic diester ID-1; reacting pyrrole cyclopropyl hydroxycarboxylic diester ID-1 with hydrobromic acid in methanol to obtain bromo-butenyl pyrrole diester ID-2; reducing bromo-butenyl pyrrole diester ID-2 in anhydrous ethanol by hydrogen catalyzed by palladium/carbon at room temperature to obtain bromo-butyl pyrrole diester ID-3; reacting bromo-butyl pyrrole diester ID-3 with different amines in dichloromethane under reflux to obtain pyrrole amide dicarboxylic diester ID-4; reacting pyrrole amide dicarboxylic diester ID-4 with trimethyl aluminmum in toluene under reflux to obtain the pyrrolofused eight-membered aza-heterocyclic aldehyde ID; reacting pyrrolofused eight-membered aza-heterocyclic aldehyde ID with indolinones in the presence of a base such as triethylamine or piperidine under reflux for 2~12 hours to obtain pyrrolofused eight-membered aza-heterocyclic derivatives (IB).

Wherein, the double bond of Formula (I) was Z configuration (cis), which can be confirmed by the NMR data. Generally, the chemical shift of pyrrole NH proton was about 9 ppm, but that of the pyrrole NH proton of the obtained compounds was about 14 ppm. The downfield shift of the NH proton was mainly because of intramolecular hydrogen bonding interaction between pyrrole NH proton and adjacent carbonyl oxygen atom of oxindole, which was also described in patent WO0160814(Su-11248).

This invention also relates to a pharmaceutical composition comprising compounds or salts thereof of this invention in an effective therapeutic dose, as well as pharmaceutically acceptable carrier.

Furthermore, this invention relates to a use of the compounds of formula (I) or salts thereof in the preparation of a medicament as tyrosine kinase inhibitors. In other words, this invention also provides the composition comprising the above compound in an effective therapeutic dose, and the use of the compounds and/or pharmaceutical compositions containing them in the preparation of a medicament as tyrosine kinase inhibitors.

The following examples serve to illustrate the invention, but the examples should not be considered as limiting the scope of the invention.

EXAMPLES

The structures of the compounds were confirmed by nuclear magnetic resonance (NMR) or mass spectrometry (MS). NMR shifts (δ) were given in parts per million (ppm). NMR measurements were performed on a Bruker AVANCE-400, using deutorated chloroform ($CDCl_3$) and deutorated dimethylsulfoxide ($DMSO-D_6$) as solvents and Tetramethylsilane (TMS) as an internal reference, chemical shifts are given in parts per million (ppm).

MS measurements were performed on a FINNIGAN LCQAd (ESI) mass spectrometer.

The average of inhibitory rate of kinase VEGFR was determined by the HTScan (Cell Signaling).

The average of inhibitory rate of kinase EGFR/HER-2 was determined by the NovoStar (BMG LABTECH in Germany).

Thin-layer silica gel was Yantai Huanghai HSGF254 or Qingdao GF254 silica gel plates.

Column chromatography generally used Yantai Huanghai 200-300 mesh silica gel as carrier.

$DMSO-D_6$: deutorated dimethyl sulfoxide.

$CDCl_3$: deutorated chloroform.

PREPARATION EXAMPLES

Example 1

(Z)-5-(2-Diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one

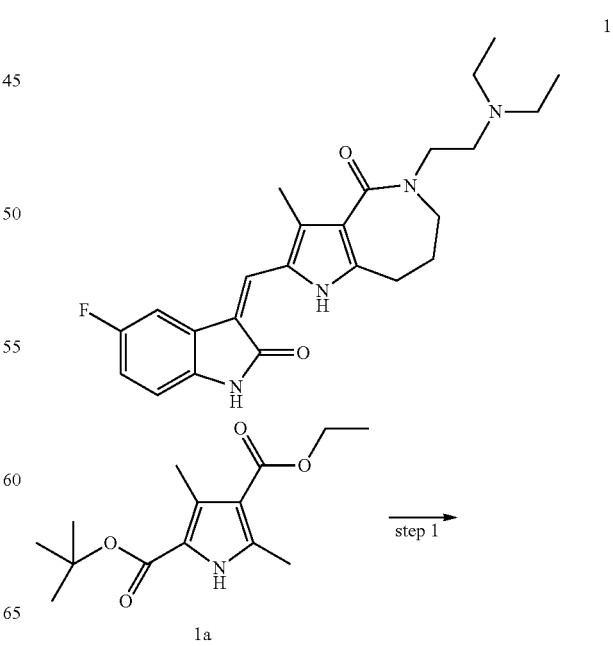

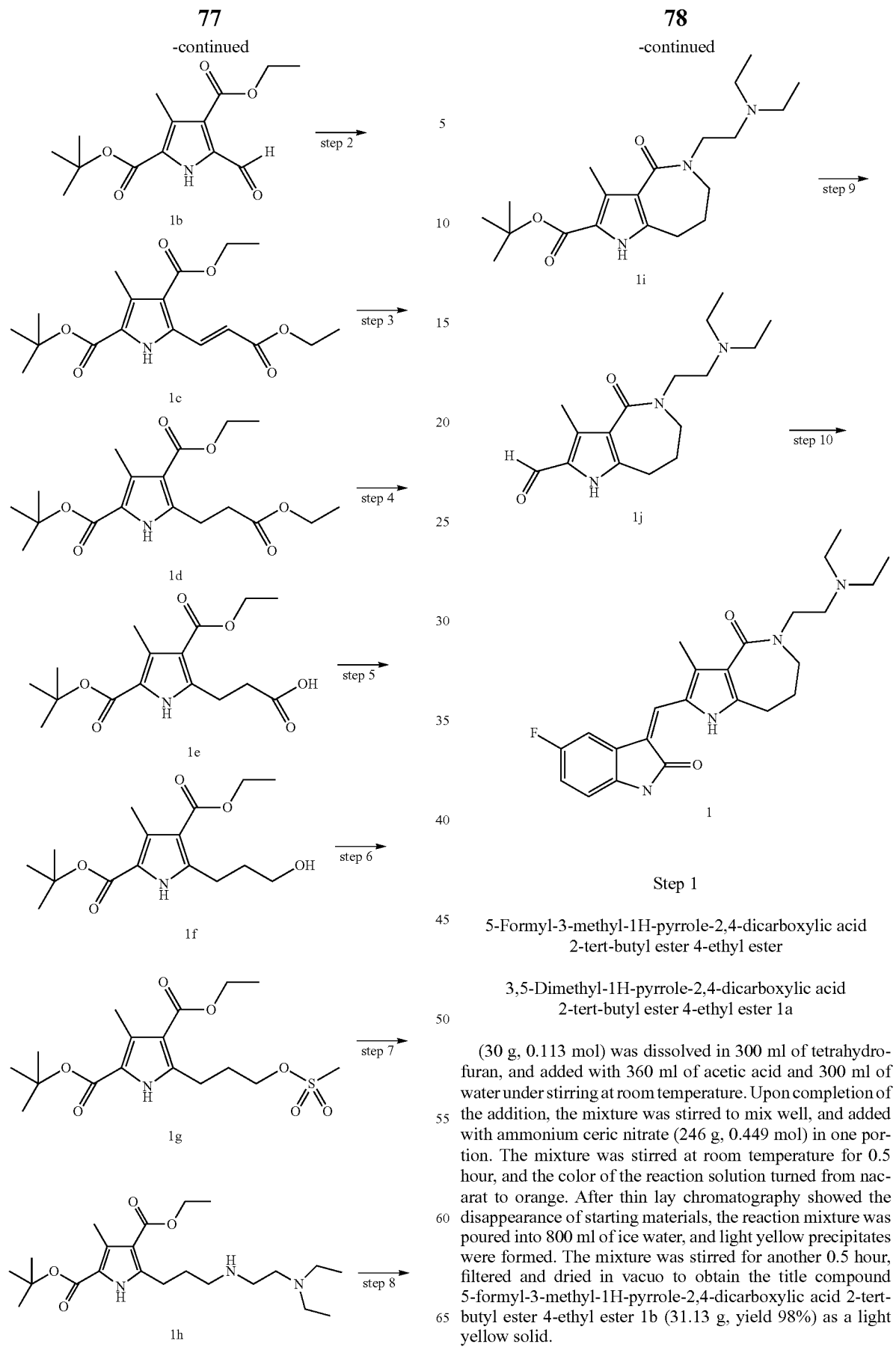

Step 1

5-Formyl-3-methyl-1H-pyrrole-2,4-dicarboxylic acid 2-tert-butyl ester 4-ethyl ester 3,5-Dimethyl-1H-pyrrole-2,4-dicarboxylic acid 2-tert-butyl ester 4-ethyl ester 1a (30 g, 0.113 mol) was dissolved in 300 ml of tetrahydrofuran, and added with 360 ml of acetic acid and 300 ml of water under stirring at room temperature. Upon completion of the addition, the mixture was stirred to mix well, and added with ammonium ceric nitrate (246 g, 0.449 mol) in one portion. The mixture was stirred at room temperature for 0.5 hour, and the color of the reaction solution turned from nacarat to orange. After thin lay chromatography showed the disappearance of starting materials, the reaction mixture was poured into 800 ml of ice water, and light yellow precipitates were formed. The mixture was stirred for another 0.5 hour, filtered and dried in vacuo to obtain the title compound 5-formyl-3-methyl-1H-pyrrole-2,4-dicarboxylic acid 2-tert-butyl ester 4-ethyl ester 1b (31.13 g, yield 98%) as a light yellow solid.

MS m/z (ESI): 282.0 [M+1]

Step 2

5-(2-Ethoxycarbonyl-vinyl)-3-methyl-1H-pyrrole-2,4-dicarboxylic acid 2-tert-butyl ester 4-ethyl ester 5-Formyl-3-methyl-1H-pyrrole-2,4-dicarboxylic acid 2-tert-butyl ester 4-ethyl ester 1 b (23 g, 81.7 mmol) and (ethoxycarbonylmethylene)triphenylphosphorane (34.66 g, 99.4 mmol) were dissolved in 450 ml of tetrahydrofuran, and stirred at room temperature overnight under an argon atmosphere. After thin lay chromatography showed the disappearance of starting materials, the reaction mixture was concentrated under reduced pressure to obtain a yellow oil. The residue was dissolved in the solvent mixture of n-hexane and ethyl acetate (V:V=20:1), and purified by sand funnel decompression column chromatography to obtain the title compound 5-(2-ethoxycarbonyl-vinyl)-3-methyl-1H-pyrrole-2,4-dicarboxylic acid 2-tert-butyl ester 4-ethyl ester 1c (24 g, yield 84%) as a light yellow solid.

MS m/z (ESI): 352.1 [M+1]

Step 3

5-(2-Ethoxycarbonyl-ethyl)-3-methyl-1H-pyrrole-2,4-dicarboxylic acid 2-tert-butyl ester 4-ethyl ester 5-(2-Ethoxycarbonyl-vinyl)-3-methyl-1H-pyrrole-2,4-dicarboxylic acid 2-tert-butyl ester 4-ethyl ester 1c (24 g, 68.3 mmol) was dissolved in anhydrous ethanol (180 ml) under stirring, and added with palladium on activated carbon (2.44 g, 10%) to the solution. The resulting solution was stirred at room temperature overnight under a hydrogen atmosphere. After thin lay chromatography showed the disappearance of starting materials, the reaction mixture was filtered to remove palladium on activated carbon, and washed with a little ethanol. The filtrate was concentrated under reduced pressure to obtain the title compound 5-(2-ethoxycarbonyl-ethyl)-3-methyl-1H-pyrrole-2,4-dicarboxylic acid 2-tert-butyl ester 4-ethyl ester 1d (23 g, yield 95%) as a white solid.

MS m/z (ESI): 354.40 [M+1]

Step 4

5-(2-Carboxy-ethyl)-3-methyl-1H-pyrrole-2,4-dicarboxylic acid 2-tert-butyl ester 4-ethyl ester 5-(2-Ethoxycarbonyl-ethyl)-3-methyl-1H-pyrrole-2,4-dicarboxylic acid 2-tert-butyl ester 4-ethyl ester 1d (23.6 g, 66.8 mmol) was dissolved in 190 ml of tetrahydrofuran and 90 ml of methanol under stirring, and added with aqueous lithium hydroxide solution (80 ml, 10 mol/L, 0.8 mol) at room temperature. The color of the reaction solution gradually turned from light yellow to cyan, and stirred for another 1 hour. After thin lay chromatography showed the disappearance of starting materials, the resulting mixture was concentrated under reduced pressure to evaporate organic solvent. The residue was adjusted pH to 2 with hydrochloric acid solution (2 mol/L) in an ice-water bath under stirring. White precipitates were formed. The mixture was filtered, and the filter cake was dried to obtain the title compound 5-(2-carboxy-ethyl)-3-methyl-1H-pyrrole-2,4-dicarboxylic acid 2-tert-butyl ester 4-ethyl ester 1e (24 g, yield 98%) as a white solid.

MS m/z (ESI): 326.1 [M+1]

Step 5

5-(3-Hydroxy-propyl)-3-methyl-1H-pyrrole-2,4-dicarboxylic acid 2-tert-butyl ester 4-ethyl ester 5-(2-Carboxy-ethyl)-3-methyl-1H-pyrrole-2,4-dicarboxylic acid 2-tert-butyl ester 4-ethyl ester 1e (9.75 g, 30 mmol) was dissolved in 90 ml of anhydrous tetrahydrofuran under stirring, and added dropwise slowly with a solution of borane in tetrahydrofuran (90 ml, 1 mol/L, 90 mmol) to the solution while maintaining the temperature at −10~−5° C. in an ice-salt bath under an argon atmosphere. Upon completion of the addition, the ice-salt bath was removed and the reaction mixture was allowed to warm up to room temperature and stirred for 2-3 hours. After thin lay chromatography showed the disappearance of starting materials, the reaction mixture was concentrated under reduced pressure to evaporate the solvent. The residue was added with 100 ml of saturated sodium bicarbonate solution and 100 ml of ethyl acetate, and stirred until dissolved. The resulting mixture was extracted with ethyl acetate (100 ml×3). The combined organic extracts were washed with 100 ml of saturated brine, dried over anhydrous magnesium sulfate, filtered to remove the drying agent and concentrated under reduced pressure to obtain the title compound 5-(3-hydroxy-propyl)-3-methyl-1H-pyrrole-2,4-dicarboxylic acid 2-tert-butyl ester 4-ethyl ester 1f (9.2 g, yield 98%) as a light yellow oil.

MS m/z (ESI): 312.3 [M+1]

Step 6

5-(3-Methanesulfonyloxy-propyl)-3-methyl-1H-pyrrole-2,4-dicarboxylic acid 2-tert-butyl ester 4-ethyl ester 5-(3-Hydroxy-propyl)-3-methyl-1H-pyrrole-2,4-dicarboxylic acid 2-tert-butyl ester 4-ethyl ester 1f (9.20 g, 30 mmol) was dissolved in 150 ml of dichloromethane under stirring, and added with triethylamine (7.0 ml, 50 mmol) to the solution while maintaining the temperature at about −10° C. in an ice-salt bath under an argon atmosphere. Upon completion of the addition, the mixture was added slowly with methanesulfonyl chloride (3.5 ml, 45 mmol). After stirring to mix well, the reaction system was allowed to warm up to room temperature and stirred for 4 hours. After thin lay chromatography showed the disappearance of starting materials, the reaction mixture was quenched with ice. The reaction mixture was washed successively with dilute hydrochloric acid (0.5 mol/L, 80 ml×2) to remove triethylamine, saturated sodium carbonate solution (80 ml×2) to remove excess hydrochloric acid and saturated brine (80 ml), and concentrated under reduced pressure to obtain the title compound 5-(3-methanesulfonyloxy-propyl)-3-methyl-1H-pyrrole-2,4-dicarboxylic acid 2-tert-butyl ester 4-ethyl ester 1 g (11.4 g, yield 99%) as a brown oil.

MS m/z (ESI): 390.5 [M+1]

Step 7

5-[3-(2-Diethylamino-ethylamino)-propyl]-3-methyl-1H-pyrrole-2,4-dicarboxylic acid 2-tert-butyl ester 4-ethyl ester 5-(3-Methanesulfonyloxy-propyl)-3-methyl-1H-pyrrole-2,4-dicarboxylic acid 2-tert-butyl ester 4-ethyl ester 1 g (8.24 g, 21 mmol) was dissolved in N,N-diethylethylenediamine (15 ml, 100 mmol) under stirring at room temperature, and stirred overnight. After thin lay chromatography showed the disappearance of starting materials, the reaction mixture was added with 100 ml of ethyl acetate and 100 ml of saturated brine, stirred for 5 minutes, and separated into layers. The organic phase was washed with saturated brine (100 ml×4), dried over anhydrous magnesium sulfate, filtered to remove the drying agent and concentrated under reduced pressure to obtain brown oil. The residue was purified by silica gel column chromatography to obtain the title compound 5-[3-(2-diethylamino-ethylamino)-propyl]-3-methyl-1H-pyrrole-2,4-dicarboxylic acid 2-tert-butyl ester 4-ethyl ester 1 h (8.2 g, yield 95%) as a colorless oil.

MS m/z (ESI): 410.2 [M+1]

Step 8

5-(2-Diethylamino-ethyl)-3-methyl-4-oxo-1,4,5,6,7,8-hexahydro-pyrrolo[3,2-c]azepine-2-carboxylic acid tert-butyl ester 5-[3-(2-Diethylamino-ethylamino)-propyl]-3-methyl-1H-pyrrole-2,4-dicarboxylic acid 2-tert-butyl ester 4-ethyl ester 1 h (3.547 g, 8.67 mmol) was dissolved in 70 ml of toluene and stirred for 10 minutes at room temperature under an argon atmosphere. The mixture was added with a solution of trimethyl aluminum in toluene (5.6 ml, 2 mol/L, 11.27 mmol), and stirred for another 30 minutes at room temperature until no white smoke was released. The reaction mixture was heated to reflux for 4 hours in an oil bath. After thin lay chromatography showed the disappearance of starting materials, the reaction mixture was naturally cooled down to room temperature, quenched with ethanol (10 ml, 95%), and added with anhydrous ethanol (60 ml). The resulting mixture was filtered through a pad of Celite, washed with anhydrous ethanol (200 ml×4) and concentrated under reduced pressure. The residue was purified by silica gel column chromatography to obtain the title compound 5-(2-diethylamino-ethyl)-3-methyl-4-oxo-1,4,5,6,7,8-hexahydro-pyrrolo[3,2-c]azepine-2-carboxylic acid tert-butyl ester 1i (0.413 g, yield 75.7%) as a white solid.

MS m/z (ESI): 364.1 [M+1]

Step 9

5-(2-Diethylamino-ethyl)-3-methyl-4-oxo-1,4,5,6,7,8-hexahydro-pyrrolo[3,2-c]azepine-2-carbaldehyde 5-(2-Diethylamino-ethyl)-3-methyl-4-oxo-1,4,5,6,7,8-hexahydro-pyrrolo[3,2-c]azepine-2-carboxylic acid tert-butyl ester 1i (0.413 g, 1.14 mmol) was dissolved in trifluoroacetic acid (1.5 ml, 20 mmol) under stirring, heated to 40° C. for 5 minutes in an oil bath under an argon atmosphere, and cooled down to −5° C. in an ice-salt bath under stirring, and added with triethoxy methane (0.34 ml, 1.7 mmol) and stirred for 2 minutes. Then the ice-salt bath was removed, and the reaction mixture was allowed to warm up to room temperature and stirred for another about 2 hours. After thin lay chromatography showed the disappearance of starting materials, the reaction mixture was added with 3 ml of ice water and 10 ml of dichloromethane, adjusted to pH 11 with aqueous sodium hydroxide solution (2 mol/L) and extracted with dichloromethane (10 ml×3). The combined organic extracts were dried over anhydrous magnesium sulfate, filtered to remove the drying agent and concentrated under reduced pressure to obtain yellow oil. The residue was purified by silica gel column chromatography to obtain the title compound 5-(2-diethylamino-ethyl)-3-methyl-4-oxo-1,4,5,6,7,8-hexahydro-pyrrolo[3,2-c]azepine-2-carbaldehyde 1j (0.271 g, yield 55%) as a light brown oil.

MS m/z (ESI): 292.3 [M+1]

Step 10

(Z)-5-(2-Diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one 5-(2-Diethylamino-ethyl)-3-methyl-4-oxo-1,4,5,6,7,8-hexahydro-pyrrolo[3,2-c]azepine-2-carbaldehyde 1j (0.271 g, 0.93 mmol) and 5-fluoro-1,3-dihydro-indol-2-one (0.127 g, 0.84 mmol) were dissolved in 1.4 ml of anhydrous ethanol under stirring at room temperature, the resulting mixture was stirred for 10 minutes in dark, and added with piperidine (0.15 ml, 1.49 mmol). The mixture was refluxed at 70° C. for about 1.5 hours in an oil bath under an argon atmosphere and lots of orange precipitates were formed. After thin lay chromatography showed the disappearance of starting materials, the ice-salt bath was removed, and the reaction mixture was naturally cooled to room temperature, filtered and dried to obtain the title compound (Z)-5-(2-diethylamino-ethyl)-2-(5-fluoro-2-oxo-1,2-dihydro-indol-3-ylidenemethyl)-3-methyl-3 a,5,6,7,8,8a-hexahydro-1H-pyrrolo[3,2-c]azepin-4-one 1 (0.288 g, yield 80.76%) as an orange solid.

MS m/z (ESI): 425.3 [M+1]

$^1$HNMR (400 MHz, DMSO-d6) δ13.710 (s, 1H, pyrrole-NH), 10.903 (s, 1H, indole-NH), 7.753~7.782 (dd, 1H, —ArH), 7.744 (s, 1H, —CH═C), 6.914~6.965 (m, 1H, ArH), 6.834~6.867 (m, 1H, —ArH), 3.483~3.518 (t, 2H, seven-membered ring intra-$CH_2N$), 3.336~3.364 (t, 2H, amide N seven-membered ring outer-$CH_2$), 2.907~2.944 (t, 2H, seven-membered ring intra-$CH_2C$═C), 2.529~2.581 (m, 6H, 3×—$CH_2N$), 2.455 (s, 3H, pyrrole-$CH_3$), 2.040~2.079 (m, 2H, seven-membered ring intra —$CH_2$), 0.956~0.992 (t, 6H, 2×—$CH_3$).

Example 2

(Z)-2-(5-Chloro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one

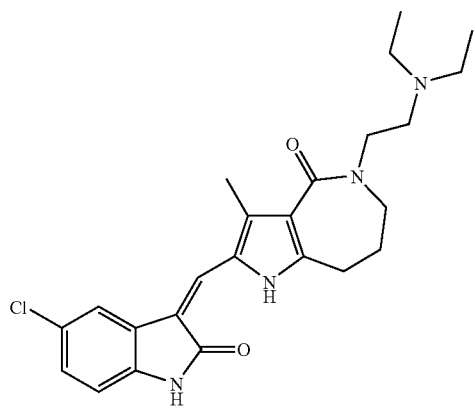

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 5-chloro-1,3-dihydro-indol-2-one as starting materials to obtain (Z)-2-(5-chloro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one 2 (27 mg, yield 60.0%) as a nacarat solid.

MS m/z (ESI): 441.1 [M+1]

$^1$HNMR (400 MHz, DMSO-d6) δ13.663 (s, 1H, pyrrole-NH), 11.002 (s, 1H, indole-NH), 7.987~7.991 (d, 1H, —ArH), 7.798 (s, 1H, —CH=C), 7.132~7.158 (dd, 1H, —ArH), 6.867~6.888 (d, 1H, —ArH), 3.483~3.518 (t, 2H, seven-membered ring intra-CH$_2$N), 3.336~3.364 (t, 2H, amide N seven-membered ring outer-CH$_2$), 2.907~2.944 (t, 2H, seven-membered ring intra-CH$_2$C=C), 2.529~2.581 (m, 6H, 3×—CH$_2$N), 2.455 (s, 3H, pyrrole-CH$_3$), 2.040~2.079 (m, 2H, seven-membered ring intra-CH$_2$), 0.956~0.992 (t, 6H, 2×—CH$_3$).

Example 3

(Z)-5-(2-Diethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin

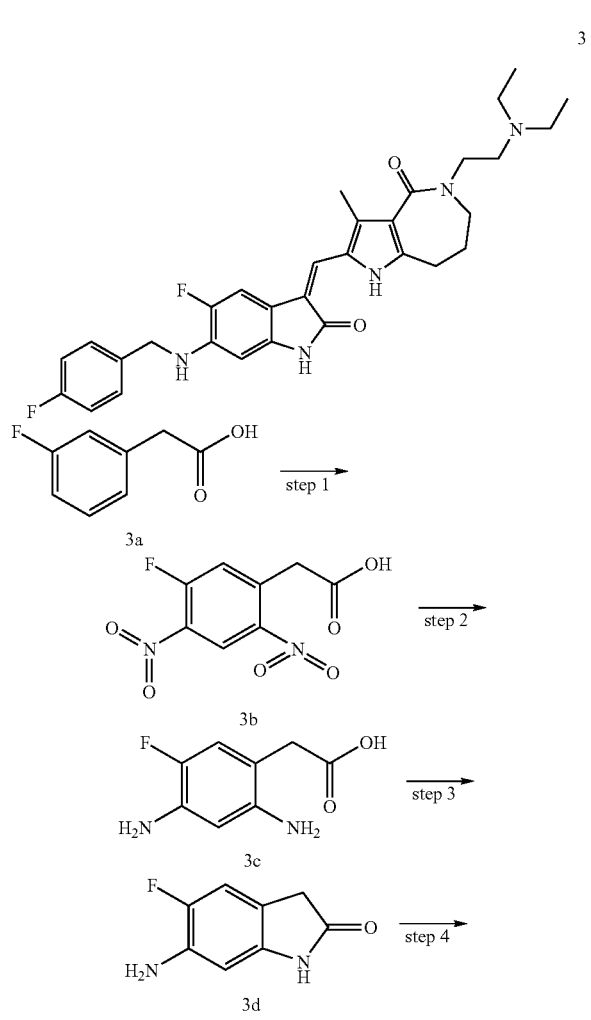

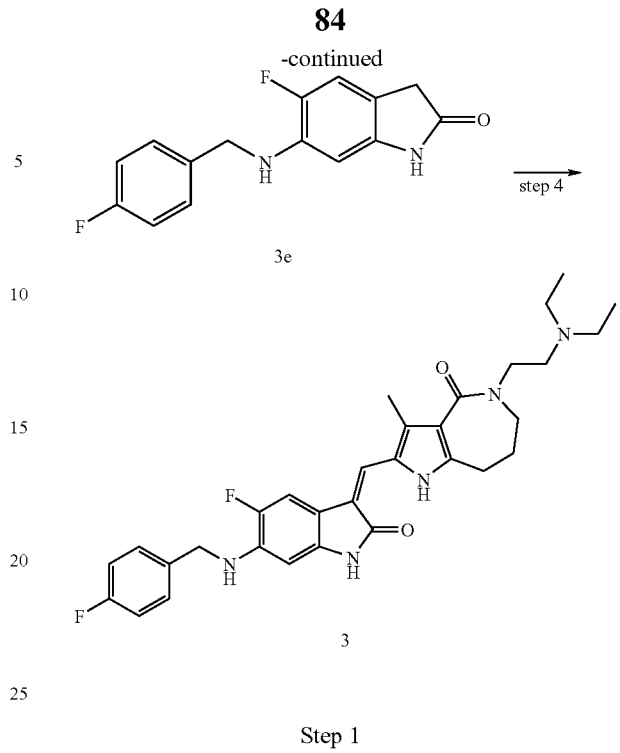

Step 1

(5-Fluoro-2,4-dinitro-phenyl)-acetic acid (3-Fluoro-phenyl)-acetic acid 3a (31.5 g, 0.204 mol) was dissolved in sulfuric acid (64 ml, 98%) under stirring at room temperature, and added dropwise with the mixture (V:V=1:1, 100 ml) of nitric acid (65%-68%) and sulfuric acid (98%) while maintaining the temperature at about 35° C. Upon completion of the addition, the mixture was stirred at 35° C. After thin lay chromatography showed the disappearance of starting materials, the reaction mixture was added with ice and filtered after ice-out to obtain the title compound (5-fluoro-2,4-dinitro-phenyl)-acetic acid 3b (49 mg) as a light yellow oil.

MS m/z (ESI): 243.5 [M−1]

Step 2

(2,4-Diamino-5-fluoro-phenyl)-acetic acid (5-Fluoro-2,4-dinitro-phenyl)-acetic acid 3b (10 g, 38.7 mmol) was dissolved in 150 ml of methanol under stirring, and added with palladium on activated carbon (1.5 g, 5%) to the solution at room temperature. The reaction mixture was hydrogenated under 0.3 Mpa of hydrogen. After thin lay chromatography showed the disappearance of starting materials, the reaction mixture was filtered twice, and concentrated under reduced pressure to obtain the title compound (2,4-diamino-5-fluoro-phenyl)-acetic acid 3c (7.12 g) as a brown solid to the next step.

Step 3

5-Fluoro-6-amino-indol-2-one (2,4-Diamino-5-fluoro-phenyl)-acetic acid 3c (7.12 g, 38.7 mmol) was dissolved in hydrochloric acid (100 ml, 1 mol/L) under stirring at room temperature. The solution was heated to reflux for 1 hour. After thin lay chromatography showed the disappearance of starting materials, the reaction mixture was cooled down to room temperature, neutralized with sodium hydroxide solution (100 ml, 1 mol/L) in an ice-water bath, extracted with ethyl acetate (125 ml×4). The combined organic extracts were washed with saturated brine (100 ml), dried over anhydrous magnesium sulfate, filtered to remove the drying agent and concentrated under reduced pressure to obtain the title compound 5-fluoro-6-amino-indol-2-one 3d (5.3 g, yield 82.8%) as a yellow solid.

MS m/z (ESI): 165.3 [M−1]

Step 4

5-Fluoro-6-(4-fluoro-benzylamino)-1,3-dihydro-indol-2-one

6-Amino-5-fluoro-1,3-dihydro-indol-2-one 3d (2.26 g, 13.6 mmol) was dissolved in 40 ml of ethanol under stirring at room temperature, the resulting solution was cooled down to 0° C. in an ice-water bath, and added with 4-fluoro-benzaldehyde (1.5 ml, 13.6 mmol) to the solution. Upon completion of the addition, the resulting solution was stirred for 1 hour at room temperature, added with sodium borohydride (1.08 g, 28.5 mmol) and heated to reflux for 18 hours. After thin lay chromatography showed the disappearance of starting materials, the reaction mixture was naturally cooled down to room temperature, added with ice water and lots of precipitates were formed, filtered and washed with water (50 ml×3). The residue was purified by silica gel column chromatography to obtain the title compound 5-fluoro-6-(4-fluoro-benzylamino)-1,3-dihydro-indol-2-one 3e (1.67 g, yield 45%) as a white solid.

MS m/z (ESI): 275 [M+1]

Step 5

(Z)-5-(2-Diethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 5-fluoro-6-(4-fluoro-benzylamino)-1,3-dihydro-indol-2-one 3e as starting materials to obtain (Z)-5-(2-diethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one 3 (61 mg, yield 62.2%) as a henna solid.

MS m/z (ESI): 548.3 [M+1]

$^1$HNMR (400 MHz, DMSO-d6) δ13.416 (s, 1H, pyrrole-NH), 10.520 (s, 1H, indole-NH), 7.573~7.602 (d, 1H, —ArH), 7.366~7.401 (m, 2H, —ArH), 7.350 (s, 1H, —CH═C), 7.141~7.185 (m, 2H, —ArH), 6.410~6.415 (m, 1H, —ArH), 6.038~6.057 (d, 1H, —ArH), 4.346~4.361 (d, 2H, aniline-CH$_2$), 3.466~3.501 (t, 2H, seven-membered ring intra-CH$_2$N), 3.336~3.364 (t, 2H, amide N seven-membered ring outer-CH$_2$), 2.907~2.944 (t, 2H, seven-membered ring intra-CH$_2$C═C), 2.529~2.581 (m, 6H, 3×—CH$_2$N), 2.388 (s, 3H, pyrrole-CH$_3$), 2.011~2.039 (m, 2H, seven-membered ring intra-CH$_2$), 0.967~1.063 (t, 6H, 2×—CH$_3$).

Example 4

(Z)-2-(7-Bromo-5-fluoro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one Step 1

7-Bromo-5-fluoro-1,3-dihydro-indol-2-one

5-Fluoro-1,3-dihydro-indol-2-one 4a (1.5 g, 0.01 mol) was dissolved in 15 ml of acetonitrile under stirring, and added dropwise with N-bromosuccinimide (1.8 g, 0.01 mol) at room temperature. Upon completion of the addition, the mixture was stirred overnight and lots of precipitate was formed. After thin lay chromatography showed the disappearance of starting materials, the reaction mixture was filtered to obtain 7-bromo-5-fluoro-1,3-dihydro-indol-2-one 4b (2 g, yield 87%) as a gray solid.

MS m/z (ESI): 228.3 [M−1]

Step 2

(Z)-2-(7-Bromo-5-fluoro-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 7-bromo-5-fluoro-1,3-dihydro-indol-2-one 4b as starting materials to obtain (Z)-2-(7-bromo-5-fluoro-2-oxo-1,2-dihydro-indol-3-ylidenemethyl)-5-(2-diethylamino-ethyl)-3-m ethyl-5,6,7,8-tetrahydro-1H-pyrrolo[3,2-c]azepin-4-one 4 (55 mg, yield 61.1%) as a yellow solid.

MS m/z (ESI): 503.6 [M+1]
$^1$HNMR (400 MHz, DMSO-d6) δ13.653 (s, 1H, pyrrole-NH), 11.181 (s, 1H, indole-NH), 7.848~7.876 (dd, 1H, —ArH), 7.794 (s, 1H, —CH═C), 7.242~7.270 (dd, 1H, —ArH), 3.485~3.520 (t, 2H, seven-membered ring intra-CH$_2$N), 3.338~3.366 (t, 2H, amide N seven-membered ring outer-CH$_2$), 2.932~2.969 (t, 2H, seven-membered ring intra-CH$_2$C═C), 2.527~2.582 (m, 6H, 3×—CH$_2$N), 2.470 (s, 3H, pyrrole-CH$_3$), 2.031~2.093 (m, 2H, seven-membered ring intra-CH$_2$), 0.954~0.990 (t, 6H, 2×—CH$_3$).

Example 5

(Z)-2-(5-Bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one

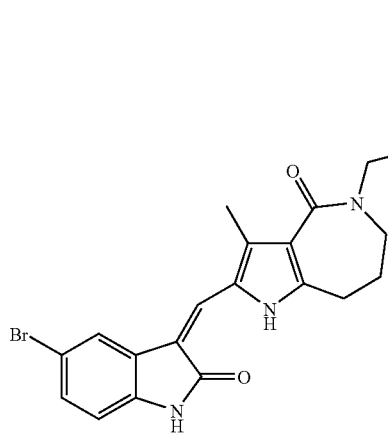

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 5-bromo-1,3-dihydro-indol-2-one as starting materials to obtain (Z)-2-(5-bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one 5 (59 mg, yield 67.8%) as a yellow solid.

MS m/z (ESI): 485.5 [M+1]
$^1$HNMR (400 MHz, DMSO-d6) δ13.660 (s, 1H, pyrrole-NH), 11.008 (s, 1H, indole-NH), 8.113~8.117 (d, 1H, —ArH), 7.803 (s, 1H, —CH═C), 7.260~7.286 (dd, 1H, —ArH), 6.825~6.845 (d, 1H, —ArH), 3.482~3.516 (t, 2H, seven-membered ring intra-CH$_2$N), 3.336~3.364 (t, 2H, amide N seven-membered ring outer-CH$_2$), 2.907~2.944 (t, 2H, seven-membered ring intra-CH$_2$C═C), 2.490~2.578 (m, 6H, 3×—CH$_2$N), 2.464 (s, 3H, pyrrole-CH$_3$), 2.039~2.067 (m, 2H, seven-membered ring intra-CH$_2$), 0.954~0.990 (t, 6H, 2×—CH$_3$).

Example 6

(Z)-5-(2-Diethylamino-ethyl)-2-[4-(2,3-difluorophenyl)-2-oxo-1,2-dihydro-indol-3-ylidenemethyl]-3-methyl-5,6,7,8-tetrahydro-1H-pyrrolo[3,2-c]azepin-4-one

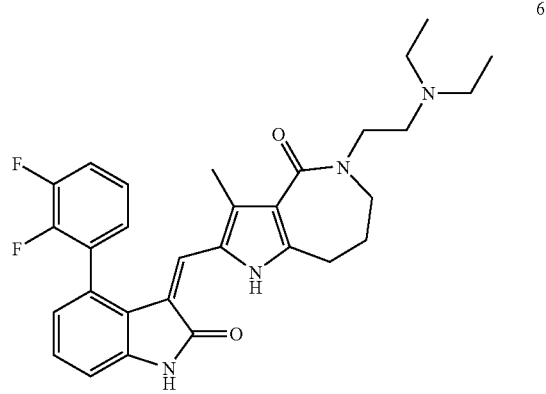

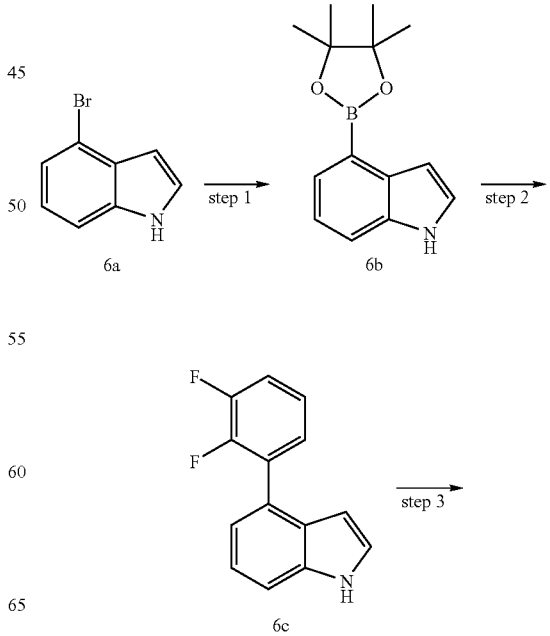

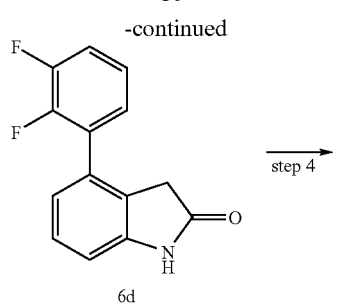

6d

Step 1

4-(4,4,5,5-Tetramethyl-[1,3,2]dioxaborolan-2-yl)-1H-indole

4-Bromo-1H-indole 6a (29.4 g, 150 mmol) was dissolved in 600 ml of dimethyl sulfoxide under stirring, and added successively with bis(pinacolato)diboron (41.9 g, 165 mmol), potassium acetate (44.1 g, 450 mmol) and [1,1'-bis(diphenylphosphino)ferrocene]dichloropalladium (3.6 g, 4.8 mmol) under an argon atmosphere. Upon completion of the addition, the reaction mixture was stirred at 80° C. in an oil bath for 22 hours. After thin lay chromatography showed the disappearance of starting materials, the reaction mixture was added with water (2 L) and extracted with ethyl acetate (2 L×3). The combined organic extracts were washed with saturated brine (2 L×5), dried over anhydrous sodium sulfate, filtered to remove the drying agent and concentrated under reduced pressure. The residue was purified by silica gel column chromatography and recrystallized to obtain 4-(4,4,5,5-tetramethyl-[1,3,2]dioxaborolan-2-yl)-1H-indole 6b (20 g, yield 60%) as a white solid.

MS m/z (ESI): 243.9 [M+1]

Step 2

4-(2,3-Difluoro-phenyl)-1H-indole 4-(4,4,5,5-Tetramethyl-[1,3,2]dioxaborolan-2-yl)-1H-indole 6b (1.22 g, 5 mmol) was dissolved in 20 ml of tetrahydrofuran under stirring, and added with 1-bromo-2,3-difluoro-benzene (0.97 g, 5 mmol), tetrakis(triphenylphosphine)palladium (0.17 g, 0.15 mmol) and sodium hydroxide solution (7 ml, 2 mol/L) under an argon atmosphere. Upon completion of the addition, the reaction system was stirred at 75° C. in an oil bath overnight. After thin lay chromatography showed the disappearance of starting materials, the reaction mixture was naturally cooled down to room temperature and extracted with ethyl acetate (20 ml×3). The combined organic extracts were washed with saturated brine (10 ml), dried over anhydrous sodium sulfate, filtered to remove the drying agent and concentrated under reduced pressure. The residue was purified by silica gel column chromatography to obtain 4-(2,3-difluoro-phenyl)-1H-indole 6c (800 mg, yield 70%) as a white solid.

MS m/z (ESI): 228.4 [M−1]

Step 3

4-(2,3-Difluoro-phenyl)-1,3-dihydro-indol-2-one 4-(2,3-difluoro-phenyl)-1H-indole 6c (744 mg, 3.25 mmol) was dissolved in 12 ml of ethanol under stirring, and added successively with tert-butanol (21 ml), glacial acetic acid (6.4 ml) and pyridinium tribromide (3.12 g, 9.7 mmol) at room temperature. Upon completion of the addition, the reaction mixture was stirred for 3 hours, added with glacial acetic acid (16 ml) and zinc dust (1.1 g, 16.25 mmol), and stirred for another 1 hour. The reaction mixture was filtered and concentrated under reduced pressure. The residue was added with ethyl acetate (30 ml), washed successively with water (10 ml), saturated sodium bicarbonate solution (10 ml) and saturated brine (10 ml), dried over anhydrous sodium sulfate, filtered to remove the drying agent and concentrated under reduced pressure to obtain 4-(2,3-difluoro-phenyl)-1,3-dihydro-indol-2-one 6d (780 mg, yield 97%) as a white solid.

MS m/z (ESI): 246.6 [M+1]

Step 4

(Z)-5-(2-Diethylamino-ethyl)-2-[4-(2,3-difluoro-phenyl)-2-oxo-1,2-dihydro-indol-3-ylidenemethyl]-3-methyl-5,6,7,8-tetrahydro-1H-pyrrolo[3,2-c]azepin-4-one The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 4-(2,3-difluoro-phenyl)-1,3-dihydro-indol-2-one 6d as starting materials to obtain (Z)-5-(2-diethylamino-ethyl)-2-[4-(2,3-difluoro-phenyl)-2-oxo-1,2-dihydro-indol-3-ylidenemethyl]-3-methyl-5,6,7,8-tetrahydro-1H-pyrrolo[3,2-c]azepin-4-one 6 (43 mg, yield 61.4%) as a yellow solid.

MS m/z (ESI): 519.6 [M+1]

¹HNMR (400 MHz, DMSO-d6) δ13.531 (s, 1H, pyrrole-NH), 11.133 (s, 1H, indole-NH), 7.617~7.640 (m, 1H, —ArH), 7.429~7.442 (m, 1H, —ArH), 7.305~7.340 (m, 1H, —ArH), 7.232~7.270 (m, 1H, —ArH), 6.997~7.017 (d, 1H, —ArH), 6.874~6.893 (d, 1H, —ArH), 6.710 (s, 1H, —CH=C), 3.445~3.478 (t, 2H, seven-membered ring intra-$CH_2N$), 3.313 (m, 2H, amide N seven-membered ring outer-$CH_2$), 2.868~3.904 (t, 2H, seven-membered ring intra-$CH_2C$=C), 2.465~2.542 (m, 6H, 3×—$CH_2N$), 2.002~2.032

(m, 2H, seven-membered ring intra-CH$_2$), 1.794 (s, 3H, pyrrole-CH$_3$), 0.930~0.965 (t, 6H, 2×—CH$_3$).

Example 7

(Z)—N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide

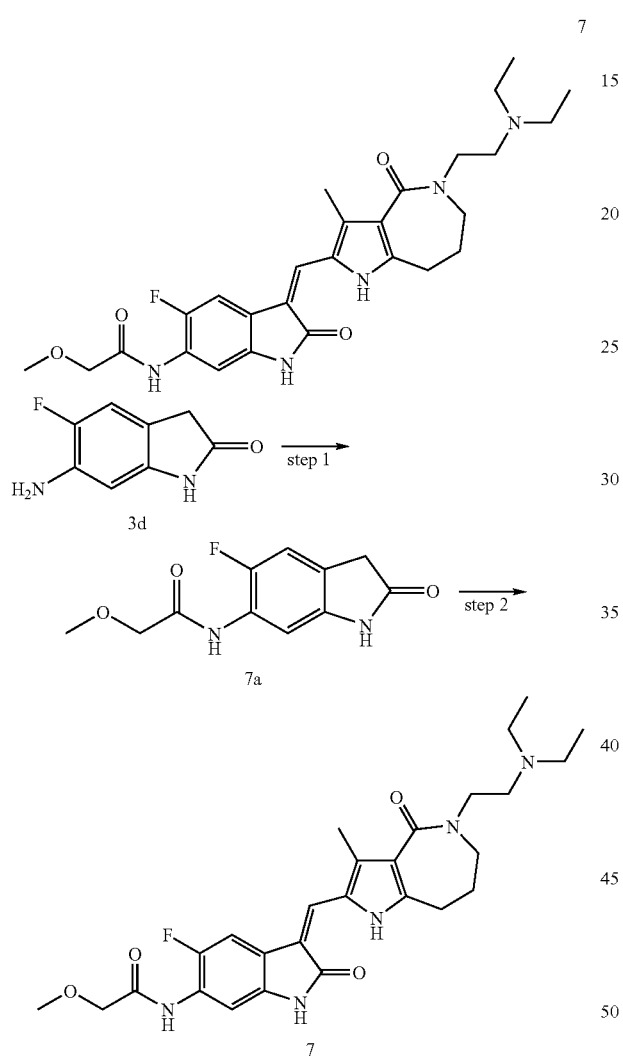

Step 1

N-(5-Fluoro-2-oxo-2,3-dihydro-1H-indol-6-yl)-2-methoxy-acetamide

6-Amino-5-fluoro-1,3-dihydro-indol-2-one 3d (2.028 g, 12.2 mmol) was dissolved in 30 ml of tetrahydrofuran under stirring, and added with 1.3 ml of pyridine to the solution at room temperature. The reaction system was cooled down to about −50° C. in a dry ice-ethanol bath. A solution of methoxy-acetyl chloride (1.35 g, 12.5 mmol) in tetrahydrofuran (20 ml) was added dropwise to the above reaction system. Upon completion of the addition, the ice-ethanol bath was removed, and the reaction mixture was allowed to warm up to room temperature and stirred overnight. After thin lay chromatography showed the disappearance of starting materials, the reaction mixture was filtered. The resulting solid was washed with water (10 mL×3) and recrystallized with methanol to obtain N-(5-fluoro-2-oxo-2,3-dihydro-1H-indol-6-yl)-2-methoxy-acetamide 7a (1.18 mg, yield 40.6%) as a gray solid.

MS m/z (ESI): 239.3 [M+1]

Step 2

(Z)-N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and N-(5-fluoro-2-oxo-2,3-dihydro-1H-indol-6-yl)-2-methoxy-acetamide 7a as starting materials to obtain (Z)—N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide 7 (37 mg, yield 53.6%) as a brown solid.

MS m/z (ESI): 512.5 [M+1]

$^1$HNMR (400 MHz, DMSO-d6) δ13.605 (s, 1H, pyrrole-NH), 10.893 (s, 1H, indole-NH), 9.320 (s, 1H, amide-NH), 7.838~7.866 (d, 1H, —ArH), 7.350 (s, 1H, —CH═C), 7.540~7.556 (d, 1H, —ArH), 4.064 (s, 2H, —CH$_2$O), 3.483~3.517 (t, 2H, seven-membered ring intra-CH$_2$N), 3.336~3.362 (t, 2H, amide N seven-membered ring outer-CH$_2$), 3.314 (s, 3H, —CH$_3$O), 2.902~2.939 (t, 2H, seven-membered ring intra-CH$_2$C═C), 2.530~2.562 (m, 6H, 3×—CH$_2$N), 2.444 (s, 3H, pyrrole-CH$_3$), 2.037~2.066 (m, 2H, seven-membered ring intra-CH$_2$), 0.958~0.993 (t, 6H, 2×—CH$_3$).

Example 8

(S,Z)—N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-propionamide

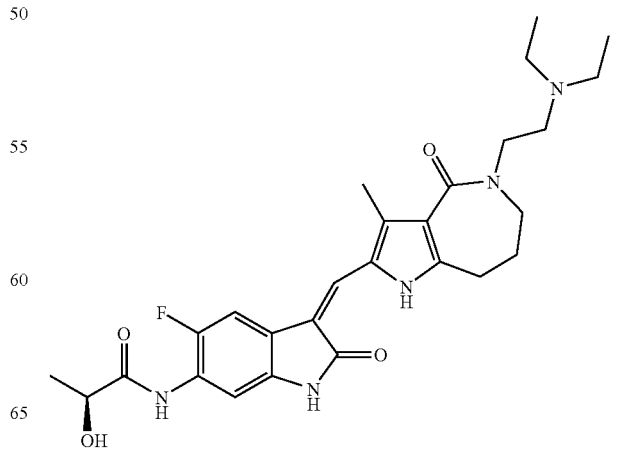

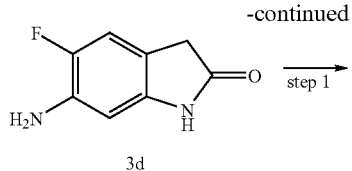

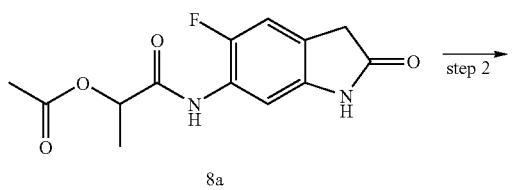

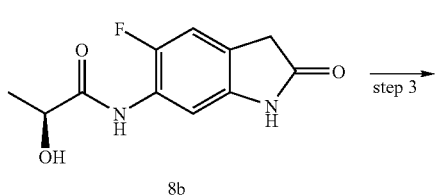

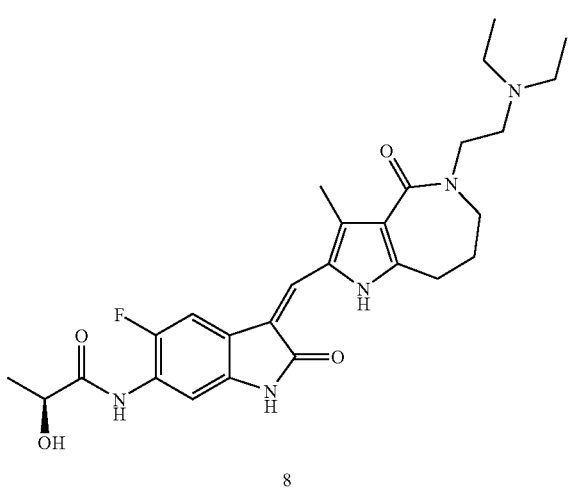

Step 1

Acetic acid 1-(5-fluoro-2-oxo-2,3-dihydro-1H-indol-6-ylcarbamoyl)-ethyl ester

5-Fluoro-6-amino-1,3-dihydro-indol-2-one 3d (450 mg, 2.71 mmol) was dissolved in 10 ml of tetrahydrofuran under stirring at room temperature. The mixture was cooled down to −45° C. in a dry ice-acetone bath and added with 364 μl of piperidine. A solution of acetic acid 1-chlorocarbonyl-ethyl ester (423 mg, 2.71 mmol) in 10 ml of tetrahydrofuran was added dropwise to the above reaction system. Upon completion of the addition, the ice-acetone bath was removed, and the reaction mixture was allowed to warm up to room temperature and stirred overnight. After thin lay chromatography showed the disappearance of starting materials, the reaction mixture was filtered. The filter cake was washed with water, and the resulting solid was dried to obtain the title compound acetic acid 1-(5-fluoro-2-oxo-2,3-dihydro-1H-indol-6-ylcarbamoyl)-ethyl ester 8a (840 mg) as a white solid to be used directly in the next step.

MS m/z (ESI): 281.5 [M+1]

Step 2

N-(5-Fluoro-2-oxo-2,3-dihydro-1H-indol-6-yl)-2-hydroxy-propionamide

Acetic acid 1-(5-fluoro-2-oxo-2,3-dihydro-1H-indol-6-ylcarbamoyl)-ethyl ester 8a (1.86 g, 6.4 mmol) was dissolved in 20 ml of methanol under stirring, and added with 10 ml of water and sodium hydroxide solution (10 ml, 0.7 mol/L) to the solution and stirred for 4 hours at room temperature. After thin lay chromatography showed the disappearance of starting materials, the reaction mixture was neutralized with hydrochloride acid (1 mol/L) and concentrated under reduced pressure. The residue was purified by silica gel column chromatography and dried to obtain N-(5-fluoro-2-oxo-2,3-dihydro-1H-indol-6-yl)-2-hydroxy-propionamide 8b (1.0 g, yield 70%) as a white solid.

MS m/z (ESI): 239.6 [M+1]

Step 3

(S,Z)—N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-propionamide The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and N-(5-fluoro-2-oxo-2,3-dihydro-1H-indol-6-yl)-2-hydroxy-propionamide 8b as starting materials to obtain (S,Z)—N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-propionamide 8 (28 mg, yield 40.8%) as a yellow solid.

MS m/z (ESI): 512.4 [M+1]

$^1$HNMR (400 MHz, DMSO-d6) δ13.594 (s, 1H, pyrrole-NH), 10.902 (s, 1H, indole-NH), 9.245 (s, 1H, amide-NH), 7.856~7.884 (d, 1H, —ArH), 7.725~7.741 (d, 1H, —ArH), 7.663 (s, 1H, —CH=C), 6.057~6.070 (d, 1H, —ArH), 4.206~4.236 (q, 1H, —CHO), 3.480~3.514 (t, 2H, seven-membered ring intra-CH$_2$N), 3.336~3.362 (t, 2H, amide N seven-membered ring outer-CH$_2$), 2.902~2.939 (t, 2H, seven-membered ring intra-CH$_2$C=C), 2.530~2.562 (m, 6H, 3×—CH$_2$N), 2.443 (s, 3H, pyrrole-CH$_3$), 2.037~2.066 (m, 2H, seven-membered ring intra-CH$_2$), 1.328~1.345 (d, 3H, —CH$_3$), 0.958~0.993 (t, 6H, 2×—CH$_3$).

Example 9

(Z)—N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-2-methyl-propionamide

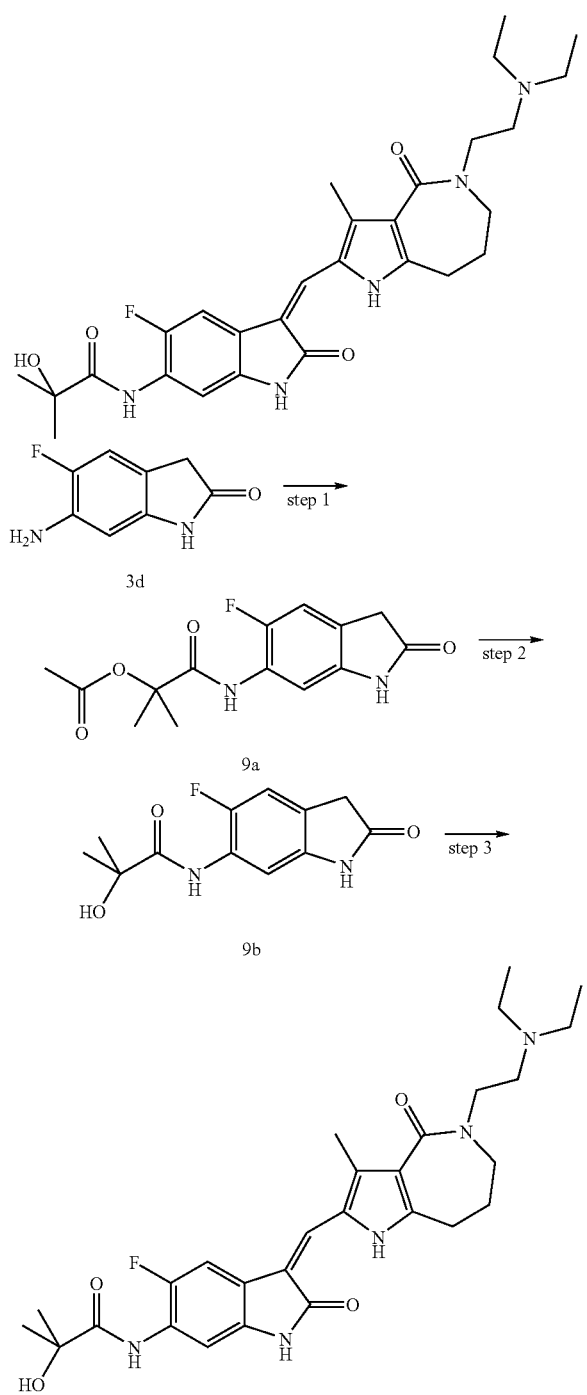

Step 1

Acetic acid 1-(5-fluoro-2-oxo-2,3-dihydro-1H-indol-6-ylcarbamoyl)-1-methyl-ethyl ester 5-Fluoro-6-amino-1,3-dihydro-indol-2-one 3d (410 mg, 2.47 mmol) was dissolved in 10 ml of tetrahydrofuran under stirring at room temperature. The mixture was cooled down to −45° C. in a dry ice-acetone bath and added with piperidine (322 μl). A solution of acetic acid 1-chlorocarbonyl-1-methyl-ethyl ester (423 mg, 2.71 mmol) in tetrahydrofuran (10 ml) was added dropwise to the above reaction system. Upon completion of the addition, the ice-acetone bath was removed, and the reaction mixture was allowed to warm up to room temperature and stirred overnight. After thin lay chromatography showed the disappearance of starting materials, the reaction mixture was filtered. The filter cake was washed with water, and the resulting solid was dried to obtain acetic acid 1-(5-fluoro-2-oxo-2,3-dihydro-1H-indol-6-ylcarbamoyl)-1-methyl-ethyl ester 9a (792 mg) as a white solid to the next step.

MS m/z (ESI): 293.7 [M−1]

Step 2

N-(5-Fluoro-2-oxo-2,3-dihydro-1H-indol-6-yl)-2-hydroxy-2-methyl-propionamide

Acetic acid 1-(5-fluoro-2-oxo-2,3-dihydro-1H-indol-6-ylcarbamoyl)-ethyl ester 9a (2.035 g, 6.9 mmol) was dissolved in 20 ml of methanol under stirring, added with sodium hydroxide solution (20 ml, 0.7 mol/L) (20 ml) to the solution and stirred for 4 hours at room temperature. After thin lay chromatography showed the disappearance of starting materials, the reaction mixture was neutralized with hydrochloride acid (1 mol/L) and concentrated under reduced pressure. The residue was purified by silica gel column chromatography and dried to obtain N-(5-fluoro-2-oxo-2,3-dihydro-1H-indol-6-yl)-2-hydroxy-2-methyl-propionamide 9b (900 mg, yield 59.2%) as a white solid.

MS m/z (ESI): 253.6 [M+1]

Step 3

(Z)—N-{3-[5-(2-Diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-2-methyl-propionamide The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and N-(5-fluoro-2-oxo-2,3-dihydro-1H-indol-6-yl)-2-hydroxy-2-methyl-propionamide 9b as starting materials to obtain (Z)—N-{3-[5-(2-diethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-2-methyl-propionamide 9 (39 mg, yield 62.4%) as a yellow solid.

MS m/z (ESI): 526.4 [M+1]

$^1$HNMR (400 MHz, DMSO-d6) δ13.591 (s, 1H, pyrrole-NH), 10.900 (s, 1H, indole —NH), 9.284 (s, 1H, amide-NH), 7.862~7.890 (d, 1H, —ArH), 7.774~7.791 (d, 1H, —ArH), 7.661 (s, 1H, —CH═C), 6.052 (s, 1H, —OH), 3.480~3.514 (t, 2H, seven-membered ring intra-CH$_2$N), 3.334~3.361 (t, 2H, amide N seven-membered ring outer-CH$_2$), 2.902~2.939

(t, 2H, seven-membered ring intra-CH$_2$C=C), 2.530~2.562 (m, 6H, 3×—CH$_2$N), 2.443 (s, 3H, pyrrole-CH$_3$), 2.037~2.066 (m, 2H, seven-membered ring intra-CH$_2$), 1.377 (s, 6H, 2×—CH$_3$), 0.958~0.993 (t, 6H, 2×—CH$_3$).

Example 10

(Z)-2-(5-Chloro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one

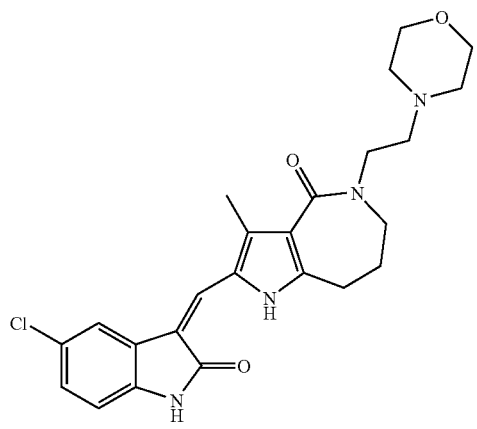

10

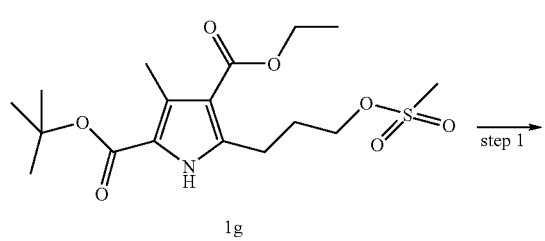

1g

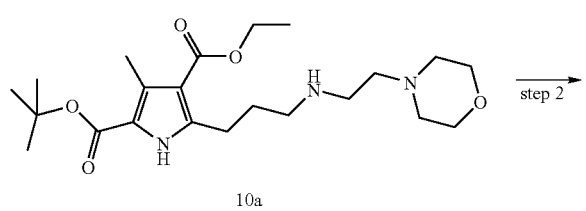

10a

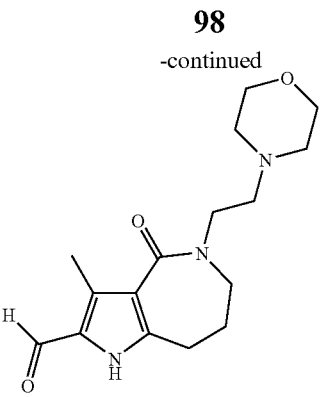

10c

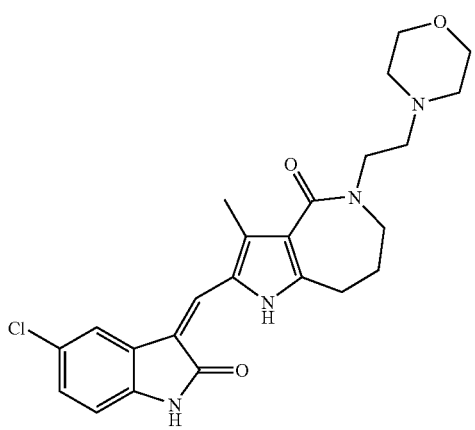

10

Step 1

3-Methyl-5-[3-(2-morpholin-4-yl-ethylamino)-propyl]-1H-pyrrole-2,4-dicarboxylic acid 2-tert-butyl ester 4-ethyl ester 5-(3-Methanesulfonyloxy-propyl)-3-methyl-1H-pyrrole-2,4-dicarboxylic acid 2-tert-butyl ester 4-ethyl ester 1 g (5.812 g, 15 mmol) obtained from step 6 of Example 1 and 2-morpholin-4-yl-ethylamine (10.725 g, 82.5 mmol) was dissolved in water bath at 30° C. and stirred for 5.5 hours at room temperature. After thin lay chromatography showed the disappearance of starting materials, the reaction mixture was added with ethyl acetate (100 ml) and saturated brine (100 ml), stirred for 5 minutes, and separated into layers. The organic phase was washed with saturated brine (100 ml×4), dried over anhydrous magnesium sulfate, filtered to remove the drying agent and concentrated under reduced pressure. The residue was purified by silica gel column chromatography to obtain 3-methyl-5-[3-(2-morpholin-4-yl-ethylamino)-propyl]-1H-pyrrole-2,4-dicarboxylic acid 2-tert-butyl ester 4-ethyl ester 10a (2.238 g, yield 87%) as a light yellow oil.

MS m/z (ESI): 424.9 [M+1]

Step 2

3-Methyl-5-(2-morpholin-4-yl-ethyl)-4-oxo-1,4,5,6,7,8-hexahydro-pyrrolo[3,2-c]azepine-2-carboxylic acid tert-butyl ester

3-Methyl-5-[3-(2-morpholin-4-yl-ethylamino)-propyl]-1H-pyrrole-2,4-dicarboxylic acid 2-tert-butyl ester 4-ethyl ester 10a (2.238 g, 5.29 mmol) was dissolved in 50 ml of toluene under stirring, and added slowly with a solution of trimethyl aluminum in toluene (3.9 ml, 2 mol/L, 7.9 mmol) under an argon atmosphere. The reaction system was stirred for 30 minutes at room temperature until no white smoke was released, and refluxed for another 3 hours in an oil bath. After thin lay chromatography showed the disappearance of starting materials, the oil bath was removed, and the reaction mixture was quenched with a little water, adjusted to pH 8-10 with dilute sodium hydroxide solution (2 mol/L), added with saturated brine (50 ml) and extracted with ethyl acetate (50 ml×3). The combined organic extracts were filtered through a pad of Celite, concentrated under reduced pressure to obtain the title compound 3-methyl-5-(2-morpholin-4-yl-ethyl)-4-oxo-1,4,5,6,7,8-hexahydro-pyrrolo[3,2-c]azepine-2-carboxylic acid tert-butyl ester 10b (1.218 g, yield 61%) as a light yellow solid MS m/z (ESI): 378.2 [M+1]

Step 3

3-Methyl-5-(2-morpholin-4-yl-ethyl)-4-oxo-1,4,5,6,7,8-hexahydro-pyrrolo[3,2-c]azepine-2-carbaldehyde

3-Methyl-5-(2-morpholin-4-yl-ethyl)-4-oxo-1,4,5,6,7,8-hexahydro-pyrrolo[3,2-c]azepine-2-carboxylic acid tert-butyl ester 10b (725 mg, 1.92 mmol) was dissolved in trifluoroacetic acid (2.6 ml, 34.2 mmol) in an ice-water bath under stirring. The reaction mixture was stirred at 40° C. in a water bath for 5 minutes, added with triethoxy methane (0.42 ml, 2.5 mmol) in one portion at −5° C. in an ice-water bath, and stirred for 2 minutes. Then the ice-salt bath was removed, and the reaction mixture was allowed to warm up to room temperature, became brown and stirred for another 2 hours. After thin lay chromatography showed the disappearance of starting materials, the reaction mixture was quenched with a little water, adjusted to pH 8 with dilute sodium hydroxide solution (2 mol/L) and extracted with dichloromethane (50 ml×3). The combined organic extracts were concentrated under reduced pressure to obtain henna solid. The solid was purified by silica gel column chromatography to obtain the title compound 3-methyl-5-(2-morpholin-4-yl-ethyl)-4-oxo-1,4,5,6,7,8-hexahydro-pyrrolo[3,2-c]azepine-2-carbaldehyde 10c (240 mg, yield 40%) as a light yellow solid.

MS m/z (ESI): 306.3 [M+1]

Step 4

(Z)-2-(5-Chloro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one

3-Methyl-5-(2-morpholin-4-yl-ethyl)-4-oxo-1,4,5,6,7,8-hexahydro-pyrrolo[3,2-c]azepine-2-carbaldehyde 10c (53 mg, 0.174 mmol) and 5-chloro-1,3-dihydro-indol-2-one (29 g, 0.84 mmol) was dissolved in 0.9 ml of ethanol under stirring, and added with piperidine (0.1 ml, 1.0 mmol) to the solution at room temperature. The mixture was heated to reflux for 2 hours in an oil bath and lots of precipitates were formed. Then the ice-salt bath was removed, and the reaction mixture was naturally cooled down to room temperature, filtered to obtain the title compound (Z)-2-(5-chloro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one 10 (30 g, yield 38%) as a red solid.

MS m/z (ESI): 455.2 [M+1]

$^1$HNMR (400 MHz, DMSO-d6) δ13.682 (s, 1H, pyrrole-NH), 11.009 (s, 1H, indole-NH), 7.992~7.997 (d, 1H, —ArH), 7.804 (s, 1H, —CH═C), 7.138~7.164 (dd, 1H, —ArH), 6.873~6.894 (d, 1H, —ArH), 3.572~3.583 (m, 6l~1, N seven-membered ring —CH$_2$, 2×—CH$_2$O), 3.346~3.360 (t, 2H, amide N seven-membered ring outer-CH$_2$), 2.938~2.974 (t, 2H, —CH$_2$C═C), 2.463 (s, 3H, pyrrole-CH$_3$), 2.438—2.510 (m, 6H, 2×—CH$_2$N), 2.054~2.083 (m, 2H, seven-membered ring intra-CH$_2$).

Example 11

(Z)-2-(5-Fluoro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one

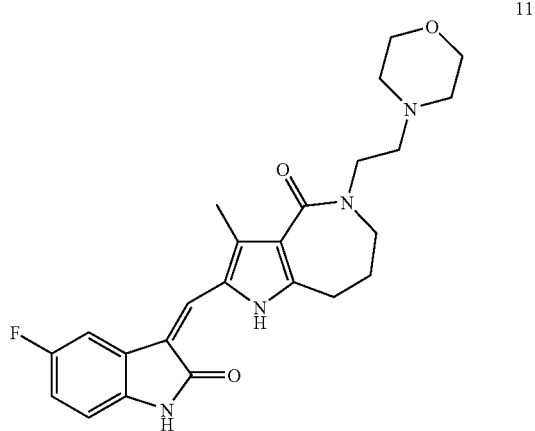

11

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and 5-fluoro-1,3-dihydro-indol-2-one as starting materials to obtain (Z)-2-(5-fluoro-2-oxo-1,2-dihydro-indol-3-ylidenemethyl)-3-methyl-5-(2-morpholin-4-yl-ethyl)-5,6,7,8-tetrahydro-1H-pyrrolo[3,2-c]azepin-4-one 11 (29 mg, yield 51.5%) as a yellow solid.

MS m/z (ESI): 439.3 [M+1]

$^1$HNMR (400 MHz, DMSO-d6) δ13.727 (s, 1H, pyrrole-NH), 10.908 (s, 1H, indole-NH), 7.756~7.785 (dd, 1H, —ArH), 7.746 (s, 1H, —CH═C), 6.917~6.968 (m, 1H, —ArH), 6.838~6.871 (m, 1H, —ArH), 3.571~3.600 (m, 6H, N seven-membered ring-CH$_2$, 2×—CH$_2$O), 3.344~3.371 (t, 2H, amide N seven-membered ring outer-CH$_2$), 2.934~2.971 (t, 2H, —CH$_2$C═C), 2.454 (s, 3H, pyrrole-CH$_3$), 2.438~2.510 (m, 6H, 2×—CH$_2$N), 2.053~2.082 (m, 2H, seven-membered ring intra-CH$_2$).

Example 12

(Z)-2-[4-(2,3-Difluoro-phenyl)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one

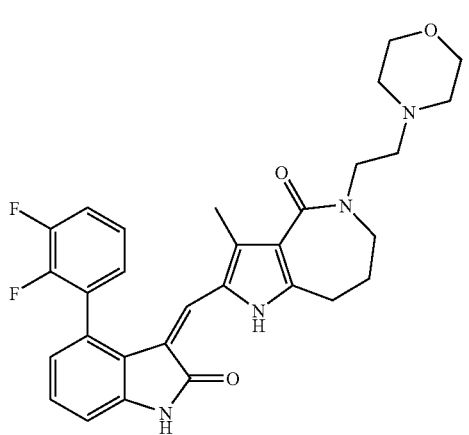

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and 4-(2,3-difluoro-phenyl)-1,3-dihydro-indol-2-one 6d obtained from step 3 of Example 6 as starting materials to obtain (Z)-2-[4-(2,3-difluoro-phenyl)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one 12 (20 mg, yield 29%) as a yellow solid.

MS m/z (ESI): 533.3 [M+1]

$^1$HNMR (400 MHz, DMSO-d6) δ13.546 (s, 1H, pyrrole-NH), 11.135 (s, 1H, indole-NH), 7.598~7.662 (m, 1H, —ArH), 7.409~7.461 (m, 1H, —ArH), 7.306~7.343 (m, 1H, —ArH), 7.234~7.273 (m, 1H, —ArH), 6.700~7.019 (d, 1H, —ArH), 6.875~6.894 (d, 1H, —ArH), 6.712 (s, 1H, —CH=C), 3.547~3.560 (m, 6H, N seven-membered ring-CH$_2$, 2×—CH$_2$O), 3.295~3.310 (t, 2H, amide N seven-membered ring outer-CH$_2$), 2.897~2.933 (t, 2H, —CH$_2$C=C), 2.410~2.510 (m, 6H, 2×—CH$_2$N), 1.999~2.061 (m, 2H, seven-membered ring intra-CH$_2$), 1.794 (s, 3H, pyrrole-CH$_3$).

Example 13

(Z)-2-(4-Bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one

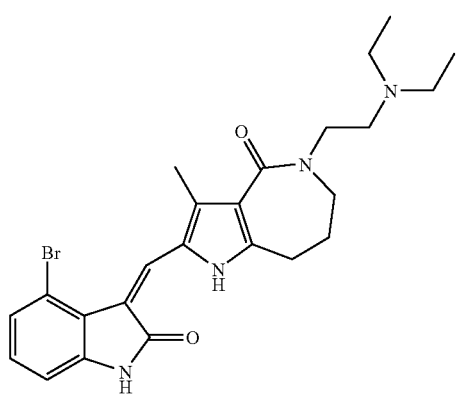

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 4-bromo-1,3-dihydro-indol-2-one as starting materials to obtain (Z)-2-(4-bromo-2-oxo-1,2-dihydro-indol-3-ylidenemethyl)-5-(2-diethylamino-ethyl)-3-methyl-5,6,7,8-tetrahydro-1H-pyrrolo[3,2-c]azepin-4-one 13 (30 mg, yield 45.5%) as an orange solid.

MS m/z (ESI): 585.1 [M+1]

$^1$HNMR (400 MHz, DMSO-d6) δ13.634 (s, 1H, pyrrole-NH), 11.184 (s, 1H, indole-NH), 8.589 (s, 1H, —CH=C), 7.220~7.240 (d, 1H, —ArH), 7.056~7.096 (m, 1H, —ArH), 6.938~6.957 (d, 1H, —ArH), 3.491~3.524 (t, 2H, seven-membered ring intra-CH$_2$N), 3.346—3.373 (t, 2H, amide N seven-membered ring outer-CH$_2$), 2.930~2.966 (t, 2H, seven-membered ring intra-CH$_2$C=C), 2.508~2.569 (m, 6H, 3×—CH$_2$N), 2.412 (s, 3H, pyrrole-CH$_3$), 2.030~2.095 (m, 2H, seven-membered ring intra-CH$_2$), 0.959~0.994 (t, 6H, 2×—CH$_3$).

Example 14

(Z)-2-(5-Bromo-2-oxo-1,2-dihydro-pyrrolo[2,3-b]pyridin-3-ylidenemethyl)-5-(2-diethylamino-ethyl)-3-methyl-5,6,7,8-tetrahydro-1H-pyrrolo[3,2-c]azepin-4-one

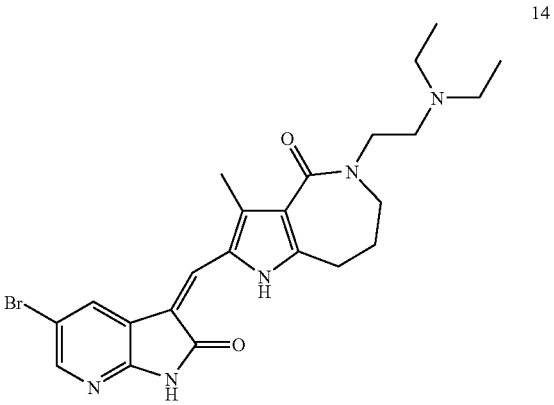

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 5-bromo-1,3-dihydro-pyrrolo[2,3-b]pyridin-2-one as starting materials to obtain (Z)-2-(5-bromo-2-oxo-1,2-dihydro-pyrrolo[2,3-b]pyridin-3-ylidenemethyl)-5-(2-diethylamino-ethyl)-3-methyl-5,6,7,8-tetrahydro-1H-pyrrolo[3,2-c]azepin-4-one 14 (23 mg, yield 33.8%) as an orange solid.

MS m/z (ESI): 486.2 [M+1]

$^1$HNMR (400 MHz, DMSO-d6) δ13.472 (s, 1H, pyrrole-NH), 11.636 (s, 1H, indole-NH), 8.487 (s, 1H, pyridine-CH), 8.116 (s, 1H, pyridine-CH), 7.889 (s, 1H, —CH=C), 3.505 (t, 2H, seven-membered ring intra-CH$_2$N), 3.354 (t, 2H, amide N seven-membered ring outer-CH$_2$), 2.930~2.966 (t, 2H, seven-membered ring intra-CH$_2$C=C), 2.508~2.569 (m, 6H, 3×—CH$_2$N), 2.472 (s, 3H, pyrrole-CH$_3$), 2.030~2.095 (m, 2H, seven-membered ring intra-CH$_2$), 0.959~0.994 (t, 6H, 2×—CH$_3$).

Example 15

(Z)-5-(2-Diethylamino-ethyl)-2-(6-methoxy-2-oxo-1,2-dihydro-indol-3-ylidenemethyl)-3-methyl-5,6,7,8-tetrahydro-1H-pyrrolo[3,2-c]azepin-4-one

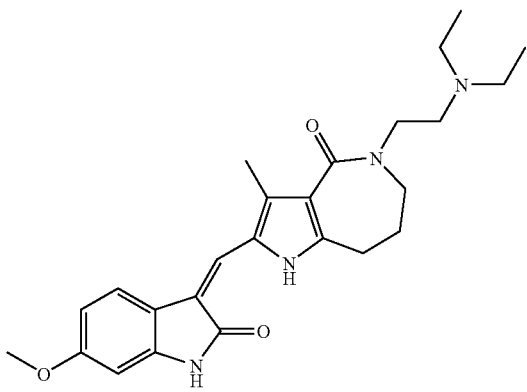

15

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 6-methoxy-1,3-dihydro-indol-2-one as starting materials to obtain (Z)-5-(2-diethylamino-ethyl)-2-(6-methoxy-2-oxo-1,2-dihydro-indol-3-ylidenemethyl)-3-methyl-5,6,7,8-tetrahydro-1H-pyrrolo[3,2-c]azepin-4-one 15 (31 mg, yield 52.7%) as a red solid.

MS m/z (ESI): 437.4 [M+1]

$^1$HNMR (400 MHz, DMSO-d6) δ13.466 (s, 1H, pyrrole-NH), 10.852 (s, 1H, indole-NH), 7.670~7.691 (d, 1H, —ArH), 7.496 (s, 1H, —CH=C), 6.575~6.596 (d, 1H, —ArH), 6.463 (s, 1H, —ArH), 3.769 ((s, 3H, —CH$_3$), 3.477~3.510 (t, 2H, seven-membered ring intra-CH$_2$N), 3.316~3.347 (t, 2H, amide N seven-membered ring outer-CH$_2$), 2.888~2.924 (t, 2H, seven-membered ring intra-CH$_2$C=C), 2.489~2.573 (m, 6H, 3 x-CH$_2$N), 2.416 (s, 3H, pyrrole-CH$_3$), 2.030~2.095 (m, 2H, seven-membered ring intra-CH$_2$), 0.954~0.982 (t, 6H, 2x—CH$_3$).

Example 16

(Z)-5-(2-Diethylamino-ethyl)-3-methyl-2-(4-methyl-2-oxo-1,2-dihydro-indol-3-ylidenemethyl)-5,6,7,8-tetrahydro-1H-pyrrolo[3,2-c]azepin-4-one

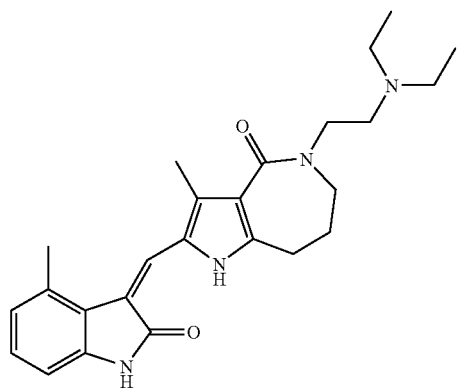

16

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 4-methyl-1,3-dihydro-indol-2-one as starting materials to obtain (Z)-5-(2-diethylamino-ethyl)-3-methyl-2-(4-methyl-2-oxo-1,2-dihydro-indol-3-ylidenemethyl)-5,6,7,8-tetrahydro-1H-pyrrolo[3,2-c]azepin-4-one 16 (25 mg, yield 44.1%) as a yellow solid.

MS m/z (ESI): 421.5 [M+1]

$^1$HNMR (400 MHz, DMSO-d6) δ13.710 (s, 1H, pyrrole-NH), 10.927 (s, 1H, indole-NH), 7.566 (s, 1H, —CH=C), 7.034~7.072 (m, 1H, —ArH), 6.768~6.835 (dd, 2H, —ArH), 3.483~3.517 (t, 2H, seven-membered ring intra-CH$_2$N), 3.339~3.366 (t, 2H, amide N seven-membered ring outer-CH$_2$), 2.909~2.946 (t, 2H, seven-membered ring intra-CH$_2$C=C), 2.489~2.573 (m, 6H, 3x—CH$_2$N), 2.590 (s, 3H, benzene-CH$_3$), 2.386 (s, 3H, pyrrole-CH$_3$), 2.041~2.069 (m, 2H, seven-membered ring intra-CH$_2$), 0.956~0.991 (t, 6H, 2x—CH$_3$).

Example 17

(Z)-5-(2-Diethylamino-ethyl)-2-[4-(2-hydroxy-ethyl)-2-oxo-1,2-dihydro-indol-3-ylidenemethyl]-3-methyl-5,6,7,8-tetrahydro-1H-pyrrolo[3,2-c]azepin-4-one

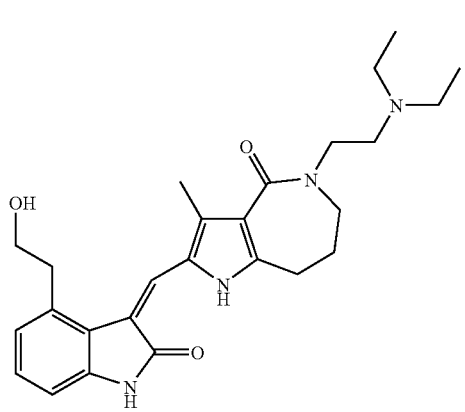

17

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and 4-(2-hydroxy-ethyl)-1,3-dihydro-indol-2-one as starting materials to obtain (Z)-5-(2-diethylamino-ethyl)-2-[4-(2-hydroxy-ethyl)-2-oxo-1,2-dihydro-indol-3-ylidenemethyl]-3-methyl-5,6,7,8-tetrahydro-1H-pyrrolo[3,2-c]azepin-4-one 17 (18 mg, yield 29.5%) as a yellow solid.

MS m/z (ESI): 451.5 [M+1]

$^1$HNMR (400 MHz, DMSO-d6) δ13.722 (s, 1H, pyrrole-NH), 10.924 (s, 1H, indole-NH), 7.652 (s, 1H, —CH=C), 7.045~7.065 (m, 1H, —ArH), 6.772~6.847 (dd, 2H, —ArH), 4.871 (s, 1H, —OH), 3.726~3.739 (t, 2H, amide N seven-membered ring outer-CH$_2$O), 3.486~3.502 (t, 2H, seven-membered ring intra-CH$_2$N), 3.342~3.556 (t, 2H, —CH$_2$), 3.095 (t, 2H, benzene-CH$_2$), 2.910~2.946 (t, 2H, seven-membered ring intra-CH$_2$C=C), 2.504~2.566 (m, 6H, 3x—CH$_2$N), 2.398 (s, 3H, pyrrole-CH$_3$), 2.092 (m, 2H, seven-membered ring intra-CH$_2$), 0.957~0.993 (t, 6H, 2x—CH$_3$).

Example 18

(Z)—N-{5-Fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-methoxy-acetamide

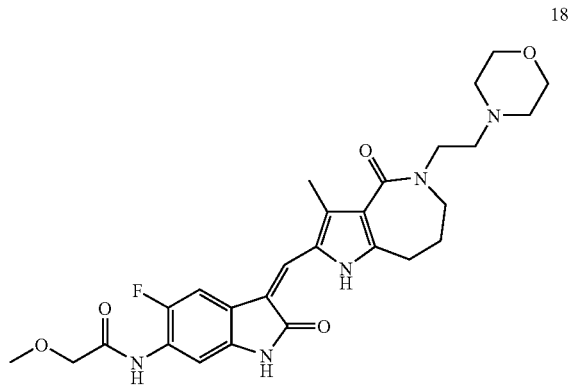

18

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and N-(5-fluoro-2-oxo-2,3-dihydro-1H-indol-6-yl)-2-methoxy-acetamide 7a obtained from step 1 of Example 7 as starting materials to obtain (Z)—N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-methoxy-acetamide 18 (47 mg, yield 60%) as a yellow solid.

MS m/z (ESI): 526.1 [M+1]

$^1$HNMR (400 MHz, DMSO-d6) δ13.608 (s, 1H, pyrrole-NH), 10.884 (s, 1H, indole-NH), 9.308 (s, 1H, —NHCO), 7.827—7.854 (d, 1H, —ArH), 7.659 (s, 1H, —CH═C), 7.534~7.550 (d, 1H, —ArH), 4.056 (s, 2H, —CH$_2$O), 3.561~3.571 (m, 6H, N seven-membered ring-CH$_2$, 2×—CH$_2$O), 3.397 (s, 3H, —CH$_3$O), 3.331~3.345 (t, 2H, amide N seven-membered ring outer-CH$_2$), 2.918~2.954 (t, 2H, —CH$_2$C═C), 2.432 (s, 3H, pyrrole-CH$_3$), 2.431~2.500 (m, 6H, 2×—CH$_2$N), 2.0402.067 (m, 2H, seven-membered ring intra-CH$_2$).

Example 19

(Z)-2-[5-Fluoro-6-(4-fluoro-benzylamino)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one

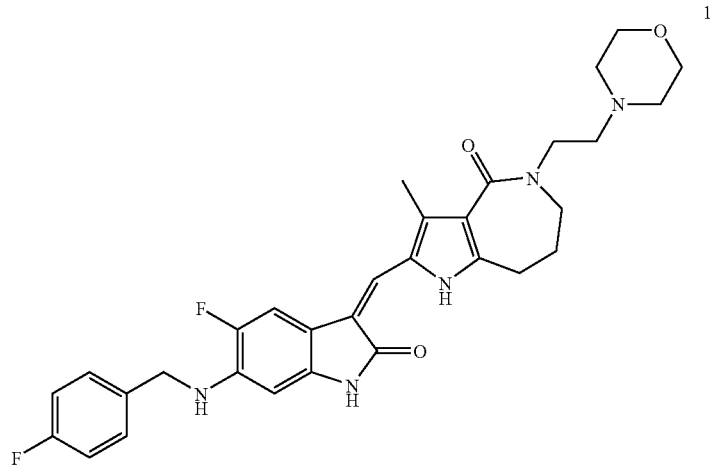

19

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and 5-fluoro-6-(4-fluoro-benzylamino)-1,3-dihydro-indol-2-one 3e obtained from step 4 of Example 3 as starting materials to obtain (Z)-2-[5-fluoro-6-(4-fluoro-benzylamino)-2-oxo-1,2-dihydro-indol-3-ylidenemethyl]-3-methyl-5-(2-morpholin-4-yl-ethyl)-5,6,7,8-tetrahydro-1H-pyrrolo[3,2-c]azepin-4-one 19 (57 mg, yield 69%) as a carmine solid.

MS m/z (ESI): 526.1 [M+1]

$^1$HNMR (400 MHz, DMSO-d6) δ13.423 (s, 1H, pyrrole-NH), 10.515 (s, 1H, indole-NH), 7.565~7.595 (d, 1H, —ArH), 7.359~7.394 (m, 2H, —ArH), 7.343 (s, 1H, —CH═C), 7.134~7.177 (m, 1H, —ArH), 6.404 (m, 1H, —NH), 6.032~3.051 (d, 1H, —ArH), 4.399~4.353 (d, 2H, anilne-CH$_2$), 3.544~3.555 (m, 6H, N seven-membered ring-CH$_2$, 2×—CH$_2$O), 3.310~3.326 (t, 2H, amide N seven-membered ring outer-CH$_2$), 2.870~2.906 (t, 2H, —CH$_2$C═C), 2.378 (s, 3H, pyrrole-CH$_3$), 2.416~2.500 (m, 6H, 2×—CH$_2$N), 2.014~2.041 (m, 2H, seven-membered ring intra-CH$_2$).

Example 20

(Z)—N-{5-Fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-7-yl}-formamide

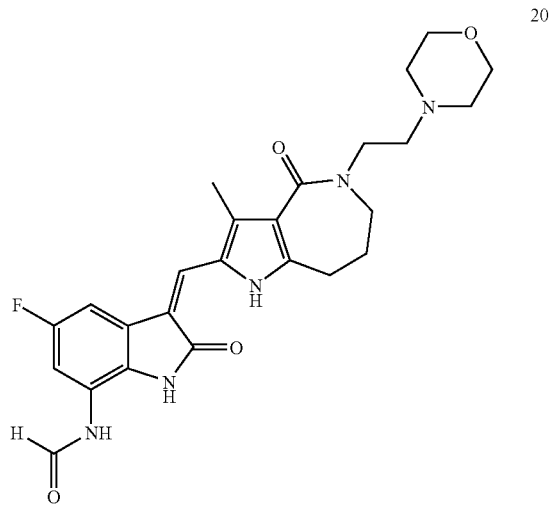

20

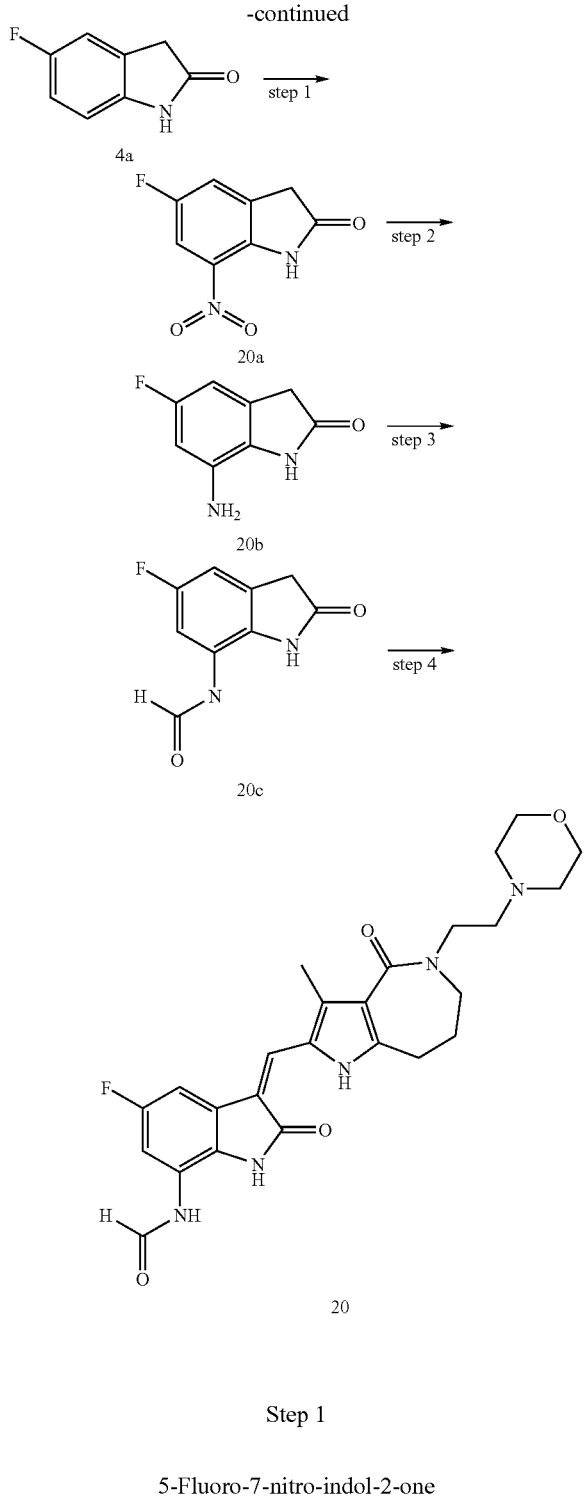

Step 1

5-Fluoro-7-nitro-indol-2-one

5-Fluoro-1,3-dihydro-indol-2-one 4a (5.0 g, 33 mmol) was dissolved in sulfuric acid (17.6 ml, 98%) under stirring at −5° C., and nitric acid (2.1 ml, 65%-68%) was added to the solution while maintaining the temperature below 0° C. Upon completion of the addition, the mixture was stirred at room temperature for 1 hour. After thin lay chromatography showed the disappearance of starting materials, the reaction mixture was poured into ice water and filtered after ice-out. The filter cake was washed with water for three times, and the resulting solid was recrystallized to obtain the title compound 5-fluoro-7-nitro-1,3-dihydro-indol-2-one 20a (4.0 g, yield 62.5%) as an orange solid.

MS m/z (ESI): 196.3 [M+1]

Step 2

7-Amino-5-fluoro-1,3-dihydro-indol-2-one

5-Fluoro-7-nitro-1,3-dihydro-indol-2-one 20a (4.0 g, 20 mmol) was dissolved in 200 ml of acetic acid under stirring, and added with palladium on activated carbon (1.0 g, 5%) at room temperature. The reaction system was stirred under a hydrogen atmosphere. After thin lay chromatography showed the disappearance of starting materials, the reaction mixture was filtered, and concentrated under reduced pressure to obtain the title compound 7-amino-5-fluoro-1,3-dihydro-indol-2-one 20b (3.2 g, yield 97.5%) as a white solid.

MS m/z (ESI): 167.4 [M+1]

Step 3

5-Fluoro-7-formamido-indol-2-one

A mixture of acetic anhydride (0.8 ml) and formic acid (0.6 ml) was stirred for 1 hour at room temperature, and added with 7-amino-5-fluoro-1,3-dihydro-indol-2-one 20b (2.0 g, 12 mmol) in 30 ml of tetrahydrofuran to the above mixture, followed by piperidine (0.02 ml). The resulting mixture was stirred for 3 hours until precipitates were formed, filtered to provide the crude product (1.95 g), and recrystallized from methanol to obtain the title compound 5-fluoro-7-formamido-indol-2-one 20c (700 mg, yield 30.4%) as a white solid.

MS m/z (ESI): 195.1 [M+1]

Step 4

(Z)—N-{5-Fluoro-3-[3-methyl-5-(2-morpholin-4-yl-ethyl)-4-oxo-1,4,5,6,7,8-hexa hydro-pyrrolo[3,2-c]azepin-2-ylmethylene]-2-oxo-2,3-dihydro-1H-indol-7-yl}-form amide The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and (Z)—N-(5-fluoro-2-oxo-2,3-dihydro-1H-indol-7-yl)-formamide 20c as starting materials to obtain (Z)—N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-7-yl}-formamide 20 (37 mg, yield 52%) as an orange solid.

MS m/z (ESI): 480.2 [M−1]

¹HNMR (400 MHz, DMSO-d6) δ13.655 (s, 1H, pyrrole-NH), 10.424 (s, 1H, indole-NH), 9.801 (s, 1H, —NHCO), 8.330 (s, 1H, —CHO), 7.757 (s, 1H, —CH═C), 7.610~7.633 (d, 1H, —ArH), 7.428~7.461 (dd, 1H, —ArH), 3.562~3.592 (m, 6H, N seven-membered ring-CH₂, 2×—CH₂O), 3.331~3.345 (t, 2H, amide N seven-membered ring outer-CH₂), 2.935~2.971 (t, 2H, —CH₂C═C), 2.451 (s, 3H, pyrrole-CH₃), 2.431~2.500 (m, 6H, 2×—CH₂N), 2.046~2.074 (m, 2H, seven-membered ring intra-CH₂).

Example 21

(S,Z)—N-{5-Fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-hydroxy-propionamide

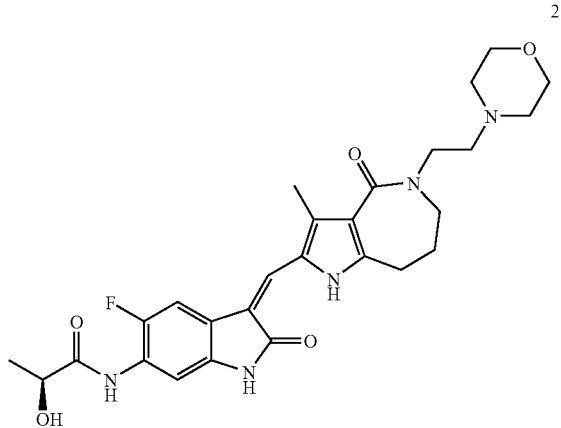

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and (S,Z)—N-(5-fluoro-2-oxo-2,3-dihydro-1H-indol-6-yl)-2-hydroxy-propionamide 8b obtained from step 2 of Example 8 as starting materials to obtain (S,Z)—N-{5-fluoro-3-[3-methyl-5-(2-morpholin-4-yl-ethyl)-4-oxo-1,4,5,6,7,8-hexahydro-pyrrolo[3,2-c]azepin-2-ylmethylene]-2-oxo-2,3-dihydro-1H-indol-6-yl}-2-hydroxy-propionamide 21 (44 mg, yield 58%) as an orange solid.

MS m/z (ESI): 526.1 [M+1]

$^1$HNMR (400 MHz, DMSO-d6) δ13.599 (s, 1H, pyrrole-NH), 10.895 (s, 1H, indole-NH), 9.236 (s, 1H, —NHCO), 7.846~7.874 (d, 1H, —ArH), 7.718~7.734 (d, 1H, —ArH), 7.663 (s, 1H, —CH═C), 6.051~6.064 (d, 1H, —OH), 4.199~4.229 (t, 1H, —CHO), 3.560~3.586 (m, 6H, N seven-membered ring-CH$_2$, 2×—CH$_2$O), 3.331~3.345 (t, 2H, amide N seven-membered ring outer-CH$_2$), 2.918~2.954 (t, 2H, —CH$_2$C═C), 2.456 (s, 3H, pyrrole-CH$_3$), 2.431~2.500 (m, 6H, 2×-CH$_2$N), 2.048~2.077 (m, 2H, seven-membered ring intra-CH$_2$), 1.321~1.338 (d, 2H, —CH$_3$).

Example 22

(Z)-2-(5-Bromo-2-oxo-1,2-dihydro-pyrrolo[2,3-b]pyridin-3-ylidenemethyl)-3-m ethyl-5-(2-morpholin-4-yl-ethyl)-5,6,7,8-tetrahydro-1H-pyrrolo[3,2-c]azepin-4-one

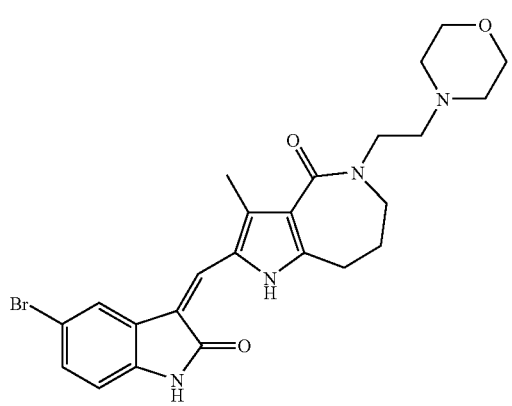

The title compound was prepared under the same conditions as described in step 4 of Example 10 with 3-methyl-5-(2-morpholin-4-yl-ethyl)-4-oxo-1,4,5,6,7,8-hexahydro-pyrrolo[3,2-c]azepine-2-carbaldehyde 10c obtained from step 3 of Example 10 and 5-bromo-1,3-dihydro-pyrrolo[2,3-b]pyridin-2-one as starting materials to obtain (Z)-2-(5-bromo-2-oxo-1,2-dihydro-pyrrolo[2,3-b]pyrid in-3-ylidenemethyl)-3-methyl-5-(2-morpholin-4-yl-ethyl)-5,6,7,8-tetrahydro-1H-pyrrolo[3,2-c]azepin-4-one 22 (59 mg, yield 60%) as an orange solid.

MS m/z (ESI): 500.0 [M+1]

$^1$HNMR (400 MHz, DMSO-d6) δ13.474 (s, 1H, pyrrole-NH), 11.004 (s, 1H, indole-NH), 8.475 (d, 1H, pyridine-CH), 8.102~8.107 (d, 1H, pyridine-CH), 7.873 (s, 1H, —CH═C), 3.560~3.591 (m, 6H, N seven-membered ring-CH$_2$, 2×—CH$_2$O), 3.336~3.364 (t, 2H, amide N seven-membered ring outer-CH$_2$), 2.946~2.983 (t, 2H, —CH$_2$C═C), 2.456 (s, 3H, pyrrole-CH$_3$), 2.425~2.500 (m, 61~1, 2×—CH$_2$N), 2.048~2.077 (m, 2H, seven-membered ring intra-CH$_2$).

Example 23

(Z)-2-(5-Chloro-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one

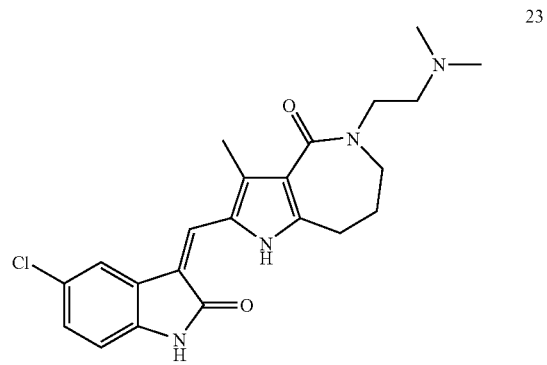

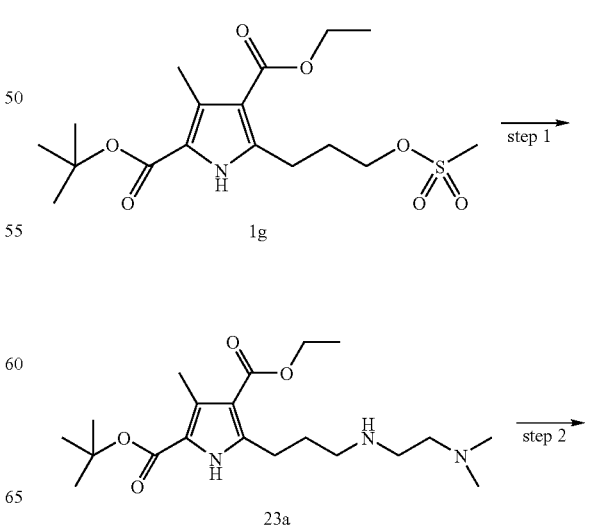

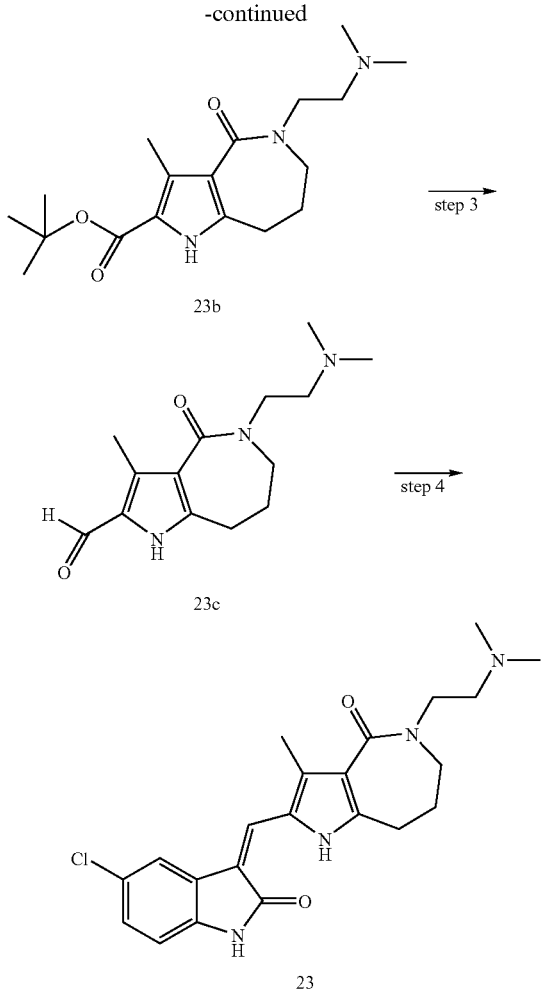

Step 1

5-[3-(2-Dimethylamino-ethylamino)-propyl]-3-methyl-1H-pyrrole-2,4-dicarboxylic acid 2-tert-butyl ester 4-ethyl ester 5-(3-Methanesulfonyloxy-propyl)-3-methyl-1H-pyrrole-2,4-dicarboxylic acid 2-tert-butyl ester 4-ethyl ester 1 g (11.964 g, 25.7 mmol) obtained from step 6 of Example 1 was dissolved in N,N-dimethylethylenediamine (12 ml, 97 mmol), the resulting solution was stirred for 5 hours at room temperature. After thin lay chromatography showed the disappearance of starting materials, the reaction mixture was added with ethyl acetate (80 ml) and saturated brine (80 ml), stirred for 5 minutes, and separated into layers. The organic phase was washed with saturated brine (80 ml×4) to remove N,N-dimethylethylenediamine, dried over anhydrous magnesium sulfate, filtered to remove the drying agent and concentrated under reduced pressure to obtain brown oil. The residue was purified by silica gel column chromatography to obtain the title compound 5-[3-(2-dimethylamino-ethylamino)-propyl]-3-methyl-1H-pyrrole-2,4-dicarboxylic acid 2-tert-butyl ester 4-ethyl ester 23a (5.85 g, yield 45.9%) as a yellow oil.

MS m/z (ESI): 382.2 [M+1]

Step 2

5-(2-Dimethylamino-ethyl)-3-methyl-4-oxo-1,4,5,6,7,8-hexahydro-pyrrolo[3,2-c]azepine-2-carboxylic acid tert-butyl ester 5-[3-(2-Dimethylamino-ethylamino)-propyl]-3-methyl-1H-pyrrole-2,4-dicarboxylic acid 2-tert-butyl ester 4-ethyl ester 23a (5.85 g, 13.8 mmol) was dissolved in 130 ml of toluene under stirring, and added slowly with a solution of trimethyl aluminum in toluene (12 ml, 2 mol/L, 24 mmol) to the solution under an argon atmosphere. Upon the completion of the addition, the reaction mixture was stirred for 10 minutes at room temperature until no white smoke was released, and heated to reflux for 3 hours in an oil bath. After thin lay chromatography showed the disappearance of starting materials, the reaction mixture was quenched with ice water. After the reaction system was naturally cooled down to room temperature, the mixture was added with hydrochloric acid solution (50 ml, 2 mol/L) and stirred for 10 minutes. The mixture was adjusted to pH 9 with aqueous sodium hydroxide solution (2 mol/L), and extracted with dichloromethane (50 ml×4). The combined organic extracts were dried over anhydrous magnesium sulfate, filtered to remove the drying agent and concentrated under reduced pressure to obtain the title compound 5-(2-dimethylamino-ethyl)-3-methyl-4-oxo-1,4,5,6,7,8-hexahydro-pyrrolo[3,2-c]azepine-2-carboxylic acid tert-butyl ester 23b (3.3 g, yield 71.4%) as a yellow solid.

MS m/z (ESI): 336.2 [M+1]

Step 3

5-(2-Dimethylamino-ethyl)-3-methyl-4-oxo-1,4,5,6,7,8-hexahydro-pyrrolo[3,2-c]azepine-2-carbaldehyde 5-(2-Dimethylamino-ethyl)-3-methyl-4-oxo-1,4,5,6,7,8-hexahydro-pyrrolo[3,2-c]azepine-2-carboxylic acid tert-butyl ester 23b (774 mg, 2.3 mmol) was dissolved in trifluoroacetic acid (3.1 ml, 20 mmol) under stirring, the resulting solution was heated at 40° C. for 5 minutes in an oil bath under an argon atmosphere. The reaction mixture was cooled down to −5° C. in an ice-salt bath under stirring, added with triethoxy methane (0.5 ml, 3.0 mmol) and stirred for 2 minutes. Then the ice-salt bath was removed, and the reaction mixture was allowed to warm up to room temperature and stirred for another 1 hour. After thin lay chromatography showed the disappearance of starting materials, the reaction mixture was added with ice water (3 ml) and dichloromethane (10 ml), adjusted to pH 11 with aqueous sodium hydroxide solution (2 mol/L) and extracted with dichloromethane (10 ml×3). The combined organic extracts were dried over anhydrous magnesium sulfate, filtered to remove the drying agent and concentrated under reduced pressure to obtain a henna oil. The residue was purified by silica gel column chromatography to obtain the title compound 5-(2-dimethylamino-ethyl)-3-methyl-4-oxo-1,4,5,6,7,8-hexahydro-pyrrolo[3,2-c]azepine-2-carbaldehyde 23c (223 mg, yield 37%) as a yellow oil.

MS m/z (ESI): 264.2 [M+1]

Step 4

(Z)-2-(5-Chloro-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one 5-(2-Dimethylamino-ethyl)-3-methyl-4-oxo-1,4,5,6,7,8-hexahydro-pyrrolo[3,2-c]azepine-2-carbaldehyde 23c (53 mg, 0.2 mmol) was dissolved in 1 ml of methanol under stirring, and added with 5-chloro-1,3-dihydro-indol-2-one (34 mg, 0.2 mmol) and piperidine (0.1 ml) to the solution. Upon the completion of the addition, the mixture was stirred to mix well in dark, heated to reflux for 2 hours and lots of precipitate was formed. After thin lay chromatography showed the disappearance of starting materials, the reaction mixture was naturally cooled down to room temperature, and filtered. The filter cake was washed with ethanol and dried to obtain the title compound (Z)-2-(5-chloro-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one 23 (62 mg, yield 75%) as an orange powder.

MS m/z (ESI): 413.1 [M+1]

$^1$HNMR (400 MHz, DMSO-d6) δ13.667 (s, 1H, pyrrole-NH), 11.004 (s, 1H, indole-NH), 7.990 (s, 1H, —ArH), 7.799 (s, 1H, —CH═C), 7.134~7.159 (m, 1H, —ArH), 6.869~6.890 (m, 1H, —ArH), 3.533~3.567 (t, 2H, N seven-membered ring-CH$_2$), 3.336~3.364 (t, 2H, amide N seven-membered ring outer-CH$_2$), 2.909~2.945 (t, 2H, —CH$_2$C═C), 2.463 (s, 3H, pyrrole-CH$_3$), 2.401~2.434 (t, 2H, —CH$_2$N), 2.204 (s, 6H, 2×—CH$_3$N), 2.035~2.079 (m, 2H, seven-membered ring intra —CH$_2$).

Example 24

(Z)-2-(5-Bromo-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one

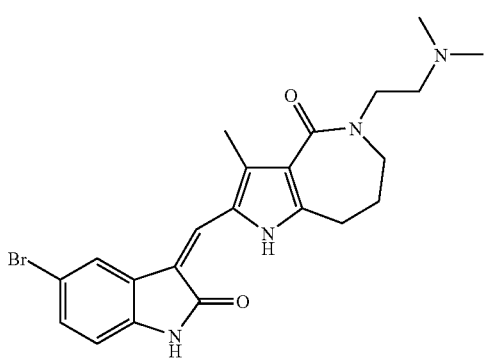

24

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 5-bromo-1,3-dihydro-indol-2-one as starting materials to obtain (Z)-2-(5-bromo-2-oxo-1,2-dihydro-indol-3-ylidenemethyl)-5-(2-dimethylamino-ethyl)-3-methyl-5,6,7,8-tetrahydro-1H-pyrrolo[3,2-c]azepin-4-one 24 (71 mg, yield 77%) as a red solid.

MS m/z (ESI): 457.0 [M+1]

$^1$HNMR (400 MHz, DMSO-d6) δ13.663 (s, 1H, pyrrole-NH), 11.011 (s, 1H, indole-NH), 8.118 (s, 1H, —ArH), 7.804 (s, 1H, —CH═C), 7.262~7.287 (m, 1H, —ArH), 6.826~6.847 (m, 1H, —ArH), 3.533~3.567 (t, 2H, N seven-membered ring-CH$_2$), 3.336~3.364 (t, 2H, amide N seven-membered ring outer-CH$_2$), 2.909~2.945 (t, 2H, —CH$_2$C═C), 2.465 (s, 3H, pyrrole-CH$_3$), 2.401~2.434 (t, 2H, —CH$_2$N), 2.204 (s, 6H, 2×—CH$_3$N), 2.035~2.079 (m, 2H, seven-membered ring intra-CH$_2$).

Example 25

(Z)-5-(2-Dimethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one

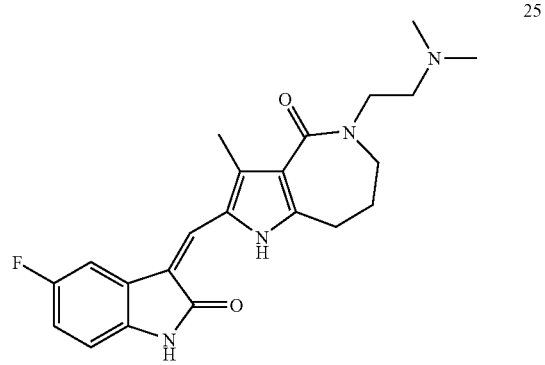

25

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 5-fluoro-1,3-dihydro-indol-2-one as starting materials to obtain (Z)-5-(2-dimethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one 25 (205 mg, yield 68%) as a red solid.

MS m/z (ESI): 397.0 [M+1]

$^1$HNMR (400 MHz, DMSO-d6) δ13.714 (s, 1H, pyrrole-NH), 10.904 (s, 1H, indole-NH), 7.760~7.783 (m, 1H, —ArH), 7.744 (s, 1H, —CH═C), 6.915~6.943 (m, 1H, —ArH), 6.836~6.868 (m, 1H, —ArH), 3.533~'3.567 (t, 2H, N seven-membered ring-CH$_2$), 3.336~3.364 (t, 2H, amide N seven-membered ring outer-CH$_2$), 2.909~2.945 (t, 2H, —CH$_2$C═C), 2.457 (s, 3H, pyrrole-CH$_3$), 2.401~2.434 (t, 2H, —CH$_2$N), 2.204 (s, 6H, 2×—CH$_3$N), 2.035~2.079 (m, 2H, seven-membered ring intra-CH$_2$).

Example 26

(Z)—N-{3-[5-(2-Dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-7-yl}-formamide

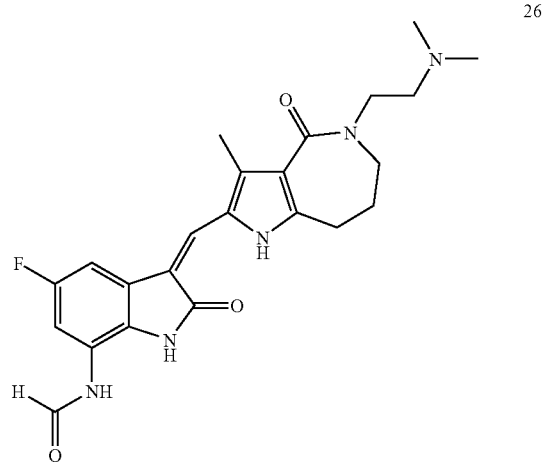

26

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and N-(5-fluoro-2-oxo-2,3-dihydro-1H-indol-7-yl)-formamide 20c obtained from step 3 of Example 20 as starting materials to obtain (Z)—N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-7-yl}-formamide 26 (71 mg, yield 79%) as a red solid.

MS m/z (ESI): 440.1 [M+1]

$^1$HNMR (400 MHz, DMSO-d6) δ13.653 (s, 1H, pyrrole-NH), 10.437 (s, 1H, indole-NH), 9.814 (s, 1H, —NHCO), 8.339 (s, 1H, —CH=O), 7.768 (s, 1H, —CH=C), 7.621~7.649 (m, 1H, —ArH), 7.440~7.473 (m, 1H, —ArH), 3.533~3.567 (t, 2H, N seven-membered ring-CH$_2$), 3.336~3.364 (t, 2H, amide N seven-membered ring outer-CH$_2$), 2.919~2.955 (t, 2H, —CH$_2$C=C), 2.463 (s, 3H, pyrrole-CH$_3$), 2.403~2.436 (t, 2H, —CH$_2$N), 2.204 (s, 6H, 2×—CH$_3$N), 2.035~2.079 (m, 2H, seven-membered ring intra-CH$_2$).

Example 27

(Z)—N-{3-[5-(2-Dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-acetamide

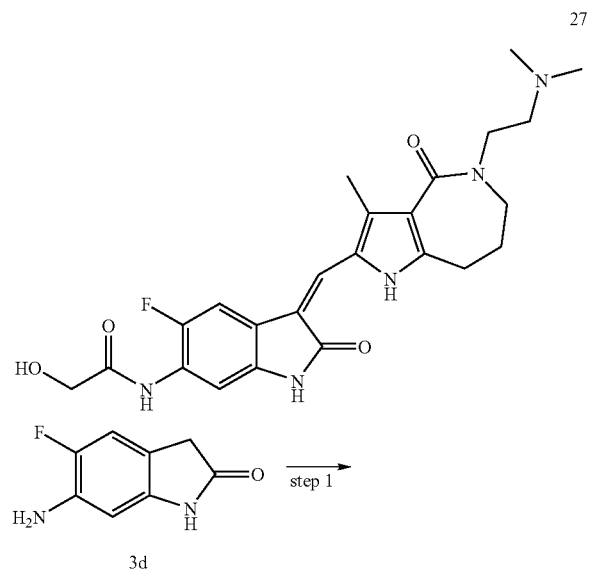

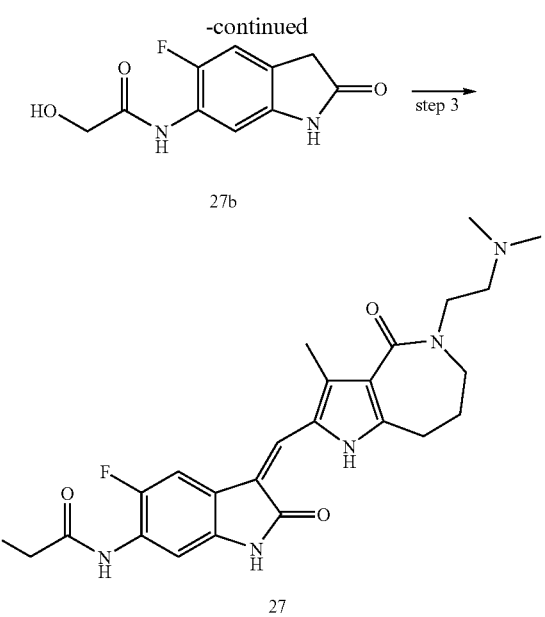

Step 1

Acetic acid (5-fluoro-2-oxo-2,3-dihydro-1H-indol-6-ylcarbamoyl)-methyl ester

6-Amino-5-fluoro-1,3-dihydro-indol-2-one 3d (500 mg, 3.0 mmol) was dissolved in 10 ml of tetrahydrofuran under stirring, and added with 0.4 ml of pyridine to the solution at room temperature. After stirring to mix well, the mixture was cooled down to −40° C. in a dry ice-acetone bath. A solution of acetic acid chlorocarbonylmethyl ester (420 mg, 3.0 mmol) in 10 ml of tetrahydrofuran was added dropwise to the above reaction system. Upon completion of the addition, the dry ice-acetone bath was removed, and the reaction mixture was allowed to warm up to room temperature and stirred overnight. After thin lay chromatography showed the disappearance of starting materials, the reaction mixture was filtered. The resulting solid was washed with water for three times and dried to obtain the title compound acetic acid (5-fluoro-2-oxo-2,3-dihydro-1H-indol-6-ylcarbamoyl)-methyl ester 27a (562 mg, yield 70.4%) as a gray solid.

MS: 265.3 [M−1]

Step 2

N-(5-Fluoro-2-oxo-2,3-dihydro-1H-indol-6-yl)-2-hydroxy-acetamide

Acetic acid (5-fluoro-2-oxo-2,3-dihydro-1H-indol-6-ylcarbamoyl)-methyl ester 27a (58 mg, 0.22 mmol) was dissolved in 1 ml of methanol under stirring, and added with 1 ml of water and sodium hydroxide (15 mg, 0.375 mmol) to the solution at room temperature. Upon completion of the addition, the reaction mixture was stirred for another 1 hour. After thin lay chromatography showed the disappearance of starting materials, the reaction mixture was filtered. The resulting solid was washed with water for three times and dried to obtain the title compound N-(5-fluoro-2-oxo-2,3-dihydro-1H-indol-6-yl)-2-hydroxy-acetamide 27b (46 mg, yield 93.8%) as a gray solid.

MS: 223.7 [M−1]

Step 3

(Z)—N-{3-[5-(2-Dimethylamino-ethyl)-3-methyl-4-oxo-1,4, 5, 6,7,8-hexahydro-pyrrol o[3,2-c]azepin-2-ylmethylene]-5-fluoro-2-oxo-2,3-dihydro-1H-indol-6-yl}-2-hydroxy-acetamide The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and N-(5-fluoro-2-oxo-2,3-dihydro-1H-indol-6-yl)-2-hydroxy-acetamide 27b as starting materials to obtain (Z)—N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-hydroxy-acetamide 27 (80 mg, yield 83.4%) as an orange solid.

MS m/z (ESI): 470.1 [M+1]

$^1$HNMR (400 MHz, DMSO-d6) δ13.599 (s, 1H, pyrrole-NH), 10.893 (s, 1H, indole-NH), 9.233 (s, 1H, —NHCO), 7.854~7.879 (m, 1H, —ArH), 7.725 (s, 1H, —CH═C), 7.663~7.688 (m, 1H, —ArH), 5.950 (s, 1H, —OH), 4.053 (s, 2H, —CH$_2$O), 3.544 (t, 2H, N seven-membered ring-CH$_2$), 3.315~3.340 (t, 2H, amide N seven-membered ring outer-CH$_2$), 2.924 (t, 2H, —CH$_2$C═C), 2.464 (t, 2H, —CH$_2$N), 2.442 (s, 3H, pyrrole-CH$_3$), 2.199 (s, 6H, 2×—CH$_3$N), 2.044 (m, 2H, seven-membered ring intra-CH$_2$).

Example 28

(Z)-2-[4-(2,3-Difluoro-phenyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one

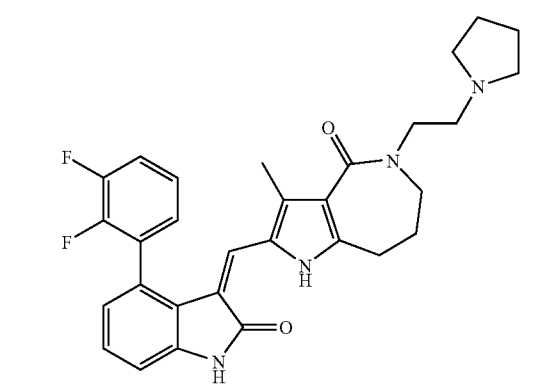

28

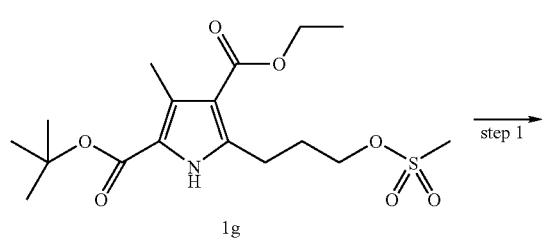

1g

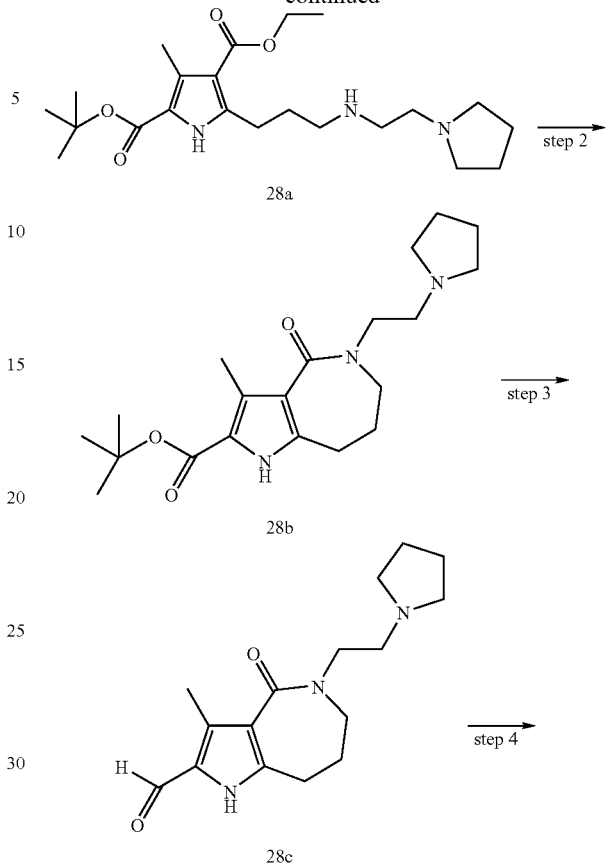

Step 1

3-Methyl-5-[3-(2-pyrrolidin-1-yl-ethylamino)-propyl]-1H-pyrrole-2,4-dicarboxylic acid 2-tert-butyl ester 4-ethyl ester 5-(3-Methanesulfonyloxy-propyl)-3-methyl-1H-pyrrole-2,4-dicarboxylic acid 2-tert-butyl ester 4-ethyl ester 1 g (8.462 g, 21.75 mmol) was dissolved in 2-pyrrolidin-1-yl-ethylamine (6.3 ml, 49.79) under stirring, the resulting solution was stirred at room temperature overnight. After thin lay chromatography showed the disappearance of starting materials, the reaction mixture was added with ethyl acetate (200 ml) and a little methanol until a clear solution was obtained. The mixture was washed with water (30 ml×3), saturated brine (40 ml×2) and concentrated under reduced pressure to obtain light brown oil. The oil was purified by silica gel column chromatography to obtain the title compound 3-methyl-5-[3-(2-pyrrolidin-1-yl-ethylamino)-propyl]-1H-pyrrole-2,4-dicarboxylic acid 2-tert-butyl ester 4-ethyl ester 28a (4.488 g, yield 63.5%) as a yellow oil.

MS m/z (ESI): 406.5 [M−1]

Step 2

3-Methyl-4-oxo-5-(2-pyrrolidin-1-yl-ethyl)-1,4,5,6,7,8-hexahydro-pyrrolo[3,2-c]azepine-2-carboxylic acid tert-butyl ester 3-Methyl-5-[3-(2-pyrrolidin-1-yl-ethylamino)-propyl]-1H-pyrrole-2,4-dicarboxylic acid 2-tert-butyl ester 4-ethyl ester 28a (6.754 g, 16.6 mmol) was dissolved in 150 ml of toluene under stirring, and added slowly with a solution of trimethyl aluminum in toluene (16.6 ml, 2 mol/L, 33.2 mmol) to the solution under an argon atmosphere. The reaction mixture was stirred for 20 minutes at room temperature until no white smoke was released, and refluxed for another 3.5 hours in an oil bath. After thin lay chromatography showed the disappearance of starting materials, the oil bath was removed. The reaction mixture was quenched with little ethanol (95%), added with ethyl acetate (100 ml), filtered through a pad of Celite and concentrated under reduced pressure. The residue was purified by silica gel column chromatography to obtain the title compound 3-methyl-4-oxo-5-(2-pyrrolidin-1-yl-ethyl)-1,4,5,6,7,8-hexahydro-pyrrolo[3,2-c]azepine-2-carboxylic acid tert-butyl ester 28b (3.894 g, yield 65%) as a yellow oil.

MS m/z (ESI): 362.2 [M+1]

Step 3

3-Methyl-4-oxo-5-(2-pyrrolidin-1-yl-ethyl)-1,4,5,6,7,8-hexahydro-pyrrolo[3,2-c]azepine-2-carbaldehyde 3-Methyl-4-oxo-5-(2-pyrrolidin-1-yl-ethyl)-1,4,5,6,7,8-hexahydro-pyrrolo[3,2-c]azepine-2-carboxylic acid tert-butyl ester 28b (3.562 g, 9.87 mmol) was dissolved in 50 ml of dichloromethane under stirring, and added with trifluoroacetic acid (19.7 ml, 260 mmol) to the solution at room temperature. Upon the completion of the addition, the mixture was heated to reflux for 30 minutes in an oil bath. After thin lay chromatography showed the disappearance of starting materials, the reaction mixture was cooled down to −5° C. in an ice-salt bath, added with triethoxy methane (2.96 ml, 14.8 mmol) in one portion, stirred at −5° C. for 5 minutes, for another 1 hour at room temperature. The reaction system was added with water (25 ml), adjusted to about pH 11 with dilute sodium hydroxide solution (2 mol/L) and extracted with dichloromethane (100 ml×3). The combined organic extracts were concentrated under reduced pressure to obtain a henna oil. The oil was purified by silica gel column chromatography to obtain the title compound 3-methyl-4-oxo-5-(2-pyrrolidin-1-yl-ethyl)-1,4,5,6,7,8-hexahydro-pyrrolo[3,2-c]azepine-2-carbaldehyde 28c (1.116 g, yield 49%) as a yellow solid.

MS m/z (ESI): 290.2 [M+1]

Step 4

(Z)-2-[4-(2,3-Difluoro-phenyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one 3-Methyl-4-oxo-5-(2-pyrrolidin-1-yl-ethyl)-1,4,5,6,7,8-hexahydro-pyrrolo[3,2-c]azepine-2-carbaldehyde 28c (40 mg, 0.134 mmol) and 4-(2,3-difluoro-phenyl)-1,3-dihydro-indol-2-one 6d obtained from step 3 of Example 6 were dissolved in 0.3 ml of methanol under stirring, and added with piperidine (0.03 ml, 0.3 mmol) to the solution. Upon the completion of the addition, the mixture was stirred at room temperature overnight. After thin lay chromatography showed the disappearance of starting materials, the reaction mixture was concentrated under reduced pressure to obtain the title compound (Z)-2-[4-(2,3-difluoro-phenyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one 28 (40 mg, yield 57%) as a yellow solid.

MS m/z (ESI): 517.2 [M+1]

¹HNMR (400 MHz, DMSO-d6) δ13.532 (s, 1H, pyrrole-NH), 11.132 (s, 1H, indole-NH), 7.598~7.620 (m, 1H, —ArH), 7.421~7.434 (m, 1H, —ArH), 7.307~7.323 (m, 1H, —ArH), 7.232~7.271 (m, 1H, —ArH), 7.001~7.021 (d, 1H, —ArH), 6.865~6.884 (d, 1H, —ArH), 6.698 (s, 1H, —CH═C), 3.499~3.533 (t, 2H, amide N seven-membered ring outer-CH₂), 3.273~3.302 (t, 2H, N seven-membered ring-CH₂), 2.854~2.891 (t, 2H, —CH₂C═C), 2.536~2.570 (t, 2H, —CH₂N), 2.498~2.515 (m, 4H, five-membered ring-CH₂N), 1.982~2.012 (m, 2H, seven-membered ring-CH₂), 1.777 (s, 3H, pyrrole-CH₃), 1.657 (m, 4H, five-membered ring-CH₂).

Example 29

(Z)—N-{5-Fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-7-yl}-formamide

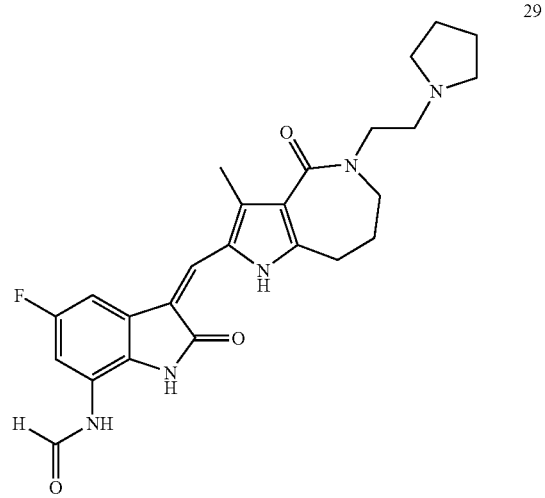

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and N-(5-fluoro-2-oxo-2,3-dihydro-1H-indol-7-yl)-formamide 20c obtained from step 3 of Example 20 as starting materials to obtain (Z)—N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-7-yl}-formamide 29 (59 mg, yield 95%) as a yellow solid.

MS m/z (ESI): 466.2 [M+1]

¹HNMR (400 MHz, DMSO-d6) δ13.679 (s, 1H, pyrrole-NH), 10.868 (s, 1H, indole-NH), 8.324 (s, 1H, —HCO), 7.796 (s, 1H, —ArH), 7.747 (s, 1H, —CH=C), 7.601~7.629 (dd, 1H, —ArH), 7.424~7.454 (dd, 1H, —ArH), 3.543~3.577 (t, 2H, amide N seven-membered ring outer-CH$_2$), 3.330~3.357 (t, 2H, N seven-membered ring-CH$_2$), 2.907~2.944 (t, 2H, —CH$_2$C=C), 2.576~2.610 (t, 2H, —CH$_2$N), 2.498~2.515 (m, 4H, five-membered ring-CH$_2$N), 2.449 (s, 3H, pyrrole-CH$_3$), 2.026~2.055 (m, 2H, seven-membered ring-CH$_2$), 1.679 (m, 4H, five-membered ring-CH$_2$).

Example 30

(Z)—N-{3-[3-Methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-5-yl}-acetamide

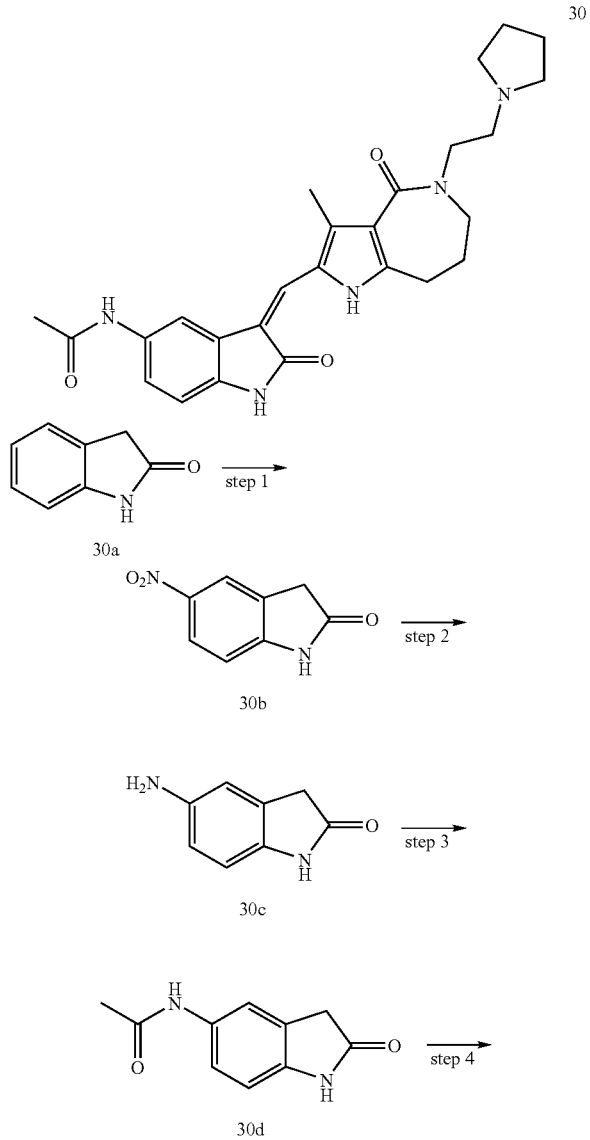

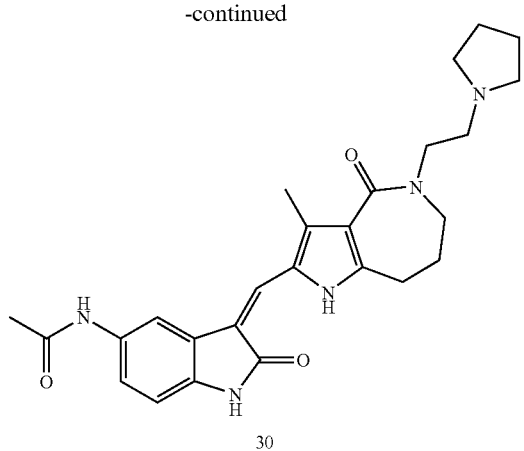

Step 1

5-Nitro-indol-2-one 1,3-Dihydro-indol-2-one 30a (20.0 g, 150 mmol) was dissolved in sulfuric acid (100 ml, 98%) in an ice-water bath under stirring, and added dropwise with nitric acid (10 ml, 65%-68%) while maintaining the temperature below 0° C. Upon completion of the addition, the mixture was stirred for 1 hour at 0° C. After thin lay chromatography showed the disappearance of starting materials, the reaction mixture was added with ice and filtered after ice-out. The filter cake was washed with water (20 ml×3), and the resulting solid was recrystallized to obtain the title compound 5-nitro-indol-2-one 30b (25.3 g, yield 92.4%) as an orange solid.
MS m/z (ESI): 177.3 [M−1]

Step 2

5-Amino-1,3-dihydro-indol-2-one

5-Nitro-1,3-dihydro-indol-2-one 30b (3.56 g, 20 mmol) was dissolved in 200 ml of acetic acid under stirring, and added with palladium on activated carbon (1.0 g, 5%) to the solution at room temperature. The reaction mixture was stirred under a hydrogen atmosphere. After thin lay chromatography showed the disappearance of starting materials, the reaction mixture was filtered, and concentrated under reduced pressure to obtain the title compound 5-amino-1,3-dihydro-indol-2-one 30c (2.04 g, yield 68.9%) as a white solid.
MS m/z (ESI): 149.4 [M+1]

Step 3

N-(2-Oxo-2,3-dihydro-1H-indol-5-yl)-acetamide

5-Amino-1,3-dihydro-indol-2-one 30c (3.5 g, 23.6 mmol) was dissolved in 20 ml of tetrahydrofuran under stirring, and added with triethylamine (3.6 ml, 26 mmol) to the solution at room temperature. Upon completion of the addition, the mixture was cooled down to −30° C. in a dry ice-acetone bath, and added slowly with acetyl chloride (1.8 ml, 24.8 mmol) while maintaining the temperature below −20° C. Upon completion of the addition, the dry ice-acetone bath was removed, and the reaction mixture was allowed to warm up to room temperature and stirred for 20 minutes.

After thin lay chromatography showed the disappearance of starting materials, the reaction mixture was added with ethyl acetate (20 ml), gray solids were formed and filtered. The filter cake was washed with water (70 ml×3) to obtain 2.5 g of solids. The filtrate was extracted with ethyl acetate (200 ml×3). The combined organic extracts were concentrated under reduced pressure, combined with the above solids to obtain the title compound N-(2-oxo-2,3-dihydro-1H-indol-5-yl)-acetamide 30d (4.0 g, yield 89%) as a gray solid.

MS m/z (ESI): 191.2 [M+1]

Step 4

(Z)—N-{3-[3-Methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-5-yl}-acetamide The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and N-(2-oxo-2,3-dihydro-1H-indol-5-yl)-acetamide 30d as starting materials to obtain (Z)—N-{3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-5-yl}-acetamide 30 (50 mg, yield 80%) as a yellow solid.

MS m/z (ESI): 462.2 [M+1]

$^1$HNMR (400 MHz, DMSO-d6) δ13.679 (s, 1H, pyrrole-NH), 10.868 (s, 1H, indole-NH), 9.806 (s, 1H, —NHCO), 7.796 (s, 1H, ArH), 7.447 (s, 1H, —CH═C), 7.231~7.256 (dd, 1H, —ArH), 6.789~6.710 (s, 1H, —ArH), 3.513~3.547 (t, 2H, amide N seven-membered ring outer-CH$_2$), 3.303~3.330 (t, 2H, N seven-membered ring-CH$_2$), 2.866~2.903 (t, 2H, —CH$_2$C═C), 2.540~2.574 (t, 2H, —CH$_2$N), 2.461~2.513 (m, 4H, five-membered ring-CH$_2$N), 2.388 (s, 3H, pyrrole-CH$_3$), 2.002~2.024 (m, 2H, seven-membered ring-CH$_2$), 2.024 (s, 3H, —CH$_3$), 1.648 (m, 4H, five-membered ring —CH$_2$).

Example 31

(Z)—N-{5-Fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-acetamide The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and N-(5-fluoro-2-oxo-2,3-dihydro-1H-indol-6-yl)-2-hydroxy-acetamide 27b obtained from step 2 of Example 27 as starting materials to obtain (Z)—N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-acetamide 31 (50 mg, yield 76%) as a yellow solid.

MS m/z (ESI): 496.2 [M+1]

$^1$HNMR (400 MHz, DMSO-d6) δ13.658 (s, 1H, pyrrole-NH), 10.857 (s, 1H, indole-NH), 9.426 (s, 1H, —NHCO), 7.826~7.854 (d, 1H, —ArH), 7.694~7.710 (d, 1H, —ArH), 7.640 (s, 1H, —CH═C), 5.717 (s, 1H, —HO), 4.035 (d, 2H, —CH$_2$O), 3.536~3.570 (t, 2H, N seven-membered ring-CH$_2$), 3.339 (t, 2H, amide N seven-membered ring outer-CH$_2$), 2.889~2.926 (t, 2H, —CH$_2$C═C), 2.562~2.596 (t, 2H, —CH$_2$N), 2.483~2.513 (m, 4H, five-membered ring —CH$_2$N), 2.427 (s, 3H, pyrrole-CH$_3$), 2.034 (m, 2H, seven-membered ring-CH$_2$), 1.673 (m, 4H, five-membered ring-CH$_2$).

Example 32

(Z)-2-(5-Fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one

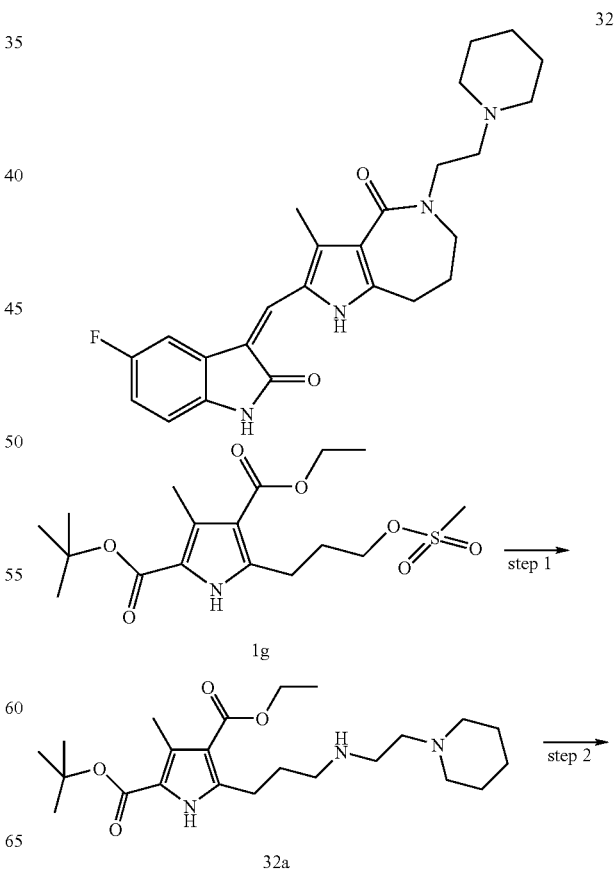

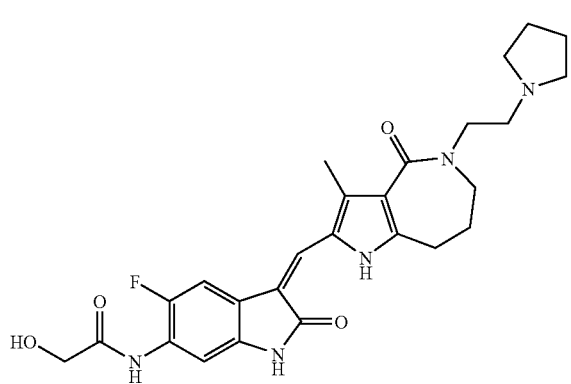

125
-continued

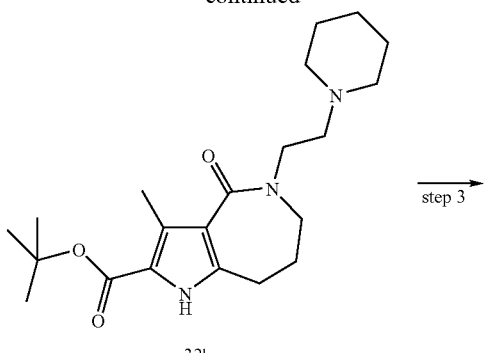

32b

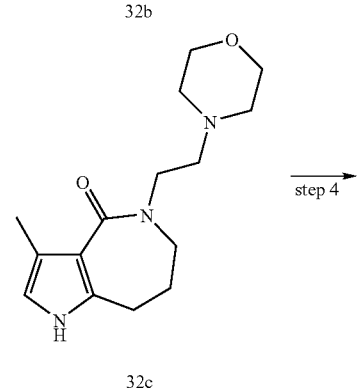

32c

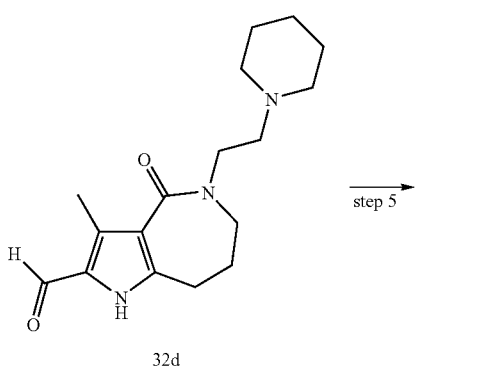

32d

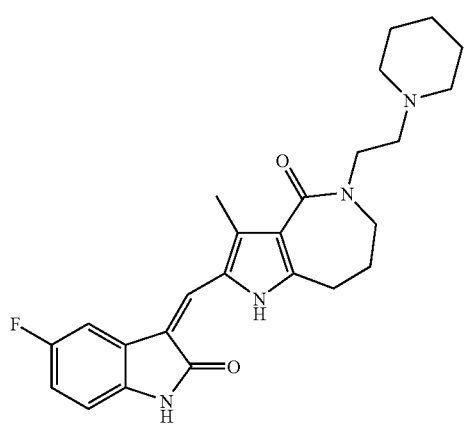

32

126

Step 1

3-Methyl-5-[3-(2-piperidin-1-yl-ethylamino)-propyl]-1H-pyrrole-2,4-dicarboxylic acid 2-tert-butyl ester 4-ethyl ester 5-(3-Methanesulfonyloxy-propyl)-3-methyl-1H-pyrrole-2,4-dicarboxyl is acid 2-tert-butyl ester 4-ethyl ester 1 g (10.64 g, 27.3 mmol) was dissolved in 2-piperidin-1-yl-ethylamine (7 ml, 49.2 mmol), the reaction solution was stirred at room temperature overnight. After thin lay chromatography showed the disappearance of starting materials, the reaction mixture was added with ethyl acetate (200 ml) and a little methanol until a clear solution was obtained. The mixture was washed with water (30 ml×3), the organic phase was washed with saturated brine (40 ml×2), and concentrated under reduced pressure. The residue was purified by silica gel column chromatography to obtain the title compound 3-methyl-5-[3-(2-piperidin-1-yl-ethylamino)-propyl]-1H-pyrrole-2,4-dicarboxylic acid 2-tert-butyl ester 4-ethyl ester 32a (5.35 g, yield 46.5%) as a yellow oil.
MS m/z (ESI): 422.3 [M+1]

Step 2

3-Methyl-4-oxo-5-(2-piperidin-1-yl-ethyl)-1,4,5,6,7,8-hexahydro-pyrrolo[3,2-c]azepine-2-carboxylic acid tert-butyl ester 3-Methyl-5-[3-(2-piperidin-1-yl-ethylamino)-propyl]-1H-pyrrole-2,4-dicarboxylic acid 2-tert-butyl ester 4-ethyl ester 32a (225 mg, 0.534 mmol) was dissolved in 5 ml of dry toluene under stirring, the reaction system was cooled in an ice-water bath, and added with a solution of trimethyl aluminum in toluene (0.534 ml, 2 mol/L, 1.07 mmol) under an argon atmosphere. Upon completion of the addition, the reaction system was stirred for 20 minutes at room temperature until no white smoke was released, refluxed for another 3 hours in an oil bath. After thin lay chromatography showed the disappearance of starting materials, the oil bath was removed, the reaction mixture was added with saturated brine (10 ml) and ethyl acetate (20 ml), stirred for 15 minutes at room temperature and filtered. The filter cake was washed with ethyl acetate (10 ml×3). The filtrate was extracted with ethyl acetate (10 ml×2). The combined organic extracts were washed with saturated brine (10 ml×2), dried over anhydrous magnesium sulfate, filtered to remove the drying agent and concentrated under reduced pressure to obtain the title compound 3-methyl-4-oxo-5-(2-piperidin-1-yl-ethyl)-1,4,5,6,7,8-hexahydro-pyrrolo[3,2-c]azepine-2-carboxylic acid tert-butyl ester 32b (105 mg) as a colorless oil to be used directly in the next step.
MS m/z (ESI): 376.2 [M+1]

Step 3

3-Methyl-5-(2-piperidin-1-yl-ethyl)-5,6,7,8-tetrahydro-1H-pyrrolo[3,2-c]azepin-4-one 3-Methyl-4-oxo-5-(2-piperidin-1-yl-ethyl)-1,4,5,6,7,8-hexahydro-pyrrolo[3,2-c]azepine-2-carboxylic acid tert-butyl ester 32b (953 mg, 2.54 mmol) was dissolved in 3 ml of ethanol under stirring, and added dropwise with hydrochloric acid (3.2 ml, 12 mol/L) in an ice-water bath under an argon atmosphere. Upon completion of the addition, the ice-water bath was removed, and the reaction mixture was stirred at 60° C. in an oil bath for 1 hour. After thin lay chromatography showed the disappearance of starting materials, the reaction mixture was adjusted to about pH 7 with aqueous sodium hydroxide solution (10 mol/L) and concentrated under reduced pressure to evaporate ethanol. The residue was adjusted to pH 10 with aqueous sodium hydroxide solution (10 mol/L), extracted with dichloromethane (20 ml×3). The combined organic extracts were washed with saturated brine (20 ml), dried over anhydrous magnesium sulfate, filtered to remove the drying agent and concentrated under reduced pressure. The residue was purified by silica gel column chromatography to obtain the title compound 3-methyl-5-(2-piperidin-1-yl-ethyl)-5,6,7,8-tetrahydro-1H-pyrrolo[3,2-c]azepin-4-one 32c (395 m, yield 57%) as a white solid.

MS m/z (ESI): 276.1 [M+1]

Step 4

3-Methyl-4-oxo-5-(2-piperidin-1-yl-ethyl)-1,4,5,6,7,8-hexahydro-pyrrolo[3,2-c]azepine-2-carbaldehyde Dichloromethane (36 ml, 559 mmol) and N,N-dimethylformamide (1.637 ml, 20.9 mmol) were stirred for 5 minutes at −15° C. in an ice-salt bath under an argon atmosphere. The solution was added dropwise with phosphorus oxychloride (1.07 ml, 11.5 mmol) and stirred for 15 minutes while maintaining the temperature at −10° C. 3-methyl-5-(2-piperidin-1-yl-ethyl)-5,6,7,8-tetrahydro-1H-pyrrolo[3,2-c]azepin-4-one 32c (1.26 g, 4.58 mmol) was dissolved in 10 ml of dichloromethane, the resulting solution was added dropwise to the above solution. Upon completion of the addition, the ice-salt bath was removed, and the reaction mixture was stirred for 3 hours at room temperature. After thin lay chromatography showed the disappearance of starting materials, the reaction mixture was quenched with iced water, adjusted to about pH 10 with sodium hydroxide solution (10 mol/L) and stirred for 30 minutes, extracted with dichloromethane (30 ml×3). The combined organic extracts were washed with saturated brine (30 ml), dried over anhydrous magnesium sulfate, filtered to remove the drying agent and concentrated under reduced pressure. The residue was purified by silica gel column chromatography to obtain the title compound 3-methyl-4-oxo-5-(2-piperidin-1-yl-ethyl)-1,4,5,6,7,8-hexahydro-pyrrolo[3,2-c]azepine-2-carbaldehyde 32d (993 mg, yield 71.4%) as a light yellow solid.

MS m/z (ESI): 304.1 [M+1]

Step 5

(Z)-2-(5-Fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 3-Methyl-4-oxo-5-(2-piperidin-1-yl-ethyl)-1,4,5,6,7,8-hexahydro-pyrrolo[3,2-c]azepine-2-carbaldehyde 32d (50 mg, 0.165 mmol) and 5-fluoro-1,3-dihydro-indol-2-one (22.4 mg, 0.15 mmol) were dissolved in 0.3 ml of ethanol under stirring, and added with piperidine (0.05 ml, 0.5 mmol) to the solution at room temperature. Upon completion of the addition, the mixture was stirred at 40~50° C. in an oil bath for 5 hours. After thin lay chromatography showed the disappearance of starting materials, the reaction mixture was filtered to obtain yellow solid. The solid was dissolved in ethanol (2 ml), heated to reflux for 30 minutes, cooled down to room temperature and filtered to obtain the title compound (Z)-2-(5-fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 32 (38 g, yield 58%) as a yellow solid.

MS m/z (ESI): 437.1 [M+1]

¹HNMR (400 MHz, DMSO-d6) δ13.720 (s, 1H, pyrrole-NH), 10.900 (s, 1H, indole-NH), 7.749~7.779 (dd, 1H, —ArH), 7.740 (s, 1H, —CH═C), 6.912~6.963 (m, 1H, ArH), 6.834~6.867 (d, 1H, —ArH), 3.539~3.572 (t, 2H, seven-membered ring intra-CH₂N), 3.326~3.354 (t, 2H, amide N seven-membered ring outer-CH₂), 2.922~2.958 (t, 2H, seven-membered ring intra-CH₂C═C), 2.452 (s, 3H, pyrrole-CH₃), 2.386~2.431 (m, 6H, 3×—CH₂N), 2.027~2.091 (t, 2H, seven-membered ring intra-CH₂), 1.474~1.499 (m, 4H, six-membered ring 2×—CH₂), 1.379~1.391 (m, 2H, six-membered ring-CH₂).

Example 33

(Z)-2-[4-(2,3-Difluoro-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one

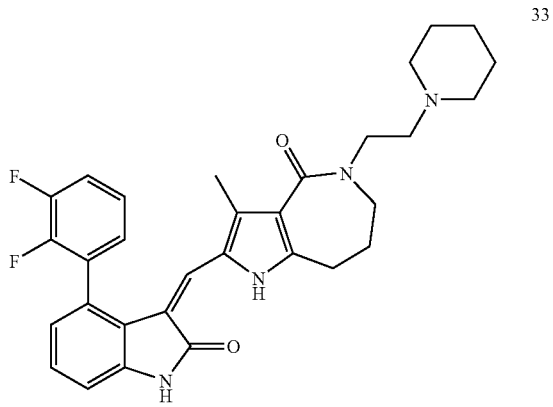

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 4-(2,3-difluoro-phenyl)-1,3-dihydro-indol-2-one 6d obtained from step 3 of Example 6 as starting materials to obtain (Z)-2-[4-(2,3-difluoro-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one 33 (51 mg, yield 80.9%) as a yellow solid.

MS m/z (ESI): 531.2 [M+1]

¹HNMR (400 MHz, DMSO-d6) δ13.540 (s, 1H, pyrrole-NH), 11.130 (s, 1H, indole-NH), 7.618~7.640 (m, 1H, —ArH), 7.429~7.461 (m, 1H, —ArH), 7.306~7.360 (m, 1H, —ArH), 7.232~7.2710 (m, 1H, —ArH), 6.998~7.017 (d, 1H, —ArH), 6.874~6.893 (d, 1H, —ArH), 6.709 (s, 1H, —CH═C), 3.504~3.536 (t, 2H, seven-membered ring intra-CH₂N), 3.289~3.312 (t, 2H, amide N seven-membered ring outer-CH₂), 2.887~2.923 (t, 2H, seven-membered ring intra-CH₂C═C), 2.365~2.417 (m, 6H, 3×—CH₂N), 2.009~2.038 (t, 2H, —CH₂), 1.792 (s, 3H, pyrrole-CH₃), 1.456~1.468 (m, 4H, six-membered ring-2×—CH₂), 1.368~1.377 (m, 2H, six-membered ring-CH₂).

Example 34

(Z)-2-[5-(4-Methoxy-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one

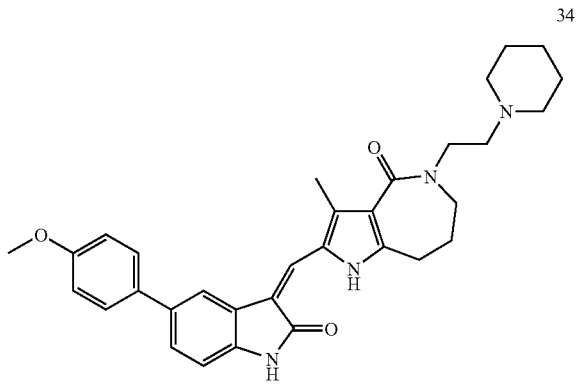

34

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 5-(4-methoxy-phenyl)-1,3-dihydro-indol-2-one as starting materials to obtain (Z)-2-[5-(4-methoxy-phenyl)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one 34 (68 mg, yield 68.7%) as a yellow solid.

MS m/z (ESI): 525.2 [M+1]

$^1$HNMR (400 MHz, DMSO-d6) δ13.653 (s, 1H, pyrrole-NH), 11.003 (s, 1H, indole-NH), 7.930~7.850 (d, 1H, —ArH), 7.668 (s, 1H, —CH=C), 7.583~7.605 (d, 2H, —ArH), 7.251~7.274 (d, 1H, —ArH), 7.017~7.071 (m, 3H, —ArH), 3.804 (s, 3H, —CH$_3$O), 3.541~3.574 (t, 2H, seven-membered ring intra-CH$_2$N), 3.343 (t, 2H, amide N seven-membered ring outer-CH$_2$), 2.926~2.962 (t, 2H, seven-membered ring intra-CH$_2$C=C), 2.386~2.449 (m, 9H, pyrrole-CH$_3$, 3×—CH$_2$N), 2.062 (m, 2H, seven-membered ring intra-CH$_2$), 1.475~1.487 (m, 4H, six-membered ring-2×—CH$_2$), 1.379~1.391 (m, 2H, six-membered ring-CH$_2$).

Example 35

(Z)-2-(5-Chloro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one

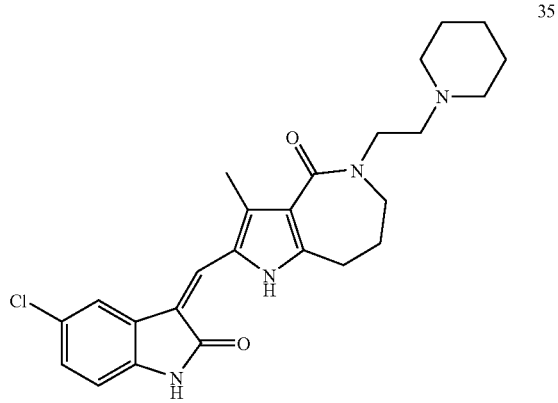

35

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 5-chloro-1,3-dihydro-indol-2-one as starting materials to obtain (Z)-2-(5-chloro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 35 (44 mg, yield 64.8%) as a yellow solid.

MS m/z (ESI): 453.2 [M+1]

$^1$HNMR (400 MHz, DMSO-d6) δ13.674 (s, 1H, pyrrole-NH), 11.003 (s, 1H, indole-NH), 7.989 (s, 1H, —ArH), 7.799 (s, 1H, —CH=C), 7.135~7.155 (d, 1H, —ArH), 6869~6.890 (d, 1H, —ArH), 3.545~3.576 (t, 2H, seven-membered ring intra-CH$_2$N), 3.313~3.342 (t, 2H, amide N seven-membered ring outer-CH$_2$), 2.925~2.962 (t, 2H, seven-membered ring intra-CH$_2$C=C), 2.399~2.459 (m, 9H, pyrrole-CH$_3$, 3 x-CH$_2$N), 2.047~2.074 (t, 2H, seven-membered ring intra-CH$_2$), 1.490 (m, 4H, six-membered ring-2×—CH$_2$), 1.385 (m, 2H, six-membered ring-CH$_2$).

Example 36

(Z)-2-(5-Bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one

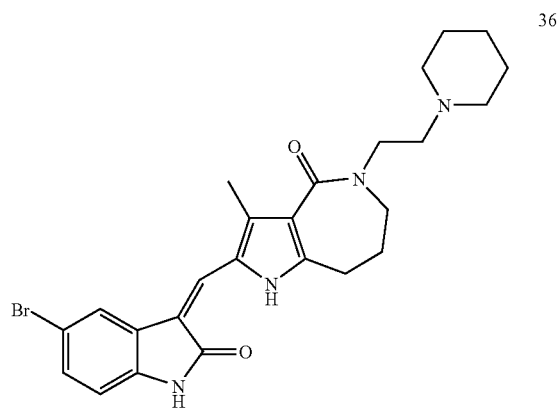

36

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 5-bromo-1,3-dihydro-indol-2-one as starting materials to obtain (Z)-2-(5-bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 36 (43 mg, yield 57.6%) as a yellow solid.

MS m/z (ESI): 497.2 [M+1]

$^1$HNMR (400 MI-1z, DMSO-d6) δ13.670 (s, 1H, pyrrole-NH), 11.010 (s, 1H, indole-NH), 8.114 (s, 1H, —ArH), 7.802 (s, 1H, —CH=C), 7.262~7.283 (d, 1H, —ArH), 6.826~6.846 (d, 1H, —ArH), 3.542~3.574 (t, 2H, seven-membered ring intra-CH$_2$N), 3.315~3.339 (t, 2H, amide N seven-membered ring outer-CH$_2$), 2.924~2.960 (t, 2H, seven-membered ring intra-CH$_2$C=C), 2.389~2.460 (m, 9H, pyrrole-CH$_3$, 3×—CH$_2$N), 2.045~2.074 (t, 2H, seven-membered ring intra-CH$_2$), 1.476~1.489 (m, 4H, six-membered ring-2×—CH$_2$), 1.381 (m, 2l1, six-membered ring-CH$_2$).

Example 37

(Z)—N-{5-Fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide

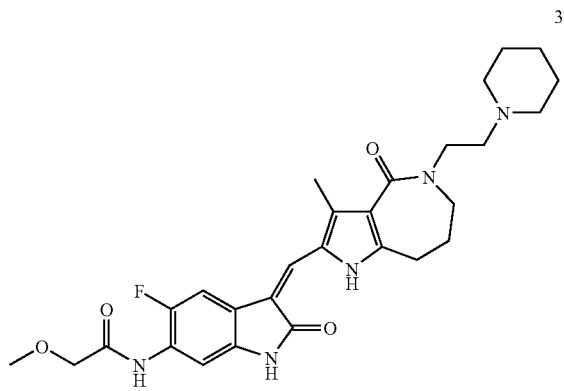

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and N-(5-fluoro-2-oxo-2,3-dihydro-1H-indol-6-yl)-2-methoxy-acetamide 7a obtained from step 1 of Example 7 as starting materials to obtain (Z)—N-{5-fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide 37 (59 mg, yield 75%) as a yellow solid.

MS m/z (ESI): 524.2 [M+1]

$^1$HNMR (400 MHz, DMSO-d6) δ13.613 (s, 1H, pyrrole-NH), 10.890 (s, 1H, indole-NH), 9.316 (s, 1H, —NHCO), 7.835~7.863 (d, 1H, —ArH), 7.668 (s, 1H, —CH═C), 7.542~7.558 (d, 1H, —ArH), 4.064 (s, 2H, —CH$_2$O), 3.540~3.572 (t, 2H, seven-membered ring intra-CH$_2$N), 3.406 (s, 3H, CH$_3$O), 3.315~3.340 (t, 2H, amide N seven-membered ring outer-CH$_2$), 2.918~2.954 (t, 2H, seven-membered ring intra-CH$_2$C═C), 2.390~2.467 (m, 9I~1, pyrrole-CH$_3$, 3×—CH$_2$N), 2.043~2.072 (t, 2H, seven-membered ring intra-CH$_2$), 1.478~1.490 (m, 4H, six-membered ring-2×—CH$_2$), 1.382~1.393 (m, 2H, six-membered ring-CH$_2$).

Example 38

(S,Z)—N-{5-Fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-propionamide

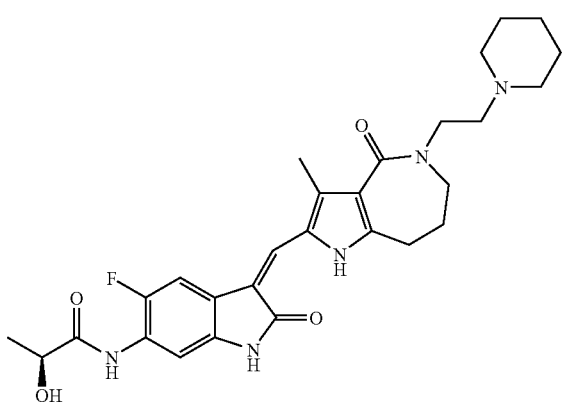

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and N-(5-fluoro-2-oxo-2,3-dihydro-1H-indol-6-yl)-2-hydroxy-propionamide 8b obtained from step 2 of Example 8 as starting materials to obtain (S,Z)—N-{5-fluoro-3-[3-methyl-4-oxo-5-(2-piperidin-1-yl-ethyl)-1,4,5,6,7,8-hexahydro-pyrrolo[3,2-c]azepin-2-ylmethylene]-2-oxo-2,3-dihydro-1H-indol-6-yl}-2-hydroxy-propionamide 38 (49 mg, yield 62.5%) as a yellow solid.

MS m/z (ESI): 524.2 [M+1]

$^1$HNMR (400 MHz, DMSO-d6) δ13.603 (s, 1H, pyrrole-NH), 10.900 (s, 1H, indole-NH), 9.246 (s, 1H, —NH), 7.853~7.881 (d, 1H, —ArH), 7.726~7.743 (d, 1H, —ArH), 7.659 (s, 1H, —CH═C), 6.058~6.070 (d, 1H, —OH), 4.207~4.237 (m, 1H, —CHO), 3.541~3.573 (t, 2H, seven-membered ring intra-CH$_2$N), 3.326~3.354 (t, 2H, amide N seven-membered ring outer-CH$_2$), 2.917~2.954 (t, 2H, seven-membered ring intra-CH$_2$C═C), 2.392~2.440 (m, 9H, pyrrole-CH$_3$, 3×—CH$_2$N), 2.025~2.089 (t, 2H, seven-membered ring intra-CH$_2$), 1.478~1.490 (m, 4H, six-membered ring-2×—CH$_2$), 1.383 (m, 2H, six-membered ring-CH$_2$), 1.330~1.347 (d, 3H, CH$_3$O).

Example 39

(Z)—N-{3-[5-(2-Dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide

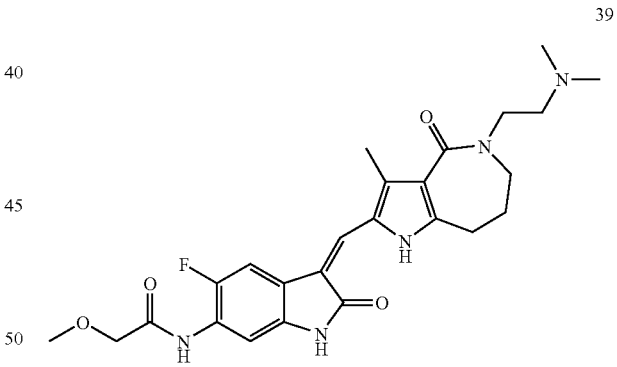

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and N-(5-fluoro-2-oxo-2,3-dihydro-1H-indol-6-yl)-2-methoxy-acetamide 7a obtained from step 1 of Example 7 as starting materials to obtain (Z)—N-{3-[5-(2-dimethylamino-ethyl)-3-methyl-4-oxo-1,4,5,6,7,8-hexahydro-pyrrolo[3,2-c]azepin-2-ylmethylene]-5-fluoro-2-oxo-2,3-dihydro-1H-indol-6-yl}-2-methoxy-acetamide 39 (75 mg, yield 76.5%) as a brown solid.

MS m/z (ESI): 484.1 [M+1]

¹HNMR (400 MHz, DMSO-d6) δ13.607 (s, 1H, pyrrole-NH), 10.894 (s, 1H, —NH), 9.320 (s, 1H, —NHCO), 7.840~7.868 (d, 1H, —ArH), 7.673 (s, 1H, —CH═C), 7.540~7.557 (d, 1H, —ArH), 4.064 (s, 2H, —CH₂O), 3.531~3.564 (t, 2H, N seven-membered ring-CH₂), 3.406 (s, 3H, —CH₃O), 3.333~3.359 (t, 2H, amide N seven-membered ring outer-CH₂), 2.904~2.941 (t, 2H, —CH₂C═C), 2.445 (s, 3H, pyrrole-CH₃), 2.404~2.420 (t, 2H, —CH₂N), 2.206 (s, 6H, 2×—CH₃N), 2.029~2.057 (m, 2H, seven-membered ring intra —CH₂).

Example 40

(Z)-2-[4-(2,6-Difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one

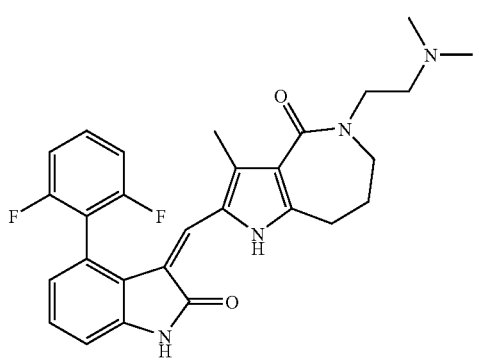

40

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 4-(2,6-difluoro-phenyl)-1,3-dihydro-indol-2-one as starting materials to obtain (Z)-2-[4-(2,6-difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one 40 (36 mg, yield 36.4%) as an orange solid.

MS m/z (ESI): 491.1 [M+1]

¹HNMR (400 MHz, DMSO-d6) δ13.552 (s, 1H, pyrrole-NH), 11.075 (s, 1H, indole-NH), 7.661 (m, 1H, —ArH), 7.338~7.378 (m, 2H, —ArH), 7.238~7.277 (m, 1H, —ArH), 7.008~7.027 (m, 1H, —ArH), 6.895~6.914 (d, 1H, —ArH), 6.652 (s, 1H, —CH═C), 3.488~3.522 (t, 2H, N seven-membered ring-CH₂), 3.280~3.316 (t, 2H, amide N seven-membered ring outer-CH₂), 2.868~2.904 (t, 2H, —CH₂C═C), 2.355~2.388 (t, 2H, —CH₂N), 2.171 (s, 6H, 2×—CH₃N), 1.992~2.021 (m, 2H, seven-membered ring intra-CH₂), 1.764 (s, 3H, pyrrole-CH₃).

Example 41

(Z)-5-(2-Dimethylamino-ethyl)-2-[4-(3-fluoro-phenyl)-2-oxo-1,2-dihydro-indol-3-ylidenemethyl]-3-methyl-5,6,7,8-tetrahydro-1H-pyrrolo[3,2-c]azepin-4-one

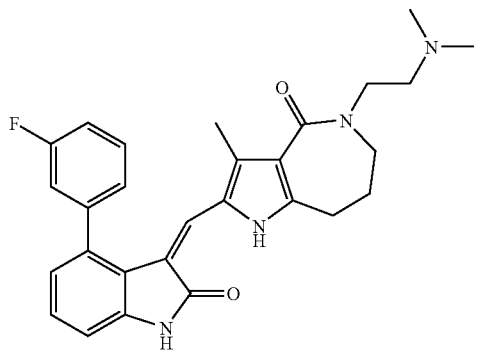

41

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 4-(3-fluoro-phenyl)-1,3-dihydro-indol-2-one as starting materials to obtain (Z)-5-(2-dimethylamino-ethyl)-2-[4-(3-fluoro-phenyl)-2-oxo-1,2-dihydro-indol-3-ylidenemethyl]-3-methyl-5,6,7,8-tetrahydro-1H-pyrrolo[3,2-c]azepin-4-one 41 (37 mg, yield 38.9%) as a yellow solid.

MS m/z (ESI): 473.2 [M+1]

¹HNMR (400 MHz, DMSO-d6) δ13.533 (s, 1H, pyrrole-NH), 11.075 (s, 1H, indole-NH), 7.595~7.610 (m, 1H, —ArH), 7.286~7.343 (m, 3H, —ArH), 7.191~7.229 (m, 1H, —ArH), 6.942~6.962 (d, 1H, —ArH), 6.830~6.844 (d, 1H, —ArH), 6.811 (s, 1H, —CH═C), 3.488~3.521 (t, 2H, N seven-membered ring-CH₂), 3.277~3.315 (t, 2H, amide N seven-membered ring outer-CH₂), 2.859~2.896 (t, 2H, —CH₂C═C), 2.361~2.394 (t, 2H, —CH₂N), 2.176 (s, 6H, 2×—CH₃N), 1.989~2.018 (m, 2H, seven-membered ring intra-CH₂), 1.774 (s, 3H, pyrrole-CH₃).

Example 42

(Z)-2-[4-(2,3-Difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one

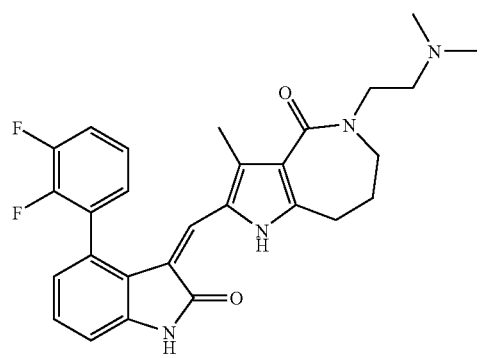

42

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 4-(2,3-difluoro-phenyl)-1,3-dihydro-indol-2-one 6d obtained from step 3 of Example 6 were used as starting materials to obtain (Z)-2-[4-(2,3-difluoro-phenyl)-2-oxo-1,2-dihydro-indol-3-ylidenemethyl]-5-(2-dimethylamino-ethyl)-3-methyl-5,6,7,8-tetrahydro-1H-pyrrolo[3,2-c]azepin-4-one 42 (25 mg, yield 25.2%) as a yellow solid.

MS m/z (ESI): 491.2 [M+1]

$^1$HNMR (400 MHz, DMSO-d6) δ13.532 (s, 1H, pyrrole-NH), 11.132 (s, 1H, indole-NH), 7.618~7.640 (m, 1H, —ArH), 7.429~7.442 (m, 1H, —ArH), 7.306~7.340 (m, 1H, —ArH), 7.232~7.271 (m, 1H, —ArH), 6.998~7.017 (d, 1H, —ArH), 6.874~6.893 (d, 1H, —ArH), 6.712 (s, 1H, —CH=C), 3.491~3.525 (t, 2H, N seven-membered ring-CH$_2$), 3.292~3.315 (t, 2H, amide N seven-membered ring outer-CH$_2$), 2.869~2.905 (t, 2H, —CH$_2$C=C), 2.362~2.395 (t, 2H, —CH$_2$N), 2.176 (s, 6H, 2×—CH$_3$N), 1.993~2.018 (m, 2H, seven-membered ring intra-CH$_2$), 1.795 (s, 3H, pyrrole-CH$_3$).

Example 43

(Z)-5-(2-Dimethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one

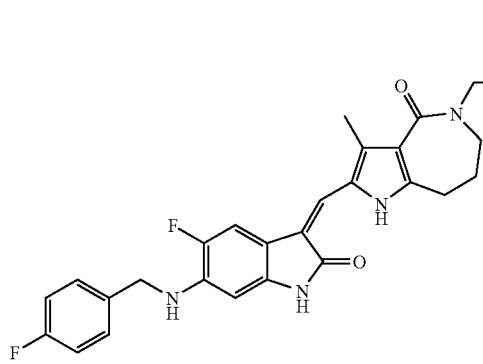

43

The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 5-fluoro-6-(4-fluoro-benzylamino)-1,3-dihydro-indol-2-one 3e obtained from step 4 of Example 3 were used as starting materials to obtain (Z)-5-(2-dimethylamino-ethyl)-2-[5-fluoro-6-(4-fluoro-benzylamino)-2-oxo-1,2-dihydro-indol-3-ylidenemethyl]-3-methyl-5,6,7,8-tetrahydro-1H-pyrrolo[3,2-c]azepin-4-one 43 (50 mg, yield 43.7%) as a red solid.

MS m/z (ESI): 520.1 [M+1]

$^1$HNMR (400 MHz, DMSO-d6) δ13.421 (s, 1H, pyrrole-NH), 10.523 (s, 1H, indole-NH), 7.574~7.603 (d, 1H, —ArH), 7.367~7.402 (m, 2H, —ArH), 7.513 (s, 1H, —CH=C), 7.142~7.186 (m, 2H, —ArH), 6.41 (t, 1H, —NH), 6.041~6.059 (d, 1H, —ArH), 4.348~4.362 (d, 2H, aniline-CH$_2$), 3.982—3.996 (d, 2H, —CH$_2$O), 3.531~3.564 (t, 2H, N seven-membered ring-CH$_2$), 3.316~3.344 (t, 2H, amide N seven-membered ring outer-CH$_2$), 2.856~2.893 (t, 2H, —CH$_2$C=C), 2.398~2.415 (t, 2H, —CH$_2$N), 2.390 (s, 3H, pyrrole-CH$_3$), 2.192 (s, 6H, 2×—CH$_3$N), 2.002~2.030 (m, 2H, seven-membered ring intra-CH$_2$).

Example 44

(Z)—N-{3-[5-(2-Dimethylamino-ethyl)-3-methyl-4-oxo-1,4,5,6,7,8-hexahydro-pyrrolo[3,2-c]azepin-2-ylmethylene]-2-oxo-2,3-dihydro-1H-indol-5-yl}-2-hydroxy-acetamide

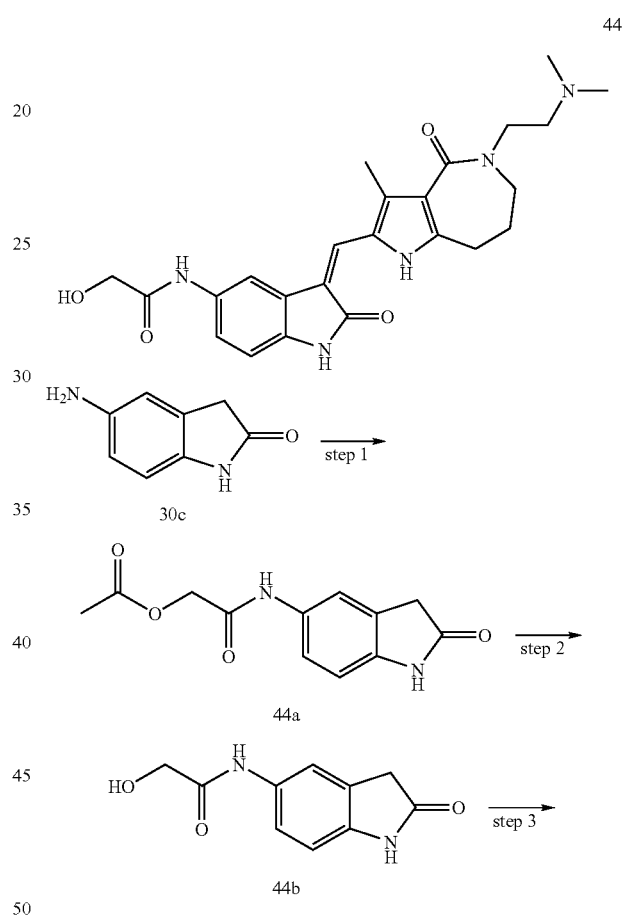

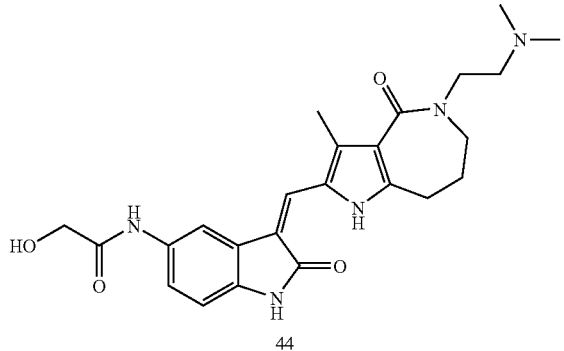

44

Step 1

Acetic acid (2-oxo-2,3-dihydro-1H-indol-5-ylcarbamoyl)-methyl ester

5-Amino-1,3-dihydro-indol-2-one 30c (500 mg, 3.38 mmol) was dissolved in 10 ml of dichloromethane under stirring at room temperature, and pyridine (470 µl, 5 mmol) was added to the solution at −40° C. in a dry ice-acetone bath. Acetic acid chlorocarbonylmethyl ester (473 mg, 3.48 mmol) was dissolved in 10 ml of dichloromethane, the resulting solution was added dropwise to the above reaction solution. Upon completion of the addition, the dry ice-acetone was removed, and the reaction mixture was allowed to warm up to room temperature and stirred overnight. After thin lay chromatography showed the disappearance of starting materials, the reaction mixture was filtered. The filter cake was washed with water (10 ml×3) and recrystallized to obtain the title compound acetic acid (2-oxo-2,3-dihydro-1H-indol-5-ylcarbamoyl)-methyl ester 44a (510 mg, yield 60.7%) as a yellow solid.

MS m/z (ESI): 247.7 [M−1]

Step 2

2-Hydroxy-N-(2-oxo-2,3-dihydro-1H-indol-5-yl)-acetamide

Acetic acid (2-oxo-2,3-dihydro-1H-indol-5-ylcarbamoyl)-methyl ester 44a (2.43 g, 10 mmol) was dissolved in 60 ml of methanol under stirring, and sodium hydroxide solution (20 ml, 2 mol/L) was added to the solution and stirred at room temperature overnight. After thin lay chromatography showed the disappearance of starting materials, the reaction mixture was neutralized with hydrochloric acid solution (6 mol/L) in ice-water bath, concentrated under reduced pressure. The resulting solid was purified by silica gel column chromatography to obtain the title compound 2-hydroxy-N-(2-oxo-2,3-dihydro-1H-indol-5-yl)-acetamide 44b (402 mg, yield 19.5%) as a yellow solid.

MS m/z (ESI): 205.3 [M−1]

Step 3

(Z)-2-Hydroxy-N-{3-[3-methyl-5-(2-methylamino-ethyl)-4-oxo-1,4,5,6,7,8-hexahydro-pyrrolo[3,2-c]azepin-2-ylmethylene]-2-oxo-2,3-dihydro-1H-indol-5-yl}-acetamide The title compound was prepared under the same conditions as described in step 4 of Example 23 with 5-(2-dimethylamino-ethyl)-3-methyl-4-oxo-1,4,5,6,7,8-hexahydro-pyrrolo[3,2-c]azepine-2-carbaldehyde 23c obtained from step 3 of Example 23 and 2-hydroxy-N-(2-oxo-2,3-dihydro-1H-indol-5-yl)-acetamide 44b as starting materials to obtain (Z)-2-hydroxy-N-{3-[3-methyl-5-(2-methylamino-ethyl)-4-oxo-1,4,5,6,7,8-hexahydro-pyrrolo[3,2-c]azepin-2-ylmethylene]-2-oxo-2,3-dihydro-1H-indol-5-yl}-acetamide 44 (52 mg, yield 50.5%) as an orange solid.

MS m/z (ESI): 452.1 [M+1]

$^1$HNMR (400 MHz, DMSO-d6) δ13.658 (s, 1H, pyrrole-NH), 10.857 (s, 1H, —NH), 9.426 (s, 1H, —NHCO), 7.939~7.942 (d, 1H, —ArH), 7.513 (s, 1H, —CH═C), 7.485~7.489 (d, 1H, —ArH), 6.820~6.841 (d, 1H, —ArH), 5.717 (s, 1H, —HO), 3.982~3.996 (d, 2H, —CH$_2$O), 3.531~3.564 (t, 2H, N seven-membered ring-CH$_2$), 3.337~3.365 (t, 2H, amide N seven-membered ring outer-CH$_2$), 2.908~2.944 (t, 2H, —CH$_2$C═C), 2.433 (s, 3H, pyrrole-CH$_3$), 2.394~2.411 (t, 2H, —CH$_2$N), 2.199 (s, 6H, 2×—CH$_3$N), 2.031~2.059 (m, 2H, seven-membered ring intra-CH$_2$).

Example 45

(Z)-2-(5-Fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one

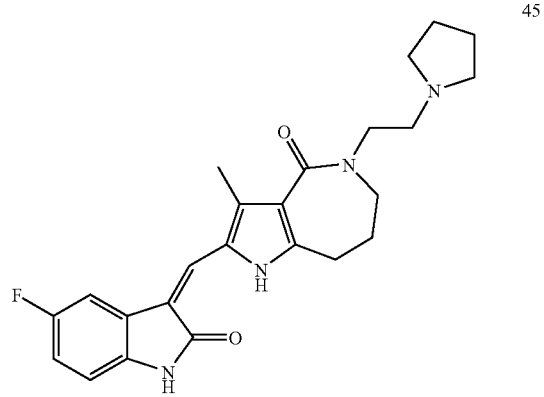

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 5-fluoro-1,3-dihydro-indol-2-one as starting materials to obtain (Z)-2-(5-fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one 45 (61 mg, yield 80.8%) as an orange solid.

MS m/z (ESI): 423.1 [M+1]

$^1$HNMR (400 MHz, DMSO-d6) δ13.715 (s, 1H, pyrrole-NH), 10.902 (s, 1H, indole-NH), 7.752~7.782 (m, 1H, —ArH), 7.743 (s, 1H, —CH═C), 6.937~6.965 (m, 1H, —ArH), 6.835~6.867 (d, 1H, —ArH), 3.548~3.582 (t, 2H, seven-membered ring intra-CH$_2$N), 3.337~3.365 (t, 2H, amide N seven-membered ring outer-CH$_2$), 3.314 (m, 4H, five-membered ring-2×—CH$_2$N), 2.990~3.027 (t, 2H, seven-membered ring intra-CH$_2$C═C), 2.573~2.607 (t, 2H, —CH$_2$N), 2.473 (s, 3H, pyrrole-CH$_3$), 2.101~2.129 (m, 2H, seven-membered ring intra-CH$_2$), 1.751 (m, 4H, five-membered ring-CH$_2$).

Example 46

(Z)-2-(5-Bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one

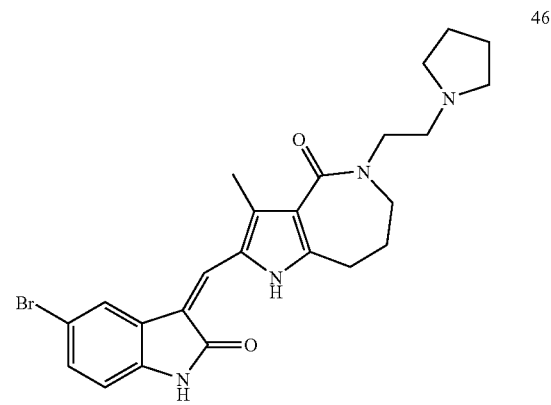

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 5-bromo-1,3-dihydro-indol-2-one as starting materials to obtain (Z)-2-(5-bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one 46 (61 mg, yield 70.4%) as a yellow solid.

MS m/z (ESI): 485.1 [M+1]

¹HNMR (400 MHz, DMSO-d6) δ13.664 (s, 1H, pyrrole-NH), 11.007 (s, 1H, indole-NH), 8.113~8.114 (d, 1H, —ArH), 7.803 (s, 1H, —CH═C), 7.261~7.286 (m, 1H, —ArH), 6.825~6.846 (d, 1H, —ArH), 3.548~3.582 (t, 2H, seven-membered ring intra-CH₂N), 3.337~3.364 (t, 2H, amide N seven-membered ring outer-CH₂), 3.312 (m, 4H, five-membered ring-2×—CH₂N), 2.905~2.942 (t, 2H, seven-membered ring intra-CH₂C═C), 2.573~2.606 (t, 2H, —CH₂N), 2.462 (s, 3H, pyrrole-CH₃), 2.028~2.057 (m, 2H, seven-membered ring intra-CH₂), 1.751 (m, 4H, five-membered ring-CH₂).

Example 47

(Z)-2-(5-Chloro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one

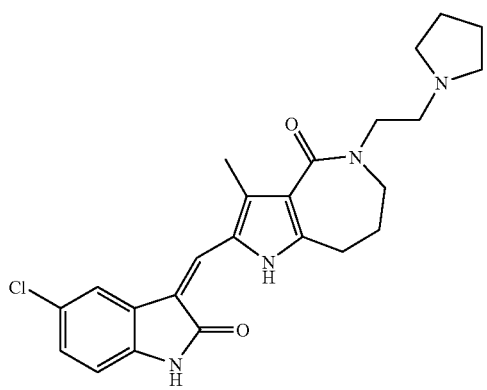

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 5-chloro-1,3-dihydro-indol-2-one as starting materials to obtain (Z)-2-(5-chloro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one 47 (61 mg, yield 77.7%) as a yellow solid.

MS m/z (ESI): 439.2 [M+1]

¹HNMR (400 MHz, DMSO-d6) δ13.714 (s, 1H, pyrrole-NH), 11.046 (s, 1H, indole-NH), 8.038 (s, 1H, —CH═C), 7.838~7.845 (d, 1H, —ArH), 7.179~7.205 (dd, 1H, —ArH), 6.915~6.935 (d, 1H, —ArH), 3.612~3.629 (t, 2H, seven-membered ring intra-CH₂N), 3.384~3.412 (t, 2H, amide N seven-membered ring outer-CH₂), 3.337~3.384 (m, 4H, five-membered ring-2×—CH₂N), 2.990~3.027 (t, 2H, seven-membered ring intra-CH₂C═C), 2.650~2.684 (t, 2H, —CH₂N), 2.473 (s, 3H, pyrrole-CH₃), 2.101~2.129 (m, 2H, seven-membered ring intra-CH₂), 1.751 (m, 4H, five-membered ring-CH₂).

Example 48

(Z)-3-Methyl-2-(2-oxo-5-phenyl-1,2-dihydro-indol-3-ylidenemethyl)-5-(2-pyrrolidin-1-yl-ethyl)-5,6,7,8-tetrahydro-1H-pyrrolo[3,2-c]azepin-4-one

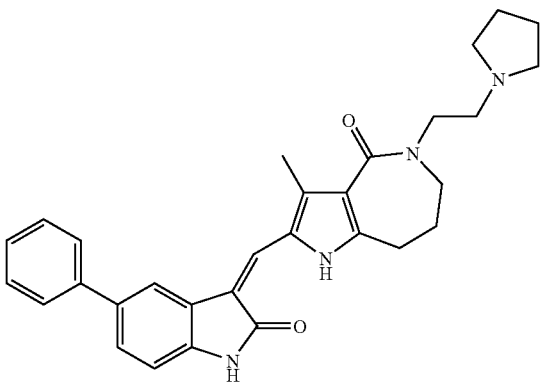

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 5-phenyl-1,3-dihydro-indol-2-one as starting materials to obtain (Z)-3-methyl-2-(2-oxo-5-phenyl-1,2-dihydro-indol-3-ylidenemethyl)-5-(2-pyrrolidin-1-yl-ethyl)-5,6,7,8-tetrahydro-1H-pyrrolo[3,2-c]azepin-4-one 48 (41 mg, yield 62.3%) as a yellow solid.

MS m/z (ESI): 481.2 [M+1]

¹HNMR (400 MHz, DMSO-d6) δ13.706 (s, 1H, pyrrole-NH), 10.070 (s, 1H, indole-NH), 8.174 (s, 1H, —CH═C), 7.843 (s, 1H, —ArH), 7.722~7.741 (d, 2H, —ArH), 7.443~7.480 (m, 3H, —ArH), 7.314~7.351 (t, 1H, —ArH), 6.961~6.981 (d, 1H, —ArH), 3.554~3.588 (t, 2H, seven-membered ring intra-CH₂N), 3.362~3.376 (t, 2H, amide N seven-membered ring outer-CH₂), 3.289~3.347 (m, 4H, five-membered ring-2×—CH₂N), 2.990~3.027 (t, 2H, seven-membered ring intra-CH₂C═C), 2.650~2.684 (t, 2H, —CH₂N), 2.473 (s, 3H, pyrrole-CH₃), 2.101~2.129 (m, 2H, seven-membered ring intra-CH₂), 1.751 (m, 4H, five-membered ring-2×—CH₂).

Example 49

(Z)-2-(4-Bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one

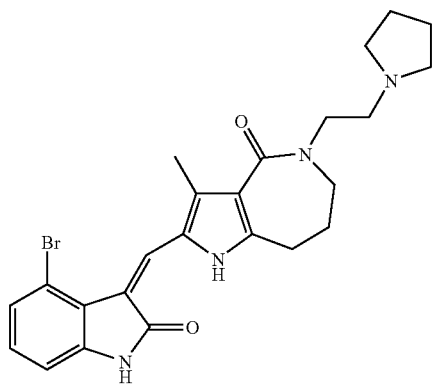

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 4-bromo-1,3-dihydro-indol-2-one as starting materials to obtain (Z)-2-(4-bromo-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one 49 (40 mg, yield 60.5%) as a yellow solid.

MS m/z (ESI): 483.2 [M−1]

$^1$HNMR (400 MHz, DMSO-d6) δ13.697 (s, 1H, pyrrole-NH), 11.244 (s, 1H, indole-NH), 8.650 (s, 1H, —CH═C), 7.281~7.301 (d, 1H, —ArH), 7.118~7.158 (m, 1H, —ArH), 7.000~7.190 (d, 1H, —ArH), 3.6183.652 (t, 2H, seven-membered ring intra-CH$_2$N), 3.410~3.438 (t, 2H, amide N seven-membered ring outer-CH$_2$), 3.356~3.378 (m, 4H, five-membered ring-2 x-CH$_2$N), 2.990~3.027 (t, 2H, seven-membered ring intra-CH$_2$C═C), 2.650~2.684 (t, 2H, —CH$_2$N), 2.473 (s, 3H, pyrrole-CH$_3$), 2.101~2.129 (m, 2H, seven-membered ring intra-CH$_2$), 1.751 (m, 4H, five-membered ring-CH$_2$).

Example 50

(Z)-2-(7-Bromo-5-fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one

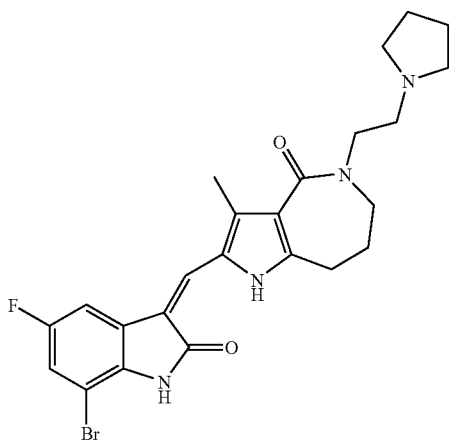

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and 7-bromo-5-fluoro-1,3-dihydro-indol-2-one 4b obtained from step 1 of Example 4 as starting materials to obtain (Z)-2-(7-bromo-5-fluoro-2-oxo-1,2-dihydro-indol-3-ylidenemethyl)-3-methyl-5-(2-pyrrolidin-1-yl-ethyl)-5,6,7,8-tetrahydro-1H-pyrrolo[3,2-c]azepin-4-one 50 (51 mg, yield 73.2%) as an orange solid.

MS m/z (ESI): 501.1 [M+1]

$^1$HNMR (400 MHz, DMSO-d6) δ13.660 (s, 1H, pyrrole-NH), 11.177 (s, 1H, indole-NH), 7.857~7.875 (d, 1H, —ArH), 7.798 (s, 1H, —CH═C), 7.251~7.269 (d, 1H, —ArH), 3.556~3.590 (t, 2H, seven-membered ring intra-CH$_2$N), 3.317~3.359 (t, 2H, amide N seven-membered ring outer-CH$_2$), 3.294~3.359 (m, 4H, five-membered ring-2x—CH$_2$N), 2.935~2.971 (t, 2H, seven-membered ring intra-CH$_2$C═C), 2.587~2.620 (t, 2H, —CH$_2$N), 2.473 (s, 3H, pyrrole-CH$_3$), 2.059 (m, 2H, seven-membered ring intra—CH$_2$), 1.751 (m, 4H, five-membered ring-CH$_2$).

Example 51

(Z)—N-{3-[5-(2-Diethylamino-ethyl)-3-methyl-4-oxo-1,4,5,6,7,8-hexahydro-pyrrolo[3,2-c]azepin-2-ylmethylene]-2-oxo-2,3-dihydro-1H-indol-5-yl}-acetamide

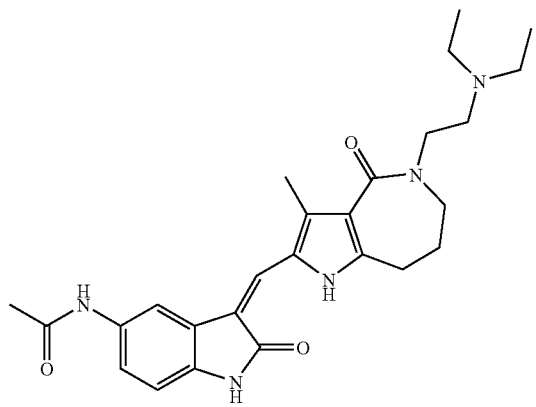

The title compound was prepared under the same conditions as described in step 10 of Example 1 with 5-(2-diethylamino-ethyl)-3-methyl-4-oxo-1,4,5,6,7,8-hexahydro-pyrrolo[3,2-c]azepine-2-carbaldehyde 1j obtained from step 9 of Example 1 and N-(2-oxo-2,3-dihydro-1H-indol-5-yl)-acetamide 30d obtained from step 3 of Example 30 as starting materials to obtain (Z)—N-{3-[5-(2-diethylamino-ethyl)-3-methyl-4-oxo-1,4,5,6,7,8-hexahydro-pyrrolo[3,2-c]azepin-2-ylmethylene]-2-oxo-2,3-dihydro-1H-indol-5-yl}-acetamide 51 (12 mg, yield 18.9%) as an orange solid.

MS m/z (ESI): 464.2 [M+1]

$^1$HNMR (400 MHz, DMSO-d6) δ13.679 (s, 1H, pyrrole-NH), 10.868 (s, 1H, indole-NH), 9.806 (s, 1H, amide-NH), 7.841 (s, 1H, —ArH), 7.472 (s, 1H, —CH═C), 7.251~7.256 (d, 1H, —ArH), 6.806~6.827 (s, 1H, —ArH), 3.499 (t, 2H, seven-membered ring intra-CH$_2$N), 3.322~3.347 (t, 2H, amide N seven-membered ring outer-CH$_2$), 2.902~2.939 (t, 2H, seven-membered ring intra-CH$_2$C═C), 2.530~2.562 (m, 6H, 3×—CH$_2$N), 2.423 (s, 3H, pyrrole-CH$_3$), 2.029~2.051 (m, 2H, seven-membered ring intra-CH$_2$), 2.029 (s, 3H, —CH$_3$CO), 0.958~0.993 (t, 6H, 2×—CH$_3$).

Example 52

(Z)—N-{5-Fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide

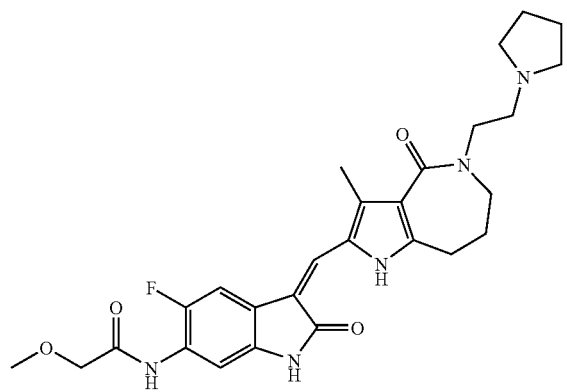

The title compound was prepared under the same conditions as described in step 4 of Example 28 with 3-methyl-4-oxo-5-(2-pyrrolidin-1-yl-ethyl)-1,4,5,6,7,8-hexahydro-pyrrolo[3,2-c]azepine-2-carbaldehyde 28c obtained from step 3 of Example 28 and N-(5-fluoro-2-oxo-2,3-dihydro-1H-indol-6-yl)-2-methoxy-acetamide 7a obtained from step 1 of Example 7 as starting materials to obtain (Z)—N-{5-fluoro-3-[3-methyl-4-oxo-5-(2-pyrrolidin-1-yl-ethyl)-1,4,5,6,7,8-hexahydro-pyrrolo[3,2-c]azepin-2-ylmethylene]-2-oxo-2,3-dihydro-1H-indol-6-yl}-2-methoxy-acetamide 52 (45 mg, yield 63.7%) as a yellow solid.

MS m/z (ESI): 510.1 [M+1]

¹HNMR (400 MHz, DMSO-d6) δ13.652 (s, 1H, pyrrole-NH), 10.936 (s, 1H, indole-NH), 9.362 (s, 1H, —NHCO), 7.882~7.910 (d, 1H, —ArH), 7.714 (s, 1H, —CH═C), 7.582~7.598 (d, 1H, —ArH), 4.110 (s, 2H, —CH₂O), 3.597~3.631 (t, 2H, seven-membered ring intra-CH₂N), 3.447 (s, 3H, —CH₃O), 3.381~3.408 (t, 2H, amide N seven-membered ring outer-CH₂), 3.331~3.355 (m, 4H, five-membered ring-2×—CH₂N), 2.945~2.981 (t, 2H, seven-membered ring intra-CH₂C═C), 2.660 (m, 2H, —CH₂N), 2.489 (s, 3H, pyrrole-CH₃), 2.069~2.099 (m, 2H, seven-membered ring intra-CH₂), 1.731 (m, 4H, five-membered ring-CH₂).

Example 53

(R,Z)-2-(5-Fluoro-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one

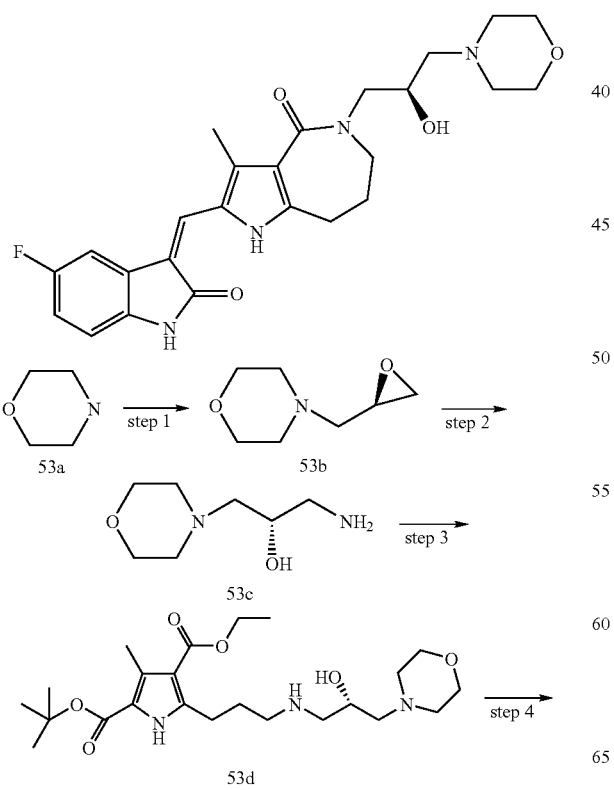

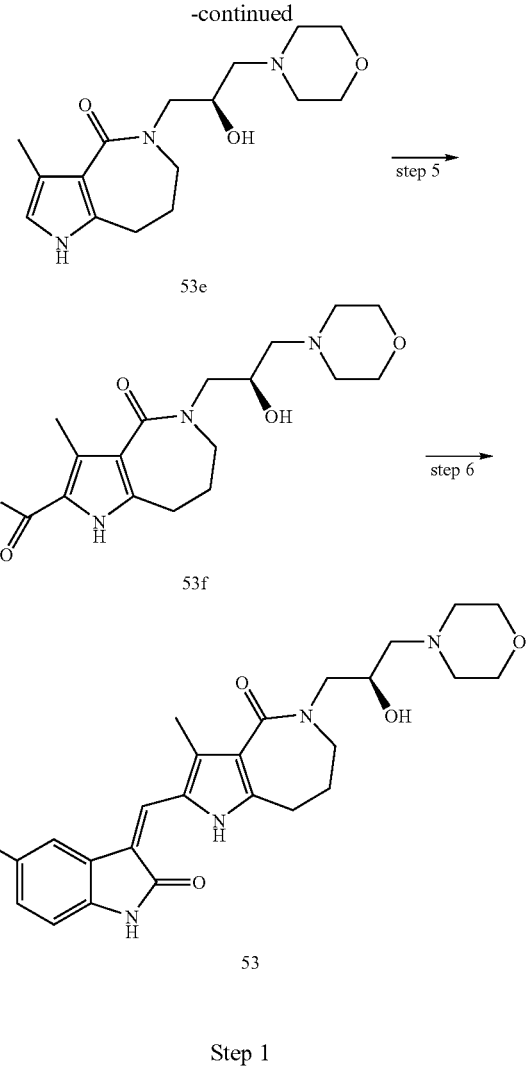

Step 1

4-Oxiranylmethyl-morpholine

Morpholine 53a (8.712 ml, 0.1 mol) was dissolved in tert-butanol (4.5 ml) under stirring at room temperature, and (R)-(−)-1-chloro-2,3-epoxypropane (8.05 ml, 0.1 mol) was added slowly to the solution at 0° C. in an ice-water bath. Upon completion of the addition, the ice-water bath was removed, and the reaction mixture was allowed to warm up to room temperature and stirred for 24 hours. After thin lay chromatography showed the disappearance of starting materials, the reaction mixture was added dropwise with a solution of potassium tert-butoxide in tetrahydrofuran (60 ml, 1.67 mol/L, 100 mmol) while maintaining the temperature below 10° C. in an ice-water bath, gradually turned from light yellow to white turbid solution and stirred for 30 minutes. After thin lay chromatography showed the disappearance of starting materials, the reaction mixture was concentrated under reduced pressure, added with water (50 ml), exacted with dichloromethane (100 ml×2). The combined organic extracts were washed with saturated brine (100 ml), dried over anhydrous magnesium sulfate, filtered to remove the drying agent and concentrated under reduced pressure to obtain the title compound 4-oxiranylmethyl-morpholine 53b (12.7 g, yield 88.8%) as a yellow oil.

MS m/z (ESI): 144.4 [M+1]

Step 2

1-Amino-3-morpholin-4-yl-propan-2-ol

4-Oxiranylmethyl-morpholine 53b (6.3 g, 44 mmol) was added slowly with ammonia (450 ml, 25%, 6.6 mol) while maintaining the temperature below 0° C. in an ice-water bath. Upon completion of the addition, the reaction mixture was allowed to warm up to room temperature and stirred for 18 hours. After thin lay chromatography showed the disappearance of starting materials, the reaction mixture was concentrated under reduced pressure to obtain the title compound 1-amino-3-morpholin-4-yl-propan-2-ol 53c (7 g, yield 99%) as a white solid.

MS m/z (ESI): 161.1 [M+1]

Step 3

5-[3-(2-Hydroxy-3-morpholin-4-yl-propylamino)-propyl]-3-methyl-1H-pyrrole-2,4-dicarboxylic acid 2-tert-butyl ester 4-ethyl ester 5-(3-methanesulfonyloxy-propyl)-3-methyl-1H-pyrrole-2,4-dicarboxylic acid 2-tert-butyl ester 4-ethyl ester 1g (1.13 g, 2.9 mmol) was dissolved in 5.6 ml of dichloromethane under stirring, and 1-amino-3-morpholin-4-yl-propan-2-ol 53c (0.93 g, 5.8 mmol) was added to the solution at room temperature. Upon completion of the addition, the reaction mixture was stirred at room temperature overnight and heated for 14 hours at 45° C. in an oil bath. After thin lay chromatography showed the disappearance of starting materials, the reaction mixture was added with saturated brine (15 ml), exacted with dichloromethane (20 ml×3). The combined organic extracts were concentrated under reduced pressure, purified by silica gel column chromatography to obtain the title compound 5-[3-(2-hydroxy-3-morpholin-4-yl-propylamino)-propyl]-3-methyl-1H-pyrrole-2,4-dicarboxylic acid 2-tert-butyl ester 4-ethyl ester 53d (600 mg, yield 72.5%) as a colorless oil.

MS m/z (ESI): 454.2 [M+1]

Step 4

5-(2-Hydroxy-3-morpholin-4-yl-propyl)-3-methyl-5,6,7,8-tetrahydro-1H-pyrrolo[3,2-c]azepin-4-one 5-[3-(2-hydroxy-3-morpholin-4-yl-propylamino)-propyl]-3-methyl-1H-pyrrole-2,4-dicarboxylic acid 2-tert-butyl ester 4-ethyl ester 53d (580 mg, 1.28 mmol) was dissolved in 6 ml of toluene under stirring, and trimethyl aluminum in toluene (1.9 ml, 2 mol/L, 3.84 mmol) was added dropwise in an ice-water bath under an argon atmosphere. Upon completion of the addition, the ice-water bath was removed, and the reaction mixture was heated to reflux for 24 hours. After thin lay chromatography showed the disappearance of starting materials, the reaction mixture was concentrated under reduced pressure, added with hydrochloric acid solution (20 ml, 6 mol/L) and stirred for 20 minutes at room temperature. The mixture was adjusted to about pH 12 with aqueous sodium hydroxide solution (12 mol/L) in an ice-water bath and extracted with dichloromethane (50 ml×2). The combined organic extracts were concentrated under reduced pressure, purified by silica gel column chromatography to obtain the title compound 5-(2-hydroxy-3-morpholin-4-yl-propyl)-3-methyl-5,6,7,8-tetrahydro-1H-pyrrolo[3,2-c]azepin-4-one 53e (300 mg, yield 57.6%) as a white solid.

MS m/z (ESI): 308.2 [M+1]

Step 5

5-(2-Hydroxy-3-morpholin-4-yl-propyl)-3-methyl-4-oxo-1,4,5,6,7,8-hexahydro-pyrrolo[3,2-c]azepine-2-carbaldehyde (Chloromethylene)dimethylammoniumchloride (130 mg, 0.977 mmol) was dissolved in 3 ml of dichloromethane under stirring, the resulting solution was cooled down to 0° C. in ice-water bath under an argon atmosphere. 5-(2-Hydroxy-3-morpholin-4-yl-propyl)-3-methyl-5,6,7,8-tetrahydro-1H-pyrrolo[3,2-c]azepin-4-one 53e (300 mg, 0.977 mmol) was dissolved in 2 ml of dichloromethane, the resulting solution was added dropwise to the above reaction system while maintaining the temperature below 0° C. and stirred for 20 minutes. After thin lay chromatography showed the disappearance of starting materials, the reaction mixture was quenched with aqueous sodium hydroxide solution (12 mol/L), added with saturated brine (10 ml), extracted with the solvent mixture (V:V=10:1, 100 ml×3) of dichloromethane and methanol. The combined organic extracts were washed with saturated brine (100 ml), dried over anhydrous magnesium sulfate, filtered to remove the drying agent and concentrated under reduced pressure. The residue was purified by silica gel column chromatography to obtain the title compound 5-(2-hydroxy-3-morpholin-4-yl-propyl)-3-methyl-4-oxo-1,4,5,6,7,8-hexahydro-pyrrolo[3,2-c]azepine-2-carbaldehyde 53f (200 mg, yield 61%) as a white solid.

MS m/z (ESI): 336.2 [M+1]

Step 6

(R,Z)-2-(5-Fluoro-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one 5-(2-Hydroxy-3-morpholin-4-yl-propyl)-3-methyl-4-oxo-1,4,5,6,7,8-hexahydro-pyrrolo[3,2-c]azepine-2-carbaldehyde 53f (50 mg, 0.149 mmol) was dissolved in 261 μl of ethanol under stirring, and added with 5-fluoro-1,3-dihydro-indol-2-one (20.28 mg, 0.134 mmol) and piperidine (7.3 μl, 0.074 mmol) to the solution at room temperature. Upon completion of the addition, the reaction mixture was stirred for 2 hours in dark at 80° C. in an oil bath. After thin lay chromatography showed the disappearance of starting materials, the oil bath was removed, and the reaction mixture was naturally cooled down to room temperature, filtered and dried to obtain the title compound (R,Z)-2-(5-fluoro-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one 53 (40 g, yield 57%) as a yellow solid.

MS m/z (ESI): 469.2 [M+1]

$^1$HNMR (400 MHz, DMSO-d6) δ13.725 (s, 1H, pyrrole-NH), 10.907 (s, 1H, indole-NH), 7.760~7.783 (m, 1H, —ArH), 7.747 (s, 1H, —CH=C), 6.914~6.939 (m, 1H, —ArH), 6.835~6.867 (m, 1H, —ArH), 4.719~4.731 (d, 1H, —OH), 3.897 (m, 1H, —CHO), 3.749~3.792 (dd, 1H, amide N seven-membered ring outer-CH$_2$), 3.570~3.592 (t, 4H, morpholine-2×—CH$_2$O), 3.384~3.351 (t, 2H, N seven-membered ring-CH$_2$), 3.138~3.191 (dd, 1H, amide N seven-membered ring outer-CH$_2$), 2.917~2.953 (t, 2H, —CH$_2$C=C), 2.457 (s, 3H, pyrrole-CH$_3$), 2.418~2.507 (m, 4H, —CH$_2$N, morpholine-CH$_2$N), 2.289~2.313 (t, 2H, morpholine-CH$_2$N), 2.076 (m, 2H, seven-membered ring-CH$_2$).

Example 54

(Z)-3-Methyl-2-(2-oxo-4-pyridin-4-yl-1,2-dihydro-indol-3-ylidenemethyl)-5-(2-piperidin-1-yl-ethyl)-5,6,7,8-tetrahydro-1H-pyrrolo[3,2-c]azepin-4-one

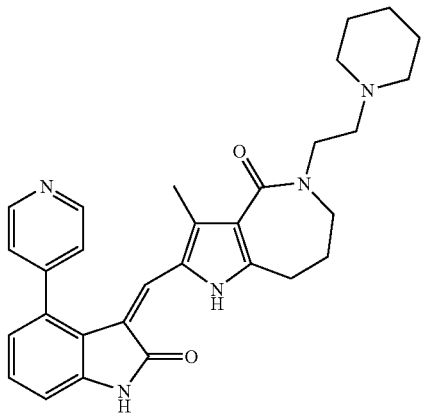

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 4-pyridin-4-yl-1,3-dihydro-indol-2-one as starting materials to obtain (Z)-3-methyl-2-(2-oxo-4-pyridin-4-yl-1,2-dihydro-indol-3-ylidenemethyl)-5-(2-piperidin-1-yl-ethyl)-5,6,7,8-tetrahydro-1H-pyrrolo[3,2-c]azepin-4-one 54 (40 mg, yield 54%) as a yellow solid.

MS m/z (ESI): 496.2 [M+1]

¹HNMR (400 MHz, DMSO-d6) δ13.530 (s, 1H, pyrrole-NH), 11.115 (s, 1H, indole-NH), 8.738~8.753 (d, 2H, —CH═N), 7.498 (s, 2H, pyridine-CH═C), 7.219~7.258 (m, 1H, —ArH), 6.976~6.996 (d, 1H, —ArH), 6.808~6.830 (d, 1H, —ArH), 6.808 (s, 1H, —CH═C), 3.499~3.532 (t, 2H, seven-membered ring intra-CH₂N), 3.270~3.298 (t, 2H, amide N seven-membered ring outer-CH₂), 2.879~2.916 (t, 2H, seven-membered ring intra-CH₂C═C), 2.361~2.413 (m, 6H, 3×—CH₂N), 2.055~2.084 (t, 2H, seven-membered ring intra-CH₂), 1.732 (s, 3H, pyrrole-CH₃), 1.453~1.478 (m, 4H, six-membered ring-2×—CH₂), 1.365~1.377 (m, 2H, six-membered ring-CH₂).

Example 55

(Z)-2-[5-Fluoro-6-(4-fluoro-benzylamino)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-one

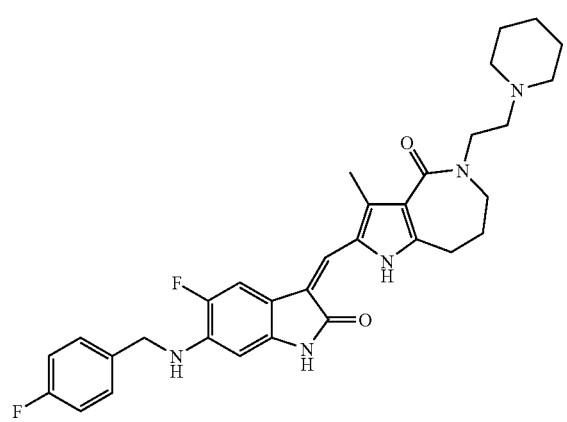

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 5-fluoro-6-(4-fluoro-benzylamino)-1,3-dihydro-indol-2-one 3e obtained from step 4 of Example 3 as starting materials to obtain (Z)-2-[5-fluoro-6-(4-fluoro-benzylamino)-2-oxo-1,2-dihydro-indol-3-ylidenemethyl]-3-methyl-5-(2-piperidin-1-yl-ethyl)-5,6,7,8-tetrahydro-1H-pyrrolo[3,2-c]azepin-4-o ne 55 (77 mg, yield 90.8%) as a yellow solid.

MS m/z (ESI): 560.1 [M+1]

¹HNMR (400 MHz, DMSO-d6) δ13.425 (s, 1H, pyrrole-NH), 10.520 (s, 1H, —NH), 7.572~7.602 (d, 1H, —ArH), 7.349 (s, 1H, —CH═C), 7.367~7.402 (m, 2H, —ArH), 7.141~7.186 (m, 2H, —ArH), 6.398~6.422 (m, 1H, —NH), 6.040~6.059 (m, 1H, —ArH), 4.347~4.361 (d, 2H, aniline-CH₂), 3.524~3.557 (t, 2H, seven-membered ring intra-CH₂N), 3.314~3.337 (t, 2H, amide N seven-membered ring outer-CH₂), 2.869~2.906 (t, 2H, seven-membered ring intra-CH₂C═C), 2.390~2.467 (m, 9H, pyrrole-CH₃, 3×—CH₂N), 1.999~2.063 (t, 2H, seven-membered ring intra-CH₂), 1.476~1.489 (m, 4H, six-membered ring-2×—CH₂), 1.383~1.393 (m, 2H, six-membered ring-CH₂).

Example 56

(Z)-2-(7-Bromo-5-fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one

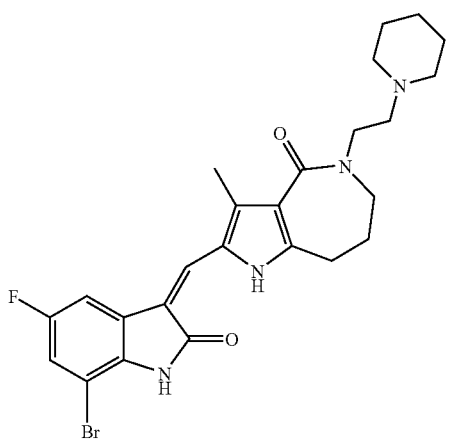

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 7-bromo-5-fluoro-1,3-dihydro-indol-2-one 4b obtained from step 1 of Example 4 as starting materials to obtain (Z)-2-(7-bromo-5-fluoro-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 56 (63 mg, yield 76.44%) as a yellow solid.

MS m/z (ESI): 515.1 [M+1]

¹HNMR (400 MHz, DMSO-d6) δ13.661 (s, 1H, pyrrole-NH), 11.184 (s, 1H, indole-NH), 7.848~7.876 (dd, 1H, —ArH), 7.794 (s, 1H, —CH=C), 7.242~7.240 (dd, 1H, —ArH), 3.545~3.571 (t, 2H, amide N seven-membered ring intra-CH$_2$), 3.331~3.358 (t, 2H, amide N seven-membered ring outer-CH$_2$), 2.950~2.986 (t, 2H, seven-membered ring intra-CH$_2$C=C), 2.390~2.467 (m, 9H, pyrrole-CH$_3$, 3×—CH$_2$N), 2.055~2.084 (t, 2H, seven-membered ring intra-CH$_2$), 1.476~1.489 (m, 4H, six-membered ring-2×—CH$_2$), 1.383~1.393 (m, 2H, six-membered ring-CH$_2$).

Example 57

(Z)-2-(4-Bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one

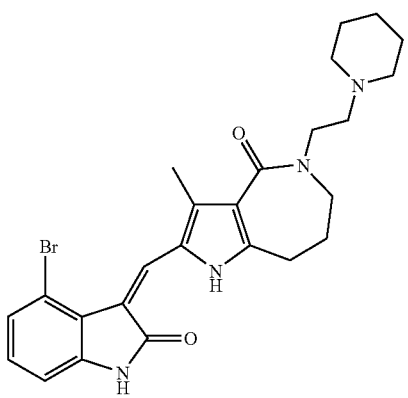

57

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 4-bromo-1,3-dihydro-indol-2-one as starting materials to obtain (Z)-2-(4-bromo-2-oxo-1,2-dihydro-indol-3-ylidenemethyl)-3-methyl-5-(2-piperidin-1-yl-ethyl)-5,6,7,8-tetrahydro-1H-pyrrolo[3,2-c]azepin-4-one 57 (68 mg, yield 91.2%) as a yellow solid.

MS m/z (ESI): 499.1 [M+1]

¹HNMR (400 MHz, DMSO-d6) δ13.682 (s, 1H, pyrrole-NH), 11.232 (s, 1H, indole-NH), 8.634 (s, 1H, —CH=C), 7.267~7.287 (m, 1H, —ArH), 7.105~7.144 (m, 1H, —ArH), 6.988~7.007 (d, 1H, —ArH), 3.595~3.627 (t, 2H, seven-membered ring intra-CH$_2$N), 3.402 (t, 2H, amide N seven-membered ring outer-CH$_2$), 2.991~3.028 (t, 2H, seven-membered ring intra-CH$_2$C=C), 2.454~2.556 (m, 9H, pyrrole-CH$_3$, 3 x-CH$_2$N), 2.102~2.131 (t, 2H, seven-membered ring intra-CH$_2$), 1.523~1.550 (m, 4H, six-membered ring-2×—CH$_2$), 1.429~1.441 (m, 2H, six-membered ring-CH$_2$).

Example 58

(Z)-3-Methyl-2-(4-methyl-2-oxo-1,2-dihydro-indol-3-ylidenemethyl)-5-(2-piperidin-1-yl-ethyl)-5,6,7,8-tetrahydro-1H-pyrrolo[3,2-c]azepin-4-one

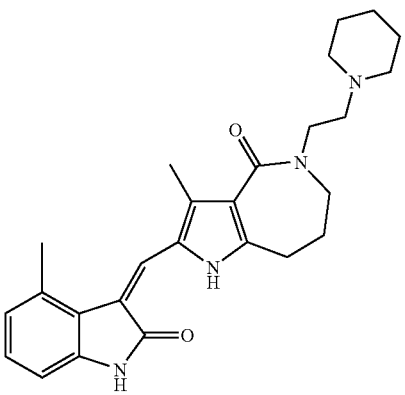

58

The title compound was prepared under the same conditions as described in step 5 of Example 32 with 3-methyl-4-oxo-5-(2-piperidin-1-yl-ethyl)-1,4,5,6,7,8-hexahydro-pyrrolo[3,2-c]azepine-2-carbaldehyde 32d obtained from step 4 of Example 32 and 4-methyl-1,3-dihydro-indol-2-one as starting materials to obtain (Z)-3-methyl-2-(4-methyl-2-oxo-1,2-dihydro-indol-3-ylidenemethyl)-5-(2-piperidin-1-yl-ethyl)-5,6,7,8-tetrahydro-1H-pyrrolo[3,2-c]azepin-4-one 58 (46 mg, yield 70.9%) as a yellow solid.

MS m/z (ESI): 433.2 [M+1]

¹HNMR (400 MHz, DMSO-d6) δ13.703 (s, 1H, pyrrole-NH), 10.926 (s, 1H, indole-NH), 7.567 (s, 1H, —CH=C), 7.035~7.074 (m, 1H, —ArH), 6.769~6.838 (dd, 2H, —ArH), 3.544~3.576 (t, 2H, seven-membered ring intra-CH$_2$N), 3.331~3.359 (t, 2H, amide N seven-membered ring outer-CH$_2$), 2.926~2.962 (t, 2H, seven-membered ring intra-CH$_2$C=C), 2.591 (s, 3H, benzene-CH$_3$), 2.383~2.437 (m, 9H, —CH$_3$, pyrrole-3×—CH$_2$N), 2.030~2.092 (t, 2H, seven-membered ring intra-CH$_2$), 1.479~1.491 (m, 4H, six-membered ring-2×—CH$_2$), 1.383~1.394 (m, 2H, six-membered ring-CH$_2$).

Example 59

(R,Z)-2-(5-Bromo-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one

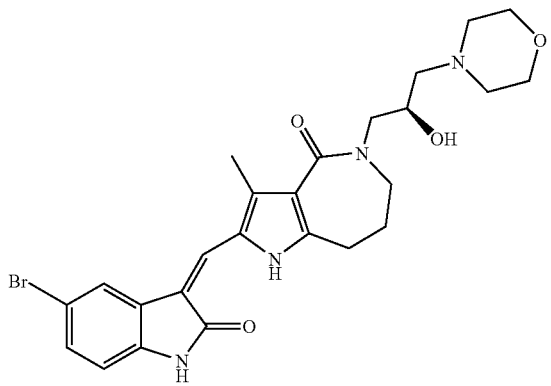

59

The title compound was prepared under the same conditions as described in step 6 of Example 53 with 5-(2-hydroxy-3-morpholin-4-yl-propyl)-3-methyl-4-oxo-1,4,5,6,7,8-hexahydro-pyrrolo[3,2-c]azepine-2-carbaldehyde 53f obtained from step 5 of Example 53 and 5-bromo-1,3-dihydro-indol-2-one as starting materials to obtain (R,Z)-2-(5-bromo-2-oxo-1,2-dihydro-indol-3-ylidenemethyl)-5-(2-hydroxy-3-morpholin-4-yl-propyl)-3-methyl-5,6,7,8-tetrahydro-1H-pyrrolo[3,2-c]azepin-4-one 59 (30 mg, yield 63%) as a yellow solid.

MS m/z (ESI): 529.1 [M+1]

¹HNMR (400 MHz, DMSO-d6) δ13.674 (s, 1H, pyrrole-NH), 11.014 (s, 1H, indole-NH), 8.116~8.120 (d, 1H, —ArH), 7.807 (s, 1H, —CH=C), 7.262~7.287 (dd, 1H, —ArH), 6.826~6.846 (d, 1H, —ArH), 4.719~4.731 (d, 1H, —OH), 3.897 (m, 1H, —CHO), 3.748~3.758 (dd, 1H, amide N seven-membered ring outer-CH₂), 3.570~3.593 (t, 4H, morpholine-2x-CH₂O), 3.433 (t, 2H, N seven-membered ring-CH₂), 3.159 (dd, 1H, amide N seven-membered ring outer-CH₂), 2.917~2.954 (t, 2H, —CH₂C=C), 2.465 (s, 3H, pyrrole-CH₃), 2.418~2.465 (m, 4H, —CH₂N, morpholine-CH₂N), 2.290~2.314 (t, 2H, morpholine-CH₂N), 2.061~2.092 (m, 2H, seven-membered ring-CH₂).

Example 60

(Z)-5-(2-Diethylamino-ethyl)-2-(5-fluoro-2-oxo-1,2-dihydro-indol-3-ylidenemethyl)-3-methyl-6,7,8,9-tetrahydro-1H,5H-1,5-diaza-cyclopentacycloocten-4-one

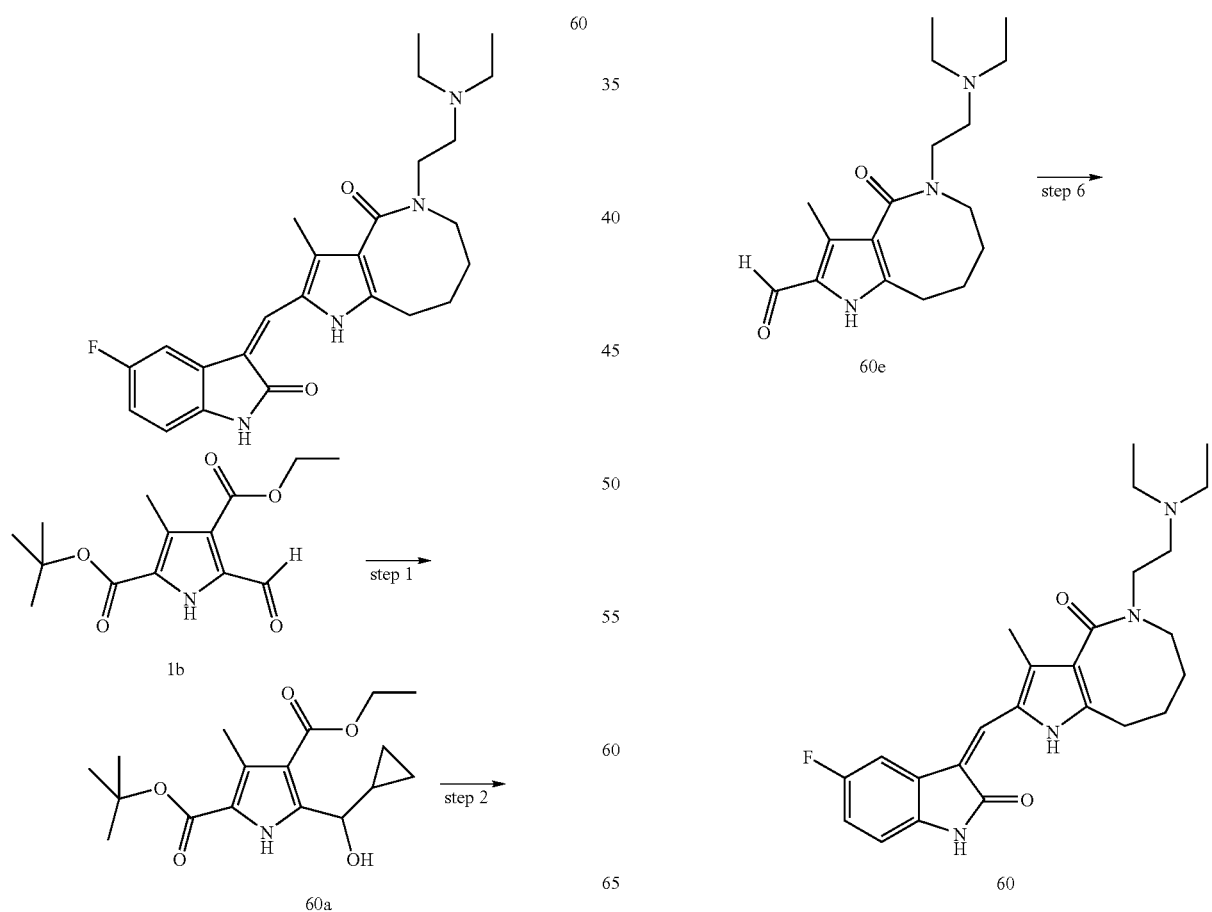

Step 1

5-(Cyclopropyl-hydroxy-methyl)-3-methyl-1H-pyrrole-2,4-dicarboxylic acid 2-tert-butyl ester 4-ethyl ester

Cyclopropylmagnesium bromide (15 m, 0.5 mol/L) was cooled down to −10° C. in an ice-salt bath under an argon atmosphere. 5-Formyl-3-methyl-1H-pyrrole-2,4-dicarboxylic acid 2-tert-butyl ester 4-ethyl ester 1b (1.26 g, 4.5 mmol) was dissolved in 10 ml of tetrahydrofuran under stirring, the resulting solution was added dropwise to the above solution while maintaining the temperature at −10° C. Upon completion of the addition, the ice-salt bath was removed, and the reaction mixture was stirred for 1 hour at room temperature. After thin lay chromatography showed the disappearance of starting materials, the reaction mixture was quenched with water, added with sulfuric acid solution (20 ml, 10%) and stirred for 30 minutes, and extracted with ethyl acetate (50 ml×3). The combined organic extracts were washed with saturated brine (50 ml), dried over anhydrous magnesium sulfate, filtered to remove the drying agent and concentrated under reduced pressure. The residue was purified by silica gel column chromatography to obtain the title compound 5-(cyclopropyl-hydroxy-methyl)-3-methyl-1H-pyrrole-2,4-dicarboxylic acid 2-tert-butyl ester 4-ethyl ester 60a (576 mg, yield 39.6%) as a white solid.

MS m/z (ESI): 322.2 [M−1]

Step 2

5-(4-Bromo-but-1-enyl)-3-methyl-1H-pyrrole-2,4-dicarboxylic acid 2-tert-butyl ester 4-ethyl ester

5-(Cyclopropyl-hydroxy-methyl)-3-methyl-1H-pyrrole-2,4-dicarboxylic acid 2-tert-butyl ester 4-ethyl ester 60a (323 mg, 1 mmol) was dissolved in 4 ml of ethanol under stirring, and added with hydrobromic acid (2.8 ml, 40%) to the solution and stirred for 30 minutes at room temperature. After thin lay chromatography showed the disappearance of starting materials, the reaction mixture was extracted with ethyl acetate (10 ml×5). The combined organic extracts were washed with saturated brine (15 ml), dried over anhydrous magnesium sulfate, filtered to remove the drying agent and concentrated under reduced pressure. The residue was purified by silica gel column chromatography to obtain the title compound 5-(4-bromo-but-1-enyl)-3-methyl-1H-pyrrole-2,4-dicarboxylic acid 2-tert-butyl ester 4-ethyl ester 60b (345 mg, yield 89.5%) as a white solid.

MS m/z (ESI): 329.4 [M+1]

Step 3

5-(4-Bromo-butyl)-3-methyl-1H-pyrrole-2,4-dicarboxylic acid 2-tert-butyl ester 4-ethyl ester

5-(4-Bromo-but-1-enyl)-3-methyl-1H-pyrrole-2,4-dicarboxylic acid 2-tert-butyl ester 4-ethyl ester 60b (30 mg, 0.08 mmol) was dissolved in 3 ml of ethanol under stirring, and added with palladium on activated carbon (6 mg, 5%) to the solution at room temperature. The reaction mixture was stirred for 45 minutes under a hydrogen atmosphere. After thin lay chromatography showed the disappearance of starting materials, the reaction mixture was filtered, concentrated under reduced pressure to obtain the title compound 5-(4-bromo-butyl)-3-methyl-1H-pyrrole-2,4-dicarboxylic acid 2-tert-butyl ester 4-ethyl ester 60c (21 mg, yield 70%) as a colorless oil.

MS m/z (ESI): 388.0 [M+1]

Step 4

5-(4-Diethylamino-butyl)-3-methyl-1H-pyrrole-2,4-dicarboxylic acid 2-tert-butyl ester 4-ethyl ester

5-(4-Bromo-butyl)-3-methyl-1H-pyrrole-2,4-dicarboxylic acid 2-tert-butyl ester 4-ethyl ester 60c (220 mg, 0.57 mmol) was dissolved in 5 ml of dichloromethane under stirring, and added with N,N-diethylethylenediamine (164 µl, 1.13 mmol) to the solution and refluxed for 30 minutes in an oil bath. The reaction mixture was concentrated to evaporate solvent and refluxed for another 1 hour. After thin lay chromatography showed the disappearance of starting materials, the reaction mixture was concentrated under reduced pressure, purified by silica gel column chromatography to obtain the title compound 5-(4-diethylamino-butyl)-3-methyl-1H-pyrrole-2,4-dicarboxylic acid 2-cert-butyl ester 4-ethyl ester 60d (187 mg, yield 78%) as a white solid.

MS m/z (ESI): 424.3 [M+1]

Step 5

5-(2-Diethylamino-ethyl)-3-methyl-4-oxo-4,5,6,7,8,9-hexahydro-1H-1,5-diaza-cyclopentacyclooctene-2-carbaldehyde

Trimethyl aluminum (489 µl, 2 mol/L) was dissolved in 3 ml of toluene under stirring, and added with the solution of 5-(4-diethylamino-butyl)-3-methyl-1H-pyrrole-2,4-dicarboxylic acid 2-tert-butyl ester 4-ethyl ester 60d (345 mg, 0.82 mmol) in 6 ml of toluene to the above solution at room temperature. Upon completion of the addition, the reaction mixture was stirred for 30 minutes at room temperature, heated to reflux for 2 hours in an oil bath, added with another trimethyl aluminum (900 µl, 2 mol/L) and refluxed for another 7 hours. After thin lay chromatography showed the disappearance of starting materials, the reaction mixture was quenched with water, added with hydrochloric acid solution (1 ml, 2 mol/L) and stirred for 30 minutes at room temperature. The mixture was adjusted to about pH 10 with aqueous sodium hydroxide solution (10%) and extracted with ethyl acetate (25 ml×3). The combined organic extracts were washed with saturated brine (25 ml), dried over anhydrous magnesium sulfate, filtered to remove the drying agent and concentrated under reduced pressure. The residue was purified by silica gel column chromatography to obtain the title compound 5-(2-diethylamino-ethyl)-3-methyl-4-oxo-4,5,6,7,8,9-hexahydro-1H-1,5-diaza-cyclopentacyclooctene-2-carbaldehyde 60e (60 mg, yield 26.7%) as a white solid.

MS m/z (ESI): 278.2 [M+1]

Step 6

(Z)-5-(2-Diethylamino-ethyl)-2-(5-fluoro-2-oxo-1,2-dihydro-indol-3-ylidenemethyl)-3-methyl-6,7,8,9-tetrahydro-1H,5H-1,5-diaza-cyclopentacycloocten-4-one

5-(2-Diethylamino-ethyl)-3-methyl-4-oxo-4,5,6,7,8,9-hexahydro-1H-1,5-diaz a-cyclopentacyclooctene-2-carbaldehyde 60e (20 mg, 0.066 mmol) was dissolved in 1 ml of ethanol under stirring, and added with 5-fluoro-1,3-dihydroindol-2-one (9.9 mg, 0.066 mmol) to the solution at room temperature. The reaction mixture was stirred in dark until dissolved, added with 0.1 ml of piperidine, and heated to reflux for 2 hours. After thin lay chromatography showed the disappearance of starting materials, the reaction mixture was naturally cooled down to room temperature, filtered to obtain the title compound (Z)-5-(2-diethylamino-ethyl)-2-(5-fluoro-2-oxo-1,2-dihydro-indol-3-ylidenemethyl)-3-methyl-6,7,8,9-tetrahydro-1H,5H-1,5-diaza-cyclopentacycloocten-4-one 60 (14 mg, yield 48.8%) as a yellow solid.

MS m/z (ESI): 439.2 [M+1]

$^1$HNMR (400 MHz, DMSO-d6) δ13.462 (s, 1H, pyrrole-NH), 10.874 (s, 1H, indole-NH), 7.739~7.758 (d, 1H, —ArH), 7.715 (s, 1H, —CH═C), 6.832~6.933 (m, 2H, —ArH), 3.406 (m, 4H, 2×—CH$_2$NCO), 2.874 (t, 2H, —CH$_2$C═C), 2.597~2.630 (t, 2H, —CH$_2$N), 2.486~2.538 (q, 4H, ethyl 2×—CH$_2$N), 2.322 (s, 3H, pyrrole-CH$_3$), 1.733 (m, 4H, eight-membered ring intra-2×—CH$_2$), 0.963~0.968 (t, 6H, 2×—CH$_3$).

Example 61

(Z)-2-(5-Bromo-2-oxo-1,2-dihydro-indol-3-ylidenemethyl)-5-(2-diethylamino-ethyl)-3-methyl-6,7,8,9-tetrahydro-1H,5H-1,5-diaza-cyclopentacycloocten-4-one

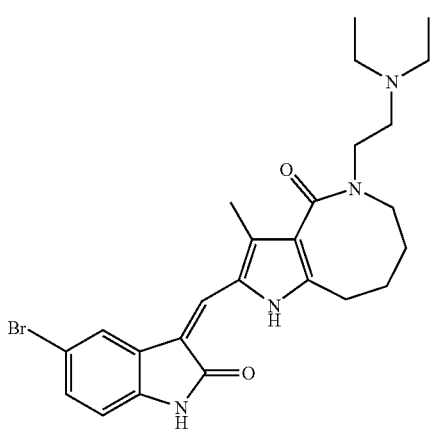

61

The title compound was prepared under the same conditions as described in step 6 of Example 60 with 5-(2-diethylamino-ethyl)-3-methyl-4-oxo-4,5,6,7,8,9-hexahydro-1H-1,5-diaza-cyclopentacyclooctene-2-carbaldehyde 60e obtained from step 5 of Example 60 and 5-bromo-1,3-dihydro-indol-2-one as starting materials to obtain (Z)-2-(5-bromo-2-oxo-1,2-dihydro-indol-3-ylidenemethyl)-5-(2-diethylamino-ethyl)-3-methyl-6,7,8,9-tetrahydro-1H,5H-1,5-diaza-cyclopentacycloocten-4-one 61 (16 mg, yield 68%) as a yellow solid.

MS m/z (ESI): 499.2 [M+1]

$^1$HNMR (400 MHz, DMSO-d6) δ13.660 (s, 1H, pyrrole-NH), 11.008 (s, 1H, indole-NH), 8.113~8.117 (d, 1H, —ArH), 7.803 (s, 1H, —CH═C), 7.260~7.286 (dd, 1H, —ArH), 6.825~6.845 (d, 1H, —ArH), 3.406 (m, 4H, 2×—CH$_2$NCO), 2.874 (t, 2H, —CH$_2$C═C), 2.597~2.630 (t, 2H, —CH$_2$N), 2.486~2.538 (q, 4H, ethyl 2×—CH$_2$N), 2.322 (s, 3H, pyrrole-CH$_3$), 1.733 (m, 4H, eight-membered ring intra-2×—CH$_2$), 0.963~0.968 (t, 6H, 2×—CH$_3$).

Example 62

(Z)-5-(2-Ethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one

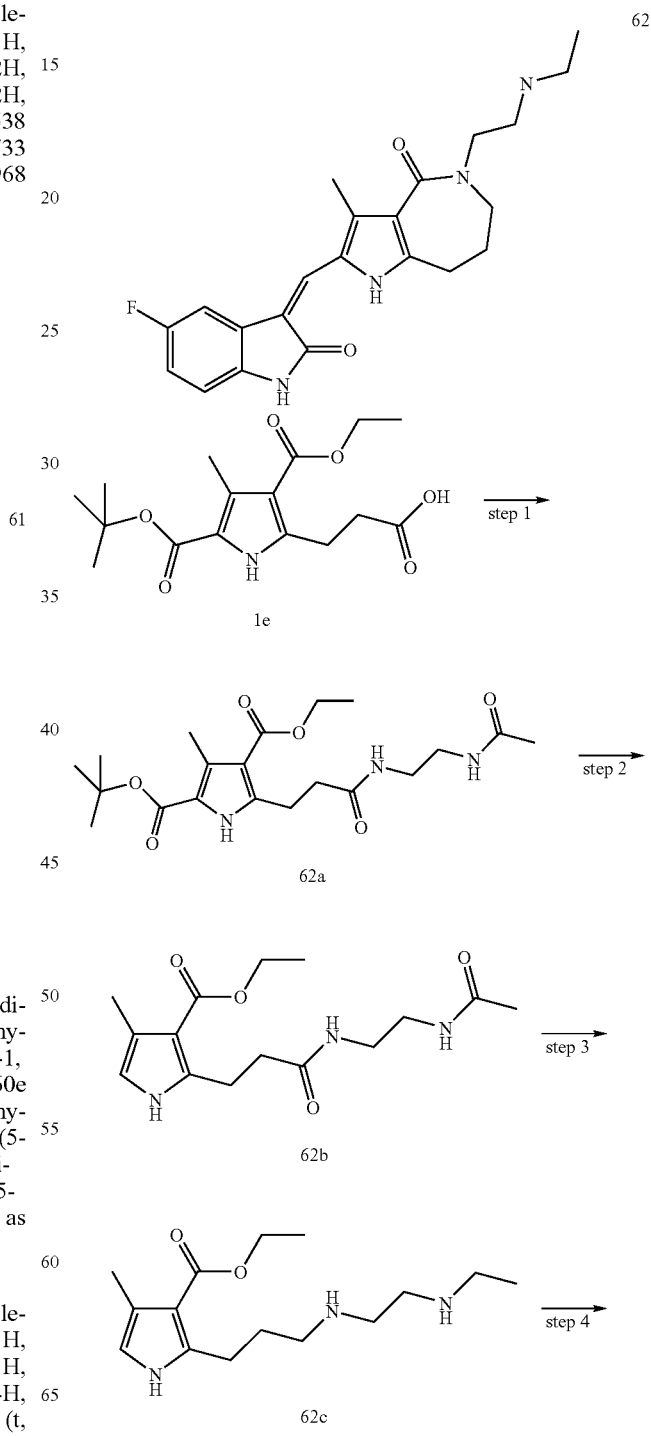

-continued

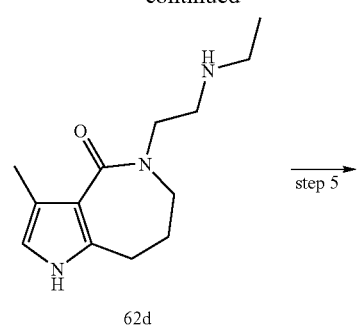

62d

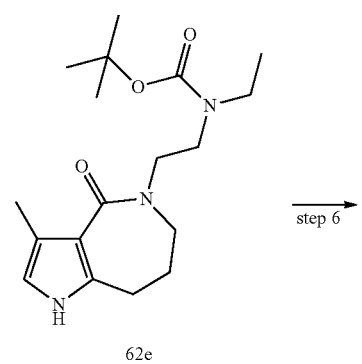

62e

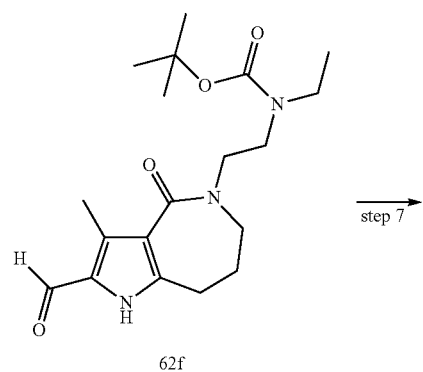

62f

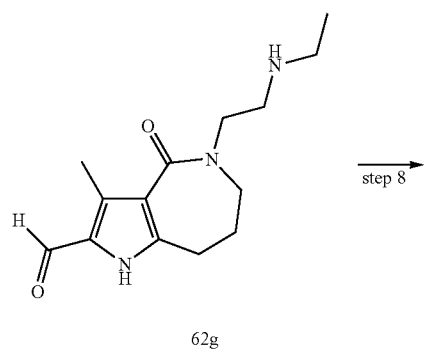

62g step 5 → step 6 → step 7 → step 8 →

-continued

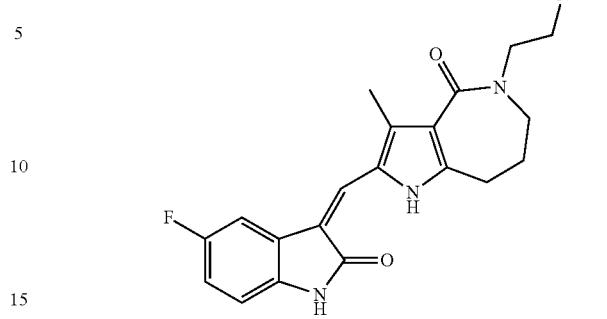

62

Step 1

5-[2-(2-Acetylamino-ethylcarbamoyl)-ethyl]-3-methyl-1H-pyrrole-2,4-dicarboxylic acid 2-tert-butyl ester 4-ethyl ester 5-(2-Carboxy-ethyl)-3-methyl-1H-pyrrole-2,4-dicarboxylic acid 2-tert-butyl ester 4-ethyl ester 1e (9.85 g, 30.3 mmol) obtained from step 4 of Example 1 was dissolved in acetonitrile (50 ml) under stirring, and added with 1-hydroxy-1H-benzotriazole (8.2 g, 60.6 mmol) and N-ethyl-N'-(3-dimethylaminopropyl)carbodiimide (11.6 g, 60.6 mmol) to the solution at room temperature. Upon completion of the addition, the reaction mixture was stirred at room temperature overnight. After thin lay chromatography showed the disappearance of starting materials, the reaction mixture was concentrated under reduced pressure, added with water (200 ml), and exacted with ethyl acetate (200 ml×4). The combined organic extracts were washed with saturated brine (100 ml), dried over anhydrous magnesium sulfate, filtered to remove the drying agent and concentrated under reduced pressure. The residue was purified by silica gel column chromatography to obtain the title compound 5-[2-(2-acetylamino-ethylcarbamoyl)-ethyl]-3-methyl-1H-pyrrole-2,4-dicarboxylic acid 2-tert-butyl ester 4-ethyl ester 62a (8 g, yield 65%) as a white solid.

MS m/z (ESI): 410.1 [M+1]

Step 2

2-[2-(2-Acetylamino-ethylcarbamoyl)-ethyl]-4-methyl-1H-pyrrole-3-carboxylic acid ethyl ester 5-[2-(2-Acetylamino-ethylcarbamoyl)-ethyl]-3-methyl-1H-pyrrole-2,4-dicarboxylic acid 2-tert-butyl ester 4-ethyl ester 62a (818 mg, 2 mmol) was dissolved in 5 ml of ethanol under stirring, and added with hydrochloric acid solution (5 ml, 12 mol/L) to the solution at room temperature. Upon completion of the addition, the reaction mixture was heated at 60° C. in an oil bath for 2 hours. After thin lay chromatography showed the disappearance of starting materials, the reaction mixture was concentrated under reduced pressure to evaporate ethanol, adjusted to about pH 12 with aqueous sodium hydroxide solution (10%) and extracted with ethyl acetate (20 ml×3). The combined organic extracts were dried over anhydrous magnesium sulfate, filtered to remove the drying agent and concentrated under reduced pressure to obtain the title compound 2-[2-(2-acetylamino-ethylcarbamoyl)-ethyl]-4-methyl-1H-pyrrole-3-carboxylic acid ethyl ester 62b (600 mg, yield 97%) as a white solid.
MS m/z (ESI): 310.1 [M+1]

Step 3

2-[3-(2-Ethylamino-ethylamino)-propyl]-4-methyl-1H-pyrrole-3-carboxylic acid ethyl ester 2-[2-Acetylamino-ethylcarbamoyl)-ethyl]-4-methyl-1H-pyrrole-3-carboxyl is acid ethyl ester 62b (600 mg, 1.94 mmol) was dissolved in 4 ml of tetrahydrofuran under stirring, and added with a solution of borane in tetrahydrofuran (7.79 ml, 1 mol/L, 7.79 mmol) to the solution in an ice-water bath under an argon atmosphere. Upon completion of the addition, the reaction mixture was heated to reflux for 2 hours. After thin lay chromatography showed the disappearance of starting materials, the reaction mixture was quenched with hydrochloric acid, stirred for 30 minutes at room temperature, adjusted to about pH 12 with aqueous sodium hydroxide solution (10%) and extracted with ethyl acetate (30 ml×3). The combined organic extracts were washed with saturated brine (30 ml), dried over anhydrous magnesium sulfate, filtered to remove the drying agent and concentrated under reduced pressure. The residue was purified by silica gel column chromatography to obtain the title compound 2-[3-(2-ethylamino-ethylamino)-propyl]-4-methyl-1H-pyrrole-3-carboxylic acid ethyl ester 62c (170 mg, yield 31%) as a white solid.
MS m/z (ESI): 282.2 [M+1]

Step 4

5-(2-Ethylamino-ethyl)-3-methyl-5,6,7,8-tetrahydro-1H-pyrrolo[3,2-c]azepin-4-one 2-[3-(2-Ethylamino-ethylamino)-propyl]-4-methyl-1H-pyrrole-3-carboxylic acid ethyl ester 62c (350 mg, 1.245 mmol) and trimethyl aluminum (1.25 ml, 2.49 mmol) were dissolved in 75 ml of toluene under stirring, the resulting mixture was heated to reflux at 140° C. in an oil bath for 24 hours. After thin lay chromatography showed the disappearance of starting materials, the reaction mixture was concentrated under reduced pressure, adjusted to about pH 3 with hydrochloric acid (6 mol/L) and stirred for 30 minutes. The mixture was adjusted to pH 14 with aqueous sodium hydroxide solution (12 mol/L) and extracted with dichloromethane (100 ml×4). The combined organic extracts were washed with saturated brine (150 ml), dried over anhydrous magnesium sulfate, filtered to remove the drying agent and concentrated under reduced pressure to obtain the title compound 5-(2-ethylamino-ethyl)-3-methyl-5,6,7,8-tetrahydro-1H-pyrrolo[3,2-c]azepin-4-one 62d (450 mg) as a yellow oil to be used directly in the next step.
MS m/z (ESI): 236.0 [M+1]

Step 5

Ethyl-[2-(3-methyl-4-oxo-4,6,7,8-tetrahydro-1H-pyrrolo[3,2-c]azepin-5-yl)-ethyl]-carbamic acid tert-butylester 5-(2-Ethylamino-ethyl)-3-methyl-5,6,7,8-tetrahydro-1H-pyrrolo[3,2-c]azepin-4-one 62d (450 mg, 1.91 mmol) was dissolved in 20 ml of dichloromethane under stirring, and added with di-tert-butyl dicarbonate (834 mg, 3.83 mmol), potassium carbonate (528 mg, 3.83 mmol) and tetrahydrofuran (30 ml) to the solution. Upon completion of the addition, the reaction mixture was stirred at room temperature overnight. After thin lay chromatography showed the disappearance of starting materials, the reaction mixture was added with water (50 ml), and exacted with ethyl acetate (50 ml×3). The combined organic extracts were washed with saturated brine (50 ml), dried over anhydrous magnesium sulfate, filtered to remove the drying agent and concentrated under reduced pressure. The residue was purified by silica gel column chromatography to obtain the title compound ethyl-[2-(3-methyl-4-oxo-4,6,7,8-tetrahydro-1H-pyrrolo[3,2-c]azepin-5-yl)-ethyl]-carbamic acid tert-butylester 62e (40 mg, yield 6%) as a yellow solid.
MS m/z (ESI): 336.2 [M+1]

Step 6

Ethyl-[2-(2-formyl-3-methyl-4-oxo-4,6,7,8-tetrahydro-1H-pyrrolo[3,2-c]azepin-5-yl)-ethyl]-carbamic acid tert-butyl ester Ethyl-[2-(3-methyl-4-oxo-4,6,7,8-tetrahydro-1H-pyrrolo[3,2-c]azepin-5-yl)-ethyl]-carbamic acid tert-butylester 62e (40 mg, 0.119 mmol) was dissolved in 25 ml of dichloromethane under stirring, and added with (chloromethylene) dimethylammoniumchloride (15.92 mg, 0.12 mmol) to the solution. Upon completion of the addition, the reaction mixture was stirred at room temperature for 10 minutes. After thin lay chromatography showed the disappearance of starting materials, the reaction mixture was quenched with aqueous sodium hydroxide solution (12 mol/L), stirred for another 15 minutes at room temperature and extracted with dichloromethane (20 ml×3). The combined organic extracts were washed with saturated brine (20 ml), dried over anhydrous magnesium sulfate, filtered to remove the drying agent and concentrated under reduced pressure to obtain the title compound ethyl-[2-(2-formyl-3-methyl-4-oxo-4,6,7,8-tetrahydro-1H-pyrrolo[3,2-c]azepin-5-yl)-ethyl]-carbamic acid tert-butyl ester 62f (54 mg) as a yellow solid to be used directly in the next step.
MS m/z (ESI): 364.1 [M+1]

Step 7

5-(2-Ethylamino-ethyl)-3-methyl-4-oxo-1,4,5,6,7,8-hexahydro-pyrrolo[3,2-c]azepine-2-carbaldehyde Ethyl-[2-(2-formyl-3-methyl-4-oxo-4,6,7,8-tetrahydro-1H-pyrrolo[3,2-c]azepin-5-yl)-ethyl]-carbamic acid tert-butyl ester 62f (43 mg, 0.118 mmol) was dissolved in 10 ml of dichloromethane under stirring, and added with trifluoroacetic acid (272 μl, 3.55 mmol) to the solution and stirred for 15 minutes in an ice-water bath. After thin lay chromatography showed the disappearance of starting materials, the reaction mixture was concentrated under reduced pressure to obtain the title compound 5-(2-ethylamino-ethyl)-3-methyl-4-oxo-1,4,5,6,7,8-hexahydro-pyrrolo[3,2-c]azepine-2-carbaldehyde 62j to be used directly in the next step.
MS m/z (ESI): 264.1 [M+1]

Step 8

(Z)-5-(2-Ethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one 5-(2-Ethylamino-ethyl)-3-methyl-4-oxo-1,4,5,6,7,8-hexahydro-pyrrolo[3,2-c]azepine-2-carbaldehyde 62j (45 mg, 0.118 mmol) was dissolved in 5 ml of ethanol under stirring, and added with 5-fluoro-1,3-dihydro-indol-2-one (16 mg, 0.106 mmol) and piperidine (0.15 ml, 1.49 mmol) to the solution. Upon completion of the addition, the reaction mixture was refluxed at 90° C. in an oil bath for 1 hour. After thin lay chromatography showed the disappearance of starting materials, the reaction mixture was concentrated under reduced pressure, added with a little ethanol, and filtered to obtain the title compound (Z)-5-(2-ethylamino-ethyl)-2-(5-fluoro-2-oxo-1,2-dihydro-indol-3-ylidenemethyl)-3-methyl-5,6,7,8-tetrahydro-1H-pyrrolo[3,2-c]azepin-4-one 62 (34 mg, yield 76%) as a yellow solid.

MS m/z (ESI): 397.1 [M+1]

$^1$H NMR (400 MHz, DMSO-d6) δ (s, 1H, pyrrole-NH), 10.920 (s, 1H, indole-NH), 7.781~7.788 (d, 1H, —ArH), 7.759 (s, 1H, —CH=C), 6.925~6.976 (td, 1H, —ArH), 6.845~6.877 (dd, 1H, —ArH), 3.637~3.688 (t, 2H, N seven-membered ring-CH$_2$), 3.371~3.398 (t, 2H, amide N seven-membered ring outer-CH$_2$), 2.959~3.026 (m, 4H, —CH$_2$C=C, —CH$_2$N), 2.864~2.918 (q, 2H, ethyl-CH$_2$), 2.488 (s, 3H, pyrrole-CH$_3$), 2.056~2.083 (m, 2H, seven-membered ring-CH$_2$), 1.136~1.172 (t, 3H, ethyl-CH$_3$)

Example 63

(Z)-5-(2-Diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one malate

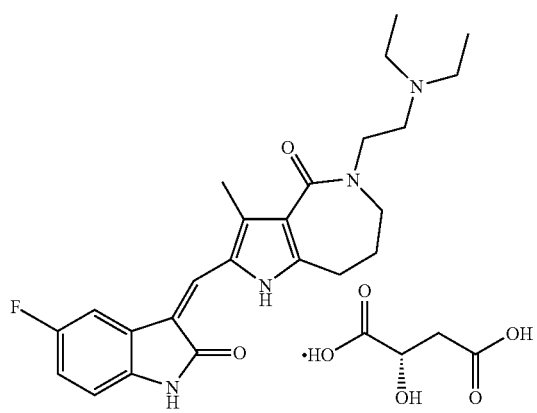

63

(Z)-5-(2-Diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one 1 (2.01 g, 4.75 mmol) obtained from Example 1 was dissolved in 279 ml of methanol under stirring, and added with 2-hydroxy-succinic acid (0.953 g, 7.11 mmol) to the solution in one portion. The orange solution was concentrated under reduced pressure, added with 45 ml of acetonitrile, heated to reflux for 30 minutes in an oil bath. The oil bath was then removed, and the reaction mixture was naturally cooled down to room temperature, filtered and dried to obtain the title compound (Z)-5-(2-diethylamino-ethyl)-2-(5-fluoro-2-oxo-1,2-dihydro-indol-3-ylidenemethyl)-3-methyl-3a,5,6,7,8,8a-hexahydro-1H-pyrrolo[3,2-c]azepin-4-one malate 63 (2.02 g, yield 76.2%) as an orange solid.

MS m/z (ESI): 425.1 [M+1]

$^1$HNMR (400 MHz, DMSO-d6) δ13.742 (s, 1H, pyrrole-NH), 10.925 (s, 1H, indole-NH), 7.784~7.790 (dd, 1H, —ArH), 7.755 (s, 1H, —CH=C), 6.922~6.951 (m, 1H, —ArH), 6.840~6.873 (m, 1H, —ArH), 3.631~3.665 (t, 2H, seven-membered ring intra-CH$_2$N), 3.374~3.401 (t, 2H, amide N seven-membered ring outer-CH$_2$), 2.911~2.958 (t, 2H, seven-membered ring intra-CH$_2$C=C), 2.536~2.575 (m, 6H, 3×—CH$_2$N), 2.471 (s, 3H, pyrrole-CH$_3$), 2.053~2.079 (m, 2H, seven-membered ring intra-CH$_2$), 1.137 (t, 6H, 2×—CH$_3$).

Example 64

2-((5-(2,6-dichlorobenzylsulfonyl)-2-oxoindolin-3-ylidene)methyl)-3-methyl-5-(2-morpholinoethyl)-5,6,7,8-tetrahydropyrrolo[3,2-c]azepin-4(1H)-one

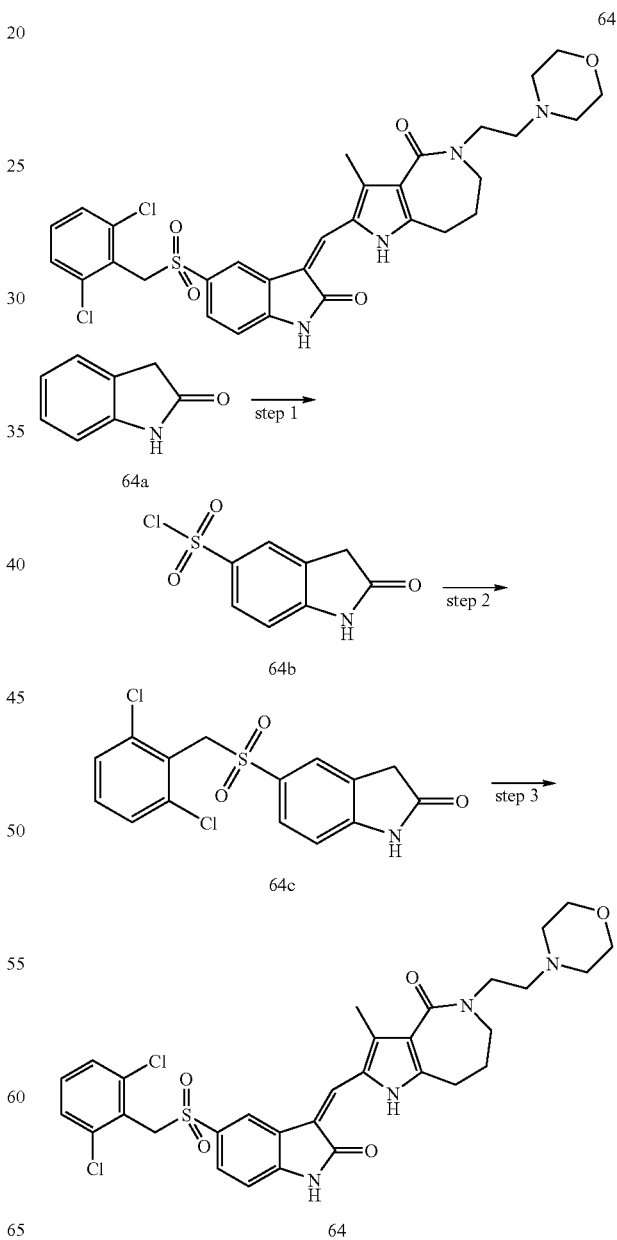

163

Step 1

5-Chlorosulfonyl-indol-2-one 1,3-Dihydro-indol-2-one 64a (13.3 g, 100 mmol) was added slowly with chlorosulfuric acid (26.6 ml, 400 mmol) in an ice-water bath. Upon completion of the addition, the reaction mixture was stirred for 1 hour in an ice-water bath, for another 1 hour at room temperature, and heated to 68° C. for 1 hour. The reaction mixture was cooled down to room temperature, added slowly with water (400 ml), stirred and yellow precipitates were formed. After standing for 1 hour at room temperature, the filter cake was washed with water (20 ml×4) and dried to obtain the title compound 5-chlorosulfonyl-indol-2-one 64b (15.0 g, yield 65%) as a yellow solid.
Reference: Acta Pharmacol Sin; 2007, 28(1), 140-152.

Step 2

5-(2,6-Dichloro-phenylmethanesulfonyl)-1,3-dihydro-indol-2-one

Sodium monohydrogen phosphate dodecahydrate (142 g, 1.0 mol) and sodium sulfite (252 g, 2.0 mol) were dissolved in 2 L of water at room temperature, heated to 30° C., and added with 2-oxo-2,3-dihydro-1H-indole-5-sulfonyl chloride 64b (232 g, 1.0 mol). Upon completion of the addition, the reaction mixture was stirred at 60° C. for 16 hours. A solution of 2,6-dichlorobenzyl bromide (240 g, 1.0 mol) in acetone (1.8 L) was added to the above solution, stirred at 60° C. for 1 hour, added with another acetone (200 ml) and stirred for another 2 hours. The reaction mixture was quenched with water (5 L), stirred at room temperature for 1 hour and filtered. The filter cake was washed with water (1 L) and acetone (1 L), and dried in vacuo to obtain the title compound 5-(2,6-dichloro-phenylmethanesulfonyl)-1,3-dihydro-indol-2-one 64c (314 g, yield 88%) as a white solid.

MS m/z (ESI): 357.3 [M+1]

$^1$HNMR (400 MHz, DMSO-d6) δ10.90 (s, 1H, indole-NH), 7.56 (m, 4H, —ArH), 7.43 (m, 1H, —ArH), 6.99 (d, 1H, —ArH), 4.59 (s, 2H, —ArCH$_2$)
Reference: Organic Process Research & Development; 2003, 7, 313-317.

Step 3

(Z)-2-((5-(2,6-dichlorobenzylsulfonyl)-2-oxoindolin-3-ylidene)methyl)-3-meth yl-5-(2-morpholinoethyl)-5,6,7,8-tetrahydropyrrolo[3,2-c]azepin-4(1H)-one 3-Methyl-5-(2-morpholin-4-yl-ethyl)-4-oxo-1,4,5,6,7,8-hexahydro-pyrrolo[3,2-c]azepine-2-carbaldehyde 10c (100 mg, 0.325 mmol) and 5-(2,6-dichloro-phenylmethanesulfonyl)-1,3-dihydro-indol-2-one 64c (104 mg, 0.293 mmol) were dissolved in 3 ml of ethanol, and added with 52 μl of piperidine to the solution at room temperature. Upon completion of the addition, the reaction mixture was heated to reflux for 2 hours. After thin lay chromatography showed the disappearance of starting materials, the reaction mixture was naturally cooled down to room temperature and filtered. The filter cake was washed with anhydrous ethanol (3 ml×2) and dried to obtain the title compound (Z)-2-(5-(2,6-dichlorobenzylsulfonyl)-2-oxoindolin-3-yl idene)methyl)-3-methyl-5-(2-morpholinoethyl)-5,6,7,8-tetrahydropyrrolo[3,2-c]azepin-4(1H)-one 64 (166 mg, yield 88%) as an orange solid.

MS m/z (ESI): 643.3 [M+1]

164

$^1$HNMR (400 MHz, DMSO-d6) δ13.63 (s, 1H, pyrrole-NH), 11.42 (s, 1H, indole-NH), 8.28 (s, 1H, —ArH), 7.90 (s, 1H, —ArH), 7.51 (m, 3H, —ArH), 7.42 (s, 1H, —CH═C), 7.06 (m, 1H, —ArH), 4.88 (s, 2H, —ArCH$_2$), 3.58~2.08 (m, 18H, aliphatic H), 2.44 (s, 3H, pyrrole-CH$_3$)

Example 65

(Z)-2-[5-(4-Fluoro-phenylmethanesulfonyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one

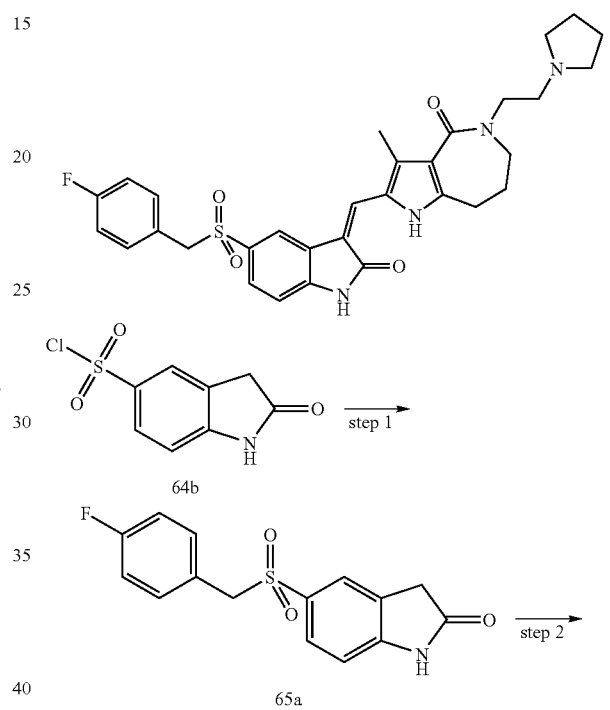

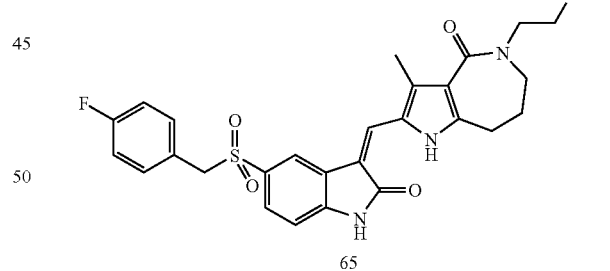

Step 1

5-(4-Fluoro-phenylmethanesulfonyl)-1,3-dihydro-indol-2-one

Sodium monohydrogen phosphate dodecahydrate (3.58 g, 10 mmol) and sodium sulfite (2.52 g, 20 mmol) were dissolved in 20 ml of water, heated to 30° C., and added with 2-oxo-2,3-dihydro-1H-indole-5-sulfonyl chloride 64b (2.32 g, 10 mmol). Upon completion of the addition, the reaction mixture was stirred at 60° C. for 16 hours. A solution of 5-fluorobenzyl bromide (1.9 g, 10 mmol) in acetone (18 ml)

was added slowly to the above solution and stirred at 60° C. for 2 hours. The reaction mixture was quenched with water (50 ml) and substantial precipitates were formed. The mixture was stirred at room temperature for another 1 hour, filtered, washed with the solvent mixture (20 ml, V:V=1:1) of water and acetone, and dried in vacuo to obtain the title compound 5-(4-fluoro-phenylmethanesulfonyl)-1,3-dihydro-indol-2-one 65a (1.8 g, yield 59%) as a light yellow solid.

MS m/z (ESI): 304.1 [M−1]

¹HNMR (400 MHz, DMSO-d6) δ10.85 (s, 1H, indole-NH), 7.42 (m, 2H, ArH), 7.21 (m, 3H, —ArH), 6.95 (d, 1H, —ArH), 4.59 (s, 2H, —ArCH₂)

Reference: Organic Process Research & Development; 2003, 7, 313-317.

Step 2

2-[5-(4-Fluoro-phenylmethanesulfonyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one 3-Methyl-4-oxo-5-(2-pyrrol 8-hexahydro-pyrrolo[3,2-c]azepine-2-carbaldehyde 28c (60.2 mg, 0.21 mmol) and 5-(4-fluoro-phenylmethanesulfonyl)-1,3-dihydro-indol-2-one 65a (57.6 mg, 0.19 mmol) were dissolved in 2 ml of ethanol, and added with 50 μl of piperidine to the solution at room temperature. Upon completion of the addition, the reaction mixture was heated to reflux for 3 hours. After thin lay chromatography showed the disappearance of starting materials, the reaction mixture was naturally cooled down to room temperature, and filtered. The filter cake was washed with anhydrous ethanol (3 ml×2) and dried to obtain the title compound (Z)-2-[5-(4-fluoro-phenylmethanesulfonyl)-2-oxo-1,2-dihydro-indol-3-ylidenemethyl]-3-methyl-5-(2-pyrrolidin-1-yl-ethyl)-5,6,7,8-tetrahydro-1H-pyrrolo[3,2-c]azepin-4-one 65 (90 mg, yield 81.8%) as an orange solid.

MS m/z (ESI): 577.3 [M+1]

¹HNMR (400 MHz, DMSO-d6) δ12.133 (s, 1H, indole-NH), 8.99 (s, 1H, —ArH), 8.61 (s, 1H, —ArH), 7.88 (s, 1H, —CH═C), 8.14~7.76 (m, 4H, —ArH), 7.75 (d, 1H, —ArH), 5.39 (s, 2H, —ArCH₂), 4.33 (m, 2H, —NCH₂), 4.11~3.25 (m, 12H, aliphatic H), 3.70 (m, 2H, —NCH₂), 2.81 (m, 2H, —NCH₂), 2.46 (s, 3H, pyrrole-CH₃).

Example 66

(Z)-2-((5-(2,6-dichlorobenzylsulfonyl)-2-oxoindol-ylidene)methyl)-3-methyl-5-(2-(pyrrolidin-8-tetrahydropyrrolo[3,2-c]azepin-4(1H)-one

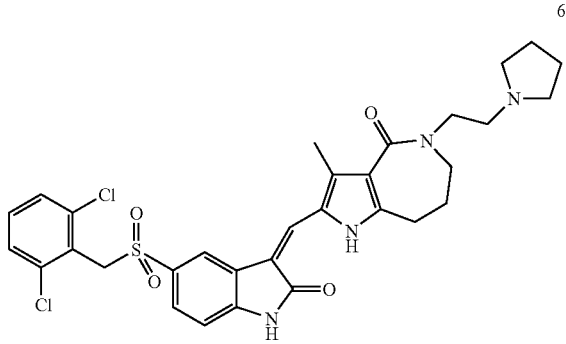

66

3-methyl-4-oxo-5-(2-pyrrolidin-1-yl-ethyl)-1,4,5,6,7,8-hexahydro-pyrrolo[3,2-c]azepine-2-carbaldehyde 28c (75 mg, 0.262 mmol) and 5-(2,6-dichloro-phenylmethanesulfonyl)-1,3-dihydro-indol-2-one 64c (84 mg, 0.236 mmol) were dissolved in 2.5 ml of ethanol, and added with 42 μl of piperidine to the solution at room temperature. Upon completion of the addition, the reaction mixture was heated to reflux for 3 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-2-((5-(2,6-dichlorobenzylsulfonyl)-2-oxoindolin-3-yl idene)methyl)-3-methyl-5-(2-(pyrrolidin-1-yl)ethyl)-5,6,7,8-tetrahydropyrrolo[3,2-c]azepin-4(1H)-one 66 (117 mg, yield 79.6%) as an orange solid.

MS m/z (ESI): 627.3 [M+1]

¹HNMR (400 MHz, DMSO-d6) δ12.18 (s, 1H, indole-NH), 9.04 (s, 1H, —ArH), 8.66 (s, 1H, —ArH), 8.25 (s, 1H, —CH═C), 8.23~8.16 (m, 3H, —ArH), 7.99 (d, 1H, —ArH), 5.64 (s, 2H, —ArCH₂), 4.34 (m, 2H, —NCH₂), 4.12~3.26 (m, 12H, aliphatic H), 3.70 (m, 2H, —NCH₂), 2.81 (m, 2H, —NCH₂), 2.46 (s, 3H, pyrrole-CH₃).

Example 67

(Z)-2-((5-(4-fluorobenzyl sulfonyl)-2-oxoindolin-3-yl idene)methyl)-3-methyl-5-(2-(piperidin-1-yl)ethyl)-5,6,7,8-tetrahydropyrrolo[3,2-c]azepin-4(1H)-one

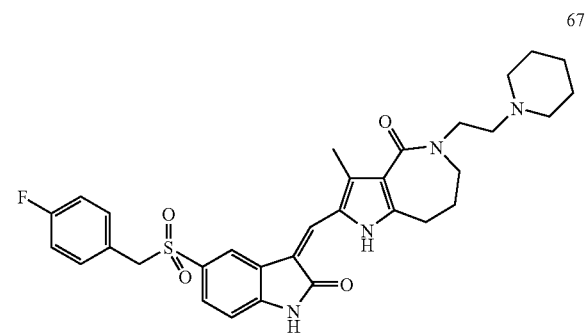

67

3-Methyl-4-oxo-5-(2-piperidin-1-yl-ethyl)-1,4,5,6,7,8-hexahydro-pyrrolo[3,2-c]azepine-2-carbaldehyde 32d (57.6 mg, 0.21 mmol) and 5-(4-fluoro-phenylmethanesulfonyl)-1,3-dihydro-indol-2-one 65a (57.6 mg, 0.19 mmol) were dissolved in 2 ml of ethanol, and added with 42 μl of piperidine to the solution at room temperature. Upon completion of the addition, the reaction mixture was heated to reflux for 3 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-2-((5-(4-fluorobenzyl sulfonyl)-2-oxoindolin-3-ylidene)methyl)-3-methyl-5-(2-(piperidin-1-yl)ethyl)-5,6,7,8-tetrahydropyrrolo[3,2-c]azepin-4(1H)-one 67 (84 mg, yield 76%) as an orange solid.

MS m/z (ESI): 591.3 [M+1]

¹HNMR (400 MHz, DMSO-d6) δ13.61 (s, 1H, pyrrole-NH), 11.39 (s, 1H, indole-NH), 8.24 (s, 1H, —HCO), 7.86 (s, 1H, —ArH), 7.17 (s, 1H, —CH═C), 7.39~7.13 (m, 4H, —ArH), 6.99 (d, 1H, —ArH), 4.64 (s, 2H, —ArCH₂), 3.58 (m, 2H, —NCH₂), 3.29~2.40 (m, 11H, aliphatic H), 2.97 (m, 2H, —NCH₂), 2.08 (m, 2H, —NCH₂), 1.49 (s, 3H, pyrrole-CH₃).

Example 68

(Z)-2-((5-(2,6-dichlorobenzylsulfonyl)-2-oxoindolin-3-ylidene)methyl)-3-methyl-5-(2-(piperidin-1-yl)ethyl)-5,6,7,8-tetrahydropyrrolo[3,2-c]azepin-4(1H)-one

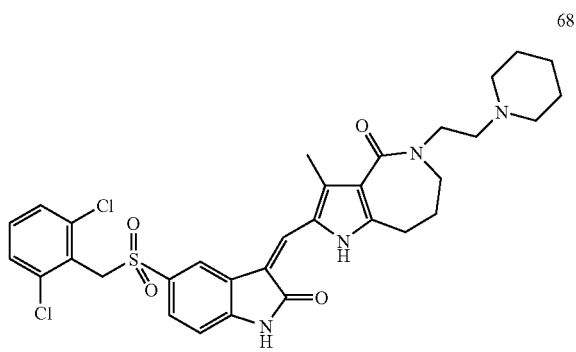

68

3-Methyl-4-oxo-5-(2-piperidin-1-yl-ethyl)-1,4,5,6,7,8-hexahydro-pyrrolo[3,2-c]azepine-2-carbaldehyde 32d (57.6 mg, 0.21 mmol) and 5-(2,6-dichloro-phenylmethanesulfonyl)-1,3-dihydro-indol-2-one 64c (67.2 mg, 0.19 mmol) were dissolved in 2.5 ml of ethanol, and added with 42 μl of piperidine to the solution at room temperature. Upon completion of the addition, the reaction mixture was heated to reflux for 3 hours. After thin lay chromatography showed the disappearance of starting materials, the reaction mixture was naturally cooled to room temperature and filtered. The filter cake was washed with anhydrous ethanol (3 ml×2), and dried to obtain the title compound (Z)-2-(5-(2,6-dichlorobenzylsulfonyl)-2-oxoindolin-3-ylidene)methyl)-3-methyl-5-(2-(piperidin-1-yl)ethyl)-5,6,7,8-tetrahydropyrrolo[3,2-c]azepin-4(1H)-one 68 (93 mg, yield 77.5%) as an orange solid.

MS m/z (ESI): 641.2 [M+1]

¹HNMR (400 MHz, DMSO-d6) δ8.79 (s, 1H, —ArH), 7.90 (s, 1H, —CH═C), 7.51~7.41 (m, 3H, —ArH), 7.05 (d, 1H, —ArH), 4.89 (m, 2H, —ArCH$_2$), 3.57 (m, 2H, —NCH$_2$), 3.35 (m, 2H, —NCH$_2$), 2.97 (m, 2H, —NCH$_2$), 3.31~2.39 (m, 15H, aliphatic H), 2.07 (m, 2H, —NCH$_2$).

Example 69

(Z)-2-(5-(4-fluorobenzylsulfonyl)-2-oxoindolin-3-ylidene)methyl)-3-methyl-5-(2-morpholinoethyl)-5,6,7,8-tetrahydropyrrolo[3,2-c]azepin-4(1H)-one

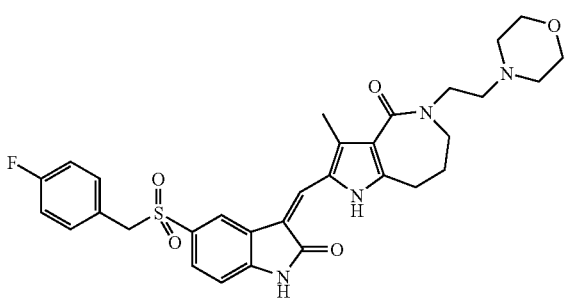

69

3-Methyl-5-(2-morpholin-4-yl-ethyl)-4-oxo-1,4,5,6,7,8-hexahydro-pyrrolo[3,2-c]azepine-2-carbaldehyde 10c (80 mg, 0.26 mmol) and 5-(4-fluoro-phenylmethanesulfonyl)-1,3-dihydro-indol-2-one 65a (72 mg, 0.24 mmol) were dissolved in 2.5 ml of ethanol, and added with 42 μA of piperidine the solution at room temperature. Upon completion of the addition, the reaction mixture was heated to reflux for 3 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-2-(5-(4-fluorobenzylsulfonyl)-2-oxoindolin-3-ylidene)methyl)-3-methyl-5-(2-morpholinoethyl)-5,6,7,8-tetrahydropyrrolo[3,2-c]azepin-4(1H)-one 69 (120 mg, yield 85.7%) as an orange solid.

MS m/z (ESI): 593.5 [M+1]

¹HNMR (400 MHz, DMSO-d6) δ13.61 (s, 1H, pyrrole-NH), 11.39 (s, 1H, indole-NH), 8.24 (s, 1H, —ArH), 7.86 (s, 1H, —ArH), 7.40 (m, 1H, —ArH), 7.24 (m, 3H, 3×—ArH), 7.21 (s, 1H, —CH═C), 7.01 (d, 1H, —ArH), 4.64 (s, 2H, —ArCH$_2$), 3.58~2.07 (m, 18H, aliphatic H), 2.44 (s, 3H, pyrrole-CH$_3$).

Example 70

(Z)-2-(5-(2,6-dichlorobenzylsulfonyl)-2-oxoindolin-3-ylidene)methyl)-5-(2-(diethylamino)ethyl)-3-methyl-5,6,7,8-tetrahydropyrrolo[3,2-c]azepin-4(1H)-one

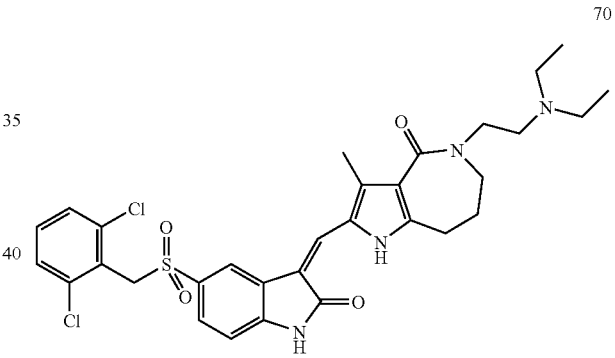

70

5-(2-Diethylamino-ethyl)-3-methyl-4-oxo-1,4,5,6,7,8-hexahydro-pyrrolo[3,2-c]azepine-2-carbaldehyde 1j (60 mg, 0.21 mmol) and 5-(2,6-dichloro-phenylmethanesulfonyl)-1,3-dihydro-indol-2-one 64c (67 mg, 0.19 mmol) were dissolved in 3 ml of ethanol, and added with 52 μl of piperidine the solution at room temperature. Upon completion of the addition, the reaction mixture was heated to reflux for 2 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-2-((5-(2,6-dichlorobenzylsulfonyl)-2-oxoindolin-3-ylidene)methyl)-5-(2-(diethylamino)ethyl)-3-methyl-5,6,7,8-tetrahydro pyrrolo[3,2-c]azepin-4(1H)-one 70 (95 mg, yield 79%) as an orange solid.

MS m/z (ESI): 629.3 [M+1]

¹HNMR (400 MHz, DMSO-d6) δ13.62 (s, 1H, pyrrole-NH), 11.42 (s, 1H, indole-NH), 8.29 (s, 1H, —ArH), 7.90 (s, 1H, —ArH), 7.49 (s, 1H, —CH═C), 7.52 (m, 2H, —NCH$_2$), 7.06 (s, 1H, —ArH), 4.89 (s, 2H, —ArCH$_2$), 3.52~2.07 (m, 14H, aliphatic H), 2.50 (s, 3H, pyrrole-CH$_3$), 1.00 (m, 6H, 2×—CH$_3$).

Example 71

(Z)-2-(5-(4-fluorobenzylsulfonyl)-2-oxoindolin-3-ylidene)methyl)-5-(2-(diethylamino)ethyl)-3-methyl-5,6,7,8-tetrahydropyrrolo[3,2-c]azepin-4(1H)-one

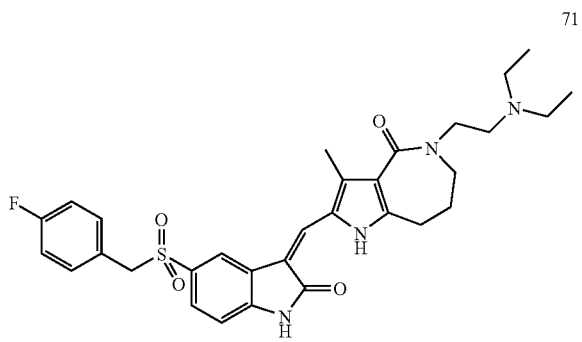

71

5-(2-Diethylamino-ethyl)-3-methyl-4-oxo-1,4,5,6,7,8-hexahydro-pyrrolo[3,2-c]azepine-2-carbaldehyde 1j (60 mg, 0.21 mmol) and 5-(4-fluoro-phenylmethanesulfonyl)-1,3-dihydro-indol-2-one 65a (58 mg, 0.19 mmol) were dissolved in 2 ml of ethanol, and added with 34 µl of piperidine the solution at room temperature. Upon completion of the addition, the reaction mixture was heated to reflux for 3 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-2-(5-(4-fluorobenzylsulfonyl)-2-oxoindolin-3-ylidene)methyl)-5-(2-(diethylamino)ethyl)-3-methyl-5,6,7,8-tetrahydropyrrolo[3,2-c]azepin-4(1H)-one 71 (73 mg, yield 66%) as an orange solid.

MS m/z (ESI): 579.3 [M+1]

$^1$HNMR (400 MHz, DMSO-d6) δ13.59 (s, 1H, pyrrole-NH), 11.39 (s, 1H, indole-NH), 8.24 (s, 1H, —ArH), 7.86 (s, 1H, —ArH), 7.21 (s, 1H, —CH═C), 7.24~7.13 (m, 3H, —ArH), 7.01 (d, 1H, —ArH), 4.64 (s, 2H, —ArCH$_2$), 3.52~2.06 (m, 14H, aliphatic H), 2.50 (s, 3H, pyrrole-CH$_3$), 1.00 (m, 6H, 2×—CH$_3$).

Example 72

(R,Z)-2-(5-(2,6-dichlorobenzylsulfonyl)-2-oxoindolin-3-ylidene)methyl)-5-(2-hydroxy-3-morpholinopropyl)-3-methyl-5,6,7,8-tetrahydropyrrolo[3,2-c]azepin-4(1H)-one

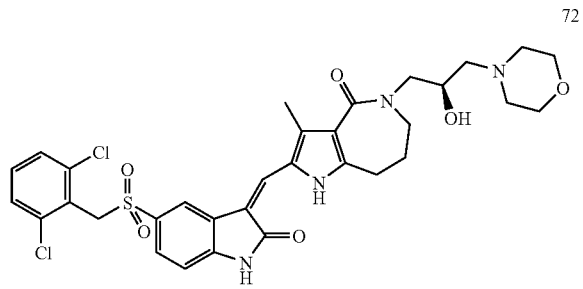

72

5-(2-Hydroxy-3-morpholin-4-yl-propyl)-3-methyl-4-oxo-1,4,5,6, 7, 8-hexahydro-pyrrolo[3,2-c]azepine-2-carbaldehyde 53f (80 mg, 0.24 mmol) and 5-(2,6-dichloro-phenyl-methanesulfonyl)-1,3-dihydro-indol-2-one 64c (75 mg, 0.21 mmol) were dissolved in 3 ml of ethanol, and added with 30 µl of piperidine to the solution at room temperature. Upon completion of the addition, after stirring for 4 minutes, the reaction mixture was reacted at 120° C. for 4 minutes under microwave and became orange turbid solution. After thin lay chromatography showed the disappearance of starting materials, the reaction mixture was naturally cooled to room temperature, and filtered. The filter cake was washed with anhydrous ethanol (2 ml×2) and dried to obtain the title compound (R,Z)-2-((5-(2,6-dichlorobenzylsulfonyl)-2-oxoindolin-3-ylidene)methyl)-5-(2-hydroxy-3-morpholinopropyl)-3-methyl-5,6,7,8-tetrahydropyrrolo[3,2-c]azepin-4(1H)-one 72 (120 mg, yield 85%) as a yellow solid.

MS m/z (ESI): 673.2 [M+1]

$^1$HNMR (400 MHz, DMSO-d6) δ13.63 (s, 1H, pyrrole-NH), 11.42 (s, 1H, indole-NH), 8.29 (d, 1H, —ArH), 7.90 (s, 1H, —ArH), 7.52 (m, 4H, —ArH), 7.42 (s, 1H, —CH═C), 7.06 (d, 1H, —ArH), 4.89 (s, 2H, —ArCH$_2$), 4.74 (m, 1H, —CHO), 3.92~2.33 (m, 18H, aliphatic H), 2.44 (s, 3H, pyrrole-CH$_3$).

Example 73

(R,Z)-2-(5-(4-fluorobenzylsulfonyl)-2-oxoindolin-3-ylidene)methyl)-5-(2-hydroxy-3-morpholinopropyl)-3-methyl-5,6,7,8-tetrahydropyrrolo[3,2-c]azepin-4(1H)-one

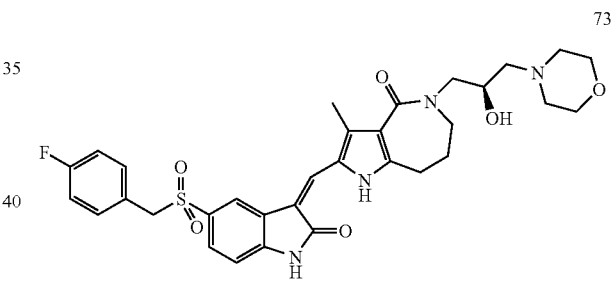

73

5-(2-Hydroxy-3-morpholin-4-yl-propyl)-3-methyl-4-oxo-1,4,5,6,7,8-hexahydro-pyrrolo[3,2-c]azepine-2-carbaldehyde 53f (80 mg, 0.24 mmol) and 5-(4-fluoro-phenyl-methanesulfonyl)-1,3-dihydro-indol-2-one 65a (64 mg, 0.21 mmol) were dissolved in 3 ml of ethanol, and added with 30 µl of piperidine to the solution at room temperature. Upon completion of the addition, after stirring for 4 minutes, the reaction mixture was reacted at 120° C. for 4 minutes under microwave and became orange turbid solution. After thin lay chromatography showed the disappearance of starting materials, the reaction mixture was naturally cooled to room temperature, and filtered. The filter cake was washed with anhydrous ethanol (2 ml×2) and dried to obtain the title compound (R,Z)-2-(5-(4-fluorobenzylsulfonyl)-2-oxoindolin-3-ylidene) methyl)-5-(2-hydroxy-3-morpholinopropyl)-3-methyl-5,6,7,8-tetrahydropyrrolo[3,2-c]azepin-4(1H)-one 73 (100 mg, yield 76%) as a yellow solid.

MS m/z (ESI): 621.3 [M−1]

$^1$HNMR (400 MHz, DMSO-d6) δ13.61 (s, 1H, pyrrole-NH), 11.38 (s, 1H, indole-NH), 8.24 (d, 1H, —ArH), 7.86 (s, 1H, —ArH), 7.40 (m, 1H, —ArH), 7.24 (m, 1H, —ArH), 7.17 (m, 1H, —ArH), 7.13 (s, 1H, —CH═C), 7.01 (d, 1H, —ArH), 4.74 (m, 1H, —CHO), 4.64 (s, 2H, —ArCH$_2$), 3.92~2.32 (m, 18H, aliphatic H), 2.44 (s, 3H, pyrrole-CH$_3$).

Example 74

(Z)-5-(2-(diethylamino)ethyl)-2-((4-(2,3-difluorophenyl)-5-fluoro-2-oxoindolin-3-ylidene)methyl)-3-methyl-5,6,7,8-tetrahydropyrrolo[3,2-c]azepin-4(1H)-one

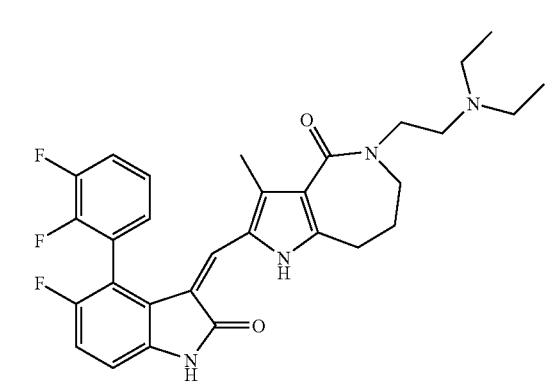

74

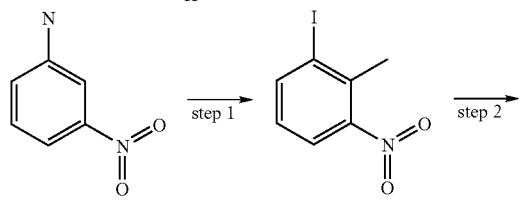

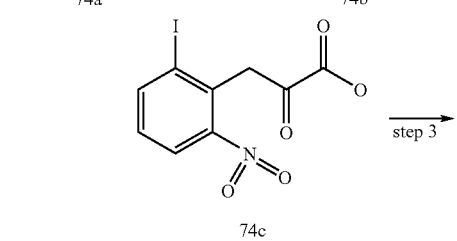

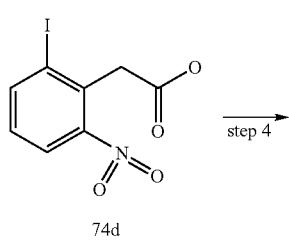

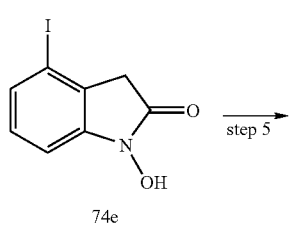

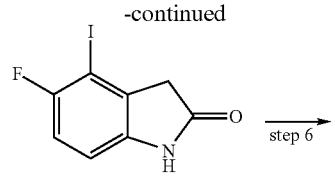

74f

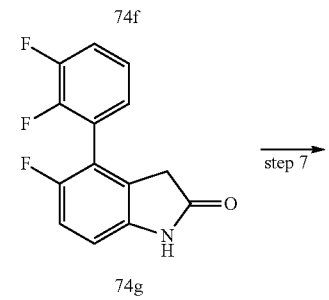

74g

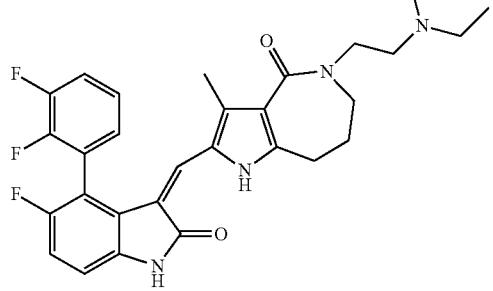

74

Step 1

1-Iodo-2-methyl-3-nitro-benzene

2-Methyl-3-nitro-phenylamine 74a (21.28 g, 0.14 mol) was dissolved in 70 ml of concentrated hydrochloric acid in an ice-water bath, added with water (40 ml), stirred at 0~5° C. and yellow-green precipitates were formed. The reaction mixture was added dropwise with nitric acid solution (40 ml, 3.6 M), stirred for 15 minutes and filtered. The filtrate was added dropwise to potassium iodide solution (280 ml, 5.25 M) at 0~5° C. Upon completion of the addition, the reaction mixture was stirred for 1 hour. After thin lay chromatography showed the disappearance of starting materials, the reaction mixture was filtered. The filter cake was dissolved in ethyl acetate, and washed with aqueous sodium hydroxide solution (10%), water, sodium thiosulfate (5%), saturated brine. The organic phase was dried over anhydrous magnesium sulfate to obtain the brown oil (34.4 g). The crude product was purified by silica gel column chromatography to obtain the title compound 1-iodo-2-methyl-3-nitro-benzene 74b (30.1 g, yield 81.7%) as a white solid.

Step 2

3-(2-Iodo-6-nitro-phenyl)-2-oxo-propionic acid

Sodium ethoxide solution (35 ml, 44 mmol) in an ice-water bath was added dropwise with a solution of 1-iodo-2-methyl-3-nitro-benzene 74b in ethanol (35 ml, 40 mmol) under an argon atmosphere. Upon completion of the addition, the reaction mixture was stirred until substantial brown precipitates were formed, and added with diethyl oxalate (6 ml, 44 mmol) in one portion. The reaction mixture was refluxed at 100° C. in an oil bath for 0.5 hour, added with water (70 ml) and refluxed for another 1 hour. The reaction mixture was concentrated under reduced pressure to evaporate ethanol, washed with ethyl acetate (50 ml) under base condition, adjusted to pH 3 with hydrochloric acid (1M), and extracted with ethyl acetate (30 ml×3). The combined organic extracts were washed with saturated brine (30 ml), dried over anhydrous sodium sulfate, filtered and concentrated under reduced pressure to obtain the title compound 3-(2-iodo-6-nitro-phenyl)-2-oxo-propionic acid 74c (2.94 g) as a brown oil to be used directly in the next step.

MS: 334.2 [M−1].

Step 3

(2-Iodo-6-nitro-phenyl)-acetic acid 3-(2-Iodo-6-nitro-phenyl)-2-oxo-propionic acid 74c (2.086 g, 6.2 mmol) was dissolved in 6 ml of methanol under stirring, and added with 20 ml of water and 7 ml of hydrogen peroxide to the solution at room temperature. Upon completion of the addition, the reaction mixture was stirred at room temperature for 1 hour. After thin lay chromatography showed the disappearance of starting materials, the reaction mixture was filtered, extracted with ethyl acetate (20 ml×2). The combined organic extracts were concentrated under reduced pressure, combined with the above filter cake, and dried to obtain the title compound (2-iodo-6-nitro-phenyl)-acetic acid 74d (1.77 g, yield 70%) as a brown solid.

Step 4

1-Hydroxy-4-iodo-1,3-dihydro-indol-2-one (2-Iodo-6-nitro-phenyl)-acetic acid 74d (0.91 g, 3 mmol) was dissolved in ethanol (30 ml, 95%), and added with palladium on activated carbon (30 mg, 3%) to the solution. Upon completion of the addition, the reaction mixture was stirred for 2 hours under a hydrogen atmosphere. After thin lay chromatography showed the disappearance of starting materials, the reaction mixture was filtered, and concentrated under reduced pressure. The residue was purified by silica gel column chromatography to obtain the title compound 1-hydroxy-4-iodo-1,3-dihydro-indol-2-one 74e (516 mg, yield 63.4%) as a white solid.

MS: 274.1 [M−1]

Step 5

5-Fluoro-4-iodo-1,3-dihydro-indol-2-one

1-Hydroxy-4-iodo-1,3-dihydro-indol-2-one 74e (326 mg, 1.19 mmol) was dissolved in 24 ml of dichloromethane in a dry ice-acetone bath, and added slowly with (diethylamino)sulfur trifluoride (0.16 ml, 1.19 mmol) while maintaining the temperature at −25° C. Upon completion of the addition, the reaction mixture was stirred at −25° C. for 15 minutes until it became clear. After thin lay chromatography showed the disappearance of starting materials, the reaction mixture was quenched with saturated sodium bicarbonate solution, added with saturated brine (30 ml), and extracted with dichloromethane (30 ml×3). The combined organic extracts were washed with saturated brine (30 ml), and dried over anhydrous sodium sulfate to obtain a yellow solid (284 mg). The crude product was purified by silica gel column chromatography to obtain the title compound 5-fluoro-4-iodo-1,3-dihydro-indol-2-one 74f (114 mg, yield 34.7%) as a white solid.

MS: 276.6 [M−1]

Step 6

4-(2,3-Difluoro-phenyl)-5-fluoro-1,3-dihydro-indol-2-one

5-Fluoro-4-iodo-1,3-dihydro-indol-2-one 74f (277 mg, 1 mmol) was dissolved in 10 ml of N,N-dimethylformamide, and added with 2,3-fluoro phenylboric acid (158 mg, 1 mmol), sodium bicarbonate (168 mg, 2 mmol) and water (10 ml) to the solution under an argon atmosphere. Upon completion of the addition, the mixture was stirred to mix well, added with tetrakis(triphenylphosphine)palladium (109 mg, 0.15 mmol) and heated to reflux overnight. After thin lay chromatography showed the disappearance of starting materials, the reaction mixture was concentrated under reduced pressure, added with hydrochloride acid solution (10 ml, 1 M), and extracted with ethyl acetate (10 ml×3). The combined organic extracts were dried over anhydrous magnesium sulfate, filtered and concentrated under reduced pressure. The residue was purified by silica gel column chromatography to obtain the title compound 4-(2,3-difluoro-phenyl)-5-fluoro-1,3-dihydro-indol-2-one 74 g (42 mg, yield 16%) as a gray solid.

MS: 262.0 [M+1].

Step 7

(Z)-5-(2-(diethylamino)ethyl)-2-(4-(2,3-difluorophenyl)-5-fluoro-2-oxoindolin-3-ylidene)methyl)-3-methyl-5,6,7,8-tetrahydropyrrolo[3,2-c]azepin-4(1H)-one 5-(2-Diethylamino-ethyl)-3-methyl-4-oxo-1,4,5,6,7,8-hexahydro-pyrrolo[3,2-c]azepine-2-carbaldehyde 1j (73 mg, 0.25 mmol) and 4-(2,3-difluoro-phenyl)-5-fluoro-1,3-dihydro-indol-2-one 74 g (60 mg, 0.23 mmol) were dissolved in 2 ml of ethanol, and added with 35 µl of piperidine to the solution at room temperature. Upon completion of the addition, the mixture was heated to reflux for 2 hours. After thin lay chromatography showed the disappearance of starting materials, the reaction mixture was naturally cooled to room temperature, and filtered. The filter cake was washed with anhydrous ethanol (3 ml×2) and dried to obtain the title compound (Z)-5-(2-(diethylamino)ethyl)-2-(4-(2,3-difluorophenyl)-5-fluoro-2-oxoindolin-3-ylidene)methyl)-3-methyl-5,6,7,8-tetrahydropyrrolo[3,2-c]azepin-4(1H)-one 74 (23 mg, yield 19%) as an orange solid.

MS m/z (ESI): 537.2 [M+1]

$^1$HNMR (400 MHz, DMSO-d6) δ13.58 (s, 1H, pyrrole-NH), 11.178 (s, 1H, indole-NH), 8.24 (s, 1H, —HCO), 7.70~6.998 (m, 5H, —ArH), 6.65 (s, 1H, —CH═C), 4.36 (m, 2H, —NCH$_2$), 2.91 (m, 2H, —NCH$_2$), 2.54 (s, 3H, pyrrole-CH$_3$), 1.2~3.4 (m, 14H, aliphatic H), 2.20 (m, 2H, —NCH$_2$).

Example 75

2-((Z)-(4-(2,3-difluorophenyl)-5-fluoro-2-oxoindolin-3-ylidene)methyl)-5-((R)-2-hydroxy-3-morpholinopropyl)-3-methyl-5,6,7,8-tetrahydropyrrolo[3,2-c]azepin-4(1H)-one

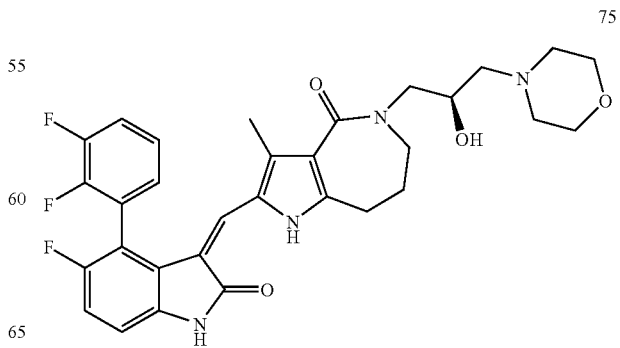

75

5-(2-Hydroxy-3-morpholin-4-yl-propyl)-3-methyl-4-oxo-1,4,5,6,7,8-hexahydro-pyrrolo[3,2-c]azepine-2-carbaldehyde 53f (84 mg, 0.25 mmol) and 4-(2,3-difluoro-phenyl)-5-fluoro-1,3-dihydro-indol-2-one 74 g (60 mg, 0.23 mmol) were dissolved in 2 ml of ethanol, and added with 35 µl of piperidine to the solution at room temperature. Upon completion of the addition, the mixture was heated to reflux for 2 hours. After thin lay chromatography showed the disappearance of starting materials, the reaction mixture was naturally cooled to room temperature, and filtered. The filter cake was washed with anhydrous ethanol (3 ml×2) and dried to obtain the title compound 2-((Z)-(4-(2,3-difluorophenyl)-5-fluoro-2-oxoindolin-3-ylidene)methyl)-5-((R)-2-hydroxy-3-morpholinopropyl)-3-methyl-5,6,7,8-tetrahydropyrrolo[3,2-c]azepin-4(1H)-one 75 (100 mg, yield 78%) as an orange solid.

MS m/z (ESI): 581.3 [M+1]

$^1$HNMR (400 MHz, DMSO-d6) δ13.57 (s, 1H, pyrrole-NH), 11.12 (s, 1H, indole-NH), 7.704~6.98 (m, 5H, —ArH), 6.65 (s, 1H, —CH═C), 4.69 (m, 1H, —CHOH), 3.86 (m, 2H, —NCH$_2$), 2.89 (m, 2H, —NCH$_2$), 2.33 (m, 2H, —NCH$_2$), 3.86~2.28 (m, 12H, aliphatic H)

Example 76

(R,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one

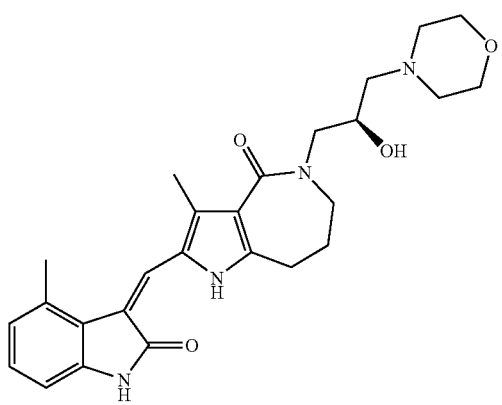

76

5-(2-Hydroxy-3-morpholin-4-yl-propyl)-3-methyl-4-oxo-1,4,5,6,7,8-hexahydro-pyrrolo[3,2-c]azepine-2-carbaldehyde 53f (30 mg, 0.09 mmol) and 4-methyl-1,3-dihydro-indol-2-one (12 mg, 0.08 mmol) were dissolved in 156 µl of ethanol, and added with 4.4 µl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (R,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one 76(12 mg, yield 30%) as an orange solid.

MS m/z (ESI): 465.2 (M+1)

$^1$HNMR (400 MHz, DMSO-d6) δ13.71 (s, 1H, pyrrole-NH), 10.92 (s, 1H, indole-NH), 7.57 (s, 1H, —CH═C), 7.07~6.77 (m, 3H, —ArH), 4.72 (d, 1H, —OH), 3.90 (m, 1H, —CHOH), 3.78 (dd, 1H, seven membered ring outer amide-NCH$_2$), 3.58 (t, 4H, morpholin intra 2×—CH$_2$O), 3.40 (m, 2H, seven membered ring —NCH$_2$), 3.17 (dd, 1H, seven membered ring outer amide-NCH$_2$), 2.94 (t, 214, pyrrole-CH$_2$), 2.59 (s, 3H, benzylmethyl), 2.44 (m, 4H, morpholin intra 2×CH$_2$N), 2.39 (s, 3H, pyrrole —CH$_3$), 2.29 (m, 2H, morpholin outer-NCH$_2$), 2.08 (m, 2H, seven membered ring CH$_2$—CH$_2$—CH$_2$).

Example 77

(R,Z)-5-(2-hydroxy-3-morpholinopropyl)-2-((6-methoxy-2-oxoindolin-3-ylidene) methyl)-3-methyl-5,6,7,8-tetrahydropyrrolo[3,2-c]azepin-4(1H)-one

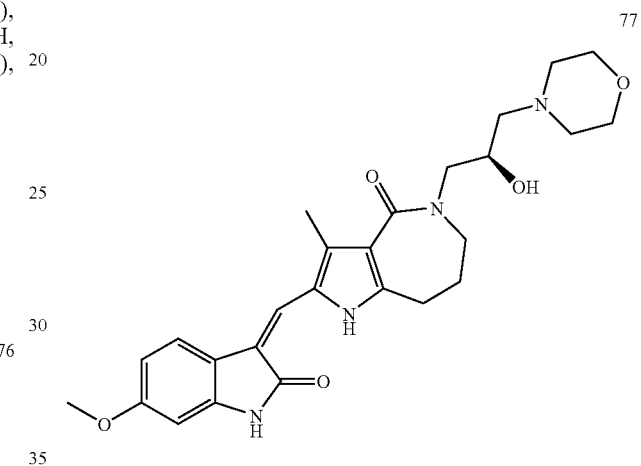

77

5-(2-Hydroxy-3-morpholin-4-yl-propyl)-3-methyl-4-oxo-1,4,5,6,7,8-hexahydro-pyrrolo[3,2-c]azepine-2-carbaldehyde 53f (30 mg, 0.09 mmol) and 6-methoxyl-1,3-dihydro-indol-2-one (13 mg, 0.08 mmol) were dissolved in 1560 of ethanol, and added with 4.4 µl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (R,Z)-5-(2-hydroxy-3-morpholinopropyl)-2-(6-methoxy-2-oxoindolin-3-ylidene) methyl)-3-methyl-5,6,7,8-tetrahydropyrrolo[3,2-c]azepin-4(1H)-one 77 (22 mg, yield 51%) as a yellow solid.

MS m/z (ESI): 481.2 (M+1)

$^1$HNMR (400 MHz, DMSO-d6) δ13.47 (s, 1H, pyrrole-NH), 10.94 (s, 1H, indole-NH), 7.68 (d, 1H, —ArH), 7.40 (s, 1H, —CH═C), 6.60 (d, 1H, —ArH), 6.46 (s, 1H, —ArH), 4.70 (d, 1H, —OH), 3.89 (m, 1H, —CHOH), 3.77 (dd, 1H, seven membered ring outer amide-NCH$_2$), 3.58 (t, 4H, morpholinintra 2×—CH$_2$O), 3.41 (m, 2H, seven membered ring —NCH$_2$), 3.17 (dd, 1H, seven membered ring outer amide-NCH$_2$), 2.93 (t, 2H, pyrrole-CH$_2$), 2.41 (s, 3H, pyrrole-CH$_3$), 2.34 (m, 4H, morpholinintra 2×—CH$_2$N), 2.29 (m, 2H, morpholin outer-NCH$_2$), 2.07 (m, 2H, seven membered ring CH$_2$—CH$_2$—CH$_2$).

Example 78

(S,Z)-2-(5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one

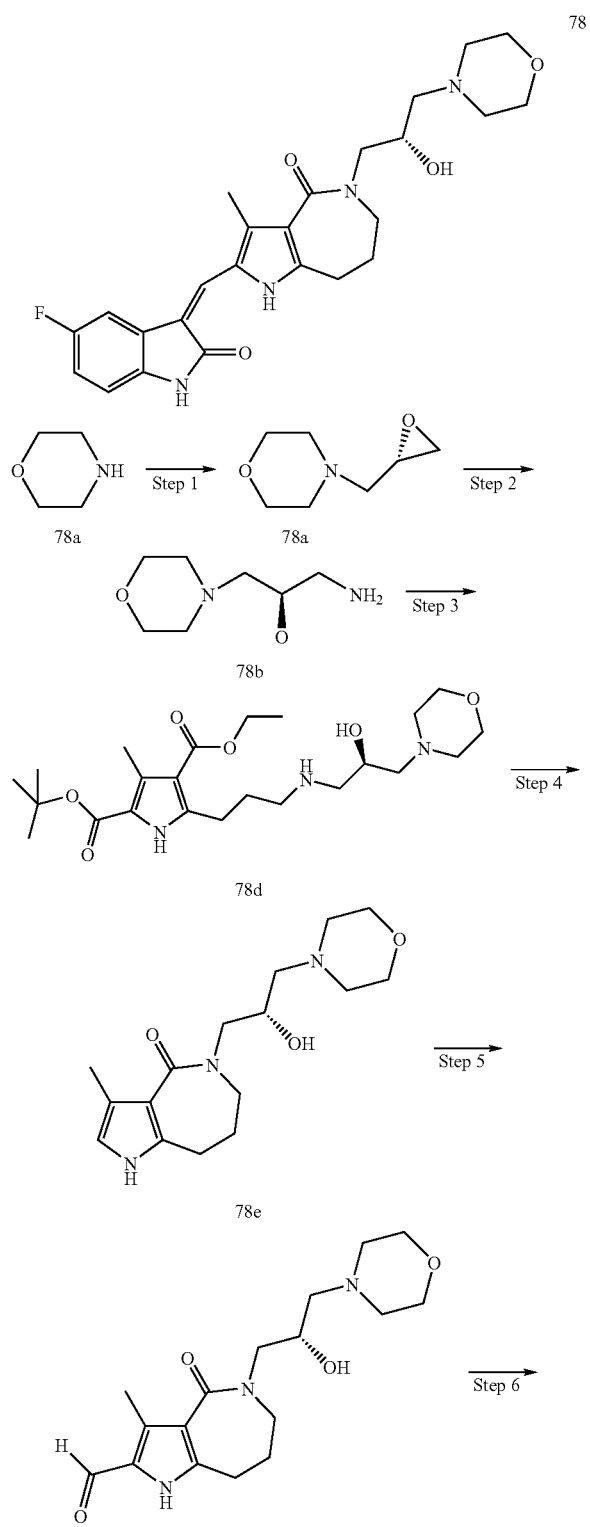

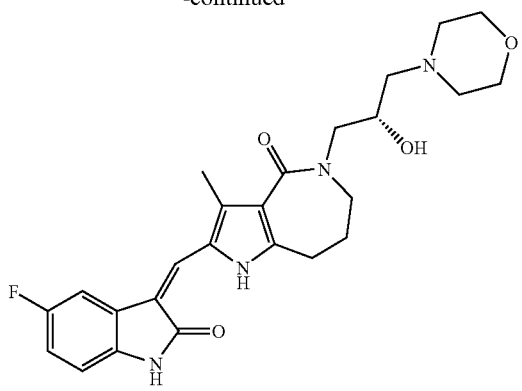

Step 1

(S)-4-Oxiranylmethyl-morpholine

Morpholine-78a (4.356 ml, 50 mmol) was dissolved in 2.5 ml of tert-butyl alcohol at room temperature, the solution was cooled to 0° C., and added slowly with (S)-(+)-2-chloromethyl-oxirane (4.02 ml, 50 mmol) to the solution. Upon the completion of the addition, the reaction system was naturally warmed to room temperature and stirred overnight. After thin lay chromatography showed the disappearance of starting materials, the reaction system was cooled to 10° C. in an ice-water bath, added with a solution of potassium tert-butoxide in tetrahydrofuran (30 ml, 1.67 mol/L, 50 mmol), the color of the solution turned from light yellow to white suspension. Upon the completion of the addition, the reaction mixture was stirred for another 30 minutes. After thin lay chromatography showed the disappearance of starting materials, the reaction was stopped. The reaction mixture was concentrated under reduced pressure, added with 20 ml of water, extracted with dichloromethane (100 ml×3). The combined organic phase was washed with saturated brine (100 ml×1), dried with anhydrous magnesium sulfate, filtered to remove the drying agent, the filtrate was concentrated to obtain the title compound (S)-4-oxiranylmethyl-morpholine-78b (5.52 g, yield 77.2%) as a yellow solid.

MS m/z (ESI): 144.4 (M+1)

Step 2

(R)-1-Amino-3-morpholin-4-yl-propan-2-ol (S)-4-oxiranylmethyl-morpholine 78b (5.52 g, 38.6 mmol) was added slowly with 395 ml of aqueous ammonia (25%, 5.8 mol) in an ice-water bath while maintaining the temperature below 0° C. Upon the completion of the addition, the reaction mixture was naturally warmed to room temperature, and stirred for another 18 hours. After thin lay chromatography showed the disappearance of starting materials, the reaction was stopped. The reaction solution was concentrated under reduced pressure to remove the reaction solvent and to obtain the title compound (R)-1-Amino-3-morpholin-4-yl-propan-2-ol 78c (6.1 g, yield 99%) as a light yellow oil.

MS m/z (ESI): 161.3 (M+1)

Step 3

(S)-5-[3-(2-Hydroxy-3-morpholin-4-yl-propylamino)-propyl]-3-methyl-1H-pyrrole-2,4-dicarboxylic acid 2-tert-butyl ester 4-ethyl ester 5-(3-methanesulfonyloxy-propyl)-3-methyl-1H-pyrrole-2,4-dicarboxylic acid 2-tert-butyl ester 4-ethyl ester 1 g (1.13 g, 2.9 mmol) was dissolved in 5.6 ml of dichloromethane under stirring, and added with (R)-1-amino-3-morpholin-4-yl-propan-2-ol 78c (0.93 g, 5.8 mmol) to the solution at room temperature. Upon the completion of the addition, the reaction mixture was heated to 45° C. for 14 hours in an oil bath. After thin lay chromatography showed the disappearance of starting materials, the reaction was stopped. The reaction solution was added with 15 ml of saturated brine, extracted with dichloromethane (20 ml×3), the combined organic phase was concentrated under reduced pressure, and the residue was purified by silica gel column chromatography to obtain the title compound (S)-5-[3-(2-hydroxy-3-morpholin-4-yl-propylamino)-propyl]-3-methyl-1H-pyrrole-2,4-dicarboxylic acid 2-tert-butyl ester 4-ethyl ester 78d (600 mg, yield 72.5%) as a yellow oil.
MS m/z (ESI): 454.2 (M+1)

Step 4

(S)-5-(2-Hydroxy-3-morpholin-4-yl-propyl)-3-methyl-5,6,7,8-tetrahydro-1H-pyrrolo[3,2-c]azepin-4-one (S)-5-[3-(2-Hydroxy-3-morpholin-4-yl-propylamino)-propyl]-3-methyl-1H-pyrrole-2 and 4-dicarboxylic acid 2-tert-butyl ester 4-ethyl ester 78d (580 mg, 1.28 mmol) were dissolved in 6 ml of toluene under an argon atmosphere, the reaction mixture was cooled in an ice-water bath, meanwhile a solution of trimethylaluminum in toluene (1.9 ml, 2 mol/L, 3.84 mmol) was added to the solution. Upon the completion of the addition, the ice-water bath was removed, and the reaction solution was heated to reflux for 24 hours. After thin lay chromatography showed the disappearance of starting materials, the reaction was stopped. The reaction solution was concentrated under reduced pressure to remove the reaction solvent, added with 20 ml hydrochloric acid (6 mol/L) and stirred for 20 minutes, adjusted to about pH 12 with sodium hydroxide solution (12 mol/L) in an ice-water bath. The resulting mixture was extracted with dichloromethane (50 ml×2), the combined organic phase was concentrated under reduced pressure, and the residue was purified by silica gel column chromatography to obtain the title compound (S)-5-(2-hydroxy-3-morpholin-4-yl-propyl)-3-methyl-5,6,7,8-tetrahydro-1H-pyrrolo[3,2-c]azepin-4-one 78e (300 mg, yield 57.6%) as a white solid.
MS m/z (ESI): 308.2 (M+1)

Step 5

(S)-5-(2-Hydroxy-3-morpholin-4-yl-propyl)-3-methyl-4-oxo-1,4,5,6,7,8-hexahydro-pyrrolo[3,2-c]azepine-2-carbaldehyde (Chloromethylene)dimethylammonium chloride (130 mg, 0.977 mmol) was dissolved in 3 ml of dichloromethane under stirring under an argon atmosphere, the solution was cooled to 0° C. in ice-water bath. (S)-5-(2-hydroxy-3-morpholin-4-yl-propyl)-3-methyl-5,6,7,8-tetrahydro-1H-pyrrolo[3,2-c]azepin-4-one 78e (300 mg, 0.977 mmol) was dissolved in 2 ml of dichloromethane under stirring, the resulting solution was added to the above solution while maintaining the temperature below 0° C. Upon the completion of addition, the reaction mixture was stirred for 20 minutes at room temperature. After thin lay chromatography showed the disappearance of starting materials, the reaction solution was added with sodium hydroxide solution (12 mol/L) to quench the reaction. The reaction solution was added with 10 ml of saturated brine, extracted with the mixture solvent of dichloromethane and methanol (V:V=10:1) (100 ml×3), the combined organic phase was washed with saturated brine (100 ml×1), dried over anhydrous magnesium sulfate, filtered to remove the drying agent, the filtrate was concentrated under reduced pressure, the residue was purified by silica gel column chromatography to obtain the title compound (S)-5-(2-Hydroxy-3-morpholin-4-yl-propyl)-3-methyl-4-oxo-1,4,5,6,7,8-hexahydro-pyrrolo[3,2-c]azepine-2-carbaldehyde 78f (200 mg, yield 61%) as a white solid.
MS m/z (ESI): 336.2 (M+1)

Step 6

(S,Z)-2-(5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one (S)-5-(2-Hydroxy-3-morpholin-4-yl-propyl)-3-methyl-4-oxo-1,4,5,6,7,8-hexahydro-pyrrolo[3,2-c]azepine-2-carbaldehyde 78f (50 mg, 0.149 mmol) was dissolved in 261 μl of ethanol under stirring, and added with 5-fluoro-1,3-dihyrdro-indole-2-one (20.28 mg, 0.134 mmol) and piperidine (7.3 μl, 0.074 mmol) to the solution at room temperature. Upon the completion of the addition, the reaction mixture was stirred for 2 hours in dark at 80° C. in an oil bath. After thin lay chromatography showed the disappearance of starting materials, the reaction was stopped, and the oil bath was removed. The reaction system was cooled to room temperature, the reaction solution was filtered and the filter cake was dried to obtain the title compound (S,Z)-2-(5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one 78(40 mg, yield 57%) as a yellow solid.
MS m/z (ESI): 469.2 (M+1) $^1$HNMR (400 MHz, DMSO-d6) δ13.73 (s, 1H, pyrrole-NH), 10.91 (s, 1H, indole-NH), 7.79~6.84 (m, 3H, —ArH), 7.56 (s, 1H, —CH=C), 4.73 (d, 1H, —OH), 3.90 (m, 1H, —CHOH), 3.76 (dd, 1H, seven-membered ring outer amide-NCH$_2$), 3.58 (t, 4H, morpholin 2×—CH$_2$O), 3.42 (m, 2H, seven-membered ring —NCH$_2$), 3.15 (dd, 1H, seven-membered ring outer amide —NCH$_2$), 2.94 (t, 2H, —CH$_2$C=C), 2.457 (s, 3H, pyrrole-CH$_3$), 2.413 (m, 4H, morpholin intra 2×—CH$_2$N), 2.306 (m, 2H, morpholin outer-NCH$_2$), 2.08 (m, 2H, seven-membered ring CH$_2$—CH$_2$—CH$_2$)

Example 79

(S,Z)-2-((5-chloro-2-oxoindolin-3-ylidene)methyl)-5-(2-hydroxy-3-morpholinoprop yl)-3-methyl-5,6,7,8-tetrahydropyrrolo[3,2-c]azepin-4(1H)-one

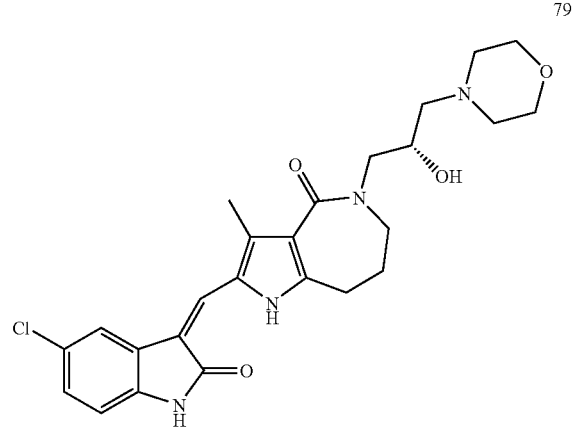

(S)-5-(2-Hydroxy-3-morpholin-4-yl-propyl)-3-methyl-4-oxo-1,4,5,6,7,8-hexa hydro-pyrrolo[3,2-c]azepine-2-carbaldehyde 78f (40 mg, 0.12 mmol 1) and 5-chloro-1,3-dihydroindol-2-one (20 mg, 0.12 mmol) were dissolved in 1.5 ml of ethanol, and added with 6 μl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (S,Z)-2-(5-chloro-2-oxoindolin-3-ylidene)methyl)-5-(2-hydroxy-3-morpholinoprop yl)-3-methyl-5,6,7,8-tetrahydropyrrolo[3,2-c]azepin-4(1H)-one 79 (46 mg, yield 79%) as a yellow solid MS m/z (ESI): 485.2 (M+1)

$^1$HNMR (400 MHz, DMSO-d6) δ13.679 (s, 1H, pyrrole-NH), 11.008 (s, 1H, indole-NH), 7.994 (s, 1H, —ArH), 7.803 (s, 1H, —CH=C), 7.159~6.869 (m, 2H, —ArH), 4.727 (d, 1H, —OH), 3.90 (m, 1H, —CHOH), 3.76 (dd, 1H, seven-membered ring outer amide —NCH$_2$), 3.58 (t, 4H, morpholin 2x—CH$_2$O), 3.418 (m, 2H, seven-membered ring —NCH$_2$), 3.15 (m, 1H, seven-membered ring outer amide —NCH$_2$), 2.937 (t, 2H, —CH$_2$C=C), 2.464 (s, 3H, pyrrole-CH$_3$), 2.428 (m, 4H, morpholin intra 2x—CH$_2$N), 2.299 (m, 2H, morpholin outer —NCH$_2$), 2.076 (m, 2H, seven-membered ring CH$_2$—CH$_2$—CH$_2$)

Example 80

(S,Z)-2-((5-bromo-2-oxoindolin-3-ylidene)methyl)-5-(2-hydroxy-3-morpholinoprop yl)-3-methyl-5,6,7,8-tetrahydropyrrolo[3,2-c]azepin-4(1H)-one

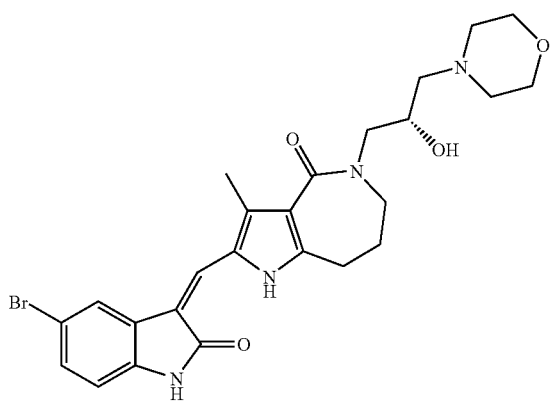

(S)-5-(2-Hydroxy-3-morpholin-4-yl-propyl)-3-methyl-4-oxo-1,4,5,6,7,8-hexa hydro-pyrrolo[3,2-c]azepine-2-carbaldehyde 78f (40 mg, 0.12 mmol) and 5-bromo-1,3-dihydroindol-2-one (25 mg, 0.12 mmol) were dissolved in 1.5 ml of ethanol, and added with 6 μl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (S,Z)-2-((5-bromo-2-oxoindolin-3-ylidene)methyl)-5-(2-hydroxy-3-morpholinoprop yl)-3-methyl-5,6,7,8-tetrahydropyrrolo[3,2-c]azepin-4(1H)-one 80 (51 mg, yield 81%) as a yellow solid.

MS m/z (ESI): 529.1 (M+1)

$^1$HNMR (400 MHz, DMSO-d6) δ13.673 (s, 1H, pyrrole-NI-1), 11.014 (s, 1H, indole-NH), 8.120~8.115 (s, 1H, —ArH), 7.807 (s, 11~1, —CH=C), 7.287~7.262 (dd, 1H, —ArH), 6.847~6.826 (d, 1H, —ArH), 4.734~4.722 (d, 1H, —OH), 3.90 (m, 1H, —CHOH), 3.792~3.748 (dd, 1H, seven membered ring outer amide-NCH$_2$), 3.58 (t, 4H, morpholin2x—CH$_2$O), 3.437~3.398 (m, 2H, seven membered ring —NCH$_2$), 3.193~3.140 (m, 1H, seven membered ring outer amide-NCH$_2$), 2.936 (t, 2H, —CH$_2$C=C), 2.465 (s, 3H, pyrrole-CH$_3$), 2.431~2.420 (m, 4H, morpholinintra 2x—CH$_2$N), 2.315 (m, 2H, morpholin outer-NCH$_2$), 2.09 (m, 2H, seven membered ring CH$_2$—CH$_2$—CH$_2$)

Example 81

(S,Z)-2-((4-bromo-2-oxoindolin-3-ylidene)methyl)-5-(2-hydroxy-3-morpholinopropyl)-3-methyl-5,6,7,8-tetrahydropyrrolo[3,2-c]azepin-4(1H)-one

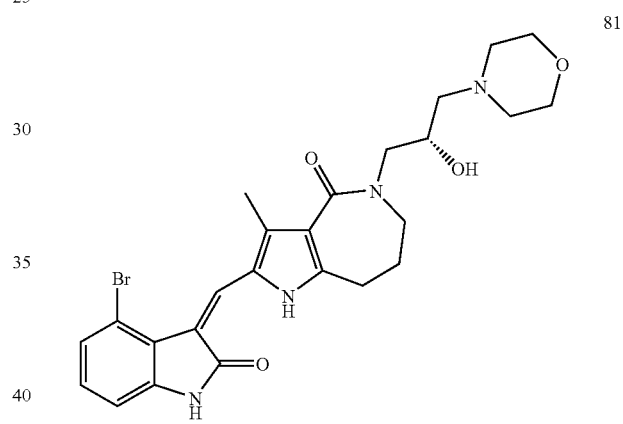

(S)-5-(2-Hydroxy-3-morpholin-4-yl-propyl)-3-methyl-4-oxo-1,4,5,6,7,8-hexa hydro-pyrrolo[3,2-c]azepine-2-carbaldehyde 78f (40 mg, 0.12 mmol) and 4-bromo-1,3-dihydroindol-2-one (25 mg, 0.12 mmol) were dissolved in 1.5 ml of ethanol, and added with 6 μl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (S,Z)-2-(4-bromo-2-oxoindolin-3-ylidene)methyl)-5-(2-hydroxy-3-morpholinoprop yl)-3-methyl-5,6,7,8-tetrahydropyrrolo[3,2-c]azepin-4(1H)-one 81 (34 mg, yield 54%) as a yellow solid.

MS m/z (ESI): 529.3 (M+1)

$^1$HNMR (400 MHz, DMSO-d6) δ13.647 (s, 1H, pyrrole-NH), 11.185 (s, 1H, indole-NH), 8.588 (s, 1H, —CH=C), 7.238~7.218 (d, 1H, —ArH), 7.095~7.055 (t, 1H, —ArH), 6.956~6.936 (d, 1H, —ArH), 4.739~4.726 (d, 1H, —OH), 3.90 (m, 1H, —CHOH), 3.800~3.757 (dd, 1H, seven membered ring outer amide-NCH$_2$), 3.593~3.570 (t, 4H, morpholin2x-CH$_2$O), 3.446 (m, 2H, seven membered ring —NCH$_2$), 3.192 (dd, 1H, seven membered ring outer amide-NCH$_2$), 2.956 (t, 2H, —CH$_2$C=C), 2.447~2.428 (m, 4H, morpholin intra2×—CH₂N), 2.411 (s, 3H, pyrrole-CH₃), 2.301 (m, 2H, morpholin outer-NCH₂), 2.08 (m, 2H, seven membered ring CH₂—CH₂—CH₂)

Example 82

(S,Z)-2((7-bromo-5-fluoro-2-oxoindolin-3-ylidene) methyl)-5-(2-hydroxy-3-morpholinopropyl)-3-methyl-5,6,7,8-tetrahydropyrrolo[3,2-c]azepin-4(1H)-one

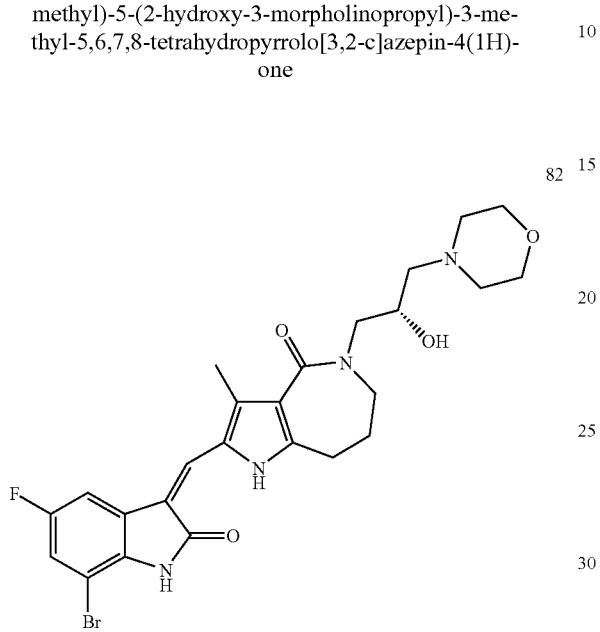

(S)-5-(2-Hydroxy-3-morpholin-4-yl-propyl)-3-methyl-4-oxo-1,4,5,6,7,8-hexa hydro-pyrrolo[3,2-c]azepine-2-carbaldehyde 78f (40 mg, 0.12 mmol) and 7-bromo-5-fluoro-1,3-dihydro-indol-2-one 4b (27 mg, 0.12 mmol) were dissolved in 1.5 ml of ethanol, and added with 6 μl of piperidine to the solution at room temperature. Upon completion of the addition, the reaction mixture was reacted at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (S,Z)-2-(7-bromo-5-fluoro-2-oxoindolin-3-ylidene)methyl)-5-(2-hydroxy-3-morpholinopropyl)-3-methyl-5,6,7,8-tetrahydropyrrolo[3,2-c]azepin-4(1H)-one 82 (48 mg, yield 73.8%) as a yellow solid.

MS m/z (ESI): 547.5 (M+1)

¹HNMR (400 MHz, DMSO-d6) δ13.665 (s, 1H, pyrrole-NH), 11.188 (s, 1H, indole-NH), 7.876~7.848 (dd, 1H, —ArH), 7.797~7.055 (s, 1H, —ArH), 7.270~7.241 (dd, 1H, —ArH), 4.74 (m, 1H, —OH), 3.93 (m, 1H, —CHOH), 3.75 (dd, 1H, seven membered ring outer amide-NCH₂), 3.583 (t, 4H, morpholin2×-CH₂O), 3.480~3.415 (m, 2H, seven-membered ring —NCH₂), 3.15 (dd, 1H, seven membered ring outer amide-NCH₂), 2.471 (s, 3H, pyrrole-CH₃), 2.430 (m, 4H, morpholin intra 2×—CH₂N), 2.310 (t, 2H, morpholin outer-NCH₂), 2.086 (m, 2H, seven membered ring CH₂—CH₂—CH₂)

Example 83

(S,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one

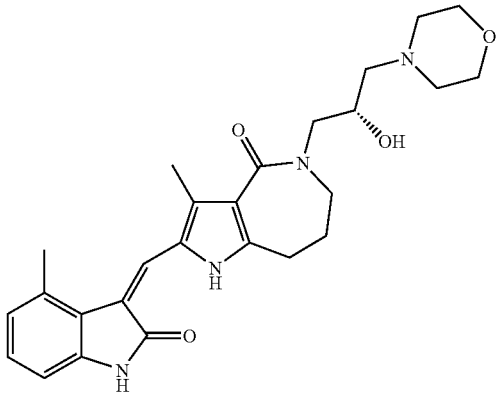

(S)-5-(2-Hydroxy-3-morpholin-4-yl-propyl)-3-methyl-4-oxo-1,4,5,6,7,8-hexahydro-pyrrolo[3,2-c]azepine-2-carbaldehyde 78f (40 mg, 0.12 mmol 1) and 4-methyl-1,3-dihydro-indol-2-one (18 mg, 0.12 mmol) were dissolved in 1.5 ml of ethanol, and added with 6 μl of piperidine to the solution at room temperature. Upon completion of the addition, the reaction mixture was stirred at 45° C. for 16 hours. After thin lay chromatography showed the disappearance of starting materials, the reaction mixture was naturally cooled to room temperature, and filtered. The filter cake was washed with anhydrous ethanol (1 ml×2) and dried to obtain the title compound (S,Z)-5-(2-hydroxy-3-morpholinopropyl)-3-methyl-2-((4-methyl-2-oxoindolin-3-ylidene)methyl)-5,6,7,8-tetrahydropyrrolo[3,2-c]azepin-4(1H)-one 83 (35 mg, yield 63.6%) as a yellow solid.

MS m/z (ESI): 465.2 (M+1)

¹HNMR (400 MHz, DMSO-d6) δ13.715 (s, 1H, pyrrole-NH), 10.934 (s, 1H, indole-NH), 7.572 (s, 1H, —CH=C), 7.057 (t, 1H, —ArH), 6.840~6.821 (d, 1H, —ArH), 6.790~6.771 (d, 1H, —ArH), 4.737~4.725 (d, 1H, —OH), 3.92 (m, 1H, —CHOH), 3.75 (dd, 1H, seven-membered ring intra amide —NCH₂), 3.58 (t, 4H, morpholin2x-CH₂O), 3.441 (m, 2H, seven-membered ring —NCH₂), 3.15 (m, 1H, seven-membered ring outer amide-NCH₂), 2.939 (t, 2H, —CH₂CH=C), 2.594 (s, 3H, pyrrole-CH₃), 2.426 (m, 4H, morpholin intra 2×—CH₂N), 2.388 (s, 3H, pyrrole-CH₃), 2.309~2.293 (m, 2H, morpholin outer-NCH₂), 2.078 (m, 2H, seven-membered ring CH₂—CH₂—CH₂)

BIOLOGICAL ASSAYS

Example 1

Inhibition of Cell Proliferation Assay

The following in vitro assay may be used to determine the level of activity and effect of different compounds of the present invention on the proliferation inhibition (cell toxic) of endothelium growth factor receptor (VEGFR) high expressing *homo sapiens* cancer cell-HUVEC cell.

The cellular assay described here is to test anti-angiogenesis and proliferation inhibition activity and effect of the compounds through VEGFR on the cancer cells in vitro. The effect and activity is represented by the $IC_{50}$ value that kills the cancer cell. The general procedures for the assay is as follows: The *homo sapiens* cells highly expressing VEGFR are chosen and seeded to 96-well cell culture plate at a suitable concentration (exp 5000 cells/ml medium). The cells then are cultured in carbon dioxide ($CO_2$) incubator till when they confluence to about 85%. The cell culture medium is then replaced by fresh one with tested compounds added in it at serial concentrations (general 6 to 7 concentrations). The cells are then returned to the incubator and cultured continuously for 72 hours. 72 hours later, the cell exposed to compounds and control cell are assayed for their proliferation using Sulforhodamine B (SRB) method. Compounds $IC_{50}$ on tested cells are calculated by the data of inhibition rates of serial concentrations of the tested compounds.

Material and Methods:
- a. Dimethyl sulfoxide (Sinophma chemical reagent company, catalog No. T20050806)
- b. HUVEC cells (Purchased from Institute of biochemistry and cell biology)
- c. Falcon 100 mm cell culture plates (Baton Dickison Labware, Baton Dickison and company, Catalog No. 18677)
- d. Corning 96-well culture cluster (Corning Incorporated, Catalog No. 3599)
- e. Fisher Pipette (Fisher scientific, Catalog No. 03-692-164)
- f. DMEM/F12 cell medium (Gibco, Catalog No. 12400-024)
- g. Fetal bovine serum, Australia origin (Gibco, Catalog No. 10099-141)
- h. Phosphate Buffered Saline (Gibco, Catalog No. 10010-072)
- i. 0.25 Trypsin-EDTA (Gibco, Catalog No. 25200-056)
- j. Sulforhodamine B (Sigma, Catalog No. 3520-42-1)
- k. Acetic Acid (Sinophma chemical reagent company, Catalog No. T20060508)
- l. Trichloroacetic Acid (Sinophma chemical reagent company, Catalog No. T20060305)
- m. Tris base (Amresco, Catalog No. 0826)
- n. Class II A/B3 Biological safety cabinet (ThermoForma, Catalog No. HB0053-03)
- o. Series II water jacketed $CO_2$ incubator (ThermoForma, Model: 3111)
- p. Centrifuge (Fisher Scientific Marathon 8 k, Catalog No. 0027-02)
- q. Novastar Plate reader (BMG Labtech, Catalog No. 700-0081)
- r. Orbital Shaker (Qilinbeier, Catalog No. TS-1)

Protocol:

The following protocol is used to assay the cell toxic activity of $IC_{50}$ value of tested compounds of the invention on HUVEC cell:

1. HUVEC cells were grown in growth media (DMEM/F12, supplemented with 10% FBS) in 100 mm coming culture plates till confluence at 37° C., 5% $CO_2$.
2. HUVEC cells were washed in 100 mm plates with FBS, then the cells were harvested by trypsinization and seeded to corning 96-well cell culture plates at a concentration of 50000 cells/ml, leaving 6 wells/each plate empty as background.
3. The cells were grown in 96-well plates at 37° C., 5% $CO_2$, till 85% confluence.
4. The compounds stock solution was prepared, using DMSO to solve candidate compounds to a concentration of 20 mM. Then DMSO was used to dilute the stock solution to a serious concentration of tested compounds solution (namely, 2 mM, 1 mM, 0.2 mM, 20 µM, 2 µM, 0.2 µM).
5. Cell culture medium was used (in this case, DMEM/F12, supplemented with 10% FBS) to dilute the compounds solution prepared above. Each DMSO serial concentration compound solution was diluted by 20 times with culture medium by adding 5 µl DMSO compound solution to 95 µl culture medium, then mixed well by vortex. This promised that the DMSO concentration at that the HUVEC cell will exposed to will not surpass 0.5%.
6. After HUVEC cell had attached to the dish bottom and confluence about 85%, the culture medium was replaced by fresh one with fresh DMEM/F12, supplemented with 10% FBS. Each well was added 180 µA medium, then 20 µl medium solution of tested compounds prepared at step 5 was added to each well. For negative control group cell, 20 µl culture medium containing 0.5% pure DMSO was added. So, HUVEC cells were exposed to each tested compound at a serial final concentration of 100 µM, 10 µM, 5 µM, 1 µM, 0.1 µM, 0.01 µM, and 0.001 µM.
7. The culture plates were put back to incubator, and cultured for 72 hours at 37° C., 5% $CO_2$.
8. 72 hours later, cultures were removed from incubator into sterile work area.
9. The fixative (50% Trichloroacetic Acid-TCA) was prepared by adding reagent grade water to the TCA, fixing the cells by gently layering 50 µl of cold TCA solution on top of the growth medium.
10. The plates were incubated for 1 hour at 4° C. and then rinsed with water several times to remove TCA, serum proteins, etc. Plates were air dried and stored until use. Bland background optical density was measured in wells incubated with growth medium without cells.
11. 0.4% Sulforhodamine B solution was prepared by using 10% acetic acid solution.

50 µl sulforhodamine B solution was added to each well of 96-well plates.

12. The cells were allowed to stain for 30 minutes.
13. The wash solution of 10% acetic acid was prepared. At the end of the staining period, the stain was removed and the cells were rinsed quickly with 1% acetic acid. Repeat until unincorporated dye was removed. Wash times were kept to a minimum to reduce desorption of protein-bound dye. After being rinsed, the cultures were air dried.
14. The incorporated dye was then dissolved in a volume of Sulforhodamine B. Solubilization solution (10 mM Tris) was equal to the original volume of culture medium. Then cultures were allowed to stand for 5 minutes at room temperature, and the mixing of the dye was enhanced by gentle stirring in a gyratory shaker.
15. The absorbance was measured by spectrophotometry at a wavelength of 565 nm. The background absorbance of 96-well plates at 690 nm was measured and subtracted from the measurement at 565 nm.
16. The inhibition rate (IR) was calculated as follows:

$$IR = 100 \times (\text{Absorbance of control cells} - \text{Absorbance of cells exposed to tested compounds at each concentration}) / \text{Absorbance of control cells} \%.$$

The $IC_{50}$ value can be derived from the IRs of compounds at different concentration gradients.

The Activity of the Compounds of the Invention:

The biological activity of the compounds of the invention is tested using the assay described above. The $IC_{50}$ values are measured and showed in table below:

| Example No. | $IC_{50}$ (VEGFR/ HUVEC) (μM) |
|---|---|
| 1 | 0.09 |
| 2 | 0.288 |
| 3 | 0.1 |
| 4 | 0.404 |
| 5 | 0.1 |
| 6 | 0.28 |
| 8 | 0.308 |
| 9 | 0.068 |
| 10 | 0.123 |
| 11 | 0.207 |
| 12 | 0.3 |
| 13 | 0.804 |
| 14 | 0.457 |
| 15 | 1.2 |
| 16 | 0.21 |
| 17 | 0.129 |
| 19 | 0.146 |

Example 2

VEGF-R2Kinase Assay

This assay is used to measure the in vitro kinase activity of recombinant human VEGF-R2 in an ELISA assay.

Materials and Reagents:
 a. Wash Buffer (PBS-T Buffer): 1×PBS (137 mM NaCl, 2.7 mM KCl, 4.3 mM $Na_2HPO_4$, 1.4 mM $KH_2PO_4$, the pH adjusted to 7.2) and 0.05% Tween-20.
 b. 1% Bovine Serum Albumin (BSA, Calbiochem #136593) in PBS-T Buffer.
 c. Stop Buffer: 50 mM EDTA, pH 8.0.
 d. DELFIA® Europium-labeled Anti-mouse IgG (PerkinElmer Life Sciences #AD0124).
 e. DELFIA® Enhancement Solution (PerkinElmer Life Sciences #1244-105).
 f. DELFIA® Streptavidin coated, 96-well, yellow plate (PerkinElmer Life Sciences #AAAND-0005).
 g. recombinant human VEGF-R2 kinase (supplied in 50 mM Tris-HCl (pH 8.0), 100 mM NaCl, 5 mM DTT, 15 mM reduced glutathione and 20% glycerol) (Cell signaling technology #7787).
 h. 10 mM ATP solution (Cell signaling technology #9804).
 i. Biotin-Gastrin Precursor (Tyr87) Peptide (Cell signaling technology #1310).
 j. Phospho-Tyrosine Mouse mAb (P-Tyr-100) (Cell signaling technology #9411).
 k. HTScan™ Tyrosine Kinase Buffer (4×)
 1× Kinase Buffer:
 60 mM HEPES
 5 mM $MgCl_2$
 5 mM $MnCl_2$
 3 μM $Na_3VO_4$
 (Cell signaling technology #9805).
 1. 1.25 M DTT (1000×) (Cell signaling technology).
Procedure:
The following protocol was used:
 1. The test compound was diluted with DMSO to the desired final assay concentration. 1 μl of test compound, the negative control (sample which does not receive any test compound), 1 μl DMSO were added for each assay.
 2. 6 μM substrate peptide (Tyr87) was diluted with $dH_2O$ (1:1), 15 μl was added to every assay.
 3. VEGF-R2 enzyme was immediately transferred from −80° C. to ice, and the enzyme was allowed to thaw on ice.
 4. 2.2 μg VEGF-R2 enzyme was taken to the enzyme tube.
 5. 10 μl of DTT (1.25 M) was added to 2.5 ml of 4×HTScan™ Tyrosine Kinase Buffer (240 mM HEPES pH 7.5, 20 mM $MgCl_2$, 20 mM $MnCl_2$, 12 μM $Na_3VO_4$) to prepare DTT/Kinase buffer.
 6. 0.75 ml of DTT/Kinase buffer was transferred to each enzyme tube to prepare 4× reaction cocktail, and 7.5 μl 4× reaction cocktail was added to every assay.
 7. 2 μl ATP (10 mM) was added to 498 μl $dH_2O$, 7.5 μl was added for every assay.
 Final Assay Conditions for a 30 μl Reaction
 60 mM HEPES pH 7.5
 5 mM $MgCl_2$
 5 mM $MnCl_2$
 3 μM $Na_3VO_4$
 1.25 mM DTT
 10 μM ATP
 1.5 μM substrate peptide
 22 ng VEGF-R2Kinase
 8. The reaction tube was incubated at 25° C. for 30 minutes.
 9. 30 μl/assay stop buffer (50 mM EDTA, pH 8.0) was added to stop the reaction.
 10. 25 μl of each reaction and 75 μl $dH_2O$/well was transferred to a 96-well streptavidin coated plate, with shaking at room temperature for 60 minutes.
 11. Each well was washed three times with 200 μl PBS-T buffer. Plate was patted on paper towel to remove excess liquid.
 12. Primary antibody, Phospho-Tyrosine mAb (P-Tyr-100) was diluted, 1:1000 in PBS-T buffer with 1% BSA, and 100 μl diluted primary antibody was added to each well.
 13. The reaction tube was incubated, with shaking at room temperature for 60 minutes.
 14. Washing was carried out as described above in step 11.
 15. Europium labeled anti-mouse IgG was diluted 1:500 in PBS-T buffer with 1% BSA, 100 μl diluted antibody was added to each well.
 16. The reaction tube was incubated, with shaking at room temperature for 30 minutes.
 17. Each well was washed five times with 200 μl PBS-T buffer. Plate was patted on paper towel to remove excess liquid.
 18. 100 μl/well DELFIA® Enhancement Solution was added.
 19. The reaction tube was incubated, with shaking at room temperature for 5 minutes.
 20. The fluorescence emission was detected at 615 nm with appropriate Time-Resolved Plate Reader.
 Calculate the inhibition rate: IR (%)=100−100*(X−B)/(N−B)
 X=the fluorescence value of the well contained test compound
 N=negative control
 B=blank
 The $IC_{50}$ value can be derived from the IRs of compounds at different concentration gradients.

The Activity of the Compounds of the Invention

The biochemical activity of the compounds of the invention is tested using the assay described above. The $IC_{50}$ values are measured and showed in table below:

| Example No. | IC$_{50}$ (VEGFR/bio) (μM) |
|---|---|
| 1 | 0.014 |
| 2 | 0.021 |
| 3 | 0.28 |
| 4 | 0.041 |
| 5 | 0.0085 |
| 6 | 0.023 |
| 7 | 0.69 |
| 8 | 0.115 |
| 9 | 0.49 |
| 10 | 0.014 |
| 11 | 0.001 |
| 12 | 0.001 |
| 13 | 0.003 |
| 14 | 0.004 |
| 15 | 0.002 |

-continued

| Example No. | IC$_{50}$ (VEGFR/bio) (μM) |
|---|---|
| 16 | 0.0013 |
| 17 | 0.001 |
| 18 | 0.01 |
| 19 | 0.012 |
| 20 | 0.072 |
| 21 | 0.16 |

PHARMACODYNAMIC ASSAYS IN VIVO

The Therapeutic Effects of the Compound of Example 63 Against Xenografts of HT-29 Human Colon Cancer in Nude Mice 1. Abstract:

The therapeutic effects of Example 63 against xenografts of HT-29 human colon cancer in nude mice were estimated. Continuous oral the compound of Example 63 markedly inhibited the growth of HT-29 human colon cancer and reduced the tumor volume, mice, can be well tolerant to the compound.

2. Purpose:

The therapeutic effects of the compound of Example 63 against xenografts of HT-29 human colon cancer in nude mice were estimated.

3. Test Drug:

Drug name and batch: the compound of Example 63 is a yellow powder.

Preparation method: the compound of Example 63 was prepared to corresponding concentration with distilled water.

4. Test Animals:

Six to seven-week-old BALB/cA-nude female mice was purchased from Slaccas Experimental Animal. Certificate No.: SCXK (Shanghai) 2003-0003. Raising Conditions: SPF level.

5. Test Protocol:

Nude mice were hypodermic inoculated HT-29 human colon cancer cell. After tumors grew to 100-300 mm$^3$, mice were randomly divided into teams (d0). The dose and dosage regimen were shown in table 1. The volume of tumors and weigh of the mice were measured for 2-3 times per week. The calculation formula of the volume of tumor (V) is: $V = \frac{1}{2} \times a \times b^2$, a: length of tumor, b: width of tumor.

TABLE 1

The therapeutic effect of the compound of Example 63 against xenografts of HT-29 human colon cancer in nude mice.

| Group | Dose (mg/kg) | Administration | Animal Numbers d0/dn | TV (X ± SD, mm$^3$) d0 | TV (X ± SD, mm$^3$) dn | RTV X ± SD | T/C (%) |
|---|---|---|---|---|---|---|---|
| Control | | p.o | 9/9 | 291 ± 66 | 729 ± 298 | 2.54 ± 1.01 | |
| The compound of Example 63 | 40 | d0~12 | 5/5 | 364 ± 46 | 300 ± 154 | 0.80 ± 0.42 | 31.5* | d0: the time of the first dosage;
dn: the 13th day after the first dosage;
TV: volume of tumor;
RTV: relative tumor volume;
*P < 0.01 vs control.

6. Conclusion:

Example 63 obviously inhibited the growth of HT-29 human colon cancer and reduced the tumor volume; mice can be well tolerant to the compound without obvious toxicity.

What is claimed is:

1. A compound of formula (I) or a pharmaceutically acceptable salt thereof:

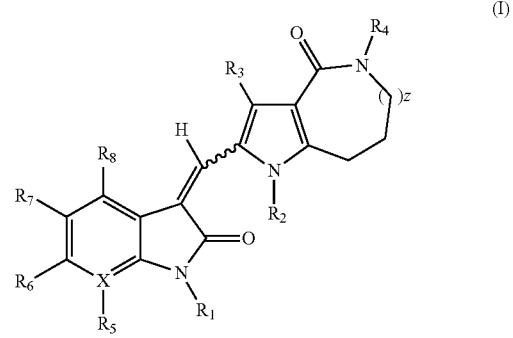

X being selected from the group consisting of carbon and nitrogen;

R$_1$ and R$_2$ each being independently selected from the group consisting of hydrogen and alkyl;

R₃ being selected from the group consisting of alkyl, trifluoromethyl, aryl, aralkyl, and methyl, at least one of said alkyl, aryl, aralkyl, and methyl being optionally further substituted by halogen;

R₄ being selected from the group consisting of alkyl, cycloalkyl, heterocyclo alkyl, aryl, heteroaryl, —(CH₂)ₙ(OCH₂CH₂)ᵣR₁₁, —[CH₂CH(OH)]ᵣCH₂NR₉R₁₀ and —(CH₂)ₙNR₉R₁₀, at least one said alkyl, cylcoalkyl, heterocyclo alkyl, aryl and heteroaryl is optionally further substituted by the group consisting of aryl, hydroxyl, amino, carboxamido, alkoxyl, aryloxy, aminoalkyl, hydroxyalkyl, heterocyclo alkyl, carboxyl, alkoxycarbonyl and —NR₉R₁₀;

when X is nitrogen, R₅ is absent, R₆, R₇, R₈ are each independently selected from the group consisting of hydrogen and halogen;

when X is carbon, R₅, R₆, R₇, R₈ are each independently selected from the group consisting of hydrogen, halogen, hydroxyalkyl, alkyl, cycloalkyl, heterocyclo alkyl, aryl, heteroaryl, hydroxyl, cyano, nitro, —OR₉, —O[CH₂CH₂O]ᵣR₁₁, —NR₉R₁₀, —(CH₂)ₙCO₂R₉, —(CH₂)ₙCONR₉R₁₀, —COR₉, —NR₉COR₁₀, —SO₂R₉ and —NHCO₂R₁₀, at least one of said aryl, heteroaryl, cycloalkyl and heterocyclo alkyl is optionally further substituted by the group consisting of alkyl, alkoxyl and halogen;

R₉ and R₁₀ each being independently selected from the group consisting of hydrogen, alkyl, cycloalkyl, aryl, heterocyclo alkyl and heteroaryl, at least one of said alkyl, cycloalkyl, aryl, heterocyclo alkyl and heteroaryl being optionally further substituted by the group consisting of alkyl, aryl, haloaryl, hydroxyl, amino, cyano, alkoxyl, aryloxy, hydroxyalkyl, heterocyclo alkyl, carboxyl, alkoxycarbonyl and —NR₉R₁₀;

R₉ and R₁₀ being taken together with the attached atom to form 4 to 8 membered hetero rings, wherein said 4 to 8 membered hetero rings contain at least one heteroatom selected from the group consisting of N, O and S, and said 4 to 8 membered rings being optionally further substituted by the group consisting of alkyl, halogen, aryl, heteroaryl, haloalkyl, hydroxyl, cyano, alkoxyl, aryloxy, aminoalkyl, hydroxyalkyl, heterocyclo alkyl, carboxyl, alkoxycarbonyl and —NR₉R₁₀;

R₁₁ is selected from the group consisting of hydrogen and alkyl;

n is an integer from 2 to 6;

z is an integer from 1 to 4; and r is an integer from 1 to 6.

2. The compound or a pharmaceutically acceptable salt thereof according to claim 1, R₁ and R₂ being hydrogen.

3. The compound or a pharmaceutically acceptable salt thereof according to claim 1, having the formula (IA) or a pharmaceutically acceptable salt thereof:

(IA)

wherein R¹ to R⁸, and X are defined as those in claim 1.

4. The compound or a pharmaceutically acceptable salt thereof according to claim 1, having the formula (IB) or a pharmaceutically acceptable salt thereof:

(IB)

wherein R¹ to R⁸, and X are defined as those in claim 1.

5. The compound or a pharmaceutically acceptable salt thereof according to claim 1 selected from the group consisting of 193
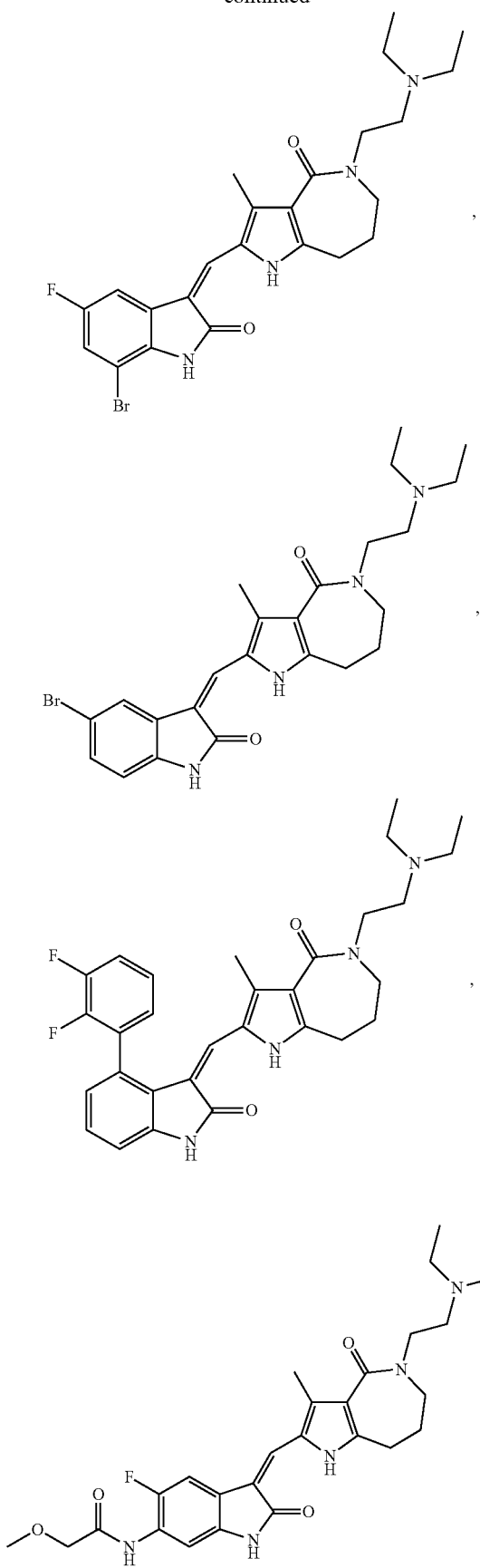
194
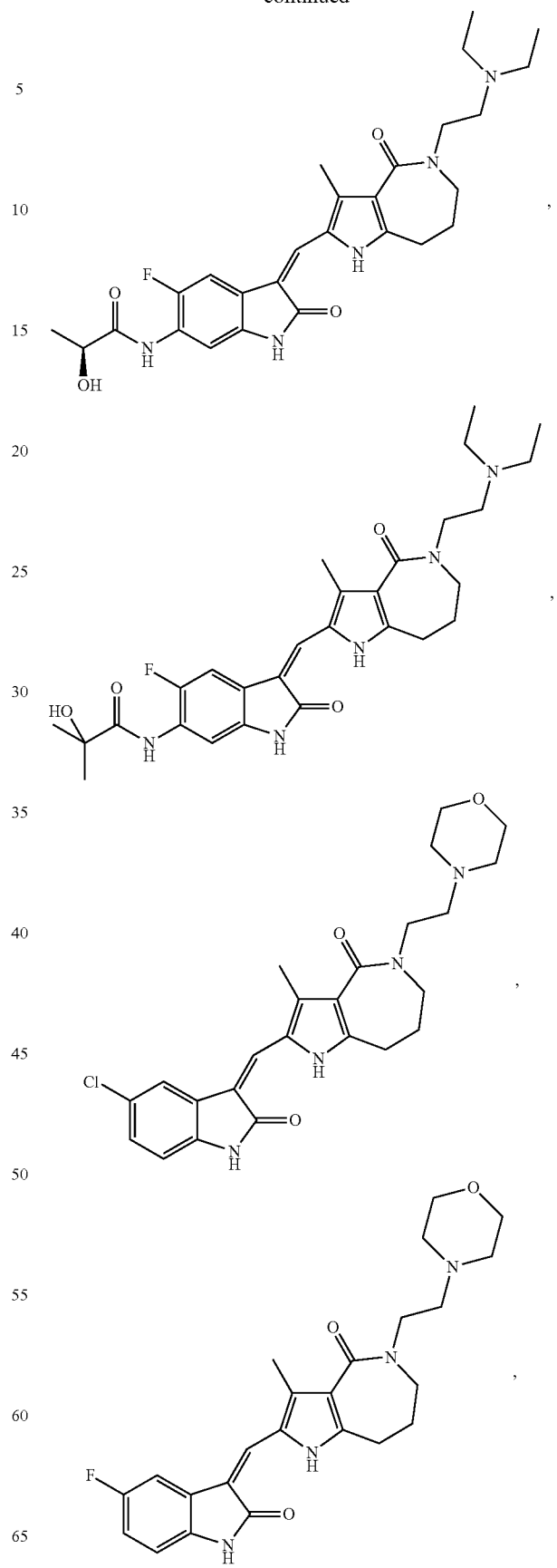

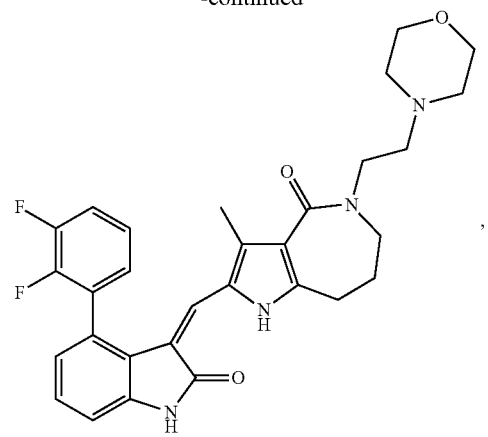
,
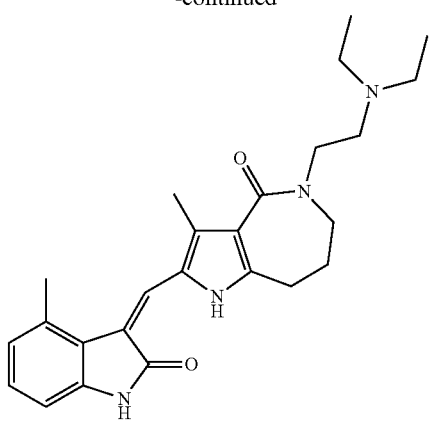
,
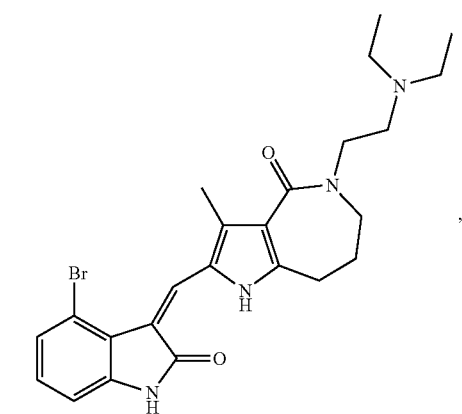
,
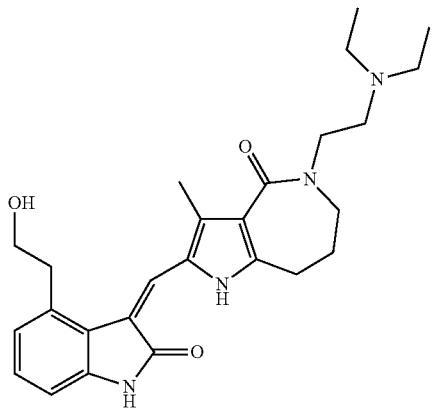
,
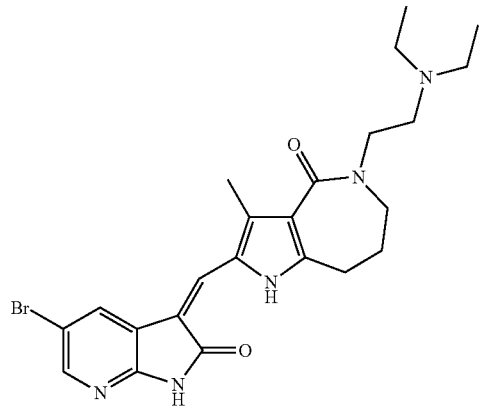
,
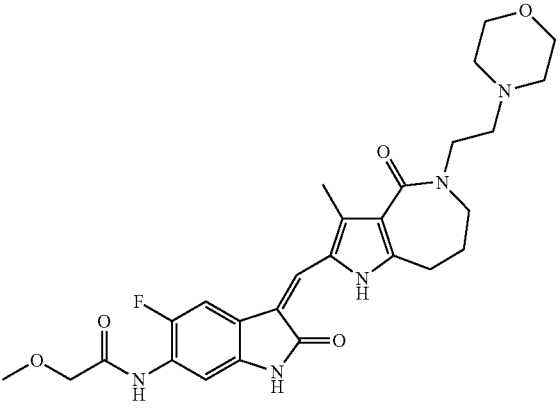
,
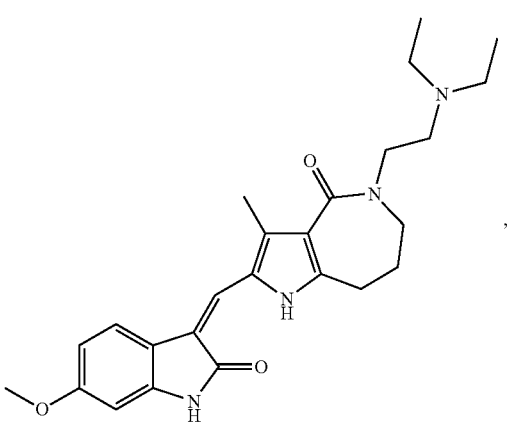
,
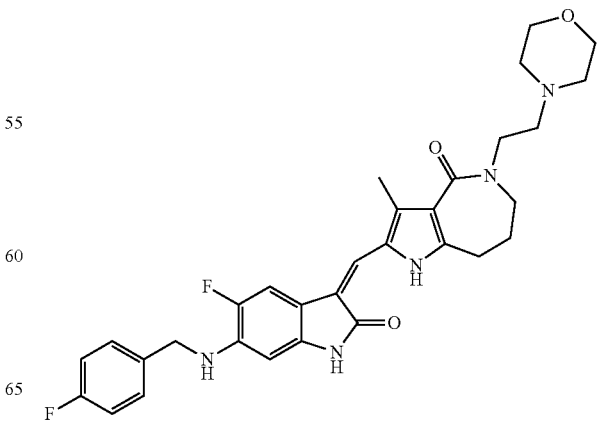
, 197
-continued
198
-continued
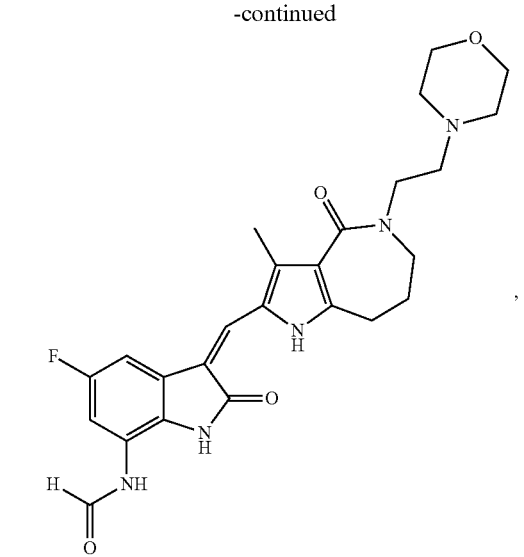
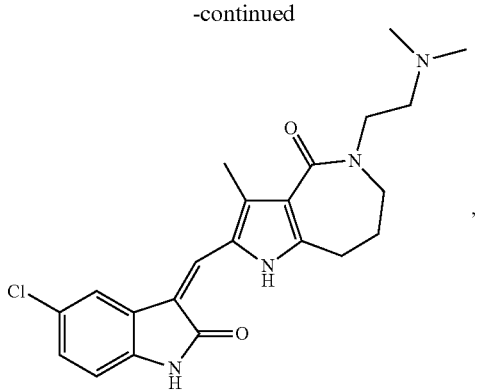

199
-continued
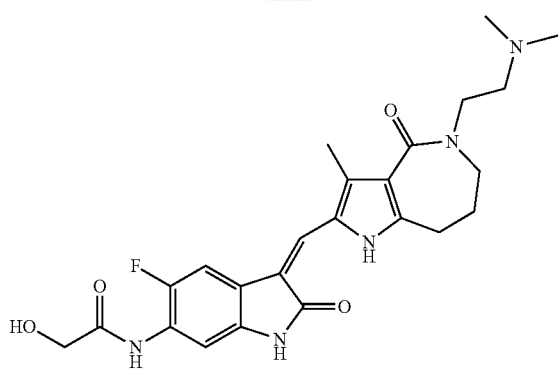
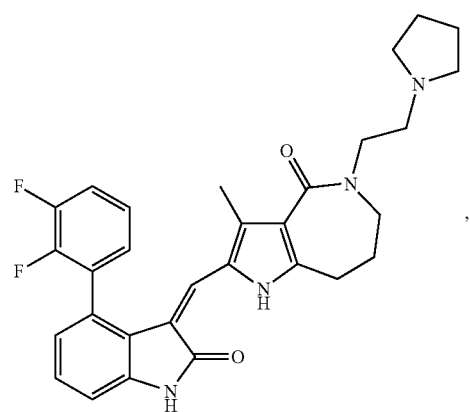
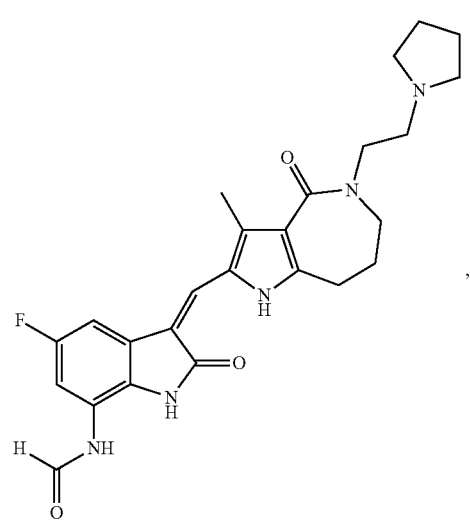
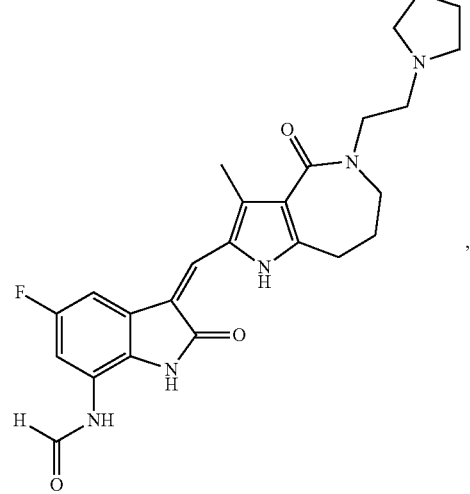
200
-continued

201
-continued
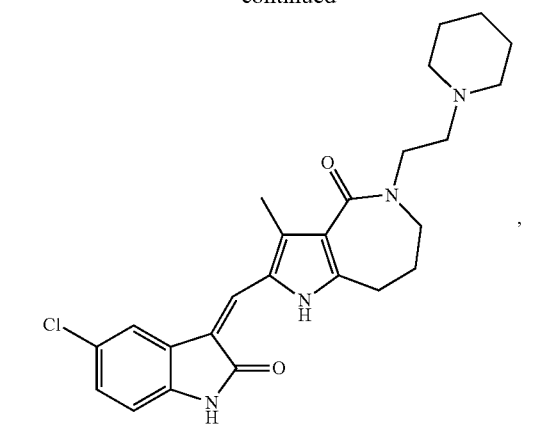
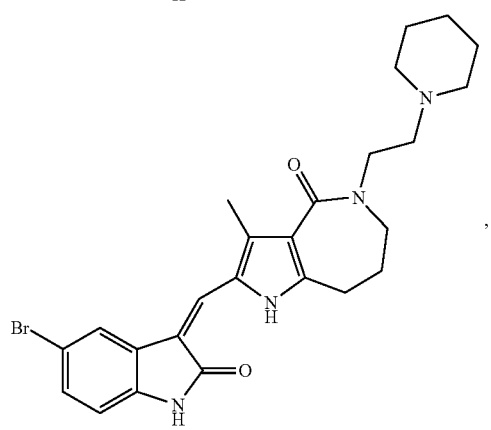
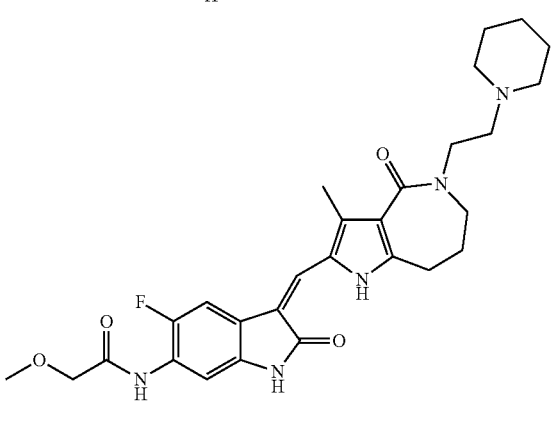
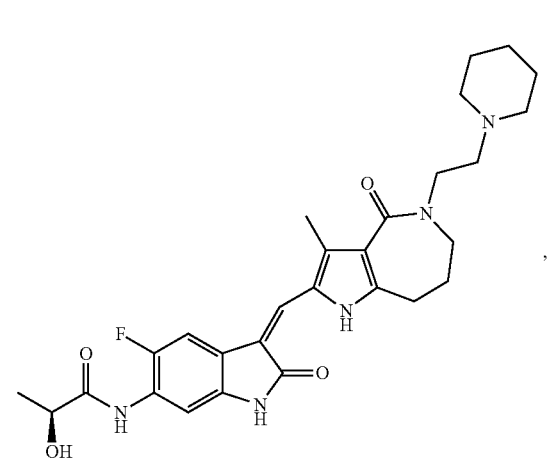
202
-continued
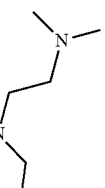
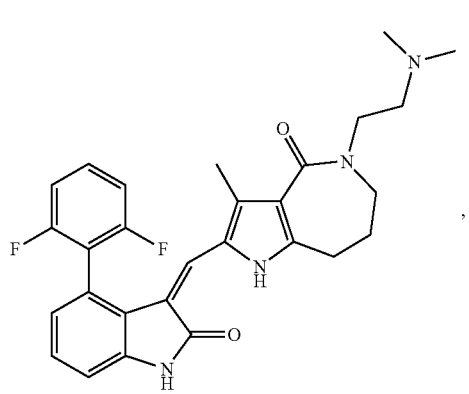
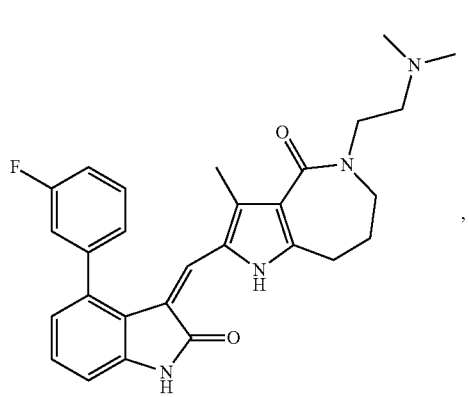
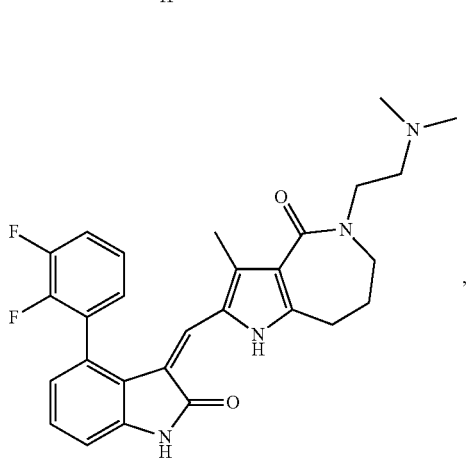

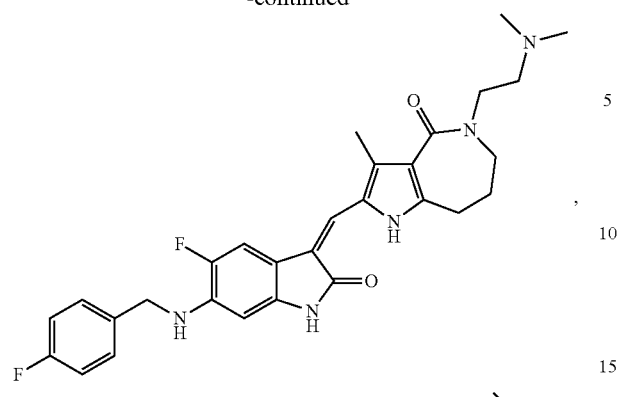
,
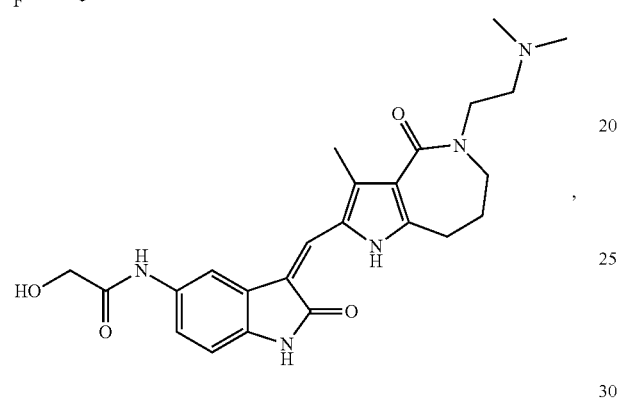
,
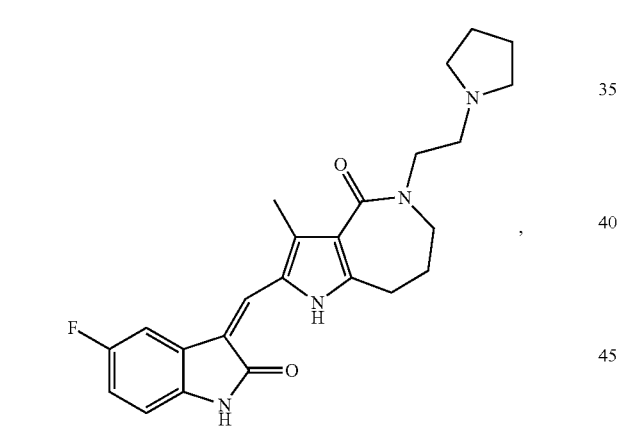
,
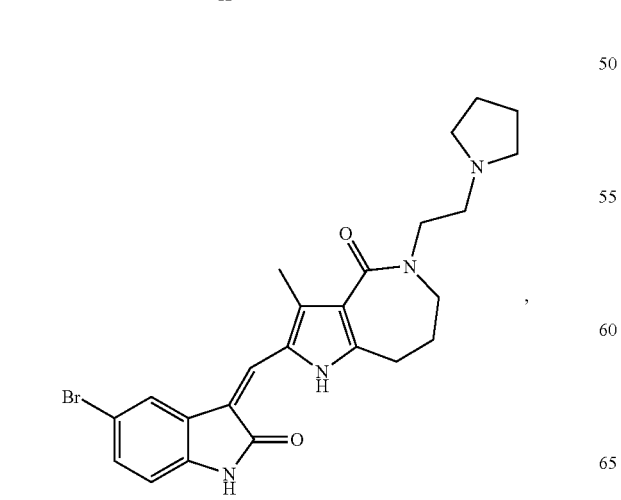
,
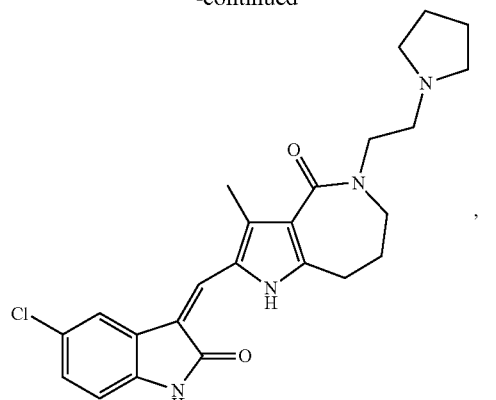
,
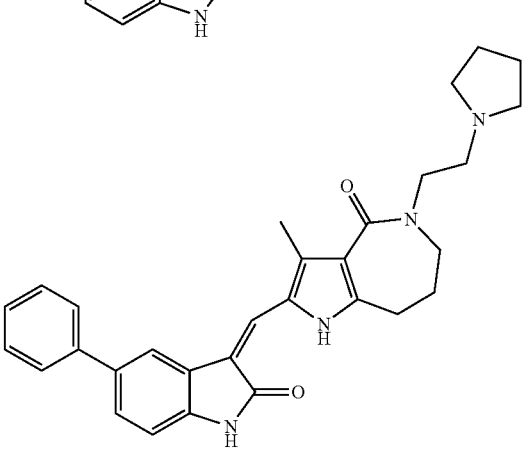
,
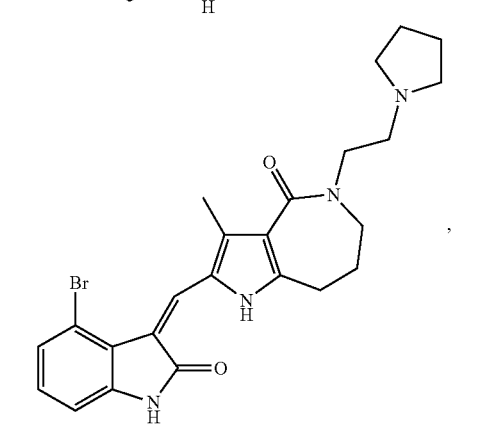
,
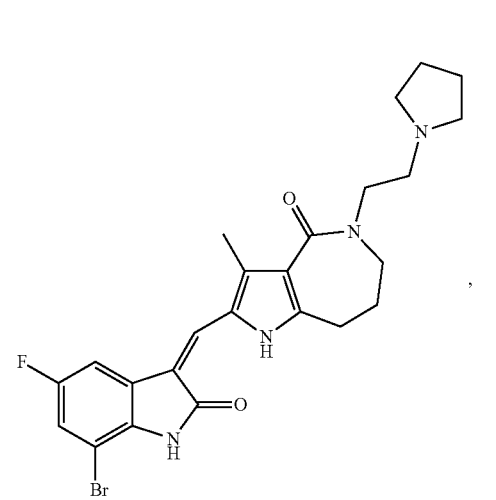
, 205
-continued
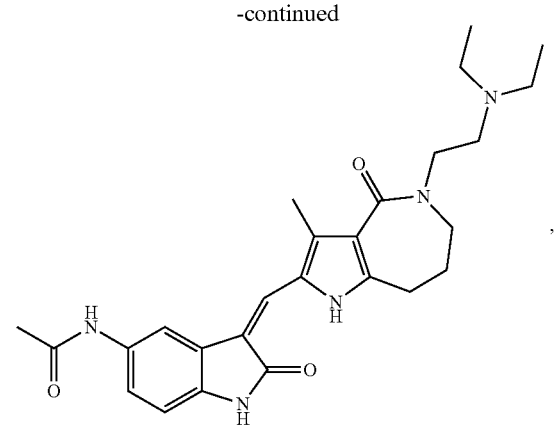
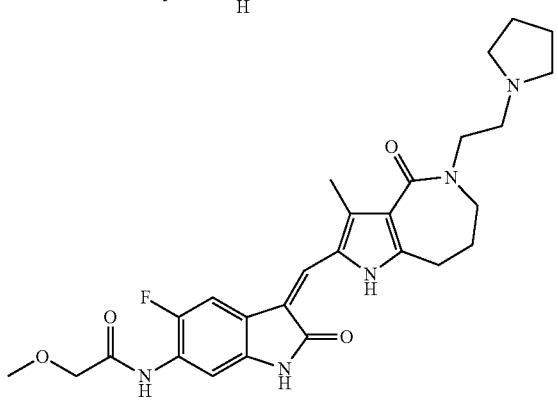
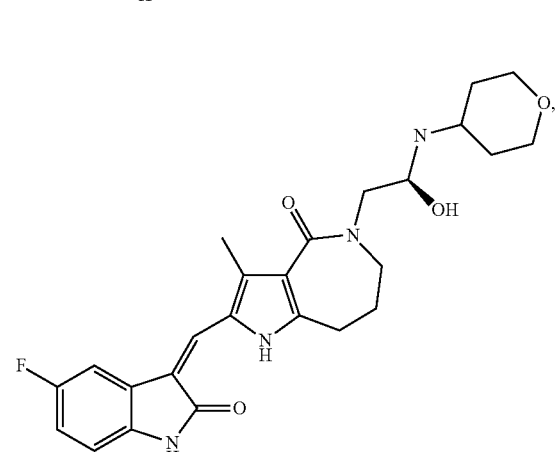
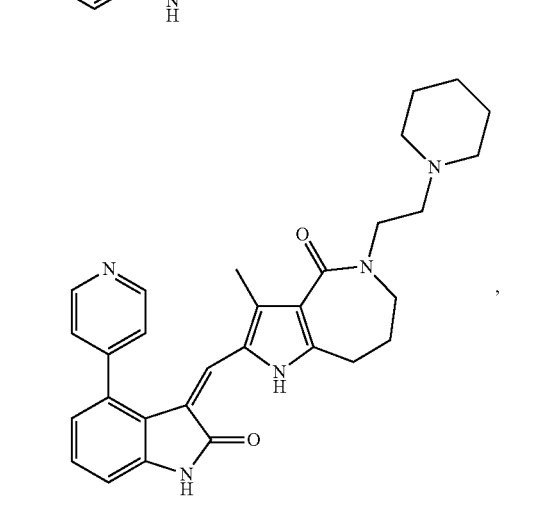
206
-continued
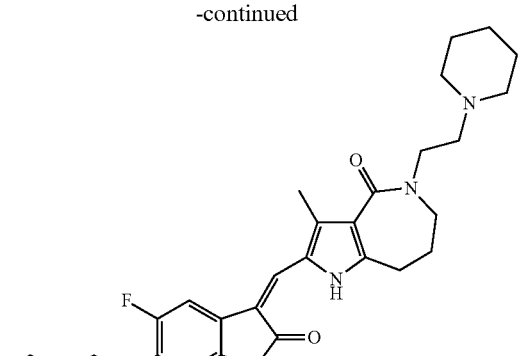
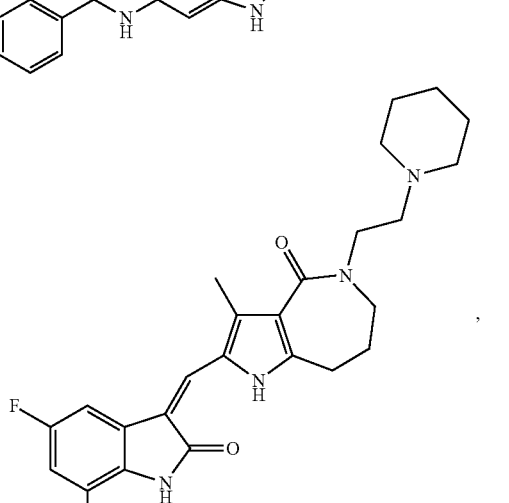
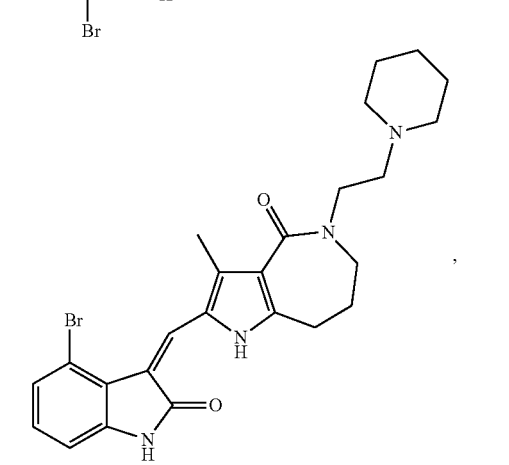
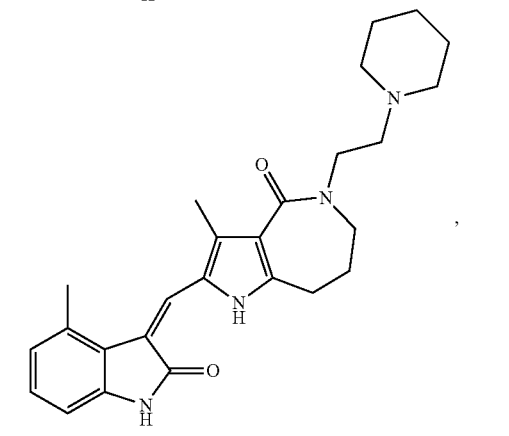

207
-continued
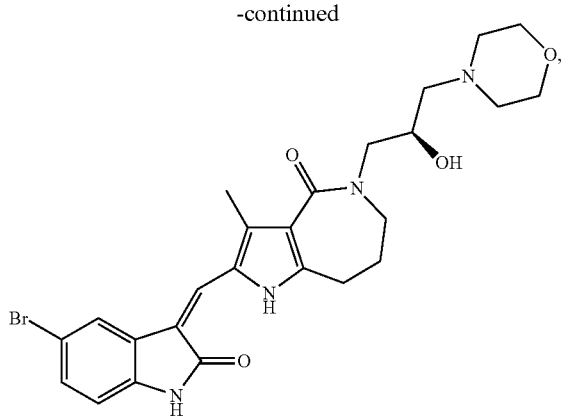
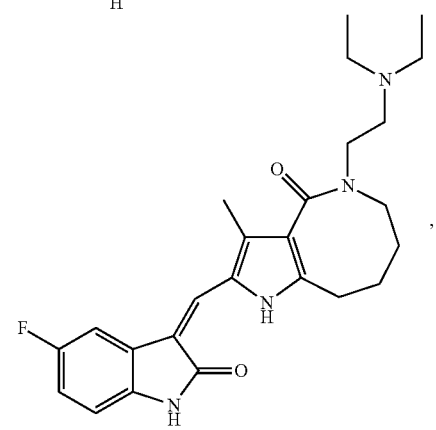
,
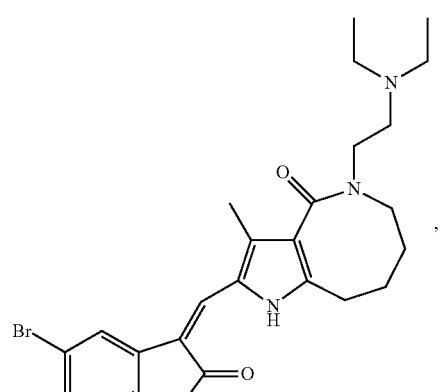
,
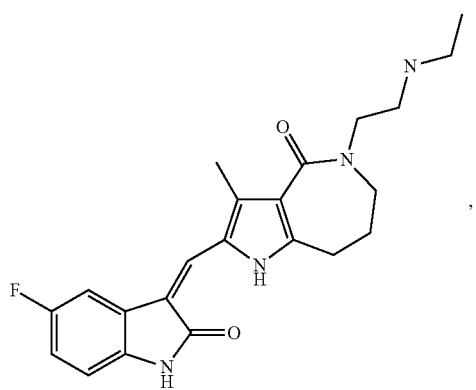
,
208
-continued
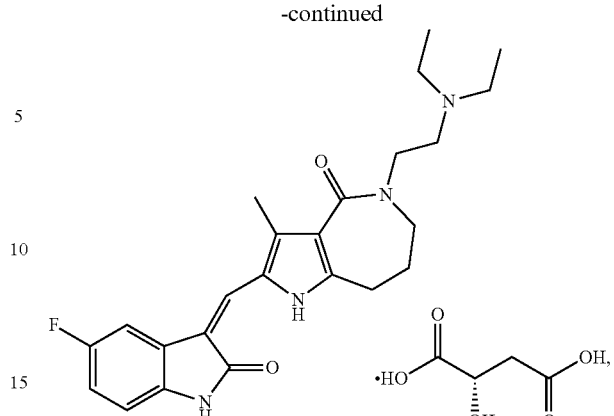
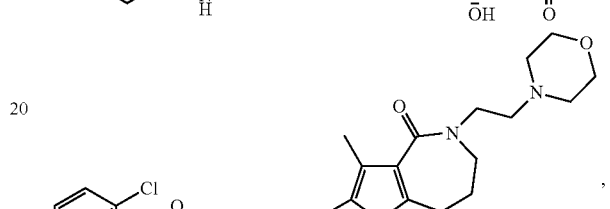
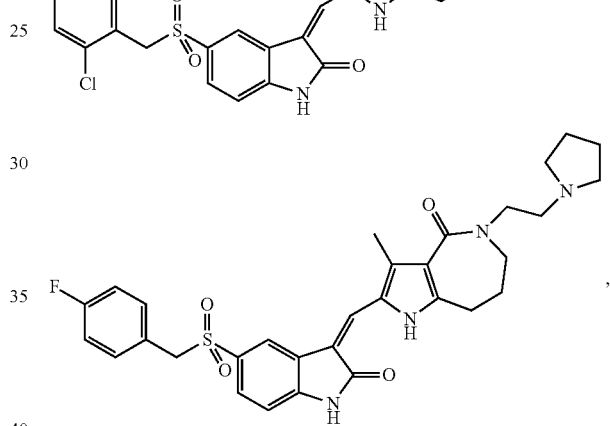
,
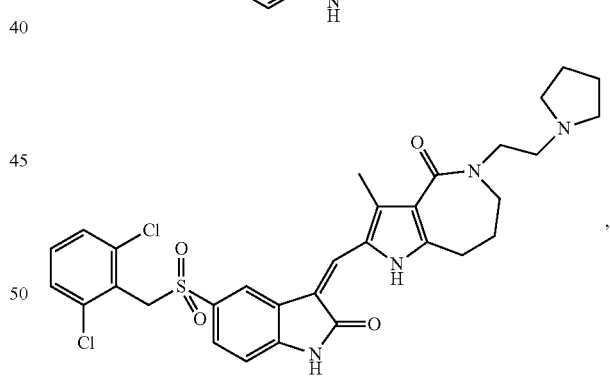
,
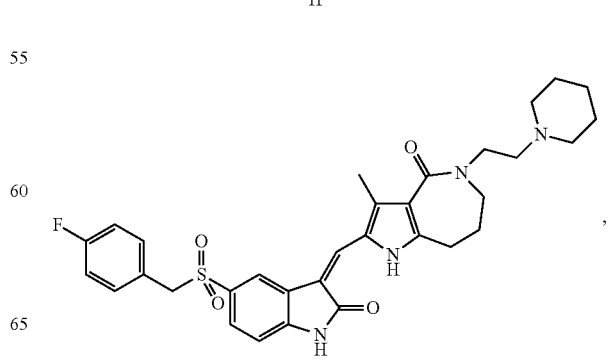
, 209
-continued
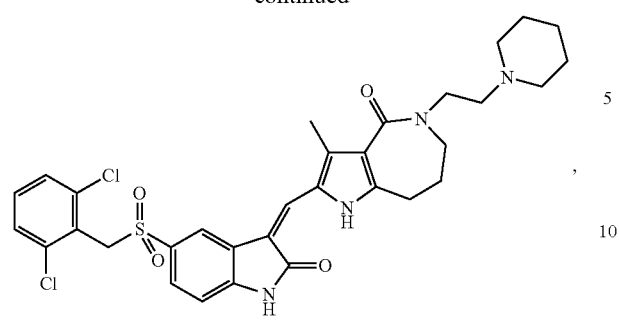,
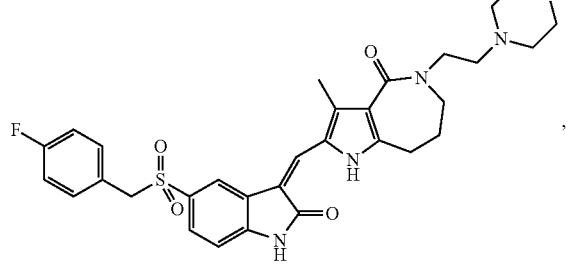,
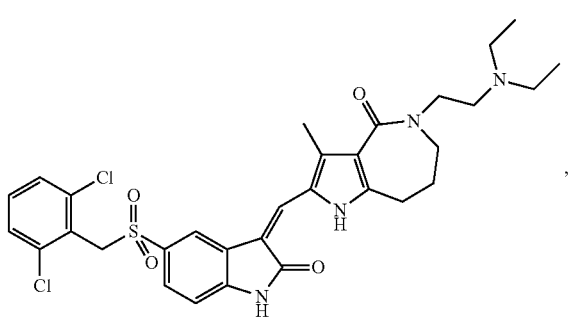,
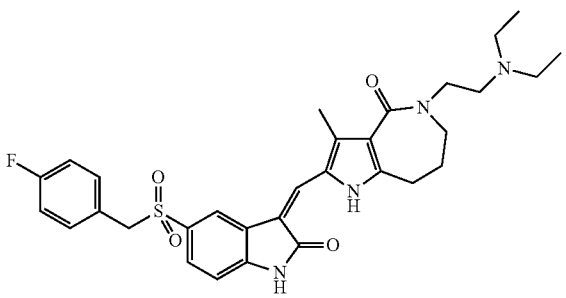,
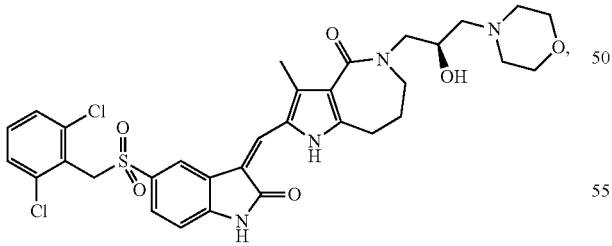,
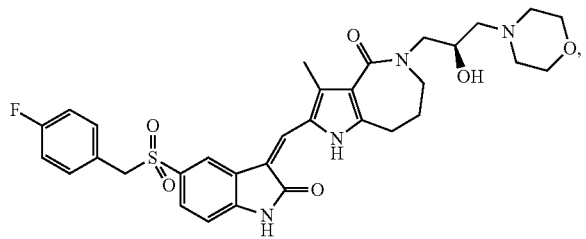,
210
-continued
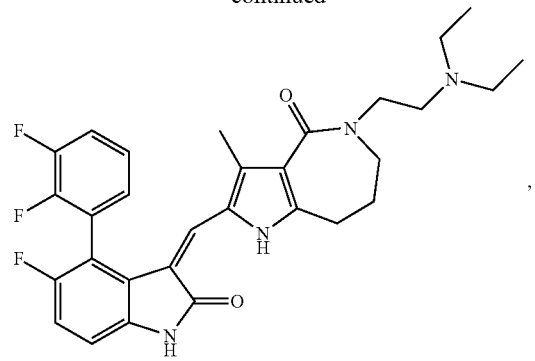,
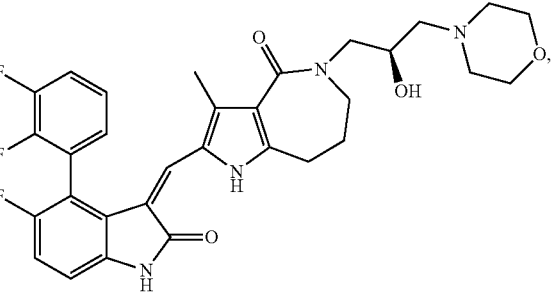,
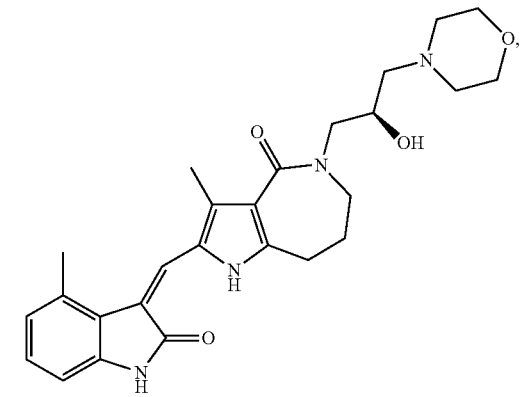,
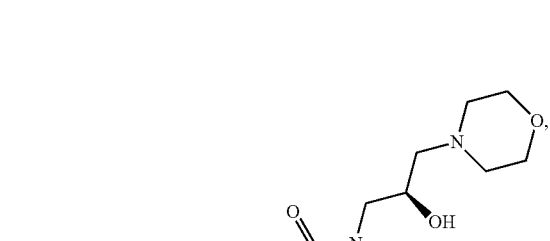,
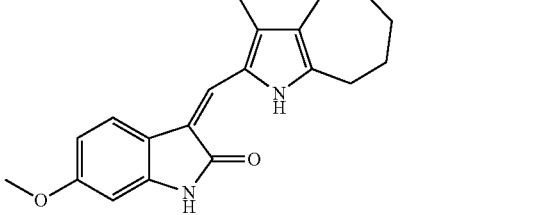, 211
-continued

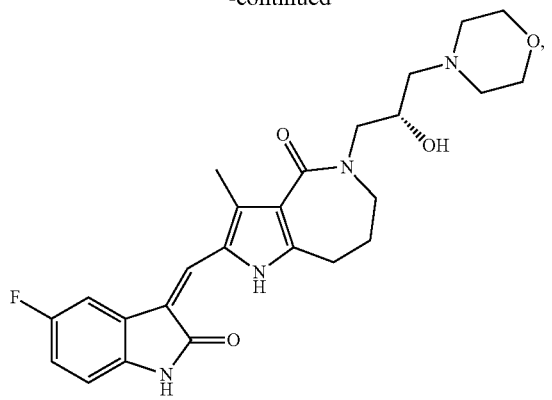

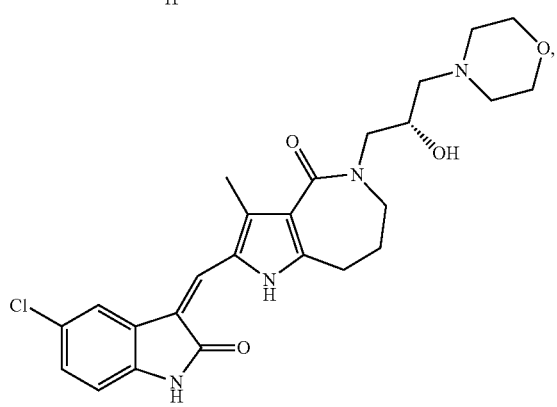

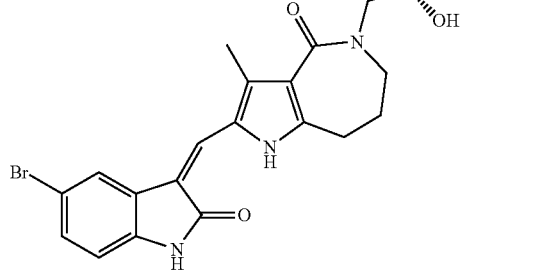

212
-continued

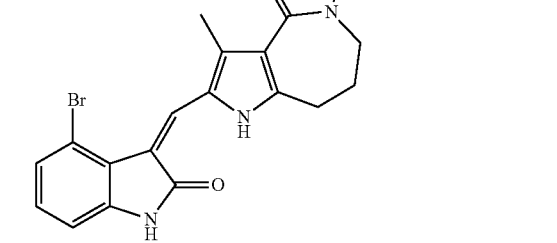

6. A pharmaceutical composition comprising an effective amount of a compound or a pharmaceutically acceptable salt thereof according to claim 1 and a pharmaceutically acceptable carrier.

7. The compound or a pharmaceutically acceptable salt thereof according to claim 1, said pharmaceutically acceptable salt are salt formed with the acid selected from the group consisting of malic acid, lactic acid, maleic acid, hydrochloric acid, methanesulfonic acid, sulfuric acid, phosphoric acid, citric acid, tartaric acid, acetic acid and trifluoroacetic acid.

8. An intermediate of formula (IC) or (ID)

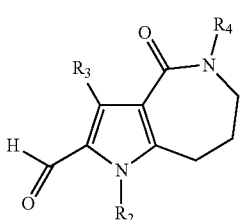
(IC)

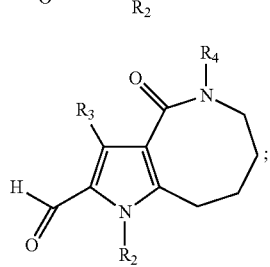
(ID)

R$_2$ being selected from the group consisting of hydrogen and alkyl;

R$_3$ being selected from the group consisting of alkyl, trifluoromethyl, aryl and aralkyl, at least one of said alkyl, aryl and aralkyl is optionally further substituted by halogen;

R$_4$ is selected from the group consisting of alkyl, cycloalkyl, heterocyclo alkyl, aryl, heteroaryl, —(CH$_2$)$_n$(OCH$_2$CH$_2$)$_r$R$_{11}$, —[CH$_2$CH(OH)]$_r$CH$_2$NR$_9$R$_{10}$ and —(CH$_2$)$_n$NR$_9$R$_{10}$, at least one of said alkyl, cylcoalkyl, heterocyclo alkyl, aryl and heteroaryl is optionally further substituted by the group consisting of aryl, hydroxyl, amino, carboxamido, alkoxyl, aryloxy, aminoalkyl, hydroxyalkyl, heterocyclo alkyl, carboxyl, alkoxycarbonyl and —NR$_9$R$_{10}$;

R$_9$ and R$_{10}$ are each independently selected from the group consisting of hydrogen, alkyl, cycloalkyl, aryl, heterocyclo alkyl and heteroaryl, at least one of said alkyl, cycloalkyl, aryl, heterocyclo alkyl and heteroaryl is optionally further substituted by the group consisting of alkyl, aryl, haloaryl, hydroxyl, amino, cyano, alkoxyl, aryloxy, hydroxyalkyl, heterocyclo alkyl, carboxyl, alkoxycarbonyl and —NR$_9$R$_{10}$;

R$_9$ and R$_{10}$ are taken together with the attached atom to form 4 to 8 membered hetero rings, said 4 to 8 membered hetero rings contain at least one heteroatom selected from the group consisting of N, O and S, and said 4 to 8 membered rings are optionally further substituted by the group consisting of alkyl, halogen, aryl, heteroaryl, haloalkyl, hydroxyl, cyano, alkoxyl, aryloxy, aminoalkyl, hydroxyalkyl, heterocyclo alkyl, carboxyl, alkoxycarbonyl, and —NR$_9$R$_{10}$;

R$_{11}$ is selected from the group consisting of hydrogen and alkyl;

n is an integer from 2 to 6;

z is an integer from 1 to 4; and r is an integer from 1 to 6.

9. A preparation process of the intermediate of formula (IC) according to claim 8, comprising:

reacting starting material pyrrole methyl carboxylic diester IC-1 in tetrahydrofuran in the presence of acetic acid with ammonium ceric nitrate at room temperature to obtain pyrrole aldehyde carboxylic diester IC-2 such that

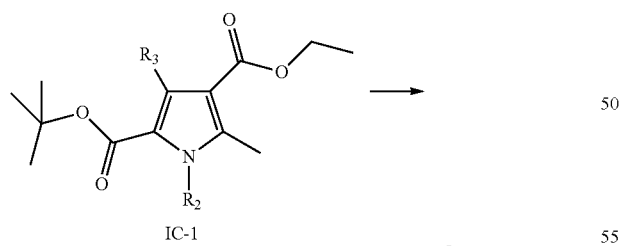

reacting pyrrole aldehyde carboxylic diester IC-2 in anhydrous tetrahydrofuran with (carbethoxy methylene) triphenylphosphorane via Witting reaction to obtain pyrrole ethoxycarbonyl ethenyl dicarboxylic ester IC-3 such that

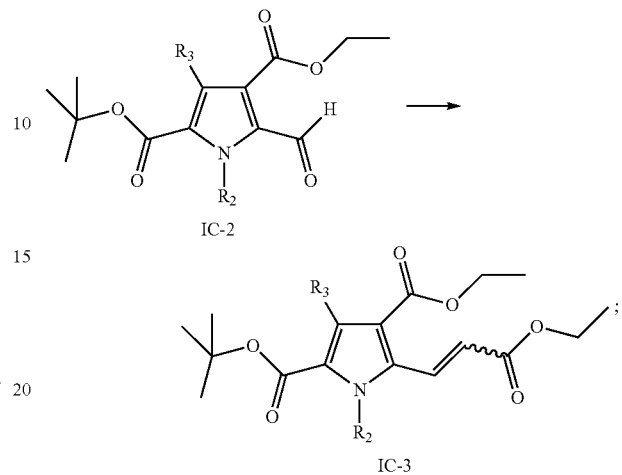

reducing pyrrole ethoxycarbonyl ethenyl dicarboxylic ester IC-3 in anhydrous ethanol by hydrogen catalyzed by palladium/carbon at room temperature to obtain pyrrole ethoxycarbony ethyl dicarboxylic ester IC-4 such that

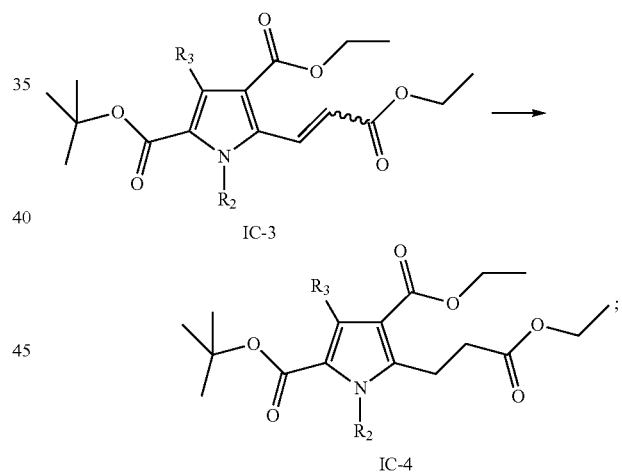

hydrolyzing pyrrole ethoxycarbony ethyl dicarboxylic ester IC-4 in aqueous lithium hydroxide solution to obtain pyrrole carboxyl ethyl dicarboxylic ester IC-5 such that

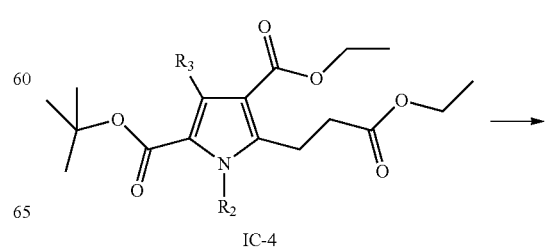

-continued

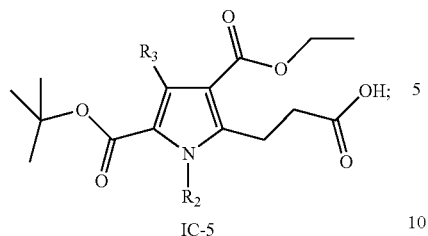
IC-5 reducing pyrrole carboxylethyl dicarboxylic ester IC-5 in anhydrous tetrahydrofuran by borane-tetrahydrofuran solution at −20~−5° C. to provide pyrrole hydroxypropyl dicarboxylic ester IC-6 such that

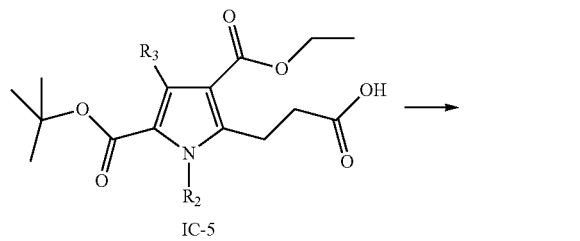
IC-5

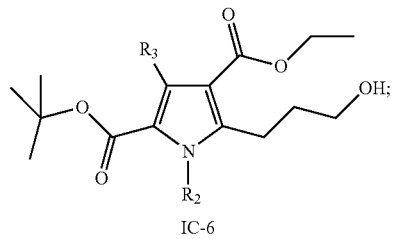
IC-6 mesylating pyrrole hydroxypropyl dicarboxylic ester IC-6 in anhydrous dichloromethane in the presence of triethylamine at −20~−5° C. to obtain pyrrole methylsulfonyloxy-propyl dicarboxylic ester IC-7 such that

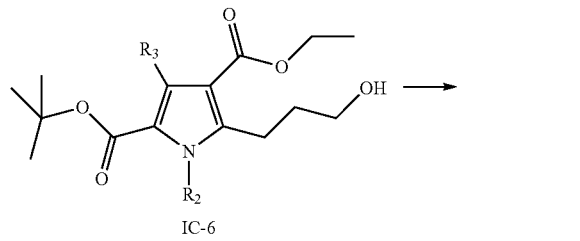
IC-6

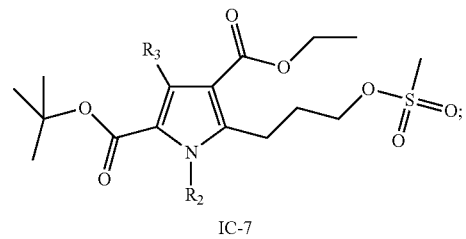
IC-7 reacting pyrrole methylsulfonyloxy-propyl dicarboxylic ester IC-7 with different amines to obtain pyrrole amide dicarboxylic ester IC-8 such that

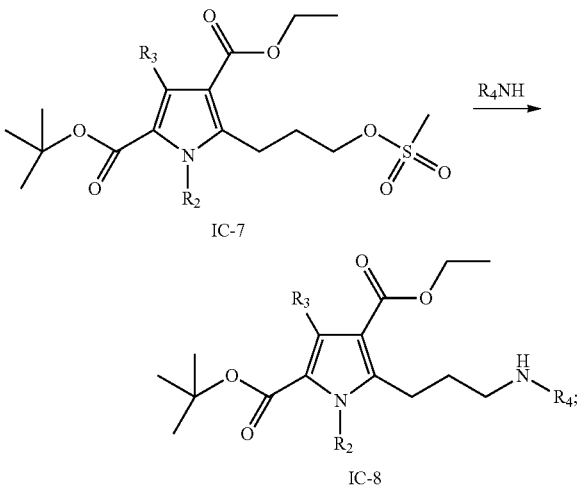
IC-7

IC-8 reacting pyrrole amide dicarboxylic ester IC-8 with trimethyl aluminmum in anhydrous toluene under reflux to obtain the pyrrolofused seven-membered aza-heterocyclic ester IC-9 such that

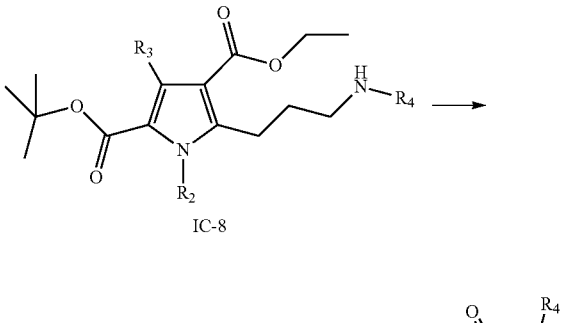
IC-8

IC-9 and reacting pyrrolofused seven-membered aza-heterocyclic ester IC-9 with trifluoroacetic acid at 30~50° C. under an argon atmosphere to obtain pyrrolofused seven-membered aza-heterocyclic formaldehyde IC

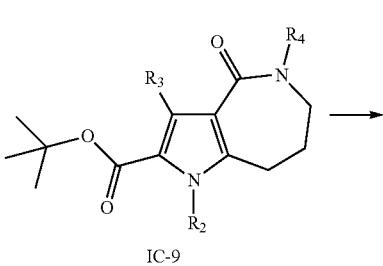
IC-9

-continued

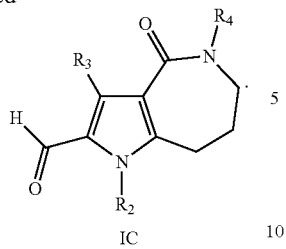

IC

10. A preparation process of the intermediate of formula (ID) according to claim 8, comprising:

reacting pyrrole aldehyde carboxylic diester IC-2 with Grignard reagent cyclopropylmagnesium bromide in anhydrous tetrahydrofuran at room temperature under an argon atmosphere to obtain pyrrole cyclopropyl hydroxycarboxylic diester ID-1 such that

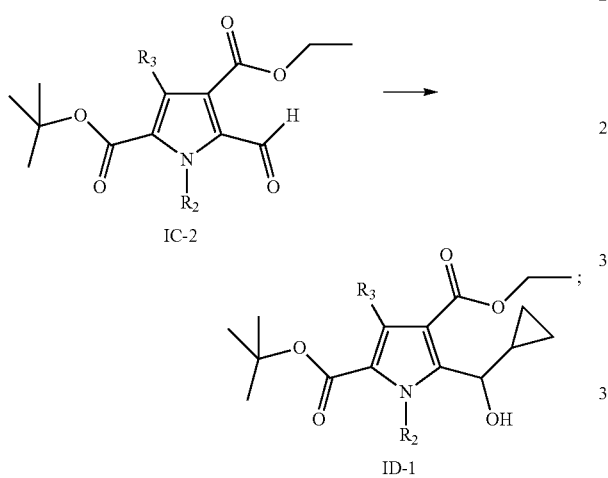

reacting pyrrole cyclopropyl hydroxycarboxylic diester ID-1 with hydrobromic acid in methanol to obtain bromo-butenyl pyrrole diester ID-2 such that

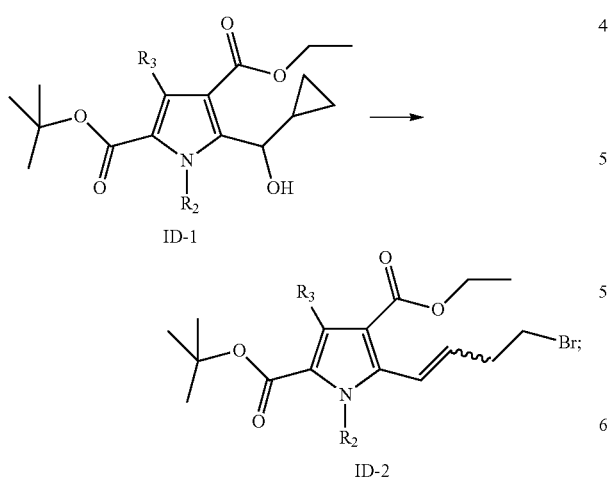

reducing bromo-butenyl pyrrole diester ID-2 in anhydrous ethanol by hydrogen catalyzed by palladium/carbon at room temperature to obtain bromo-butyl pyrrole diester ID-3 such that

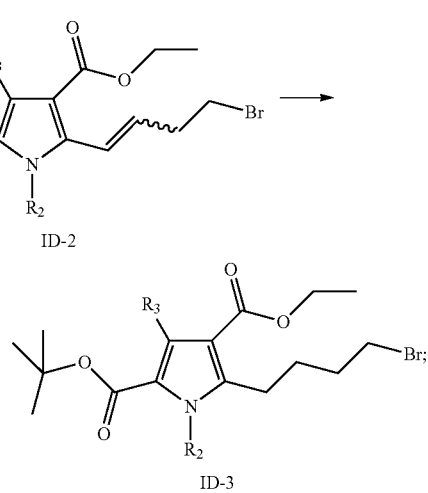

reacting bromo-butyl pyrrole diester ID-3 with different amines in dichloromethane under reflux to obtain pyrrole amide dicarboxylic diester ID-4 such that

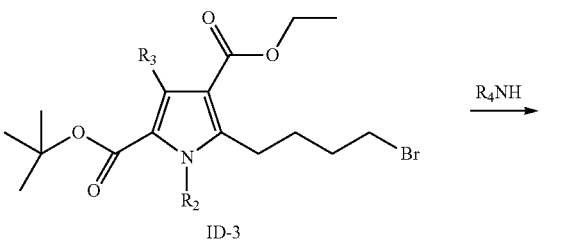

and reacting pyrrole amide dicarboxylic diester ID-4 with trimethyl aluminmum in toluene under reflux to obtain the pyrrolofused eight-membered aza-heterocyclic aldehyde ID such that

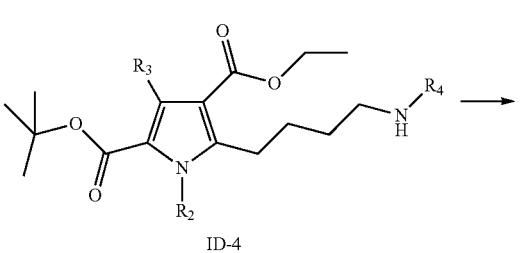

-continued

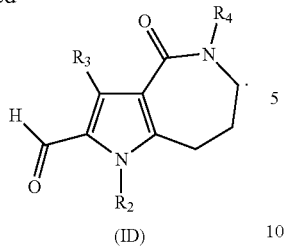

(ID)

11. A preparation process for the compound or a pharmaceutically acceptable salt thereof according to claim 1, comprising:
    reacting an oxindole with an aldehyde in the presence of at least one of triethylamine and piperidine to create a reaction mixture;
    heating said reaction mixture to reflux for 2~12 hours such that said aldehyde has the following formula:

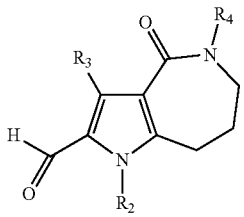

(IC)

-continued

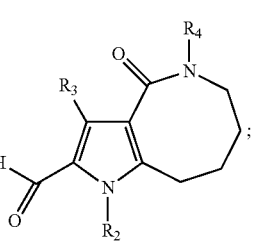

(ID)

said oxindole has the following formula:

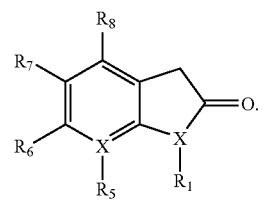

12. A method of treating colon cancer comprising a step of administering to a patient in need thereof a therapeutically effective amount of the compound or a pharmaceutically acceptable salt thereof according to claim 1.

* * * * *